US010299479B2

(12) United States Patent
Nakatani et al.

(10) Patent No.: US 10,299,479 B2
(45) Date of Patent: May 28, 2019

(54) CARBAMOYL TRIAZOLINONE BASED HERBICIDE COMBINATIONS AND METHODS OF USE

(71) Applicant: Arysta LifeScience Corporation, Tokyo (JP)

(72) Inventors: Hideo Nakatani, Tokyo (JP); Noel Burchell Leibbrandt, Mount Edgecombe (ZA); Joao M. Miyasaki, Sao Paulo (BR)

(73) Assignee: Arysta LifeScience Corporation, Chuo-ku, Tokyo (JP)

( * ) Notice: Subject to any disclaimer, the term of this patent is extended or adjusted under 35 U.S.C. 154(b) by 0 days.

(21) Appl. No.: 13/737,849

(22) Filed: Jan. 9, 2013

(65) Prior Publication Data

US 2014/0051579 A1    Feb. 20, 2014

Related U.S. Application Data

(63) Continuation-in-part of application No. 12/796,511, filed on Jun. 8, 2010, now abandoned.

(60) Provisional application No. 61/185,363, filed on Jun. 9, 2009, provisional application No. 61/747,963, filed on Dec. 31, 2012.

(51) Int. Cl.
*A01N 43/653* (2006.01)
*A01N 43/80* (2006.01)
*A01N 47/38* (2006.01)

(52) U.S. Cl.
CPC ........... *A01N 43/653* (2013.01); *A01N 43/80* (2013.01); *A01N 47/38* (2013.01)

(58) Field of Classification Search
CPC ....... A01N 43/653; A01N 43/80; A01N 47/38
USPC ........................................................ 504/134
See application file for complete search history.

(56) References Cited

U.S. PATENT DOCUMENTS

| | | | |
|---|---|---|---|
| 4,405,357 A | | 9/1983 | Chang |
| 5,506,195 A * | | 4/1996 | Ensminger et al. .......... 504/350 |
| 5,968,873 A | | 10/1999 | Dahmen et al. |
| 6,040,271 A | | 3/2000 | Thielert et al. |
| 6,821,926 B1 | | 11/2004 | Feucht et al. |
| 7,115,543 B2 | | 10/2006 | Feucht et al. |
| 2003/0211942 A1 | | 11/2003 | Feucht et al. |
| 2005/0043181 A1 | | 2/2005 | Feucht et al. |
| 2007/0032382 A1* | | 2/2007 | Volgas .................. A01N 25/32 504/101 |
| 2010/0311589 A1* | | 12/2010 | Nakatani ................ A01N 43/80 504/134 |

FOREIGN PATENT DOCUMENTS

| | | |
|---|---|---|
| BR | PI 9704565-9 | 11/1998 |
| CN | 1486609 A | 7/2004 |
| CN | 1596649 A | 3/2005 |
| DE | 19635074 A1 | 3/1998 |
| DE | 19635060 A1 | 5/1998 |
| EP | 0958742 A1 | 11/1999 |
| WO | 96/11575 A1 | 4/1996 |
| WO | 01/37652 A2 | 5/2001 |
| WO | 01/37652 A3 | 5/2001 |
| WO | 03/024224 A2 | 3/2003 |
| WO | 03/024224 A3 | 3/2003 |
| WO | 03/024225 A2 | 3/2003 |
| WO | 03/024225 A3 | 3/2003 |
| WO | 03/028450 A2 | 4/2003 |
| WO | 03/028450 A3 | 4/2003 |
| WO | WO 2008011283 A2 * | 1/2008 |

OTHER PUBLICATIONS

Elmore, M.T., Mesotrione and Amicarbazone Combinations for Annual Bluegrass (Poa Annua) Control, Jan. 2012, 66th Annual Meeting of the Northeastern Weed Science Society, American Society of Horticultural Science, vol. 66, 2 pages.*
Villa Charge. Material Safety Data Sheet [online]. Villa Crop Protection, 2011 [retrieved on Sep. 19, 2017]. Retrieved from the Internet<URL:http://www.villacrop.co.za/files/Charge_Villa_MSDS.pdf>, 3 pages.*
International Application No. PCT/IB2010/001610, International Preliminary Report on Patentability, dated Dec. 22, 2011.
Database WPI, Section CH, Week 200442 GB, AN 2004-441478; XP002639411, "Herbicide Composition Contains 2,4-D Ester, amide herbicide and clomazone", & CN 1 486 609 A (Dali-N Dalian Songliao Chem IDS CO) Apr. 7, 2004.
Database WPI; Section CH, Week 200547 GB; AN 2005-459471 "Herbicide composition containing methyl sulcotrione", & CN 1 596 649 A (Ma Yunsheng [CN]) Mar. 23, 2005.
Aldaba Meza, J.L., et al., "Eficacia de Amicarbazone en Mezcla con Acetochlor en Preemergencia en Maiz en Chihuahua", XXVIII Congresso Nacional de la Ciencia de la Maleza, Oct. 26, 2007, pp. 10-14, XP55006931, Mazatlan.
Ribet, J., et al., "Chapter 6. Research and Scientific Progress", Mauritius Chamber of Agriculture, Annual Report 2007-2008, Jan. 2008, pp. 65-73, XP55006920, URL:http://www.mchagric.org/images/pdf/research_and_scientific_progress.pdf.
Seeruttun, S., et al., "New Herbicide Tank-Mix, Krismat (R) Plus Dinamic (R): a Cost-Effective Broad-Spectrum Pre-& Post-Emergence Treatment for Managing Weeds in Sugarcane", Abstracts from the Proceedings of the 2007 International Society of Sugarcane Technologists Congress, High Wycombe GB, vol. 25, No. 6, Nov. 2007, p. 28, XP009148943, ISSN: 0265-7406.

(Continued)

Primary Examiner — John Pak
Assistant Examiner — Andriae M Holt
(74) Attorney, Agent, or Firm — Carmody Torrance Sandak & Hennessey LLP

(57) ABSTRACT

The invention relates to herbicidal active compound combinations comprising, carbamoyltriazolinones, and herbicidally active compounds, which combinations are suitable for controlling weeds.

10 Claims, 24 Drawing Sheets

(56) References Cited

OTHER PUBLICATIONS

Seeruttun, et al., "New Herbicide Tank-Mix, KRISMAT® + DINAMIC®: A Cost-Effective Broad- Spectrum Pre-& Post-Emergence Treatment for Managing Weeds in Sugarcane", XXVI Congress, Proc. International Society of Sugar Cane Technologists, ICC, Durban, South Africa, Jul. 29-Aug. 2, 2007, 2007 pp. 229-237.
Mauritius Sugar Industry, Annual Report, 2007-2008, Chamber of Agriculture, Chapter Six, Research and Scientific Progress, pp. 64-72.

\* cited by examiner

CARBAMOYL TRIAZOLINONE BASED HERBICIDE COMBINATIONS AND METHODS OF USE

RELATED APPLICATIONS

This application is a continuation-in-part of application Ser. No. 12/796,511, filed Jun. 8, 2010, and claims priority to application Ser. No. 61/747,963, filed Dec. 31, 2012, and application Ser. No. 61/185,363, filed Jun. 9, 2009, each of which applications are expressly incorporated by reference herein in their entirety.

FIELD OF THE INVENTION

The invention relates to herbicidal, active compound combinations composed of known carbamoyltriazolinones and herbicidally active compounds, which can be used successfully for controlling weeds.

INTRODUCTION

Herbicides play an important role for weed control in crop production. Applying combinations of herbicidal compounds may enhance the herbicidal effectiveness.

SUMMARY OF THE INVENTION

Figure 1:
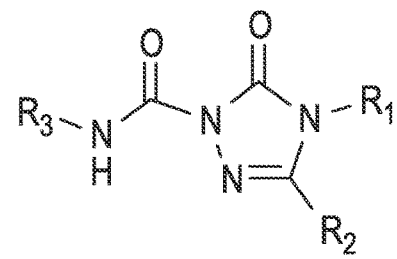
FIG. 1 shows a carbamoyltriazolinone of the general formula (I).

Embodiments herein, accordingly, provides compositions comprising a synergistic effective amount of a combination of a first compound and a second component, wherein said first compound is a compound of the formula (I)

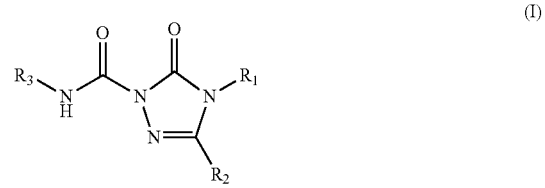

wherein:

$R_1$ is selected from the group consisting of hydrogen, hydroxyl, amino, or in each case optionally substituted alkyl, alkenyl, alkinyl, alkoxy, alkenyloxy, alkinyloxy, alkylamino, alkenylamino, alkenylamino, alkylideneamino, dialkylamino, cycloalkyl, cycloalkylalkyl, aryl and arylalkyl, any of which may be optionally substituted;

$R_2$ is selected from the group consisting of alkyl, alkenyl, alkinyl, alkoxy, alkenyloxy, alkinyloxy, alkylthio, alkenylthio, alkinylthio, alkylamino, alkenylamino, alkinylamino, dialkylamino, cycloalkyl, cycloalkyloxy, cycloalkylalkyl, aryl, aryloxy, arylthio, arylamino and arylalkyl, any of which may be optionally substituted;

$R_3$ is selected from the group consisting of alkyl, alkenyl, alkinyl, cycloalkyl, cycloalkylalkyl, arylalkyl, arylalkenyl and arylalkinyl, any of which may be optionally substituted; and said second component is selected from 2-[(2-chlorophenyl)methyl]-4,4-dimethyl-3-isoxazolidinone, 3-cyclohexyl- 6-dimethylamino-1-methyl-1,3,5-triazine-2,4(1H,3H)-dione, 4-methyl-2-chlorophenoxyacetic acid, 2-chloro-4-(ethylamine)-6-(isopropylamine)-s-triazine, 2-chloro-N-(2-ethyl-6-methylphenyl)-N-[(1-methylethoxy)methyl]acetamide, an herbicide of the chloroacetamide class, (aka, the chloroacetanilide class) and mixtures thereof.

In various aspects, an herbicide of the chloroacetamide class include 2-chloro-N-(2-ethyl-6-methylphenyl)-N-[(1-methylethoxy)methyl]acetamide (Propisochlor), 2-chloro-N-ethoxymethyl-6'-ethylacet-o-toluidide (Acetochlor), 2-chloro-N-(2-ethyl-6-methylphenyl)-N-(2-methoxy-1-methylethyl)acetamide, (Metolachlor), 2-chloro-N-(2-ethyl-6-methylphenyl)-N-[(1S)-2-methoxy-1-methylethyl]acetamide (S-Metolachlor), 2-chloro-N-(2,6-diethylphenyl)-N-(methoxymethyl)acetamide (Alachlor), and N-(butoxymethyl)-2-chloro-N-(2,6-diethylphenyl)acetamide (Butachlor), N-[[(2Z)-2-butenyloxy]methyl]-2-chloro-N-(2,6-diethylphenyl)acetamide (Butenachlor), 2-chloro-N-(2,6-dimethylphenyl)-N-[(2-methylpropoxy)methyl]acetamide (Delachlor), N-(chloroacetyl)-N-(2,6-diethylphenyl)glycine(Diethatyl), 2-chloro-N-(2,6-dimethylphenyl)-N-(2-methoxyethyl)acetamide (Dimethachlor), 2-chloro-N-(2,6-dimethylphenyl)-N-(1H-pyrazol-1-ylmethyl)acetamide (Metazachlor), 2-chloro-N-(2,6-diethylphenyl)-N-(2-propoxyethyl)acetamide (Pretilachlor), 2-chloro-N-(1-methylethyl)-N-phenylacetamide (Propachlor), 2-chloro-N-(1-methyl-2-propynyl)-N-phenylacetamide (Prynachlor), N-(butoxymethyl)-2-chloro-N-[2-(1,1-dimethylethyl)-6-methylphenyl]acetamide (Terbuchlor), 2-chloro-N-(2,6-dimethylphenyl)-N-[(3-methoxy-2-thienyl)methyl]acetamide (Thenylchlor), and 2-chloro-N-(2,3-dimethylphenyl)-N-(1-methylethyl)acetamide (Xylachlor).

In one embodiment, $R_1$ is an optionally substituted amino. In a further embodiment, $R_1$ is $NH_2$. In one embodiment, $R_2$ is an optionally substituted alkyl. In a further embodiment, $R_2$ is i-propyl. In one embodiment, $R_3$ is an optionally substituted alkyl. In a further embodiment, $R_3$ is t-butyl.

In certain embodiments, a first compound is 4-amino-5-isopropyl-2-(tert-butyl-aminocarbonyl)-2,4-dihydro-3H-1,2,4-triazol-3-one. In certain embodiments, a second component is 2-chloro-N-(2-ethyl-6-methylphenyl)-N-[(1-methylethoxy)methyl]acetamide. In certain embodiments, a second component is 2-[(2-chlorophenyl)methyl]-4,4-dimethyl-3-isoxazolidinone and 3-cyclohexyl-6-dimethylamino-1-methyl-1,3,5-triazine-2,4(1H,3H)-dione. In certain embodiments, a second component is 4-methyl-2-chlorophenoxyacetic acid.

In another embodiment, a composition further includes an adjuvant. In a further embodiment, an adjuvant is an ethoxylated propoxylated fatty amine or a polyether-polymethylsiloxane-copolymer. In yet a further embodiment, a composition further includes a herbicidally acceptable diluent or carrier.

In one embodiment, a second component is present in the composition in an amount ranging from 0.001 to 1000 parts by weight per part by weight of the first component. In a further embodiment, a second component is present in the composition in an amount ranging from 0.02 to 500 parts by weight per part by weight of the first component. In yet a further embodiment, a second component is present in the composition in an amount ranging from 0.05 to 100 parts by weight per part by weight of the first component.

In another embodiment of the invention, a composition is in a solid or liquid form of an emulsifiable concentrate, wettable powder, granule, dust, oil spray or aerosol.

In embodiments, compositions described herein provides synergistic control of one or more weeds. In one embodiment, a weed is *Amaranthus, Digitaria, Cyperus* or *Euphorbia*.

Embodiments herein also provide methods for selective control of weeds. In one aspect, a method includes contacting a composition comprising a synergistic effective amount of a combination of a first compound and a second component onto a crop plant or a non-crop area in need of weed control or at risk of undesirable weeds, in an amount effective to provide weed control in the crop, wherein said first compound is a compound of the formula (I)

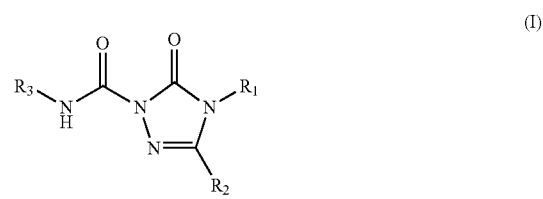

wherein:

$R_1$ is selected from the group consisting of hydrogen, hydroxyl, amino, or in each case optionally substituted alkyl, alkenyl, alkinyl, alkoxy, alkenyloxy, alkinyloxy, alkylamino, alkenylamino, alkenylamino, alkylideneamino, dialkylamino, cycloalkyl, cycloalkylalkyl, aryl and arylalkyl, any of which may be optionally substituted;

$R_2$ is selected from the group consisting of alkyl, alkenyl, alkinyl, alkoxy, alkenyloxy, alkinyloxy, alkylthio, alkenylthio, alkinylthio, alkylamino, alkenylamino, alkinylamino, dialkylamino, cycloalkyl, cycloalkyloxy, cycloalkylalkyl, aryl, aryloxy, arylthio, arylamino and arylalkyl, any of which may be optionally substituted;

$R_3$ is selected from the group consisting of alkyl, alkenyl, alkinyl, cycloalkyl, cycloalkylalkyl, arylalkyl, arylalkenyl and arylalkinyl, any of which may be optionally substituted; and said second component is selected from 2-[(2-chlorophenyl)methyl]-4,4-dimethyl-3-isoxazolidinone, 3-cyclohexyl-6-dimethylamino-1-methyl-1,3,5-triazine-2,4(1H,3H)-dione, 4-methyl-2-chlorophenoxyacetic acid, 2-chloro-4-(ethylamine)-6-(isopropylamine)-s-triazine, N-ethyl-N'-(1-methylethyl)-6-(methylthio)-1,3,5-triazine-2,4-diamine, N-(3,4-dichlophenyl)-N,N-dimethyl urea, 5-cyclopropyl-4-(2-methylsulfonyl-4-trifluoromethylbenzoyl)isoxazole, 4-amino-6-tert-butyl-4,5-dihydro-3-methyltio-1,2,4-triazin-5-one, 1-(5-tert-butyl-1,3,4-thiadiazol-2-yl)-1,3-dimethylurea, 2',4'-dichloro-5'-(4-difluoromethyl-4,5-dihydro-3-methyl-5-oxo-1H-1,2,4-triazol-1-yl)methanesulfonanilide, 2-(4-mesyl-2-nitrobenzoyl)cyclohexane-1,3-dione, N-(phosphonomethyl)glycine, dimethylamine salt of 2,4-dichlorophenoxyacetic acid, an herbicide of the chloroacetamide class, and mixtures thereof.

In various aspects, an herbicide of the chloroacetamide class includes 2-chloro-N-(2-ethyl-6-methylphenyl)-N-[(1-methylethoxy)methyl]acetamide (Propisochlor), 2-chloro-N-ethoxymethyl-6'-ethylacet-o-toluidide (Acetochlor), 2-chloro-N-(2-ethyl-6-methylphenyl)-N-(2-methoxy-1-methylethyl)acetamide(Metolachlor), 2-chloro-N-(2-ethyl-6-methylphenyl)-N-[(1S)-2-methoxy-1-methylethyl]acetamide (S-Metolachlor), 2-chloro-N-(2,6-diethylphenyl)-N-(methoxymethyl)acetamide (Alachlor), and N-(butoxymethyl)-2-chloro-N-(2,6-diethylphenyl)acetamide (Butachlor), N-[[(2Z)-2-butenyloxy]methyl]-2- chloro-N-(2,6-diethylphenyl)acetamide (Butenachlor), 2-chloro-N-(2,6-dimethylphenyl)-N-[(2-methylpropoxy) methyl]acetamide (Delachlor), N-(chloroacetyl)-N-(2,6-diethylphenyl)glycine(Diethatyl), 2-chloro-N-(2,6-dimethylphenyl)-N-(2-methoxyethyl)acetamide (Dimethachlor), 2-chloro-N-(2,6-dimethylphenyl)-N-(1H-pyrazol-1-ylmethyl)acetamide (Metazachlor), 2-chloro-N-(2,6-diethylphenyl)-N-(2-propoxyethyl)acetamide (Pretilachlor), 2-chloro-N-(1-methylethyl)-N-phenylacetamide (Propachlor), 2-chloro-N-(1-methyl-2-propynyl)-N-phenylacetamide (Prynachlor), N-(butoxymethyl)-2-chloro-N-[2-(1,1-dimethylethyl)-6-methylphenyl]acetamide (Terbuchlor), 2-chloro-N-(2,6-dimethylphenyl)-N-[(3-methoxy-2-thienyl) methyl]acetamide (Thenylchlor), and 2-chloro-N-(2,3-dimethylphenyl)-N-(1-methylethyl)acetamide (Xylachlor).

In certain embodiments, a crop plant is selected from cereals, rice, maize, sorghum, sugar cane, cotton, canola, turf, barley, potato, sweet potato, sunflower, rye, oats, wheat, corn, soybean, sugar beet, tobacco, safflower, tomato, alfalfa, pineapple and cassaya.

In one embodiment, a second component is selected from N-ethyl-N'-(1-methylethyl)-6-(methylthio)-1,3,5-triazine-2,4-diamine, N-(3,4-dichlophenyl)-N,N-dimethyl urea, 5-cyclopropyl-4-(2-methylsulfonyl-4-trifluoromethylbenzoyl) isoxazole and 4-amino-6-tert-butyl-4,5-dihydro-3-methyltio-1,2,4-triazin-5-one. In one embodiment, a crop plant is selected from the group consisting of sugar cane, pineapple, cassaya, turf and pasture.

In one embodiment, a composition further comprises 2-[(2-chlorophenyl)methyl]-4,4-dimethyl-3-isoxazolidinone and/or 3-cyclohexyl-6-dimethylamino-1-methyl-1,3,5-triazine-2,4(1H,3H)-dione. In one embodiment, a crop plant is sugar cane, turf and pasture.

In one embodiment, a composition further comprises 4-methyl-2-chlorophenoxyacetic acid. In an additional embodiment, a composition further includes an adjuvant. In a further embodiment, an adjuvant is an ethoxylated propoxylated fatty amine or a polyether-polymethylsiloxane-copolymer. In one embodiment, a crop plant is sugar cane, turf and pasture.

In one embodiment, a first compound is 4-amino-5-isopropyl-2-(tert-butyl-aminocarbonyl)-2,4-dihydro-3H-1,2,4-triazol-3-one.

In one embodiment, a composition is contacted at an application rate of from 0.01 kg/ha to 5.00 kg/ha of the first compound and from 0.5 kg/ha to 10.00 kg/ha of the second component to the crop. In a further embodiment, a composition is contacted at an application rate of from 0.03 kg/ha to 3.00 kg/ha of the first compound to the crop. In yet a further embodiment, a composition is contacted at an application rate of from 0.05 kg/ha to 5.00 kg/ha of the second component to the crop.

As used herein, "application rate" refers to the amount of a synergistic treatment composition applied over an area, that is, "application rate" is nominally an application coverage. "Application rate" is not intended to encompass an application amount per unit time as might be implied by the term "rate."

In one embodiment, a composition is applied as a pre-emergence treatment. In another embodiment, the composition is applied as a post-emergence treatment.

In certain embodiments, a weed is *Amaranthus, Digitaria, Cyperus* or *Euphorbia*.

In some embodiments, a composition comprises a synergistic amount of a combination of amicarbazone (4-amino-N-tert-butyl-4,5-dihydro-3-isopropyl-5-oxo-1H-1,2,4-triazole-1-carboxamide) and mesotrione (2-[4-(Methylsulfonyl)-2-nitrobenzoyl]cyclohexane-1,3-dione), wherein the composition is an effective herbicide.

In some embodiments, the composition further comprises an adjuvant. In some embodiments, the adjuvant is an ethoxylated propoxylated fatty amine or a polyether-polymethylsiloxane-copolymer.

In some embodiments, the composition further comprises a herbicidally acceptable diluent or carrier.

In some embodiments, the composition comprises a solid or liquid form. In some embodiments, the composition comprises an emulsifiable concentrate, wettable powder, granule, dust, oil spray or aerosol.

In some embodiments, the composition provides synergistic control of one or more weeds. In some embodiments, the one or more weeds is a broadleaf weed. In some embodiments, the one or more weeds is selected from the group consisting of mustard, *Poa annua*, green foxtail, crabgrass, blackjack, pigweed, khaki weed, crab-finger grass, large thornapple, purslane, dwarf marigold, field bindweed, anoda weed, *Rottboelia exaltata, Ipomeoea purpurea, Eleusine indica, Amaranthus spinosus*, and *Commelina benghalensis*.

In some embodiments, the mesotrione and amicarbzone are present in a ratio within a range of from about 16:1 to about 4:3, such ratios being weight ratios. In some such embodiments, the ratio of mesotrione and amicarbzone is within a range of from about 8:1 to about 4:3.

In some embodiments, a method for selective control of weeds comprises contacting a weed with the above described compositions.

In some embodiments, the method is employed to control weeds present within a crop. In some such embodiments, the crop is selected from the group consisting of cereals, rice, maize, sorghum, sugar cane, cotton, canola, grass, turf grass, barley, potato, sweet potato, sunflower, rye, oats, wheat, corn, soybean, sugar beet, tobacco, safflower, tomato, alfalfa, pineapple and cassaya. In some such embodiments, the weed is a broadleaf weed. In some such embodiments, the weed is selected from the group consisting of mustard, *Poa annua*, green foxtail, crabgrass, blackjack, pigweed, khaki weed, crab-finger grass, large thornapple, purslane, dwarf marigold, field bindweed, anoda weed, *Rottboelia exaltata, Ipomeoea purpurea, Eleusine indica, Amaranthus spinosus*, and *Commelina benghalensis*, and combinations thereof.

In some embodiments, methods apply the composition as a pre-emergence treatment. In other embodiments, methods apply the composition is applied as a post-emergence treatment.

In some embodiments, methods apply the composition at an application rate of from about 0.035 kg/ha to about 0.210 kg/ha of amicarbazone and from about 0.280 kg/ha to about 0.560 kg/ha of mesotrione to the crop. In some such embodiments, the composition is applied at an application rate of about 0.210 kg/ha of amicarbazone and about 0.560 kg/ha of mesotrione to the crop. In other such embodiments, the composition is applied at an application rate of about 0.210 kg/ha of amicarbazone and about 0.280 kg/ha of mesotrione to the crop.

In any of the aforementioned composition or methods, the composition exhibits reduced bleaching of one or more weeds as compared to application of mesotrione alone. "Bleaching," as used herein, refers to the discoloration of weeds causing it to be visually more conspicuous to the eye of an observer. This may appear as a lightening of an existing color or a washing out of pigmentation observed as a whitening of the weed.

DETAILED DESCRIPTION

A series of active compounds from the carbamoyltriazolinone series, used jointly with herbicidally active compounds from various classes of substances, show a synergistic activity with regard to the action against weeds and can be employed as products for controlling (e.g. limiting growth) monocotyledonous (e.g. glasses) or dicotyledonous weeds (e.g. board leaves) in crops of useful plants such as, for example, in barley, maize, rice, soya beans, sunflowers, wheat, pineapple, Cassaya, sugar cane, corn and Agave. but also for the selective, semi- and non-selective control of monocotyledonous and dicotyledonous weeds.

Disclosed herein are herbicidal compositions, characterized by an effective content of composition comprising
(a) a carbamoyltriazolinone of the general formula (I)

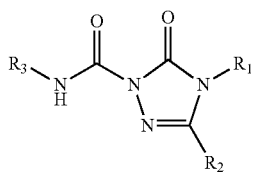

wherein:
$R_1$ represents hydrogen, hydroxyl, amino, or in each case optionally substituted alkyl, alkenyl, alkinyl, alkoxy, alkenyloxy, alkinyloxy, alkylamino, alkenylamino, alkenylamino, alkylideneamino, dialkylamino, cycloalkyl, cycloalkylalkyl, aryl and arylalkyl, any of which may be optionally substituted, $R_2$ represents alkyl, alkenyl, alkinyl, alkoxy, alkenyloxy, alkinyloxy, alkylthio, alkenylthio, alkinylthio, alkylamino, alkenylamino, alkinylamino, dialkylamino, cycloalkyl, cycloalkyloxy, cycloalkylalkyl, aryl, aryloxy, arylthio, arylamino and arylalkyl, any of which may be optionally substituted, and $R_3$ represents alkyl, alkenyl, alkinyl, cycloalkyl, cycloalkylalkyl, arylalkyl, arylalkenyl and arylalkinyl, any of which may be optionally substituted.
(active compounds of group a)
(b) one or more compounds from a second component of herbicides containing the active compounds mentioned herein below: 2-[(2-chlorophenyl)methyl]-4,4-dimethyl-3-isoxazolidinone (Clomazone), 3-cyclohexyl-6-dimethylamino-1-methyl-1,3,5-triazine-2,4(1H,3H)-dione (Hexazinone), 4-methyl-2-chlorophenoxyacetic acid (MCPA), 2-chloro-4-(ethylamine)-6-(isopropylamine)-s-triazine (Atrazine), N-ethyl-N'-(1-methylethyl)-6-(methylthio)-1,3,5-triazine-2,4-diamine (Ametryn), N-(3,4-dichlophenyl)-N,N-dimethyl urea (Diuron), 5-cyclopropyl-4-(2-methylsulfonyl-4-trifluoromethylbenzoyl)isoxazole (Isoxaflutole), 4-amino-6-tert-butyl-4,5-dihydro-3-methyltio-1,2,4-triazin-5-one (Metribuzin), 1-(5-tert-butyl-1,3,4-thiadiazol-2-yl)-1,3-dimethylurea (Tebuthiuron), 2',4'-dichloro-5'-(4-difluoromethyl-4,5-dihydro-3-methyl-5-oxo-1H-1,2,4-triazol-1-yl)methanesulfonanilide (Sulfentrazone), 2-(4-mesyl-2-nitrobenzoyl)cyclohexane-1,3-dione (Mesotrione), N-(phosphonomethyl)glycine (Glyphosate), dimethylamine salt of 2,4-dichlorophenoxyacetic acid (2,4-D Amine), an herbicide of the chloroacetamide class, for example, 2-chloro-N-(2-ethyl-6-methylphenyl)-N-[(1-methylethoxy)methyl]acetamide (Propisochlor), 2-chloro-N-ethoxymethyl-6'-ethylacet-o-toluidide (Acetochlor), 2-chloro-N-(2-ethyl-6-methylphenyl)-N-(2-methoxy-1-methylethyl)acetamide (Metolachlor), 2-chloro-N-(2-ethyl-6-methylphenyl)-N-[(1S)-2-methoxy-1-methylethyl]acetamide (S-Metolachlor), 2-chloro-N-(2,6-diethylphenyl)-N-(methoxymethyl)acetamide (Alachlor), and N-(butoxymethyl)-2-chloro-N-(2,6-diethylphenyl)acetamide (Butachlor), N-[[(2Z)-2-butenyloxy]methyl]-2-chloro-N-(2,6-diethylphenyl)acetamide (Butenachlor), 2-chloro-N-(2,6-dimethylphenyl)-N-[(2-methylpropoxy)methyl]acetamide (Delachlor), N-(chloroacetyl)-N-(2,6-diethylphenyl)glycine(Diethatyl), 2-chloro-N-(2,6-dimethylphenyl)-N-(2-methoxyethyl)acetamide (Dimethachlor), 2-chloro-N-(2,6-dimethylphenyl)-N-(1H-pyrazol-1-ylmethyl)acetamide (Metazachlor), 2-chloro-N-(2,6-diethylphenyl)-N-(2-propoxyethyl)acetamide (Pretilachlor), 2-chloro-N-(1-methylethyl)-N-phenylacetamide (Propachlor), 2-chloro-N-(1-methyl-2-propynyl)-N-phenylacetamide (Prynachlor), N-(butoxymethyl)-2-chloro-N-[2-(1,1-dimethylethyl)-6-methylphenyl]acetamide (Terbuchlor), 2-chloro-N-(2,6-dimethylphenyl)-N-[(3-methoxy-2-thienyl)methyl]acetamide (Thenylchlor), and 2-chloro-N-(2,3-dimethylphenyl)-N-(1-methylethyl)acetamide (Xylachlor), and mixtures thereof.
(active compounds of group b)

The meanings of the radicals mentioned in the above formula (I) are illustrated hereinbelow.

In certain embodiments, $R_1$ represents hydrogen, hydroxyl, amino, or represents alkyl, alkenyl, alkinyl, alkoxy, alkenyloxy, alkinyloxy, alkylamino, alkenylamino, alkinylamino, alkylideneamino or dialkylamino, each of which has up to 6 carbon atoms and each of which is optionally substituted by halogen or cyano, or represents cycloalkyl, cycloalkylalkyl, each of which has 3 to 6 carbon atoms in the cycloalkyl groups and, if appropriate, 1 to 4 carbon atoms in the alkyl group and each of which is optionally substituted by halogen, cyano or $C_1$-$C_4$-alkyl, or represents phenyl or phenyl-$C_1$-$C_4$-alkyl, each of which is optionally substituted by halogen, cyano, $C_1$-$C_4$-alkyl or $C_1$-$C_4$-alkoxy.

In certain embodiments, $R_2$ represents alkyl, alkenyl, alkinyl, alkoxy, alkenyloxy, alkinyloxy, alkylthio, alkenylthio, alkinylthio, alkylamino, alkenylamino, alkinylamino or dialkylamino, each of which has up to 6 carbon atoms and each of which is optionally substituted by halogen, cyano, $C_1$-$C_4$-alkoxy or $C_1$-$C_4$-alkylthio, or represents cycloalkyl, cycloalkyloxy or cycloalkylalkyl, each of which has 3 to 6 carbon atoms in the cycloalkyl groups and, if appropriate, 1 to 4 carbon atoms in the alkyl group and each of which is optionally substituted by halogen, cyano or $C_1$-$C_4$-alkyl, or represents phenyl, phenoxy, phenylthio, phenylamino or phenyl-$C_1$-$C_4$-alkyl, each of which is optionally substituted by halogen, cyano, $C_1$-$C_4$-alkyl or $C_1$-$C_4$-alkoxy.

In certain embodiments, $R_3$ represents alkyl, alkenyl or alkinyl, each of which has up to 10 carbon atoms and each of which is optionally substituted by halogen, cyano, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-alkylamino or di-($C_1$-$C_4$-alkyl)amino, or represents cycloalkyl or cycloalkylalkyl, each of which has 3 to 6 carbon atoms in the cycloalkyl moiety and, if appropriate,) to 4 carbon atoms in the alkyl moiety and each of which is optionally substituted by halogen, cyano or $C_1$-$C_4$-alkyl, or represents phenyl-$C_1$-$C_6$-alkyl, phenyl-$C_2$-$C_6$-alkenyl or phenyl-$C_2$-$C_6$-alkinyl, each of which is optionally substituted by halogen, cyano, $C_1$-$C_4$-alkyl or $C_1$-$C_4$-alkoxy.

In certain embodiments, $R_1$ represents hydrogen, hydroxyl, amino, or represents methyl, ethyl, n- or i-propyl, n-, i-, s- or t-butyl, propenyl, butenyl, propinyl or butinyl, methoxy, ethoxy, n- or i-propoxy, n-, i-, s- or t-butoxy, propenyloxy, butenyloxy, propinyloxy or butinyloxy, methylamino, ethylamino, n- or i-propylamino, n-, i-, s- or t-butylamino, propenylamino, butenylamino, propinylamino or butinylamino, ethylideneamino, propylideneamino, butylideneamino, dimethylamino or diethylamino, each of which is optionally substituted by fluorine, chlorine or cyano, or represents cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine, bromine, cyano, methyl, ethyl, n- or i-propyl, or represents phenyl or benzyl, each of which is optionally substituted by fluorine, chlorine, bromine, cyano, methyl, ethyl, n- or i-propyl, n-, i-, s- or t-butyl, methoxy or ethoxy.

In certain embodiments, $R_2$ represents methyl, ethyl, n- or i-propyl, n-, i-, s- or t-butyl, propenyl, butenyl, propinyl, butinyl, methoxy, ethoxy, n- or i-propoxy, n-, i-, s- or t-butoxy, propenyloxy, butenyloxy, propinyloxy, butinyloxy, methylthio, ethylthio, n or i-propylthio, n-, i-, s- or t-butylthio, propenylthio, butenylthio, propinylthio, butinylthio, methylamino, ethylamino, n- or i-propylamino, n-, i-, s- or t-butylamino, propenylamino, butenylamino, propinylamino, butinylamino, dimethyl-lamino or diethylamino, each of which is optionally substituted by fluorine, chlorine, cyano, methoxy, ethoxy, n- or i-propoxy, methylthio, ethylthio, n- or i-propylthio, or represents cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl or cyclohexylmethyl, each of which is optionally substituted by fluorine, chlorine, bromine, cyano, methyl, ethyl, n- or i-propyl, or represents phenyl, phenoxy, phenylthio, phe-nylamino or benzyl, each of which is optionally substituted by fluorine, chlorine, bromine, cyano, methyl, ethyl, n- or i-propyl, n-, i-, s- or t-butyl, methoxy or ethoxy.

In certain embodiments, $R_3$ represents methyl, ethyl, n- or i-propyl, n-, i-, s- or t-butyl, propenyl, butenyl, pentenyl, hexenyl, propinyl, butinyl, pentinyl or hexinyl, each of which is optionally substituted by fluorine, cyano, methoxy, ethoxy, n- or i-propoxy, n-, i-, s- or t-butoxy, methylthio, ethylthio, n- or i-propylthio, n-, i-, s-, or t-butylthio, methylsulphinyl, ethylsulphinyl, methylsulphonyl, ethylsulphonyl, methylamino, ethylamino, n- or i-propylamino, n-, i-, s- or t-butylamino, dimethylamino, diethylamino, dipropylamino or dibutylamino, or represents cyclopropyl, cyclobutyl, cyclopentyl, cyclohexyl, cyclopropylmethyl, cyclobutylmethyl, cyclopentylmethyl, cyclohexylmethyl, cyclohexylethyl or cyclohexylpropyl, each of which is optionally substituted by fluorine, chlorine, bromine, cyano, methyl, ethyl, n- or i-propyl, or represents benzyl, phenylethyl, phenylpropyl, phenylbutyl, phenylethenyl, phenylpropenyl, phenylbutenyl, phenylethinyl, phenyl-propinyl or phenylbutinyl, each of which is optionally substituted by fluorine, chlorine, bromine, cyano, methyl, ethyl, n- or i-propyl, n-, i-, s- or t-butyl, methoxy or ethoxy.

In certain embodiments, $R_1$ represents hydrogen, amino, or represents methyl, ethyl, n- or i-propyl, propenyl, butenyl, propinyl or butinyl, methoxy, ethoxy, n- or i-propoxy, propenyloxy or propinyloxy, each of which is optionally substituted by fluorine or chlorine, or represents methylamino, ethylamino, n- or i-propylamino, propeny-lamino or propinylamino, dimethylamino or diethylamino, or represents cyclopropyl or cyclopropylmethyl, each of which is optionally substituted by fluorine, chlorine, cyano or methyl.

In certain embodiments, $R_2$ represents methyl, ethyl, n- or i-propyl, n-, i-, s- or t-butyl, propenyl, butenyl, propinyl, butinyl, methoxy, ethoxy, n- or i-propoxy, n-, i-, s- or t-butoxy, propenyloxy, butenyloxy, propinyloxy, butinyloxy, methylthio, ethylthio, n- or i-propylthio, n-, i-, s- or t-butylthio, propenylthio, butenylthio, propinylthio, butinylthio, methylamino, ethylamino, n- or i-propylamino, n-, i-, s- or t-butylamino, propenylamino, butenylamino, propinylamino, butinylamino, dimethyl-lamino or diethylamino, each of which is optionally substituted by fluorine, chlorine, cyano, methoxy, ethoxy, methylthio or ethylthio, or represents cyclopropyl, cyclo-propyloxy or cyclopropylmethyl, each of which is option-ally substituted by fluorine, chlorine, cyano or methyl.

In certain embodiments, $R_3$ represents methyl, ethyl, n- or i-propyl, n-, i-, s- or t-butyl, propenyl, butenyl, pentenyl, hexenyl, propinyl, butinyl, pentinyl or hexinyl, each of which is optionally substituted by fluorine, cyano, methoxy, ethoxy, n- or i-propoxy, methylthio, ethylthio, n- or i-propylthio, methylsulphinyl, ethylsulphinyl, methylsulphonyl, ethylsulphonyl, methylamino, ethylamino, n- or i-propylamino, dimethylamino or diethylamino, or represents cyclopropyl, cyclobutyl, cyclopentyl, cyclohexyl, cyclopropylmethyl, cyclobutylmethyl, cyclopentylmethyl, cyclohexylmethyl, cyclohexylethyl or cyclohexylpropyl, each of which is optionally substituted by fluorine, chlorine, bromine, cyano, methyl, ethyl, n- or i-propyl, or represents benzyl, phenylethyl, phenylpropyl, phenylbutyl, phenylethenyl, phenylpropenyl, phenylbutenyl, phenylethinyl, phenyl-propinyl or phenylbutinyl, each of which is optionally substituted by fluorine, chlorine, bromine, cyano, methyl, ethyl, n- or i-propyl, n-, i-, s- or t-butyl, methoxy or ethoxy.

Non-limiting examples of individually compounds of the formula (I) to be used as components according to the invention in mixtures are:

4-amino-5-methyl-2-(1,1-dimethyl-ethyl-aminocarbonyl)-2,4-dihydro-3H-1,2,4-triazol-3-one, 4-amino-5-ethyl-2-(1,1-dimethyl-ethyl-aminocarbonyl)-2,4-dihydro-3H-1,2,4-triazol-3-one, 4-amino-5-n-propyl-2-(1,1-dimethyl-ethyl-aminocarbonyl)-2,4-dihydro-3H-1,2,4-triazol-3-one, 4-amino-5-i-propyl-2-(1,1-dimethyl-ethyl-aminocarbonyl)-2,4-dihydro-3H-1,2,4-triazol-3-one, 4-amino-5-methoxy-2-(1,1-dimethyl-ethyl-aminocarbonyl)-2,4-dihydro-3H-1,2,4-triazol-3-one, 4-amino-5-ethoxy-2-(1,1-dimethyl-ethyl-aminocarbonyl)-2,4-dihydro-3H-1,2,4-triazol-3-one, 4-amino-5-methyl-2-(2-fluoro-1,1-dimethyl-ethyl-aminocarbonyl)-2,4-dihydro-3H-1,2,4-triazol-3-one, 4-amino-5-ethyl-2-(2-fluoro-1,1-dimethyl-ethyl-aminocarbonyl)-2,4-dihydro-3H-1,2,4-triazol-3-one, 4-amino-5-n-propyl-2-(2-fluoro-1,1-dimethyl-ethyl-aminocarbonyl)-2,4-dihydro-3H-1,2,4-triazol-3-one, 4-amino-5-i-propyl-2-(2-fluoro-1,1-dimethyl-ethyl-aminocarbonyl)-2,4-dihydro-3H-1,2,4-triazol-3-one, 4-amino-5-methoxy-2-(2-fluoro-1,1-dimethyl-ethyl-aminocarbonyl)-2,4-dihydro-3H-1,2,4-triazol-3-one, 4-amino-5-ethoxy-2-(2-fluoro-1,1-dimethyl-ethyl-amino-carbonyl)-2,4-dihydro-3H-1,2,4-triazol-3-one, 4-amino-5-methyl-2-(2-chloro-1,1-dimethyl-ethyl-aminocarbonyl)-2,4-dihydro-3H-1,2,4-triazol-3-one, 4-amino-5-ethyl-2-(2-chloro-1,1-dimethyl-ethyl-aminocarbonyl)-2,4-dihydro-3H-1,2,4-triazol-3-one, 4-amino-5-n-propyl-2-(2-chloro-1,1-dimethyl-ethyl-aminocarbonyl)-2,4-dihydro-3H-1,2,4-triazol-3-one, 4-amino-5-i-propyl-2-(2-chloro-1,1-dimethyl-ethyl-amino-carbonyl)-2,4-dihydro-3H-1,2,4-triazol-3-one, 4-amino-5-methoxy-2-(2-chloro-1,1-dimethylethyl-aminocarbonyl)-2,4-dihydro-3H-1,2,4-triazol-3-one, 4-amino-5-ethoxy-2-(2-chloro-1,1-dimethyl-ethyl-aminocarbonyl)-2,4-dihydro-3H-1,2,4-triazol-3-one, 4-amino-5-i-propyl-2-i-propyl-aminocarbonyl-2,4-dihydro-3H-1,2,4-triazol-3-one, 4-amino-5-dimethylamino-2-(1,1-dimethyl-ethyl-aminocarbonyl)-2,4-dihydro-3H-1,2,4-triazol-3-one, 4-amino-5-dimethylamino-2-(2-fluoro-1,1-dimethyl-ethyl-aminocarbonyl)-2,4-dihydro-3H-1,2,4-triazol-3-one, 4-amino-5-dimethylamino-2-(2-chloro-1,1-dimethyl-ethyl-aminocarbonyl)-2,4-dihydro-3H-1,2,4-triazol-3-one and 4-methyl-5-methoxy-2-(1,1-dimethyl-ethyl-aminocarbonyl)-2,4-dihydro-3H-1,2,4-triazol-3-one.

The compound 4-amino-5-(1-methyl-ethyl)-2-(1,1-dimethyl-ethyl-aminocarbonyl)-2,4-dihydro-3H-1,2,4-triazol-3-one-in accordance with Chem. Abstracts also to be termed 4-amino-N-(1,1-dimethyl-ethyl)-4,5-dihydro-3-(1-methyl-ethyl)-5-oxo-1H-1,2,4-triazole-1-carboxamide (CAS-Reg. No.: 129909-90-6, Compound (1-1) of the use examples, proposed common name: "amicarbazone")- is a component of the formula (I) in the mixture.

A family of compositions comprising a first compound and a second component, wherein said first compound is a compound of the formula (I)

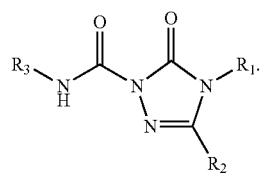

(I)

In certain embodiments, $R_1$ is an optionally substituted amino. In certain embodiments, $R_1$ is $NH_2$. In certain embodiments, $R_2$ is an optionally substituted alkyl. In certain embodiments, $R_2$ is i-propyl. In certain embodiments, $R_3$ is an optionally substituted alkyl. In certain embodiments, $R_3$ is t-butyl. In certain embodiments, the first compound is 4-amino-5-isopropyl-2-(tert-butyl-aminocarbonyl)-2,4-dihydro-3H-1,2,4-triazol-3-one (Amicarbazone).

In certain embodiments, the second component is 2-[(2-chlorophenyl)methyl]-4,4-dimethyl-3-isoxazolidinone and 3-cyclohexyl-6-dimethylamino-1-methyl-1,3,5-triazine-2,4(1H,3H)-dione. In certain embodiments, the second component is 4-methyl-2-chlorophenoxyacetic acid. In certain embodiments, the second component is one or more of N-ethyl-N'-(1-methylethyl)-6-(methylthio)-1,3,5-triazine-2,4-diamine, N-(3,4-dichlophenyl)-N,N-dimethyl urea, 5-cyclopropyl-4-(2-methylsulfonyl-4-trifluoromethylbenzoyl)isoxazole or 4-amino-6-tert-butyl-4,5-dihydro-3-methyltio-1,2,4-triazin-5-one.

Examples of a combination composition according to the invention include, but are not limited to:

Amicarbazone+clomazone+hexazinone; amicarbazone+MCPA+ethoxylated propoxylated fatty amines; amicarbazone+MCPA+polyether-polymethylsiloxane-copolymers; amicarbazone+ametryn+amtrazine; amicarbazone+diuron; amicarbazone+isoxaflutole; amicarbazone+metribuzin; amicarbazone+hexazinone; amicarbazone+hexazinone+diuron; and amicarbazone+ametrine+diuron; amicarbazone+tebuthiuron; and amicarbazone+propisochlor, amicarbazone+acetochlor, amicarbazone+metolachlor, amicarbazone+S-Metolachlor, amicarbazone+alachlor, amicarbazone+butachlor, amicarbazone+butenachlor, amicarbazone+delachlor, amicarbazone+diethatyl, amicarbazone+dimethachlor, amicarbazone+metazachlor, amicarbazone+pretilachlor, amicarbazone+propachlor, amicarbazone+prynachlor, amicarbazone+terbuchlor, amicarbazone+thenylchlor, and amicarbazone+xylachlor.

Optionally, a composition can include an adjuvant. An adjuvant may be used with the composition to enhance or improve herbicidal performance. Adjuvants may be added to the composition at the time of formulation, or by the applicator to the spray mix just prior to treatment. Adjuvants include surfactants, compatibility agents, anti-foaming agents and spray colorants (dyes), and drift control agents. In certain embodiments, the adjuvant is an ethoxylated propoxylated fatty amine or a polyether-polymethylsiloxane-copolymer.

As disclosed herein, the compound combinations, in addition to being well tolerated by crops, have herbicidal activities and can be used in a variety of crops for selectively controlling weed. Non-limiting examples of crops include maize, wheat, sugar cane, barley, rice, citrus, palm trees, pineapple, cucurbits, beans, soybeans, agave, cassava, turf and pasture.

The compound combinations can also be used for controlling undesired vegetation in non-crop areas, e.g. fallow agricultural land. The term "non-crop area" used herein refers to areas where a crop, or any intentionally planted vegetation, is not grown. The term "fallow agricultural land" used herein refers to a piece of land where no crop or pasture is growing. A fallow agricultural land that is not used for crops, may be left unused in order to restore its natural fertility.

In various embodiments, the herbicidal activity of a composition according to the invention exceeds the total of the activities of the individual active compounds. If there are two active compounds, the activity will be greater than the same of the single active compound alone. Thus, in various embodiments, herbicidal compositions include compositions synergistic for control of one or more weeds.

The compositions of the invention have been found to be active herbicides in possessing herbicidal activity against one or more species of weeds. In the broadest sense, the term "weed" refers to plants which grow in locations in which they are not desired. In other words, a weed is a plant in which in the context of a crop is undesirable due to competition for water, nutrients, sunlight, soil, etc.

As used herein the term "herbicide" refers to a compound which adversely control, or modifies (e.g. limits or reduces) the growth of plants, particularly of undesirable plants. A "herbicidally effective amount" is meant an amount of compound which causes an adverse effect on the growth of plants, such as weeds. The herbicide can affect pre- or post-emergent growth or both.

The term "plants" is meant to include germinant seeds, emerging seedlings, and established vegetation, including roots and above-ground portions (for example, leaves, stalks, flowers, fruits, etc.) Such adverse modifying and controlling effects may include all deviations from natural plant development, including killing the weed.

The compositions of the invention can be used, for example, in control of one or more of following plants (weeds):

Monocotyledonous weeds include the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds include the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Croton, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Merremia, Momordica, Mullugo, Myosotis, Papaver, Pharbitis, Plantago, Polygonum, Portulaca, Ranunculus, Raphanus, Ricinus, Rorippa, Rotala, Rumex, Salsola, Senecio, Sesbania, Sida, Sinapis, Solanum, Sonchus, Sphenoclea, Stellaria, Stizolobium, Taraxacum, Thlaspi, Trifolium, Urtica, Veronica, Viola, Xanthium.*

The use of the active compound combinations according to the invention is in no way restricted to these genera, but also extends in the same manner to other plants.

Depending on the concentration, the herbicidal compositions are suitable for selective weed control in crops, for example, cereals, rice, maize, sorghum, sugar cane, cotton, canola, soya, turf, barley, potato, sweet potato, sunflower, rye, oats, wheat, corn, soybean, sugar beet, safflower, alfalfa, cassaya, cucurbits, pineapple and pastures.

Specific weed species encountered in corn include, but not limited to, *Ixophorus unisetus, Amaranthus hybridu, Ipomoea purpurea,* and *Sicyos angulata.*

Specific weed species encountered in sugar cane include, but not limited to, *Acalypha* sp., *Boerhavia erecta, Trianthema portulacastrum, Amaranthus hybridus,* and *Amaranthus lividus.*

In particular embodiments, a synergistic effect of the compound combinations according to the invention is present. As used herein, the term "synergism" means that the herbicidal action of the active compound combination exceeds the action of the active compounds when applied individually on a given weed, either pre- or post-emergent.

The ratios by weight of an active compound (e.g. group a and group b) in the active compound combinations can be varied within relatively wide ranges. In general, 0.001 to 1000 parts by weight, 0.02 to 500 parts by weight, 0.05 to 100 by weight, 0.01 to 100 parts by weight, or 0.1 to 10 parts by weight of one or more active compound(s) of the second component (group b) are used per part by weight of the first compound (group a).

In the treatment of crops, in general, the application rate is from 0.01 kg/ha to 5.00 kg/ha or from 0.03 kg/ha to 3.00 kg/ha of the first compound, and from 0.5 kg/ha to 10.00 kg/ha or from 0.05 kg/ha to 5.00 kg/ha of the second component.

The herbicidal compositions can be in customary formulations, such as solutions, emulsions, wettable powders, suspensions, powders, dusts, pastes, soluble powders, granules, suspo-emulsion concentrates, emulsifiable concentrate, oil spray, aerosol, natural and synthetic materials impregnated with active compound, and very fine capsules in polymeric substances. In certain embodiments, the compositions is in a form of an emulsifiable concentrate, wettable powder, granule, dust, oil spray or aerosol.

These formulations can be produced, for example by mixing the active compounds with extenders, that is liquid solvents and/or solid carriers, optionally with the use of surface-active agents, such as emulsifying agents and/or dispersing agents and/or foam-forming agents.

In the case of the use of water as an extender, organic solvents can, for example, also be used as auxiliary solvents. Liquid solvents include aromatics, such as xylene, toluene or alkylnaphthalenes, chlorinated aromatics and chlorinated aliphatic hydrocarbons, such as chlorobenzenes, chloroethylenes or methylene chloride, ali-phatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable, for example, ammonium salts and ground natural minerals, such as kaolins, clays, talc, chalk, quartz, attapulgite, mont-morillonite or diatomaceous earth, and ground synthetic minerals, such as finely divided silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, poly-oxyethylene fatty alcohol ethers, for example alkylaryl polyglycol ethers, alkylsulphonates, alkyl sulphates, aryl-sulphonates as well as protein hydrolysates; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives may be mineral and vegetable oils.

Colourants can also included in the formulations. Non-limiting examples are inorganic pigments, such as iron oxide, titanium oxide and Prussian Blue, and organic dyestuffs, such as alizarin dyestuffs, azo dye-stuffs and metal phthalocyanine dyestuffs, and trace nutrients such as salts of iron, manganese, boron, copper, cobalt, molybdenum and zinc.

The formulations in general comprise between 0.1 and 95 percent by weight, or between 0.5 and 90 percent by weight, of each of the active compounds from group a (or the first compound) and group b (or the second component).

Herbicidal compositions according to the invention can be applied in the form of ready mixes. Herbicidal compositions can also be formulated individually and mixed upon use, i.e. applied in the form of tank mixes.

Herbicidal compositions can be used as such or in the form of their formulations, and furthermore also as mixtures with other known herbicides, ready mixes or tank mixes. They may also be mixed with other known active compounds, such as fungicides, insecticides, acaricides, nematicides, bird repellents, growth substances, plant nutrients and agents which improve soil structure. For particular application purposes, in particular when applied post-emergence, formulations such as mineral or vegetable oils which are tolerated by plants (for example the commercial product "Oleo DuPont 11E") or ammonium salts such as, for example, ammonium sulphate or ammonium thiocyanate, as further additives can be included.

Herbicidal compositions can be used as such, in the form of their formulations or in the forms prepared therefrom by dilution of a concentrated form, such as ready-to-use or concentrated solutions, suspensions, emulsions, powders, pastes and granules. They are used in the customary manner, for example by watering, spraying, atomizing, dusting or scattering.

Herbicidal compositions according to the invention can be applied before and after the plants have emerged, that is to say pre-emergence and post-emergence. They can also be incorporated into the soil before, during or after sowing seeds of a crop.

The invention also provides methods for controlling undesirable plants or vegetation. In one embodiment, a method includes applying to a crop where control of such vegetation is desired, an herbicidally effective amount of a composition. Such methods include a composition of the invention, optionally together with an adjuvant, an inert diluent or a carrier suitable for use with an herbicide.

The invention also provides methods for selective control of weeds. In one embodiment, a method includes contacting a composition of the invention onto a crop plant in need of weed control or at risk of undesirable weeds, in an amount effective to provide weed control in the crop.

Herbicidal activity of the compound combinations can be seen from the examples which follow. While the individual active compounds show less activity with regard to herbicidal activity, certain combinations have a herbicidal activity which exceeds a simple sum of the activity of the individual active compounds.

Activity for a given combination of two active compounds can be calculated as follows (cf. COLBY. S. R.: "Calculating synergistic and antagonistic responses of herbicide combinations". Weeds 15, Pages 20-22. 1967):

If:
X=% damage by herbicide A (active compound of group a) at an application rate of p kg/ha,
Y=% damage by herbicide B (active compound of group b) at an application rate of q kg/ha,
E=the expected % damage of herbicides A+B at an application rate of p+q kg/ha,
then $$E=X+Y-(X*Y/100).$$

Similarly, according to Colby, the activity for a given combination of three active compounds can be calculated as follows (cf. COLBY. S. R.: "Calculating synergistic and antagonistic responses of herbicide combinations". Weeds 15, Pages 20-22. 1967):

If:
X=% damage by herbicide A (active compound of group a) at an application rate of p kg/ha,
Y=% damage by herbicide B1 (a first active compound of group b) at an application rate of q kg/ha,
Y=% damage by herbicide B2 (a second active compound of group b) at an application rate of r kg/ha,
E=the expected % damage of herbicides A+B1+B2 at an application rate of p+q+r kg/ha,
then $$E=X+Y+Z-(X*Y+X*Z+Y*Z)/100)+X*Y*Z/10,000.$$

If the actual damage exceeds the calculated value (E), the combination is considered to have synergistic effect activity.

It can be seen from the use examples herein below that the found herbicidal action of the active compound combinations according to the invention exceeds the calculated value, that is to say that the new active compound combinations have a synergistic effect.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

All applications, publications, patents and other references, citations cited herein are incorporated by reference in their entirety. In case of conflict, the specification, including definitions, will control.

As used herein, the singular forms "a", "and," and "the" include plural referents unless the context clearly indicates otherwise.

As used herein, all numerical values or numerical ranges include integers within such ranges and fractions of the values or the integers within ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Herbicidal Activity Studies

Example 1

Evaluation of Synergistic Action Between Amicarbazone and Propisochlor on *Digitaria ciliaris*

The herbicide study was conducted at Aburahi Agricultural Research Trial Grass house in Shiga Prefecture, Japan. Various mixtures of DINAMIC® (Amicarbazone 70 DF) and Proponit (Propisochlor 720 EC) was applied pre-emergence using foliar application by manual sprayer in this study. The mixture was diluted in water immediately prior to application, and applied at the concentration in Table 1-1. The application rate was 1000 L water/ha. *Digitaria ciliaris* was grown in square plastic pots (10 cm×10 cm) and replicated three times.

The herbicidal effect was observed by comparing the extent of *Digitaria ciliaris* treated with the compounds against that occurring in similar non-treated control. Herbicidal effect was visually assessed and recorded at 5, 8, 14, 21 and 28 days after treatment (DAT). Damage by the herbicidal compositions was evaluated with reference to a scale of 0% to 100% in comparison with untreated control. 0% means no damage and 100% means complete destruction of the plants.

The herbicide effect of amicarbazone, in particular, at 50 g/ha and 100 g/ha, was small on *Disitaria ciliaris* at the one-leaf stage. Similarly, the herbicide effect of propisochlor was less apparent on *Disitaria ciliaris* at the one-leaf stage, for example, the weeding effect index was less than 50% at 5 DAT observation at all tested dose rate. Surprisingly, treatments with the herbicidal mixtures significantly increase the % damage on the weed. Assessment of the synergistic effect was evaluated using the Colby method. The herbicidal mixtures (amicarbazone+propisochlor) exert a greater herbicidal action than expected according to Colby on the basis of the observed effects of the individual components when used alone. Therefore, a synergistic effect between amicarbazone and propisochlor was confirmed on *Disitaria ciliaris*.

TABLE 1-1

Pre-emergence treatment effects on *Digitaria ciliaris* (one leaf-stage of weeds) with various mixtures of amicarbazone and propisochlor, expressed as percentage control

| | | | Propisochlor (Rate/ha) | | | |
|---|---|---|---|---|---|---|
| | | DAT | 0 g | 50 g | 100 g | 200 g |
| Amicarbazone (Rate/ha) | 0 g | 5 | 0 | 28 | 42 | 44 |
| | | 8 | 0 | 70 | 78 | 80 |
| | | 14 | 0 | 76 | 86 | 90 |
| | | 21 | 0 | 88 | 94 | 98 |
| | | 28 | 0 | 82 | 92 | 98 |
| | 50 g | 5 | 24 | 70 | 68 | 84 |
| | | | | (45.3) | (55.9) | (57.4) |
| | | 8 | 38 | 78 | 84 | 86 |
| | | | | (81.4) | (86.4) | (87.6) |
| | | 14 | 34 | 88 | 94 | 94 |
| | | | | (84.2) | (90.8) | (93.4) |
| | | 21 | 34 | 94 | 98 | 98 |
| | | | | (92.1) | (96.0) | (98.7) |
| | | 28 | 26 | 96 | 100 | 100 |
| | | | | (86.7) | (94.1) | (98.5) |
| | 100 g | 5 | 70 | 94 | 94 | 96 |
| | | | | (78.4) | (82.6) | (83.2) |
| | | 8 | 78 | 98 | 98 | 98 |
| | | | | (93.4) | (95.2) | (95.6) |
| | | 14 | 82 | 98 | 100 | 100 |
| | | | | (95.7) | (97.5) | (98.2) |
| | | 21 | 74 | 100 | 100 | 100 |
| | | | | (96.9) | (98.4) | (99.5) |
| | | 28 | 66 | 100 | 100 | 100 |
| | | | | (93.9) | (97.3) | (99.3) |
| | 200 g | 5 | 92 | 100 | 100 | 100 |
| | | | | (94.2) | (95.4) | (95.5) |
| | | 8 | 96 | 100 | 100 | 100 |
| | | | | (98.8) | (99.1) | (99.2) |
| | | 14 | 98 | 100 | 100 | 100 |
| | | | | (99.5) | (99.7) | (99.8) |
| | | 21 | 86 | 100 | 100 | 100 |
| | | | | (98.3) | (99.2) | (99.7) |

TABLE 1-1-continued

Pre-emergence treatment effects on *Digitaria ciliaris* (one leaf-stage of weeds) with various mixtures of amicarbazone and propisochlor, expressed as percentage control

| | | Propisochlor (Rate/ha) | | | |
|---|---|---|---|---|---|
| | DAT | 0 g | 50 g | 100 g | 200 g |
| | 28 | 86 | 100 | 100 | 100 |
| | | | (97.5) | (98.9) | (99.7) |

( ) indicates the calculated expected percent damage according to Colby method E, wherein
$E = a + b(100 - a)/100$
A: Herbicidal effect of Propisochlor as single application
B: Herbicidal effect of Amicarbazone as single application
Herbicidal effect index: 0 (No efficacy)-100 (Complete kill)

Example 2

Evaluation of Synergistic Action Between Amicarbazone and Clomazone/Hexazinone on *Cyperus esculentus*

DINAMIC® (amicarbazone) and Discover (clomazone 400 g/kg+hexazinone 100 g/kg) alone or in combination were applied pre-emergence in this study. The formulations for DINAMIC® and Discover were 700 g active ingredient a.i./kg and 500 g active ingredient a.i./kg respectively.

The herbicidal effect was observed by comparing the extent of *Cyperus esculentus* treated with the compounds against that occurring in similar non-treated control. Herbicidal effect was visually assessed and recorded at 27, 43, 46, 60, 63, 77, 83, 97 and 124 days after treatment (DAT). Damage by the herbicidal compositions was evaluated with reference to a scale of 0% to 100% in comparison with untreated control. 0% means no damage and 100% means complete destruction of the plants.

The results in Table 2 indicate synergistic effects between amicarbazone and the clomazone/hexazinone partner. Assessment of the synergistic effect was evaluated using the Colby method. The theoretical herbicidal effect index were calculated based on Colby and the values were indicated in bracket ( ) in Table 2-1. The herbicidal mixtures (amicarbazone+(clomazone/hexazinone)) exert a greater herbicidal action than expected according to Colby on the basis of the observed effects of the individual components when used alone. In both Trials 1 and 2, the observed herbicidal effects are greater than the theoretical herbicidal effects at DAT 77 and DAT 124 respectively, therefore, there exist synergistic effects between amicarbazone and the clomazone/hexazinone partner on *Cyperus esculentus*. The underlined values in the table indicate that the observed weed killing is greater than calculated from the Colby formula and therefore indicates a synergistic weed killing effect or activity.

TABLE 2-1

Pre-emergence treatment effects on *Cyperus esculentus*, expressed as percentage control

| | Application Rate | Days After Treatment (DAT) | | | | | | | | |
|---|---|---|---|---|---|---|---|---|---|---|
| Active Ingredient(s) | (kg/ha) | 27 | 43 | 46 | 60 | 63 | 77 | 83 | 97 | 124 |
| Trial 1 | | | | | | | | | | |
| Amicarbazone | 1.5 | | 40 | | | 62 | 65 | | | |
| Clomazone/Hexazinone | 2.0 | | 0 | | | 0 | 0 | | | |
| Amicarbazone + (Clomazone/Hexazinone) | 1.5 + 2.0 | | 83 | | | 94 | 96 (65) | | | |
| Trial 2 | | | | | | | | | | |
| Amicarbazone | 1.5 | 37 | | 53 | 57 | | | 68 | 53 | 23 |
| Clomazone/Hexazinone | 2.0 | 45 | | 40 | 17 | | | 17 | 5 | 0 |

TABLE 2-1-continued

Pre-emergence treatment effects on *Cyperus esculentus*, expressed as percentage control

| Active Ingredient(s) | Application Rate (kg/ha) | Days After Treatment (DAT) | | | | | | | |
|---|---|---|---|---|---|---|---|---|---|
| | | 27 | 43 | 46 | 60 | 63 | 77 | 83 | 97 | 124 |
| Amicarbazone + (Clomazone/Hexazinone) | 1.5 + 2.0 | 22 | | 86 | 82 | | | 84 | 85 | 77 (23) |

( ) indicates the calculated expected percent damage according to Colby method E, wherein E = a + b (100 − a)/100
A: Herbicidal effect of Clomazone/Hexazinone as single application
B: Herbicidal effect of Amicarbazone as single application
Herbicidal effect index: 0 (No efficacy)-100 (Complete kill)

Example 3

Evaluation of Synergistic Action Between Amicarbazone and Other Herbicides on *Cyperus rotundus*

DINAMIC® (amicarbazone) in combination of various herbicides listed in Table 3-1 were tested for herbicidal activity.

TABLE 3-1

Herbicides used in combination of amicarbazone

| Name | Active Ingredients | Source |
|---|---|---|
| Volcano-blend (adjuvant) | Ethoxylated propoxylated fatty amines 1000 g/L | Volcano Agroscience |
| Break Thru (adjuvant) | Polyether-polymethylsiloxane-copolymer 100% | Goldschmidt Chemical Corporation |
| MCPA | 4-Methyl-2-chlorophenoxyacetic acid | Volcano Agroscience |

The herbicidal effect was observed by comparing the extent of *Cyperus esculentus* treated with the compounds against that occurring in similar non-treated control. Herbicidal effect was visually assessed and recorded at 4, 8, 18 and 34 days after treatment (DAT). Damage by the herbicidal compositions was evaluated with reference to a scale of 0% to 100% in comparison with untreated control. 0% means no damage and 100% means complete destruction of the plants.

Table 3-2 provides post-emergence treatment effects on *Cyperus esculentus* between amicarbazone and 4-methyl-2-chlorophenoxyacetic acid with an adjuvant.

TABLE 3-2

Post-emergence treatment effects on *Cyperus esculentus*, expressed as percentage (by volume) control

| Active Ingredient(s) | Application Rate (kg/ha or L/ha) | Days After Treatment (DAT) | | | |
|---|---|---|---|---|---|
| | | 4 | 8 | 18 | 34 |
| Amicarbazone + Volcano-Blend (adjuvant) | 1.0 + 0.2% | 0 | 5 | 0 | 0 |
| Amicarbazone + MCPA + Volcano-Blend (adjuvant) | 1.0 + 3.5 + 0.2% | 0 | 50 | 70 | 0 |
| Amicarbazone + Break Thru (adjuvant) | 1.0 + 0.1% | 0 | 5 | 0 | 0 |
| Amicarbazone + MCPA + Break Thru (adjuvant) | 1.0 + 3.5 + 0.1% | 0 | 50 | 75 | 50 |

Example 4

Evaluation of Synergistic Action Between Amicarbazone and Other Herbicides on *Cyperus rotundus*

DINAMIC® (amicarbazone) in combination of various herbicides listed in Table 4-1 were tested for herbicidal activity.

TABLE 4-1

Herbicides used in combination of amicarbazone

| Name | Active Ingredients | Source |
|---|---|---|
| Gesapax | Ametryn: N-ethyl-N'-(1-methylethyl)-6-(methylthio)-1,3,5-triazine-2,4-diamine, 500 g/L | Syngenta |
| Karmex | Diuron: N-(3,4-dichlophenyl)-N,N-dimethyl urea, 800 g/kg | Goldschmidt Chemical Corporation DuPont (in Brazil) |
| Provence | Isoxaflutole: 5-cyclopropyl-4-isoxazolyl)[2-(methylsulfonyl)-4-(trifluoromethyl)phenyl]methanone, 750 g/kg | Bayer Group |
| Sencor | Metribuzin: 4-amino-6-(1,1-dimethylethyl)-3-(methylthio)-1,2,4-triazin-5(4H)-one, 480 g/kg | Bayer Group |

The herbicidal effect was observed by comparing the extent of *Euphorbia heterophylla* (EPHHL) treated with the compounds against that occurring in similar non-treated control. Herbicidal effect was visually assessed and recorded at 14, 23, 36, 49, 65 and 77 days after treatment (DAT). Damage by the herbicidal compositions was evaluated with reference to a scale of 0% to 100% in comparison with untreated control. 0% means no damage and 100% means complete destruction of the plants.

The results in Table 4-2 indicate synergistic effects in the herbicidal treatments with (Amicarbazone+Karmex) mixtures and (Amicarbazone+Sencor) mixtures on *Euphorbia heterophylla*. Assessment of the synergistic effect was evaluated using the Colby method. The theoretical herbicidal effect index were calculated based on Colby and the values were indicated in bracket ( ) in Table 4-2. Both of the herbicidal mixtures (amicarbazone+Karmex) and (amicarbazone+Sencor) exert a greater herbicidal action than expected according to Colby on the basis of the observed effects of the individual components when used alone. The observed herbicidal effects are greater than the theoretical herbicidal effects at DAT 49, 65 and 77, therefore, there exist synergistic effects. On the other hand, antagonistic effects were observed in the herbicidal treatments with (Amicarbazone+Gesapax) mixtures and (Amicarbazone+Provence) mixtures on *Euphorbia heterophylla*, as the observed herbicidal effects were smaller than the theoretical herbicidal effects at any of the DAT tested (i.e. DAT=14, 23, 36, 49, 65 and 77). The underlined values in the table indicate that the observed weed killing is greater than calculated from the Colby formula and therefore indicates a synergistic weed killing effect or activity.

TABLE 4-2

Pre-emergence treatment effects on *Euphorbia heterophylla*, expressed as percentage control

| Active Ingredient(s) | Application Rate (kg/ha or L/ha) | Days After Treatment (DAT) | | | | | |
|---|---|---|---|---|---|---|---|
| | | 14 | 23 | 36 | 49 | 65 | 77 |
| Amicarbazone | 1.50 | 98 | 98 | 96 | 96 | 96 | 90 |
| Amicarbazone | 1.00 | 96 | 96 | 96 | 79 | 79 | 75 |
| Amicarbazone + Gesapax | 1.00 + 3.00 | 96 | 96 | 96 | 86 | 86 | 85 |
| | | (100) | (99) | (99) | (89) | (88) | (86) |
| Gesapax | 3.00 | 96 | 84 | 80 | 47 | 45 | 45 |
| Gesapax | 5.00 | 96 | 72 | 66 | 50 | 47 | 47 |
| Amicarbazone + Karmex | 1.00 + 3.00 | 96 | 94 | 96 | 90 | 90 | 90 |
| | | (100) | (98) | (98) | <u>(86)</u> | <u>(84)</u> | <u>(81)</u> |
| Karmex | 3.00 | 96 | 60 | 60 | 35 | 23 | 23 |
| Karmex | 5.00 | 98 | 80 | 80 | 50 | 50 | 35 |
| Amicarbazone + Provence | 1.00 + 0.15 | 96 | 96 | 96 | 82 | 80 | 82 |
| | | (100) | (98) | (98) | (84) | (88) | (85) |
| Provence | 0.15 | 90 | 60 | 60 | 45 | 42 | 40 |
| Provence | 0.20 | 96 | 82 | 80 | 80 | 66 | 65 |
| Amicarbazone + Sencor | 1.00 + 2.00 | 96 | 96 | 96 | 96 | 90 | 90 |
| | | (100) | (99) | (99) | <u>(88)</u> | <u>(85)</u> | <u>(85)</u> |
| Sencor | 2.00 | 96 | 85 | 75 | 41 | 40 | 40 |
| Sencor | 3.50 | 96 | 85 | 85 | 56 | 50 | 50 |

( ) indicates the calculated expected percent damage according to Colby method E, wherein E = a + b (100 − a)/100
A: Herbicidal effect of the second active ingredients (i.e. Gesapax, Karmex, Provence or Sencor) as single application
B: Herbicidal effect of Amicarbazone as single application
Herbicidal effect index: 0 (No efficacy)-100 (Complete kill)

The herbicidal effect was observed by comparing the extent of *Ipomoea gradifolia* (IAOGR) treated with the compounds against that occurring in similar non-treated control. Herbicidal effect was visually assessed and recorded at 14, 23, 36, 49, 65 and 77 days after treatment (DAT). Damage by the herbicidal compositions was evaluated with reference to a scale of 0% to 100% in comparison with untreated control. 0% means no damage and 100% means complete destruction of the plants. The results of the observed herbicidal effect and the theoretical herbicidal effected were shown in Table 4-3. Assessment of the synergistic effect was evaluated using the Colby method. The theoretical herbicidal effect index were calculated based on Colby and the values were indicated in bracket ( ). Most of the observed herbicidal effects were smaller than the theoretical herbicidal effects in most of the tested results, which indicate antagonic effects. Some of the observed herbicidal effects were the same as the theoretical hervicidal effects, which indicate additive effects. The underlined values in the table indicate that the observed weed killing is greater than calculated from the Colby formula and therefore indicates a synergistic weed killing effect or activity.

TABLE 4-3

Pre-emergence treatment effects on *Ipomoea gradifolia*, expressed as percentage control

| Active Ingredient(s) | Application Rate (kg/ha or L/ha) | Days After Treatment (DAT) | | | | | |
|---|---|---|---|---|---|---|---|
| | | 14 | 23 | 36 | 49 | 65 | 77 |
| Amicarbazone | 1.50 | 98 | 98 | 98 | 98 | 96 | 97 |
| Amicarbazone | 1.00 | 100 | 98 | 96 | 96 | 93 | 93 |
| Amicarbazone + Gesapax | 1.00 + 3.00 | 100 | 98 | 96 | 96 | 98 | 96 |
| | | (100) | (100) | (99) | (98) | <u>(96)</u> | (96) |
| Gesapax | 3.00 | 99 | 87 | 85 | 60 | 47 | 45 |
| Gesapax | 5.00 | 100 | 96 | 96 | 60 | 60 | 58 |
| Amicarbazone + Karmex | 1.00 + 3.00 | 99 | 96 | 96 | 97 | 94 | 96 |
| | | (100) | (100) | (100) | (100) | (98) | (98) |
| Karmex | 3.00 | 99 | 97 | 96 | 77 | 70 | 70 |
| Karmex | 5.00 | 98 | 96 | 96 | 79 | 70 | 60 |
| Amicarbazone + Provence | 1.00 + 0.15 | 100 | 96 | 96 | 98 | 93 | 96 |
| | | (100) | (99) | (98) | (98) | (96) | (96) |
| Provence | 0.15 | 90 | 67 | 60 | 47 | 45 | 45 |
| Provence | 0.20 | 96 | 94 | 90 | 90 | 64 | 64 |
| Amicarbazone + Sencor | 1.00 + 2.00 | 100 | 96 | 96 | 96 | 96 | 96 |
| | | (100) | (100) | (100) | (100) | (99) | (98) |
| Sencor | 2.00 | 100 | 96 | 96 | 96 | 84 | 70 |
| Sencor | 3.50 | 100 | 96 | 96 | 96 | 80 | 67 |

( ) indicates the calculated expected percent damage according to Colby method E, wherein E = a + b (100 − a)/100
A: Herbicidal effect of the second active ingredients (i.e. Gesapax, Karmex, Provence or Sencor) as single application
B: Herbicidal effect of Amicarbazone as single application Herbicidal effect index: 0 (No efficacy)-100 (Complete kill)

The herbicidal effect was observed by comparing the extent of *Croton glandulosus* (CROTON) treated with the compounds against that occurring in similar non-treated control. Herbicidal effect was visually assessed and recorded at 14, 23, 36, 49, 65 and 77 days after treatment (DAT). Damage by the herbicidal compositions was evaluated with reference to a scale of 0% to 100% in comparison with untreated control. 0% means no damage and 100% means complete destruction of the plants. The results of the observed herbicidal effect and the theoretical herbicidal effected were shown in Table 4-4. Assessment of the synergistic effect was evaluated using the Colby method. The theoretical herbicidal effect index were calculated based on Colby and the values were indicated in bracket ( ). Some of the observed herbicidal effects were the same as the theoretical hervicidal effects, which indicate additive effects. The underlined values in the table indicate that the observed weed killing is greater than calculated from the Colby formula and therefore indicates a synergistic weed killing effect or activity.

decreased the objectionable bleaching associated with mesotrione, increased the speed of complete kill of weeds and enhanced weed control. The results disclosed in this Example were achieved without the aid of non-ionic surfactants.

Field Preparation/Maintenance

Containers were watered as needed based on species and water usage. The greenhouse was heated to keep temperatures above 50° F. (10° C.) and ventilated as needed to keep temperatures below 100° F. (38° C.). Typical daytime temperatures in the greenhouse were 80-90° F. (27-32° C.) and nighttime temperatures were between 50-60° F. (10-16° C.). The soil employed was Promix BX potting soil. Overall moisture conditions were normal and the closest weather station was on-site. Conditions and equipment employed in this Example are tabulated below in Tables 5-1 and 5-2.

TABLE 4-4

Pre-emergence treatment effects on *Croton glandulosus*, expressed as percentage control

| Active Ingredient(s) | Application Rate (kg/ha or L/ha) | Days After Treatment (DAT) | | | | | |
|---|---|---|---|---|---|---|---|
| | | 14 | 23 | 36 | 49 | 65 | 77 |
| Amicarbazone | 1.50 | 100 | 99 | 99 | 99 | 99 | 99 |
| Amicarbazone | 1.00 | 100 | 99 | 99 | 95 | 99 | 99 |
| Amicarbazone + Gesapax | 1.00 + 3.00 | 100 | 99 | 99 | 99 | 99 | 99 |
| | | (100) | (99) | (99) | (97) | (99) | (99) |
| Gesapax | 3.00 | 96 | 60 | 60 | 40 | 40 | 40 |
| Gesapax | 5.00 | 100 | 84 | 80 | 62 | 62 | 62 |
| Amicarbazone + Karmex | 1.00 + 3.00 | 100 | 99 | 99 | 99 | 99 | 99 |
| | | (100) | (99) | (99) | (99) | (99) | (99) |
| Karmex | 3.00 | 100 | 92 | 90 | 87 | 87 | 80 |
| Karmex | 5.00 | 100 | 92 | 92 | 88 | 88 | 75 |
| Amicarbazone + Provence | 1.00 + 0.15 | 100 | 99 | 99 | 99 | 93 | 90 |
| | | (100) | (99) | (99) | (97) | (99) | (99) |
| Provence | 0.15 | 100 | 65 | 65 | 42 | 42 | 40 |
| Provence | 0.20 | 99 | 90 | 90 | 60 | 60 | 60 |
| Amicarbazone + Sencor | 1.00 + 2.00 | 100 | 99 | 99 | 99 | 99 | 99 |
| | | (100) | (99) | (99) | (99) | (99) | (99) |
| Sencor | 2.00 | 100 | 96 | 96 | 98 | 99 | 98 |
| Sencor | 3.50 | 100 | 96 | 96 | 96 | 96 | 96 |

( ) indicates the calculated expected percent damage according to Colby method E, wherein E = a + b (100 − a)/100
A: Herbicidal effect of the second active ingredients (i.e. Gesapax, Karmex, Provence or Sencor) as single application
B: Herbicidal effect of Amicarbazone as single application
Herbicidal effect index: 0 (No efficacy)-100 (Complete kill)

Example 5

Evaluation of Synergistic Action Between Amicarbazone and Mesotrione on Mustard (*Sinapsis* sp.), *Poa annua*, Green Foxtail, and *Crabgrass* sp.

The experiments in this Example were designed to determine whether amicarbazone could decrease mesotrione-induced bleaching of Kentucky bluegrass, St. Augustinegrass, tall fescue and selected turf weed species and whether the combination of amicarbazone and mesotrione could increase the speed and degree of kill of common turf weeds. The experiments in this Example were also designed to determine if amicarbazone plus mesotrione tank-mixes enhance weed control over treatments with mesotrione or amicarbazone alone. This Example shows the synergistic effect of the combination of amicarbazone and mesotrione on injury and bleaching effects on Mustard (*Sinapsis* sp.), *Poa annua*, Green Foxtail, and *Crabgrass* sp. The combination of amicarbazone and mesotrione in a tank mixture

TABLE 5-1

Application Description

| | A |
|---|---|
| Time of Day: | 12-3 pm |
| Application Method: | SPRAY |
| Application Timing: | POSPOS |
| Air Temperature, Unit: | 69.4 |
| % Relative Humidity: | 71 |

TABLE 5-2

Application Equipment

| | A |
|---|---|
| Appl. Equipment: | CO2 sprayer |
| Operating Pressure, Unit: | 30 PSI |

TABLE 5-2-continued

Application Equipment

A

| Nozzle Type: | EV |
|---|---|
| Nozzle Size: | 8003 |
| Nozzle Spacing, Unit: | 24 IN |
| Nozzles/Row: | 2 |

All containers were moved outdoors from the greenhouse and arranged in blocks by treatment for the herbicide applications. A single spray application was applied to each block containing four repetitions of each species for each treatment. Plants were then immediately returned to the greenhouse and irrigated with approximately ¼" water 1-3 hrs after treatment with a hose end sprayer. Only the *Poa* plants were trimmed with scissors two days prior to treatment at a height of approximately 3 inches.

Transplanted tillering Kentucky Bluegrass was 5 to 6 months old, transplanted *Poa annua* was 5 to 6 months old. Tall fescue was seeded into the crabgrass pots. St. Augustine plants (Floratam and Saphire) were shipped from Port St. Lucie, Fla. Only two replicates of Saphire St. Augustine grass were used due to plant availability.

Both seedling and tillering stages of Kentucky bluegrass were examined. There were no treatment effects with regard to bleaching because virtually no bleaching occurred on any of the Kentucky bluegrass plants. Since Kentucky bluegrass is tolerant to both amicarbazone and mesotrione, no treatment effects were observed indicating that amicarbazone or mesotrione applied alone or in tank mixture are safe to Kentucky Bluegrass. No treatment effects were evident on the tillering bluegrass at any rating period. However, amicarbazone at the 3 oz/Acre rate and the combination of the two products using the 3 oz/acre rate of amicarbazone injured Kentucky Bluegrass seedlings, resulting in decreased stand density at 31 days after application for treatments. It has been observed that a 3 oz/acre rate of amicarbazone is injurious to seedling Kentucky Bluegrass.

Figure 2A:
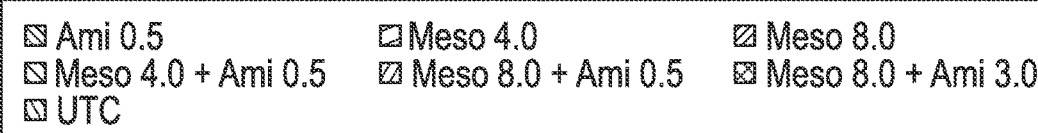
FIG. 2A shows a bar graph plot showing the injury effect of amicarbazone (4-amino-5-oxo-3-propan-2-yl-n-tert-butyl-1,2,4-triazole-1-carboxamide) and mesotrione (2-[4-(methylsulfonyl)-2-nitrobenzoyl]-1,3-cyclohexanedione) alone and in combination at different concentrations on Mustard (*Sinapsis* sp.) ten days after application.
Figure 2A:
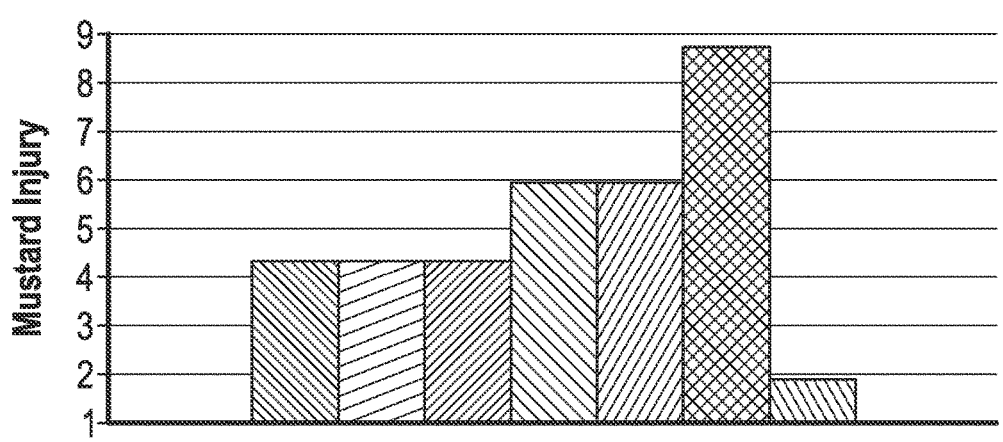
Figure 2B:
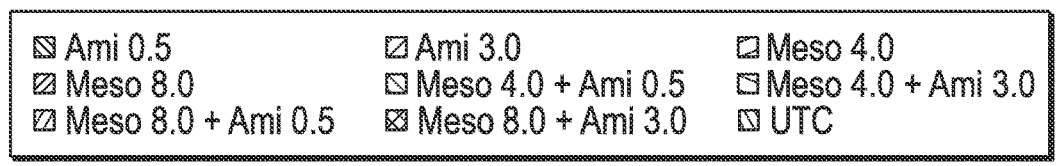
FIG. 2B shows a bar graph plot showing the bleaching effect of amicarbazone and mesotrione alone and in combination at different concentrations on Mustard (*Sinapsis* sp.) seven days after application.
Figure 2B:
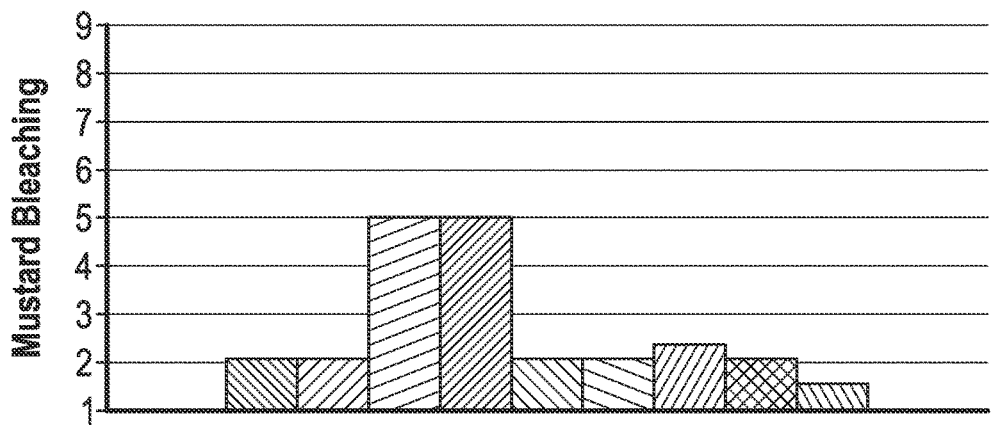
Figure 3A:
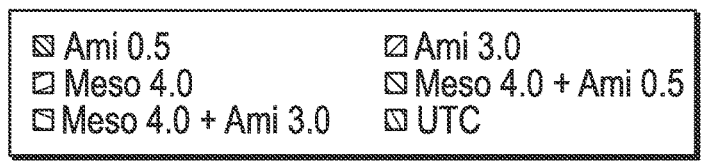
FIG. 3A shows a bar graph plot showing the injury effect of amicarbazone and mesotrione alone and in combination at different concentrations on *Poa annua* at 10, 14, and 20 days after application.
Figure 3A:
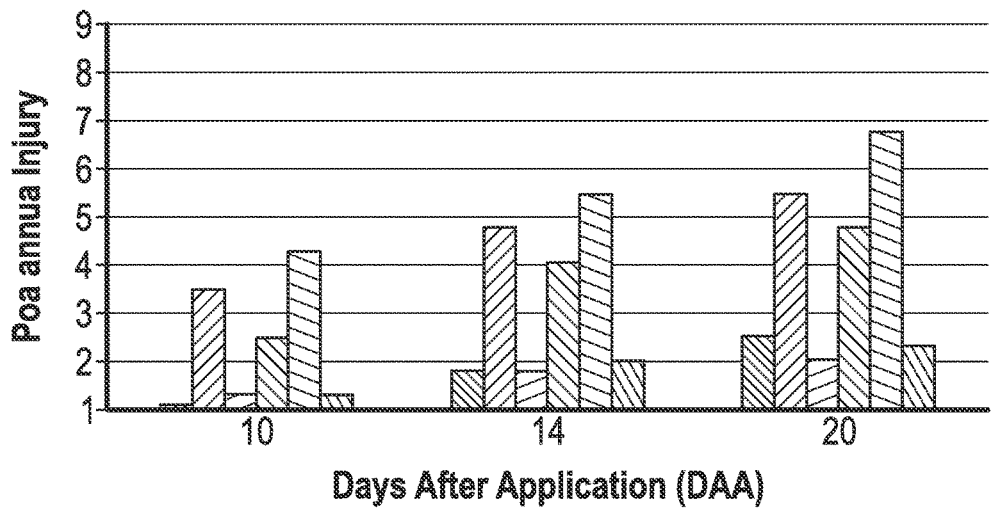
Figure 3B:
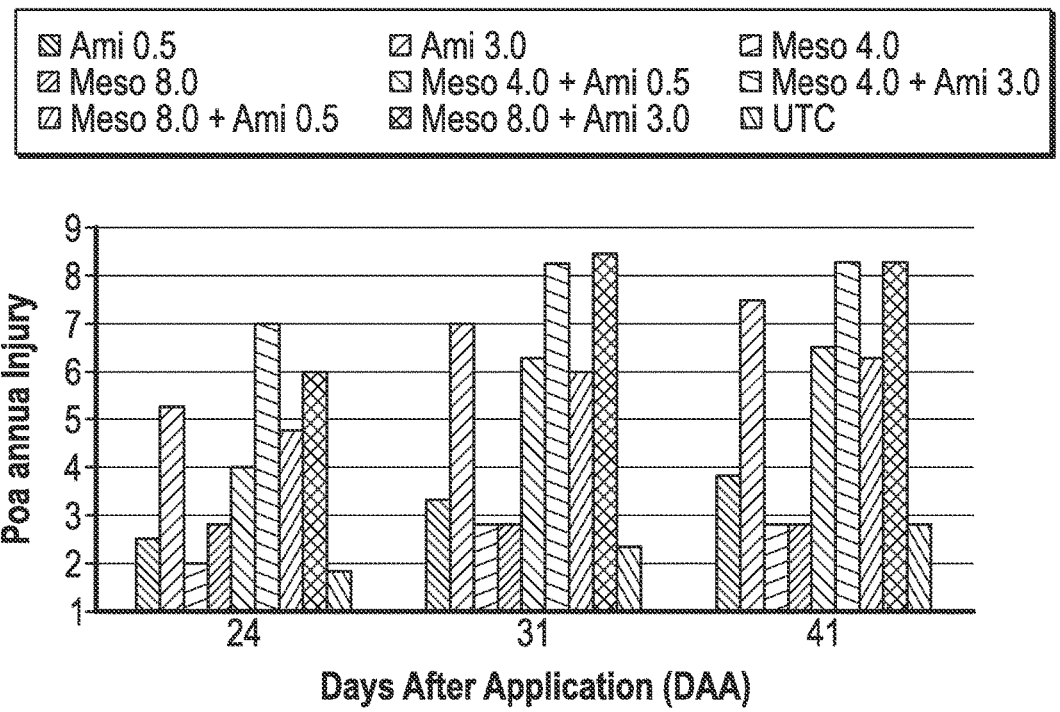
FIG. 3B shows a bar graph plot showing the injury effect of amicarbazone and mesotrione alone and in combination at different concentrations on *Poa annua* at 24, 31, and 41 days after application.
Figure 4A:
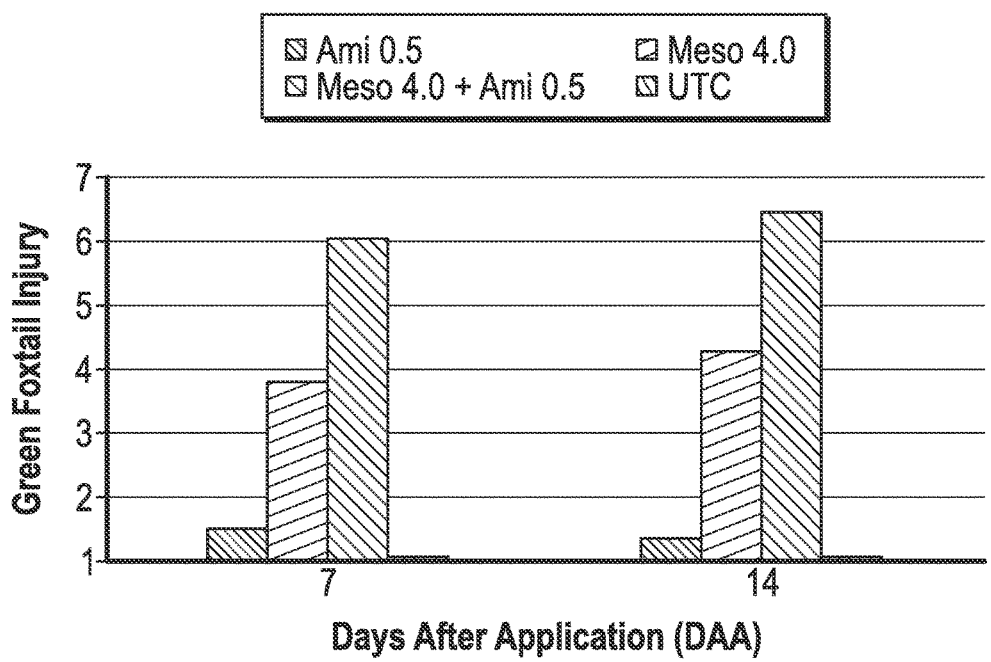
FIG. 4A shows a bar graph plot showing the injury effect of amicarbazone and mesotrione alone and in combination at different concentrations on Green Foxtail at 7 and 14 days after application.
Figure 4B:
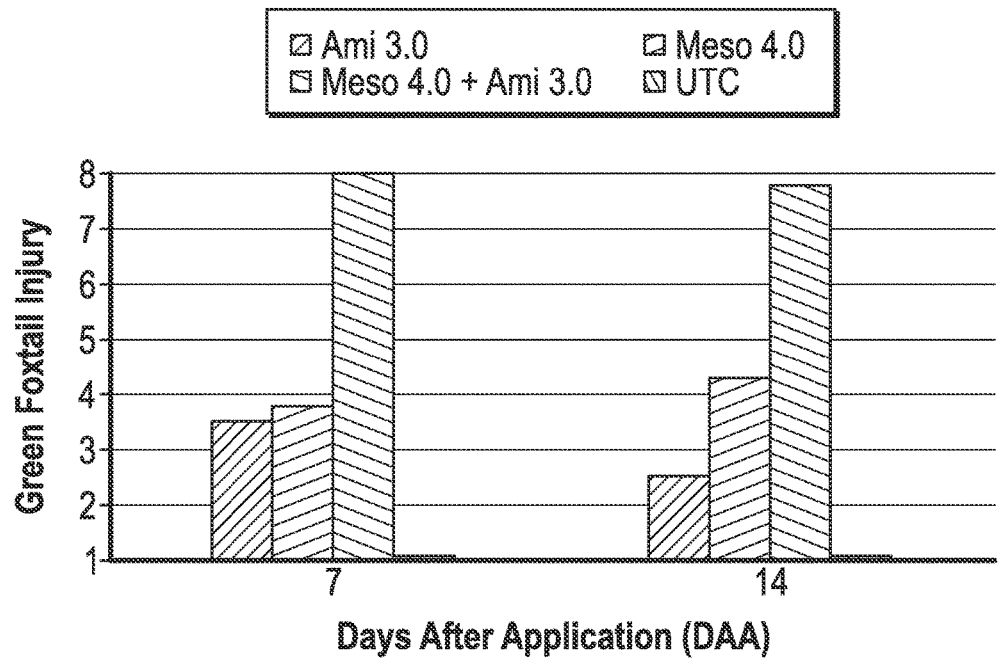
FIG. 4B shows another bar graph plot showing the injury effect of amicarbazone and mesotrione alone and in combination at different concentrations on Green Foxtail at 7 and 14 days after application.
Figure 4C:
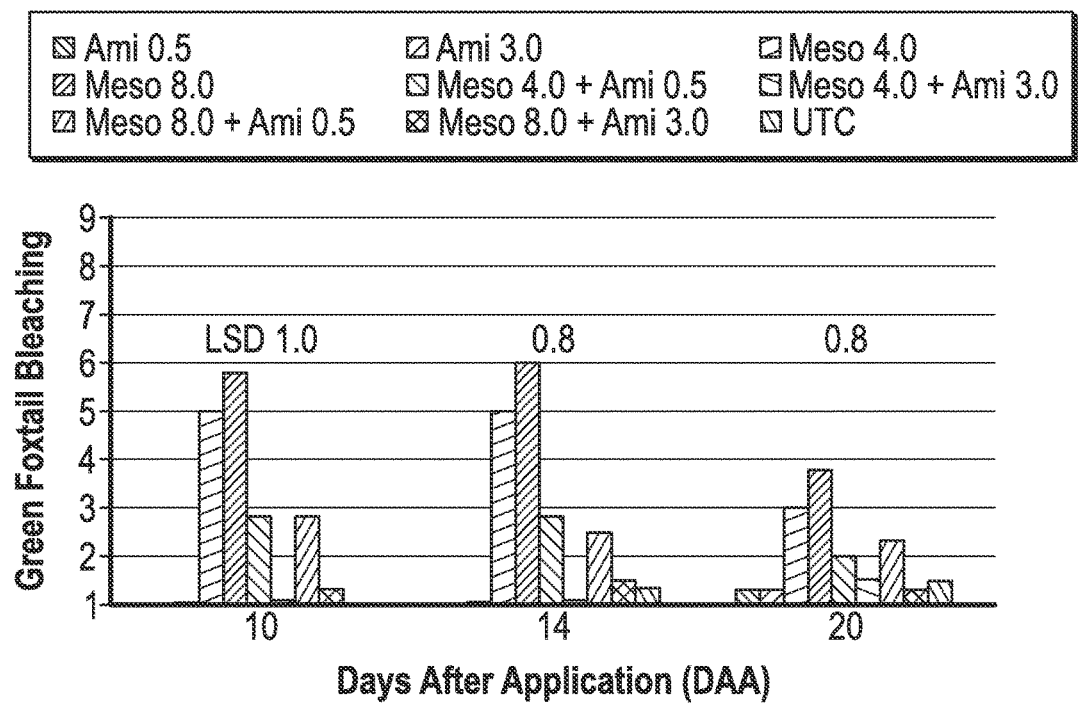
FIG. 4C shows a bar graph plot showing the bleaching effect of amicarbazone and mesotrione alone and in combination at different concentrations on Green Foxtail at 10, 14, and 20 days after application.
Figure 5A:
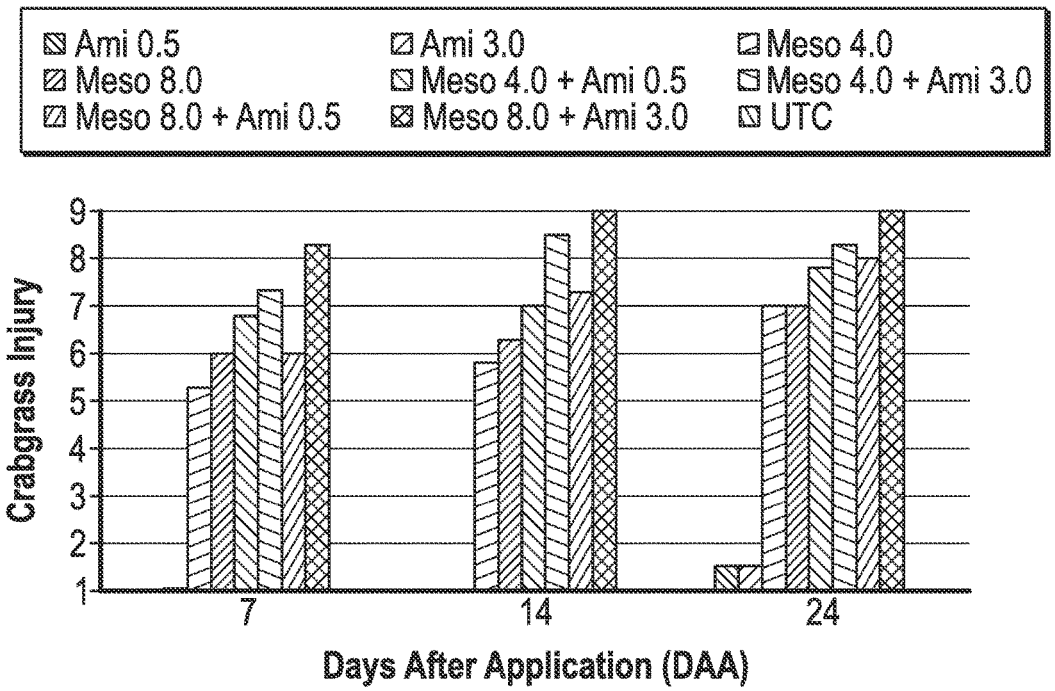
FIG. 5A shows a bar graph plot showing the injury effect of amicarbazone and mesotrione alone and in combination at different concentrations on *Crabgrass* sp. at 7, 14, and 24 days after application.
Figure 5B:
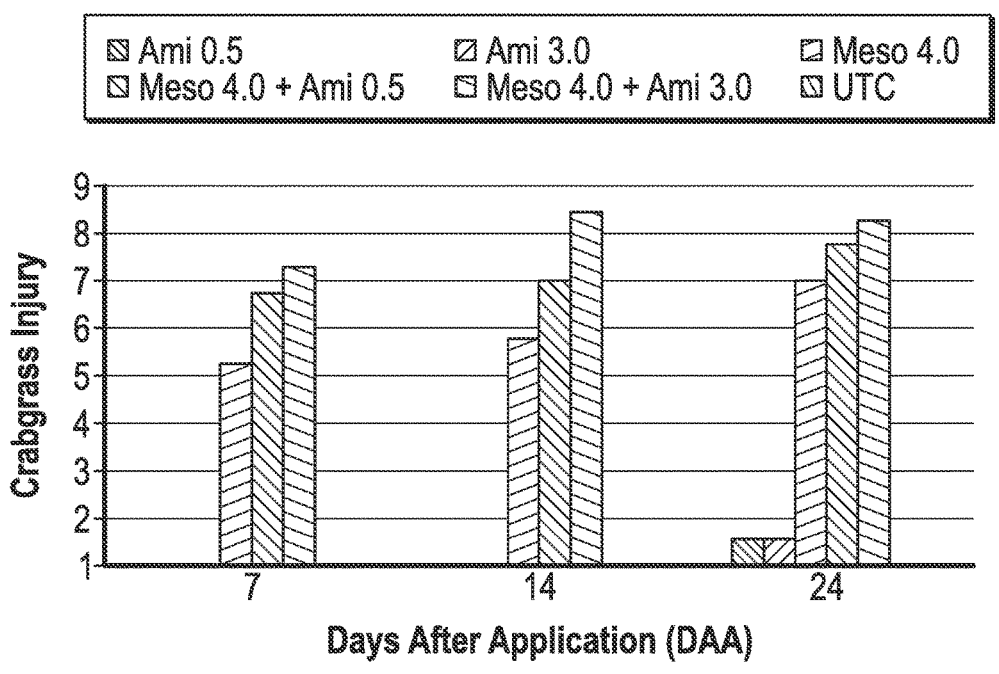
FIG. 5B shows another bar graph plot showing the injury effect of amicarbazone and mesotrione alone and in combination at different concentrations on *Crabgrass* sp. at 7, 14, and 24 days after application.
Figure 5C:
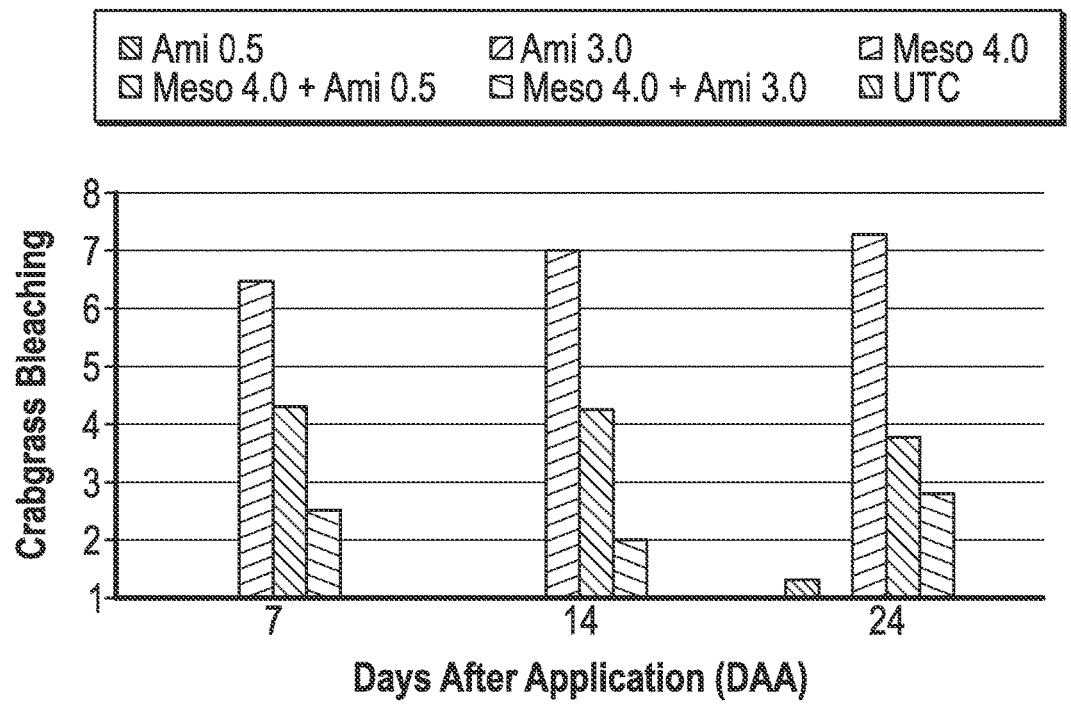
FIG. 5C shows a bar graph plot showing the bleaching effect of amicarbazone and mesotrione alone and in combination at different concentrations on *Crabgrass* sp. at 7, 14, and 20 days after application.
Figure 5D:
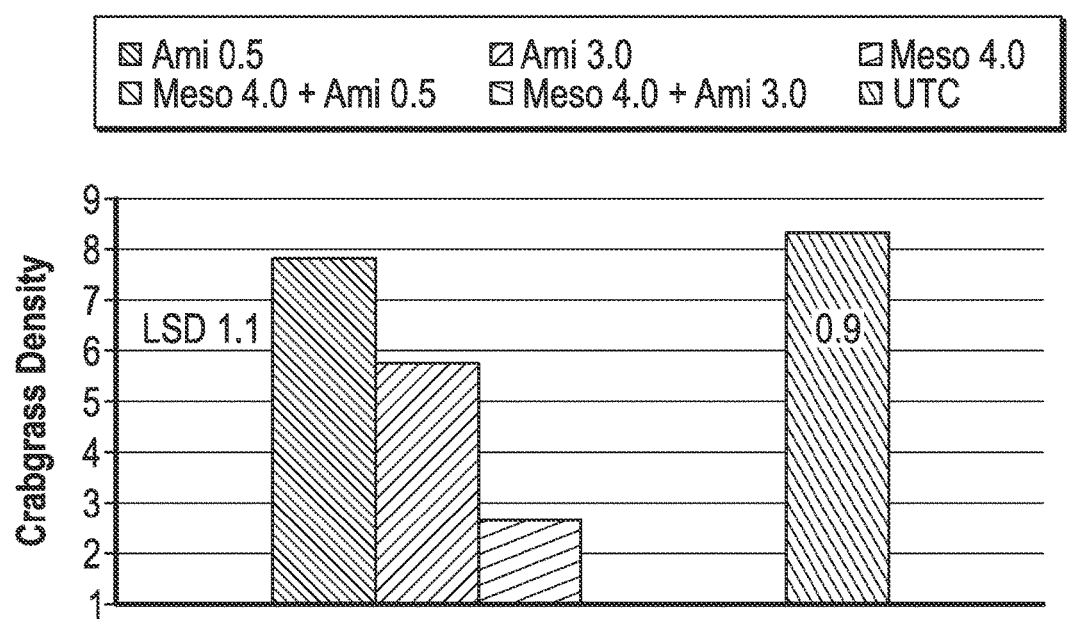
FIG. 5D shows a bar graph plot showing the effect on density of amicarbazone and mesotrione alone and in combination at different concentrations on *Crabgrass* sp. at 31 days after application.
Figure 6A:
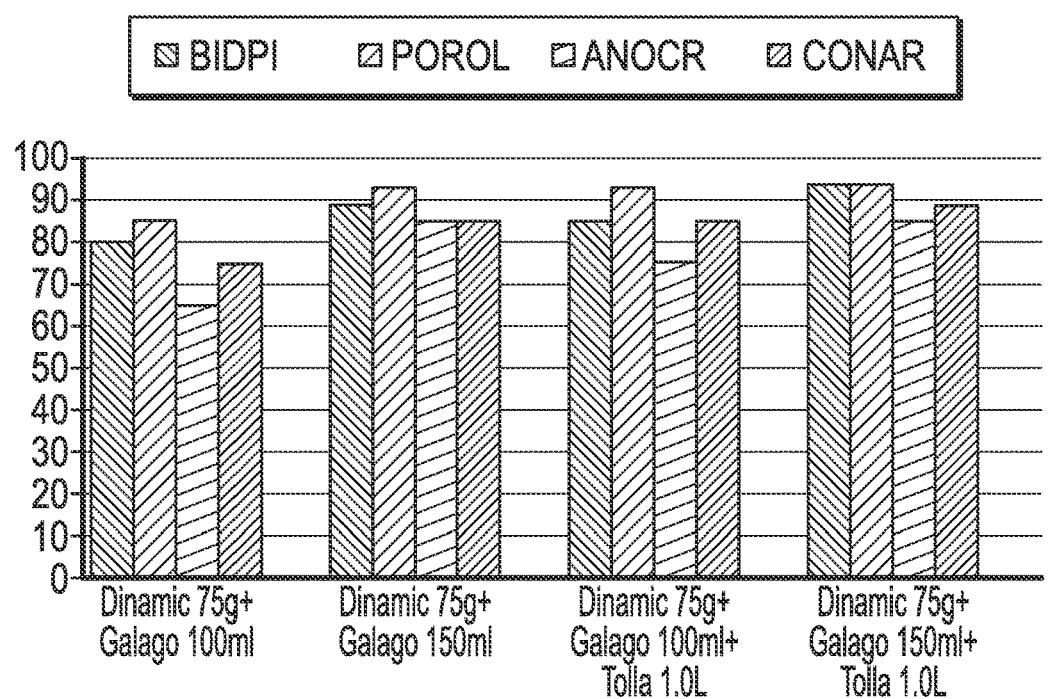
FIG. 6A shows a comparative weed control chart with tank mixtures of DINAMIC® 700 WDG (amicarbazone, 700 g/kg) at 75 g/ha with Galago (mesotrione, 480 g/L) and with Galago plus TOLLA 840 S (metolachlor, i.e. chloroacetamide, 840 g/L+Safener (dichlormid, i.e. 2,2-dichloro-N,N-di-2-propenyl acetamide)). Weed species are *Bidens pilosa* (BIDPI), *Portulaca oleracea* (POROL), *Anoda cristata* (ANOCR), and *Convolvulus arvensis* (CONAR).
Figure 6B:
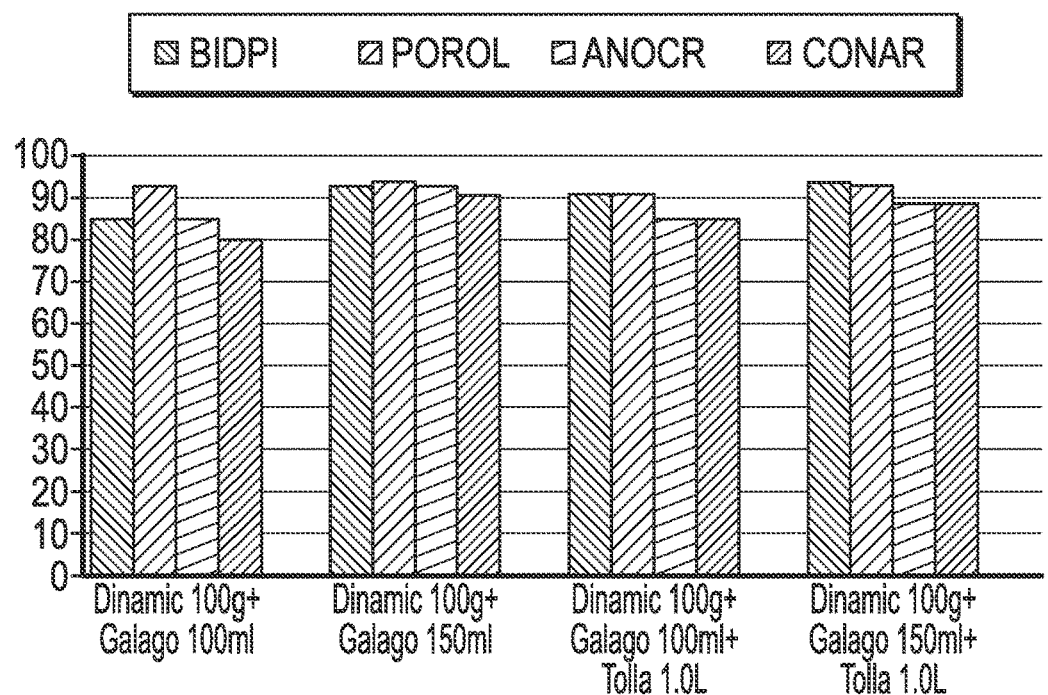
FIG. 6B shows a comparative weed control chart with tank mixtures of DINAMIC® 700 WDG at 100 g/ha with Galago and with Galago plus TOLLA 840 S. Weed species are the same as in FIG. 6A.
Figure 6C:
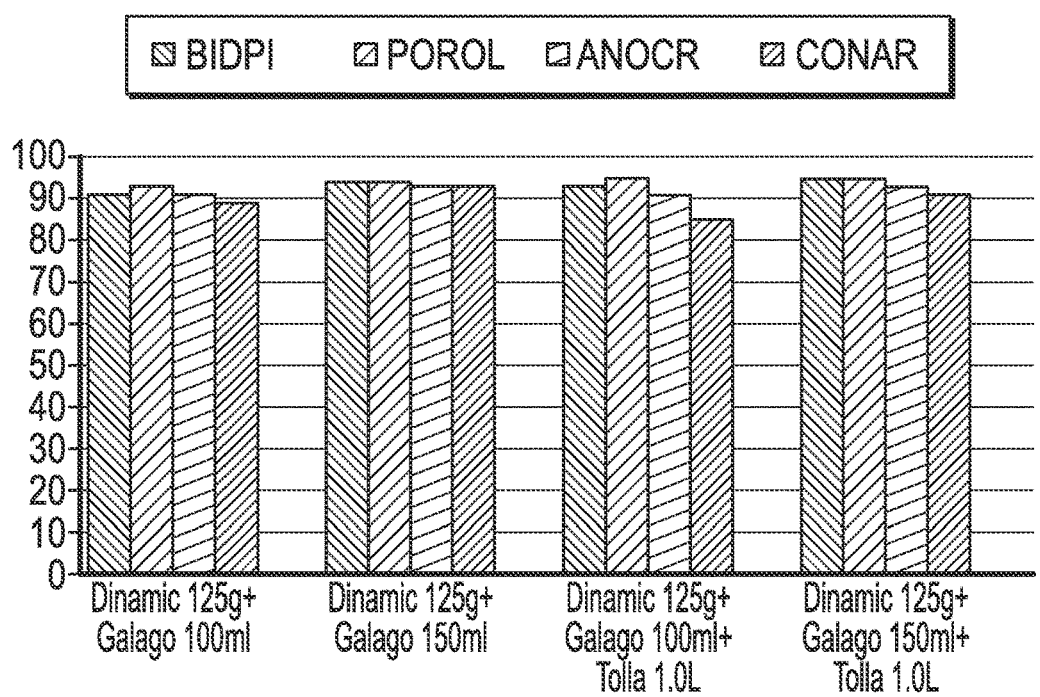
FIG. 6C shows a comparative weed control chart with tank mixtures of DINAMIC® 700 WDG at 125 g/ha with Galago and with Galago plus TOLLA 840 S. Weed species are the same as in FIG. 6A.
Figure 6D:
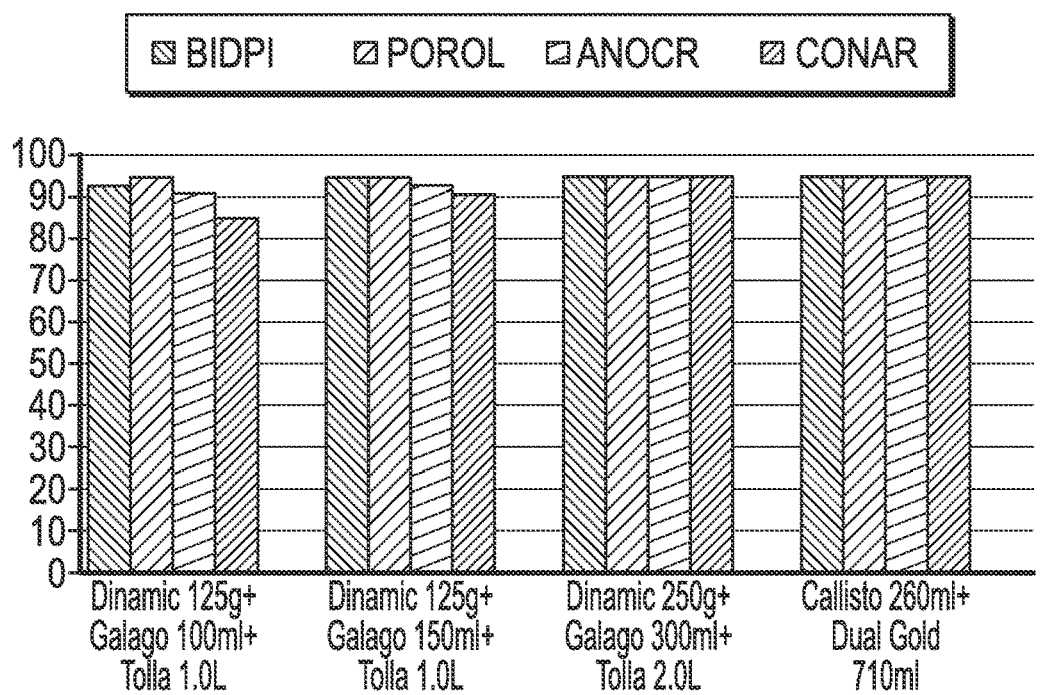
FIG. 6D shows a comparative weed control chart with tank mixtures of DINAMIC® 700 WDG with Galago plus TOLLA 840 S versus a standard tank mixture of CALLISTO® (mesotrione, 480 g/L) plus DUAL S GOLD® (S-metolachlor, 915 g/L+Safener). Weed species are the same as in FIG. 6A.
Figure 6E:
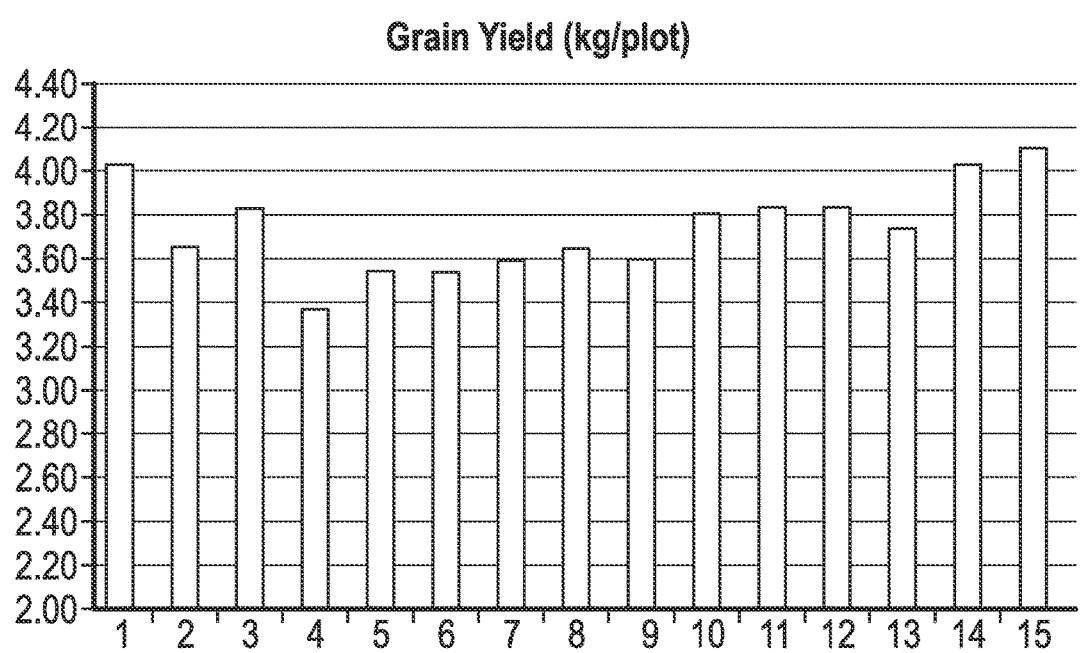
FIG. 6E shows a comparative grain yield chart of 13 different tank mixture combinations employing DINAMIC® 700 WDG (Lanes 1-13). Lane 14 is CALLISTO® plus DUAL S GOLD®. Lane 15 is an untreated control.
Figure 7A:
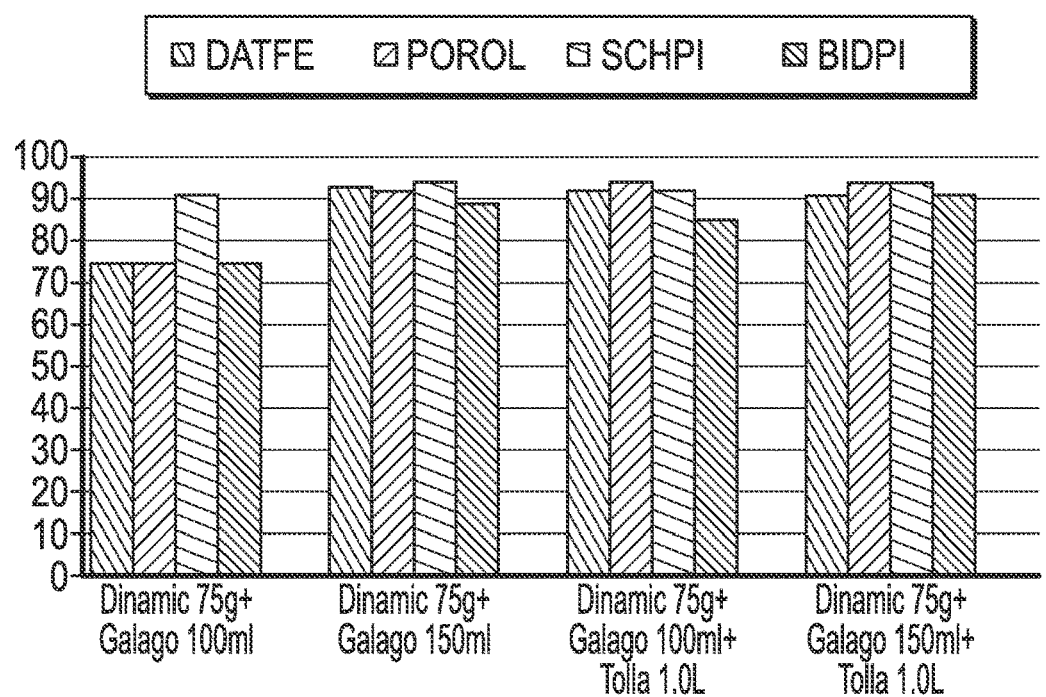
FIG. 7A shows another comparative weed control chart with tank mixtures of DINAMIC® 700 WDG at 75 g/ha with Galago and with Galago plus TOLLA 840 S. Weed species are *Datura ferox* (DATFE), *Portulaca oleracea*, (POROL), *Schkuhria pinnata* (SCHPI), and *Bidens pilosa* (BIDPI).
Figure 7B:
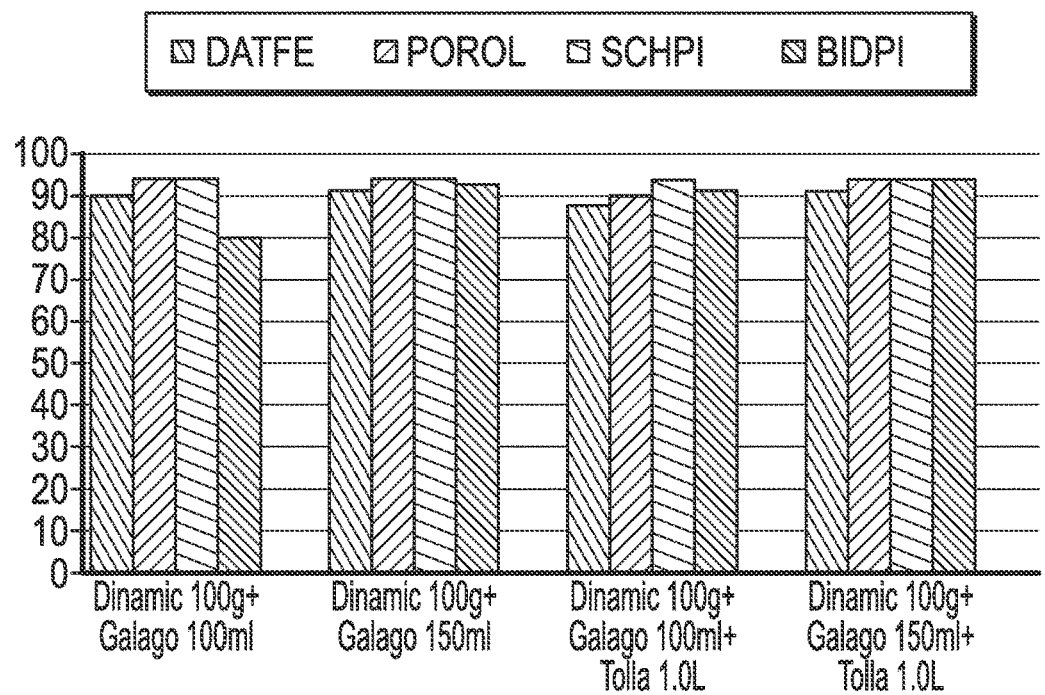
FIG. 7B shows another comparative weed control chart with tank mixtures of DINAMIC® 700 WDG at 100 g/ha with Galago and with Galago plus TOLLA 840 S. Weed species are the same as in FIG. 7A.
Figure 7C:
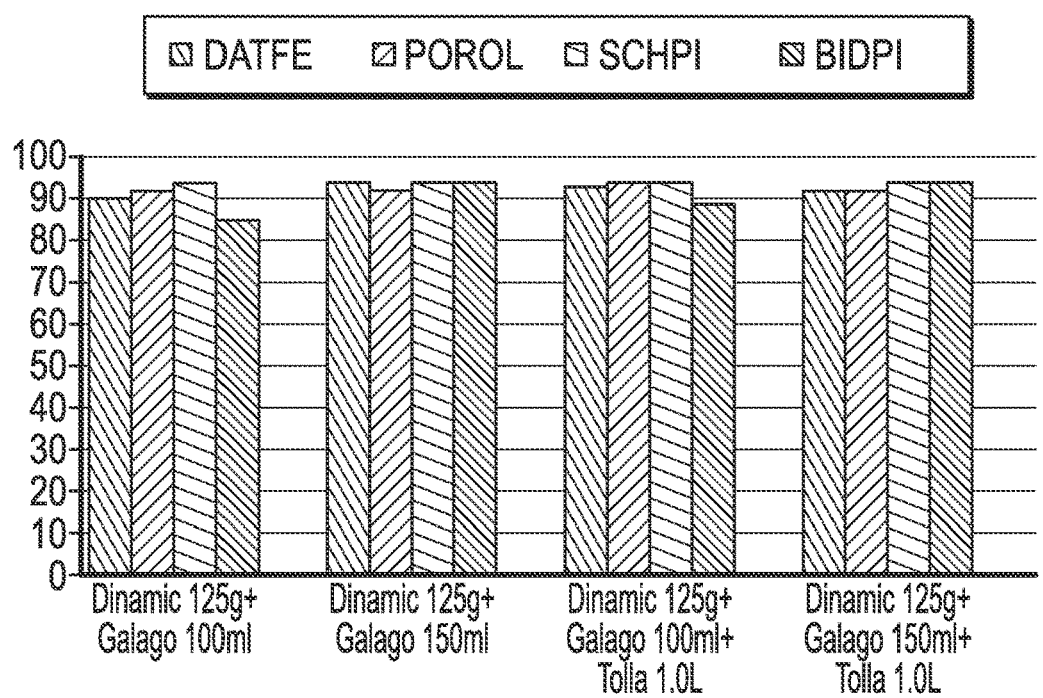
FIG. 7C shows another comparative weed control chart with tank mixtures of DINAMIC® 700 WDG at 125 g/ha with Galago and with Galago plus TOLLA 840 S. Weed species are the same as in FIG. 7A.
Figure 7D:
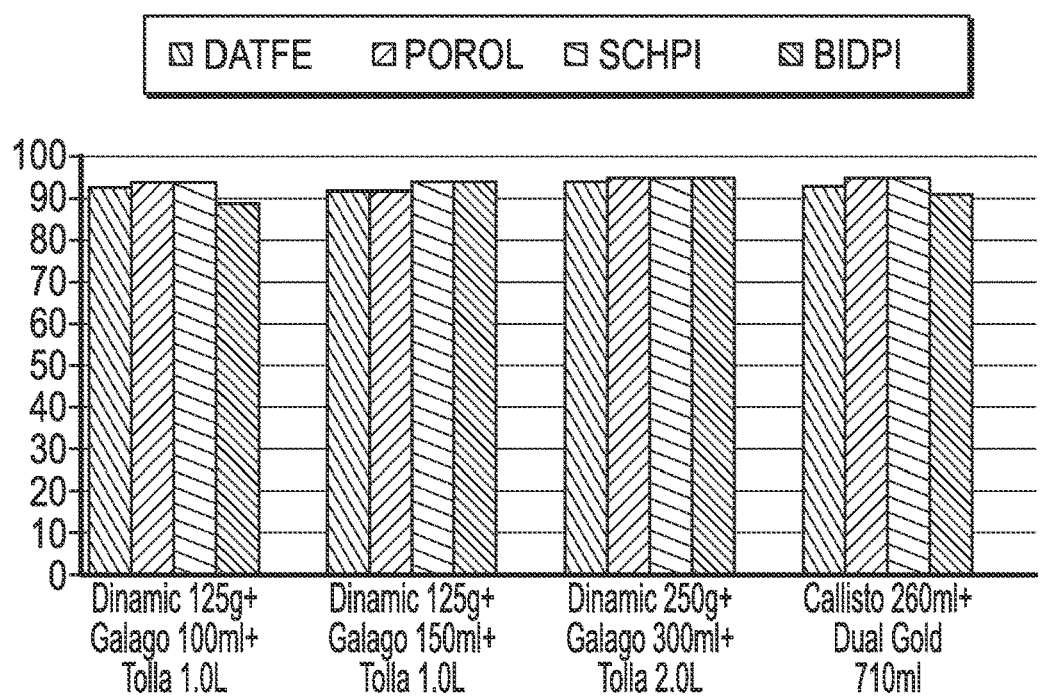
FIG. 7D shows another comparative weed control chart with tank mixtures of DINAMIC® 700 WDG with Galago plus TOLLA 840 S versus a standard tank mixture of CALLISTO® plus DUAL S GOLD®. Weed species are the same as in FIG. 7A.
Figure 7E:
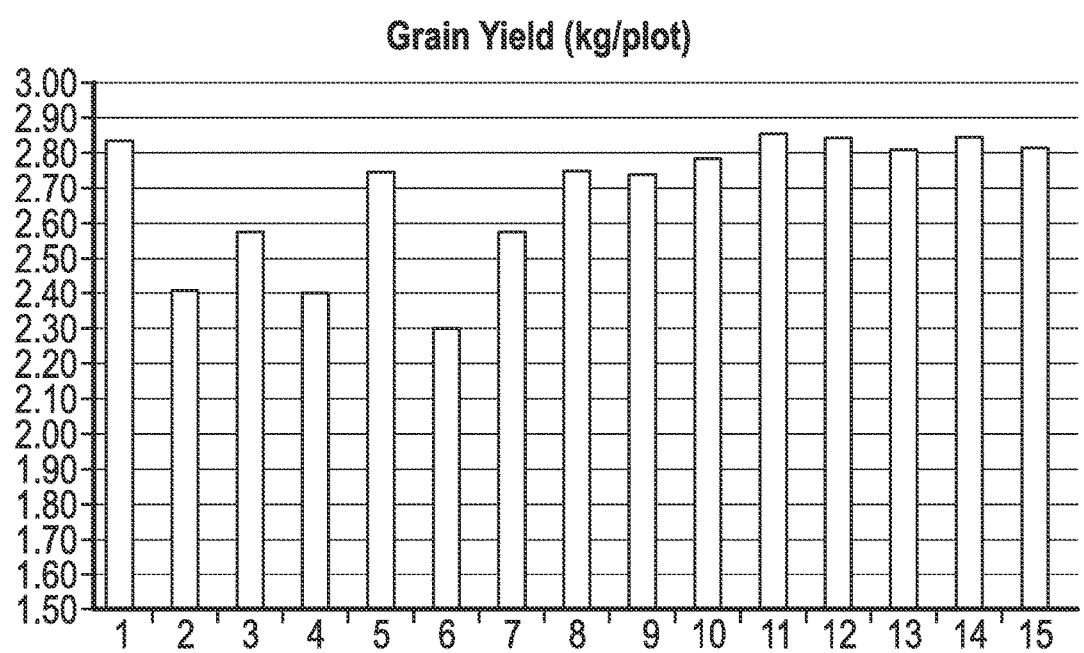
FIG. 7E shows another comparative grain yield chart of 13 different tank mixture combinations employing DINAMIC® 700 WDG (Lanes 1-13). Lane 14 is CALLISTO® plus DUAL S GOLD®. Lane 15 is an untreated control.
Figure 8A:
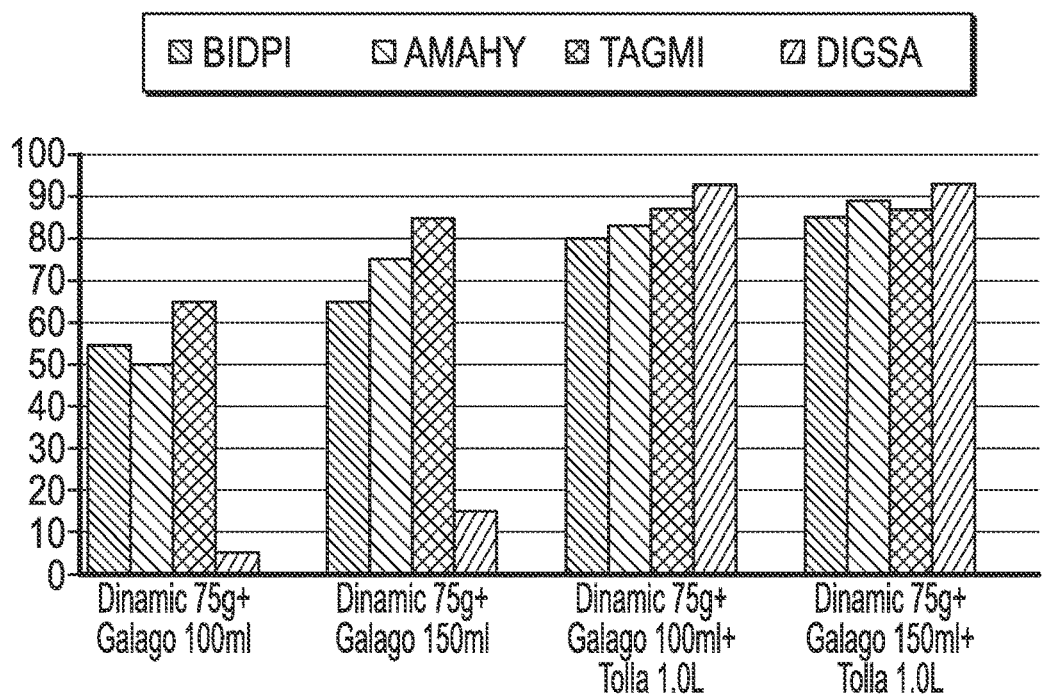
FIG. 8A shows another comparative weed control chart with tank mixtures of DINAMIC® 700 WDG at 75 g/ha with Galago and with Galago plus TOLLA. Weed species are *Bidens pilosa* (BIDPI), *Amaranthus hybridus* (AMAHY), *Tagetes minuta* (TAGMI), and *Digitaria sanquinalis* (DIGSA).
Figure 8B:
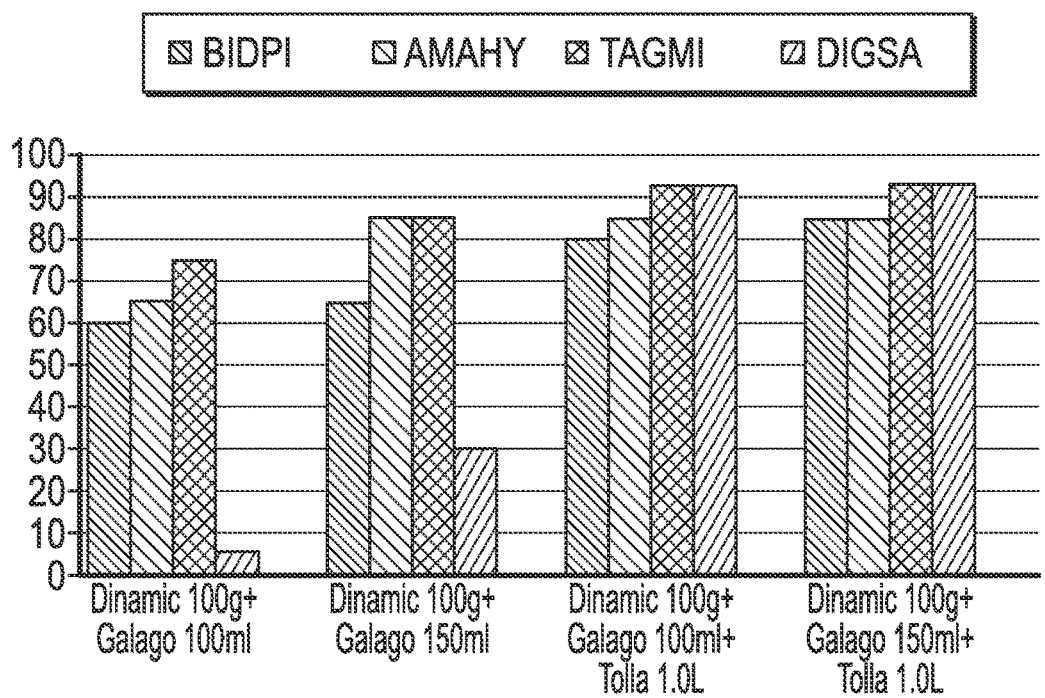
FIG. 8B shows another comparative weed control chart with tank mixtures of DINAMIC® 700 WDG at 100 g/ha with Galago and with Galago plus TOLLA 840 S. Weed species are the same as in FIG. 8A.
Figure 8C:
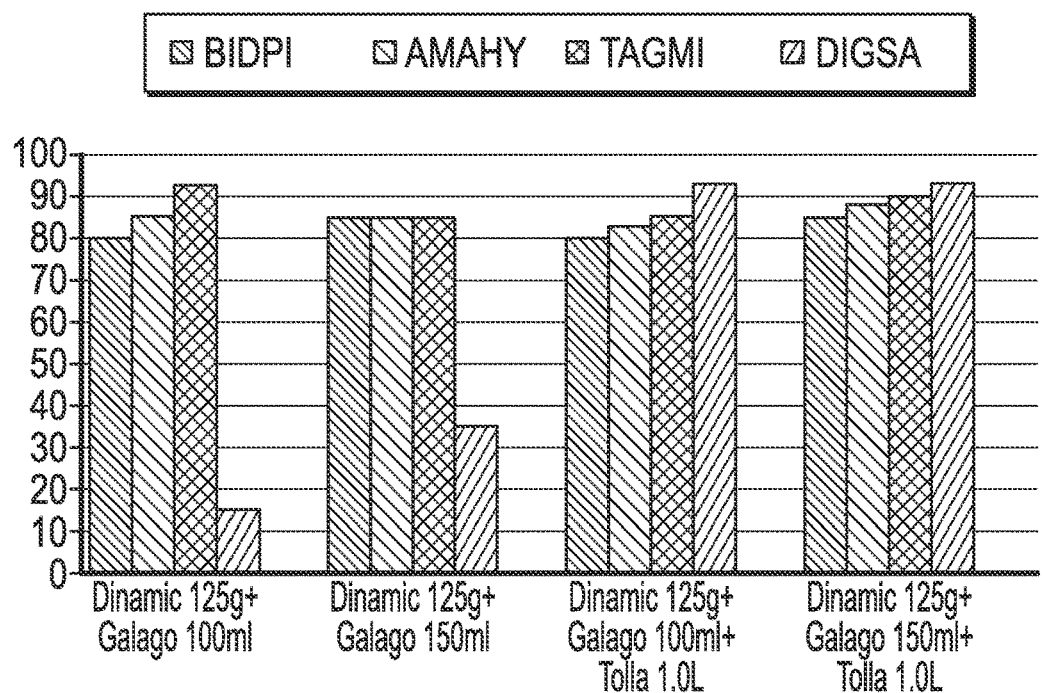
FIG. 8C shows another comparative weed control chart with tank mixtures of DINAMIC® 700 WDG at 125 g/ha with Galago and with Galago plus TOLLA 840 S. Weed species are the same as in FIG. 8A.
Figure 8D:
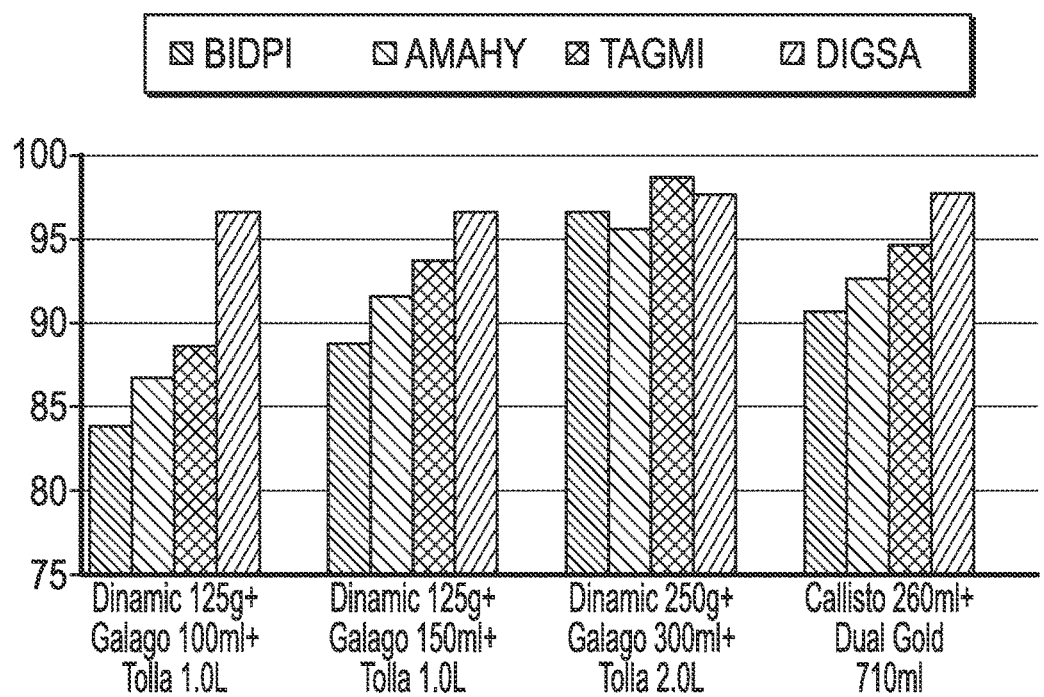
FIG. 8D shows another comparative weed control chart with tank mixtures of DINAMIC® 700 WDG with Galago plus TOLLA 840 S versus a standard tank mixture of CALLISTO® plus DUAL S GOLD®. Weed species are the same as in FIG. 8A.
Figure 8E:
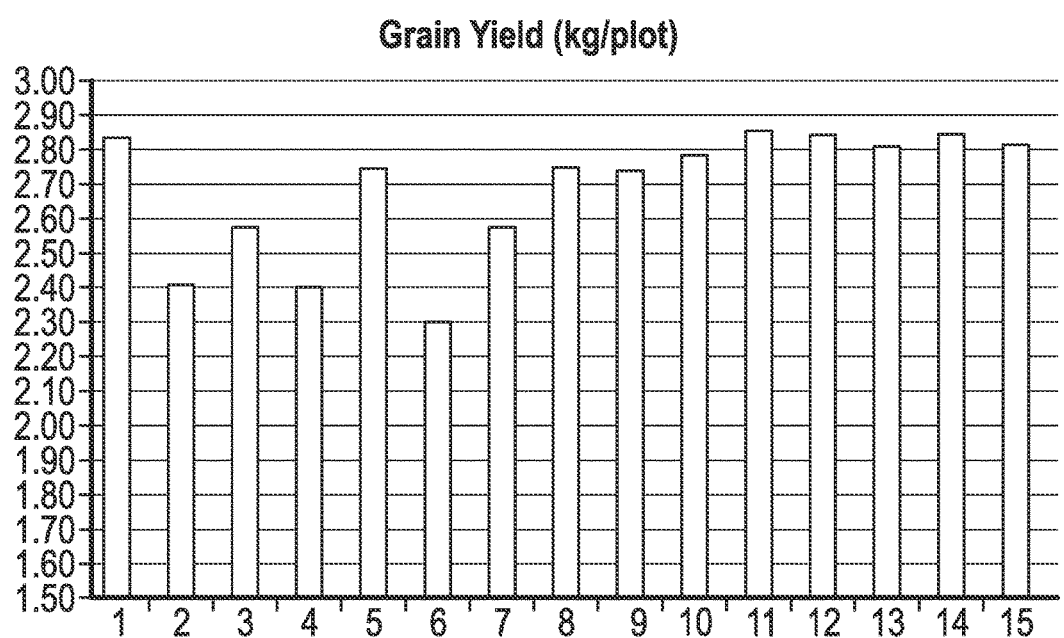
FIG. 8E shows another comparative grain yield chart of 13 different tank mixture combinations employing DINAMIC® 700 WDG (Lanes 1-13). Lane 14 is CALLISTO® plus DUAL S GOLD®. Lane 15 is an untreated control.
Figure 9A:
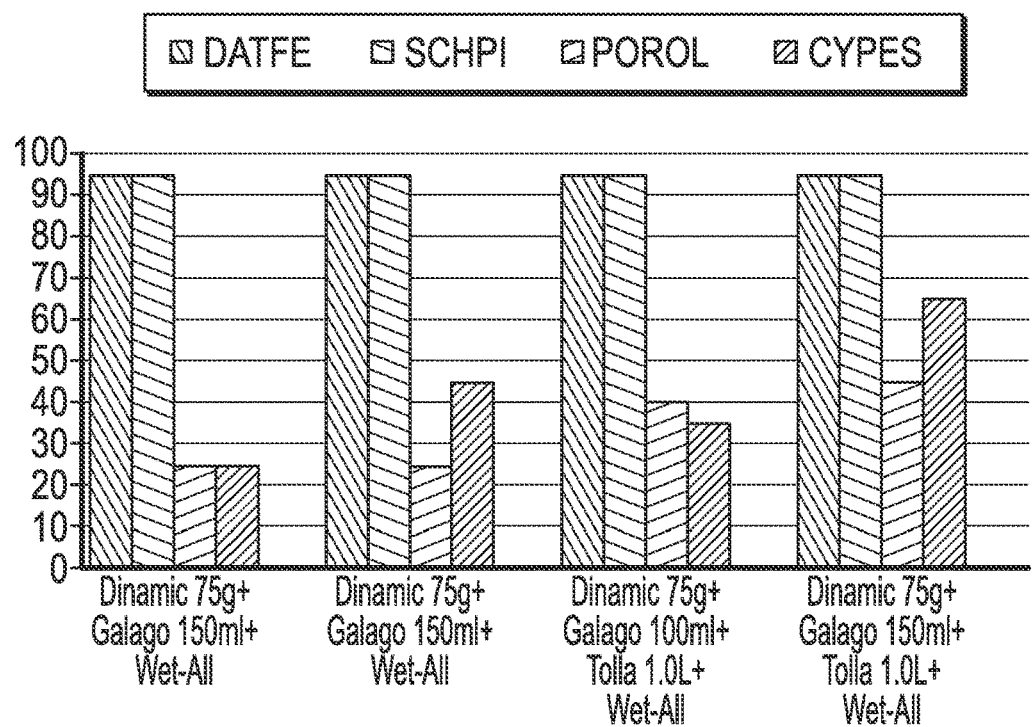
FIG. 9A shows another comparative weed control chart with tank mixtures of DINAMIC® 700 WDG at 75 g/ha with Galago plus Wet-All (alcohol ethoxylate, non-ionic surfactant) and with Galago plus TOLLA 960 (metolachlor, 960 g/L) plus Wet-All. Weed species are *Datura ferox* (DATFE), *Schkuhria pinnata* (SCHPI), *Portulaca oleracea* (POROL) and *Cyperus esculentus* (CYPES).
Figure 9B:
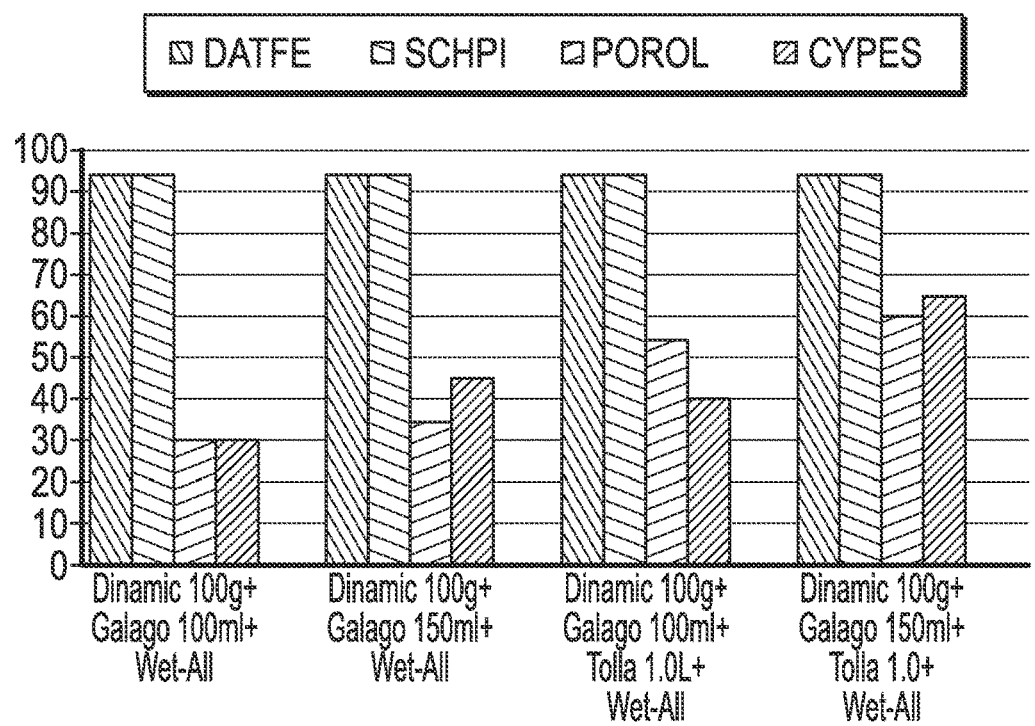
FIG. 9B shows another comparative weed control chart with tank mixtures of DINAMIC® 700 WDG at 100 g/ha with Galago plus Wet-All and with Galago plus TOLLA 960 plus Wet-All. Weed species are the same as in FIG. 9A.
Figure 9C:
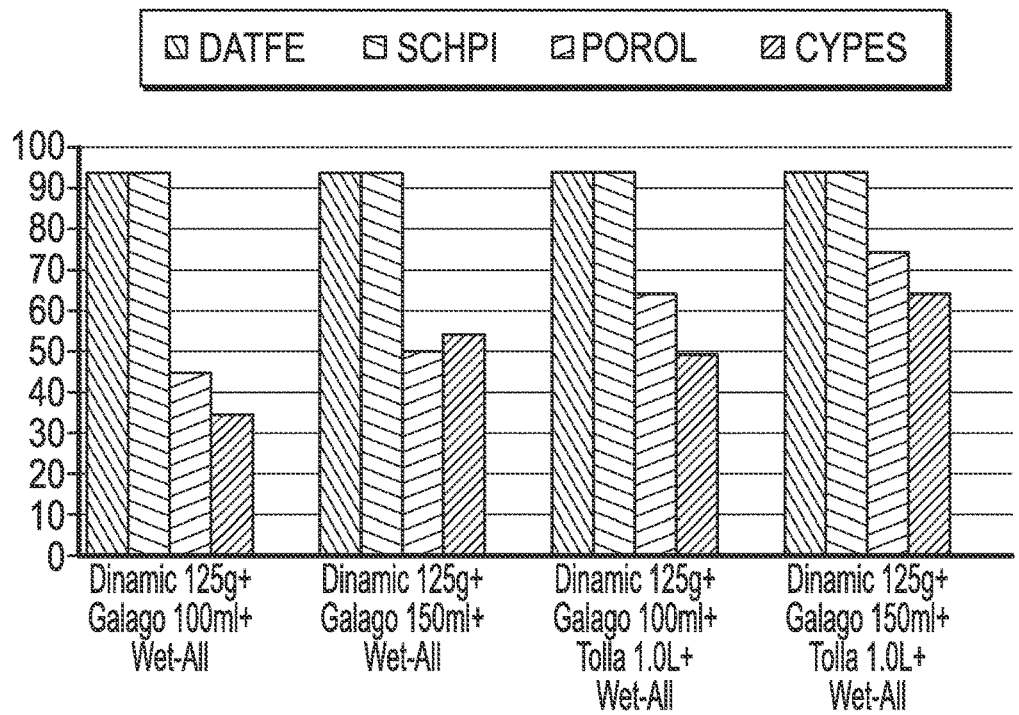
FIG. 9C shows another comparative weed control chart with tank mixtures of DINAMIC® 700 WDG at 125 g/ha with Galago plus Wet-All and with Galago plus TOLLA 960 plus Wet-All. Weed species are the same as in FIG. 9A.
Figure 9D:
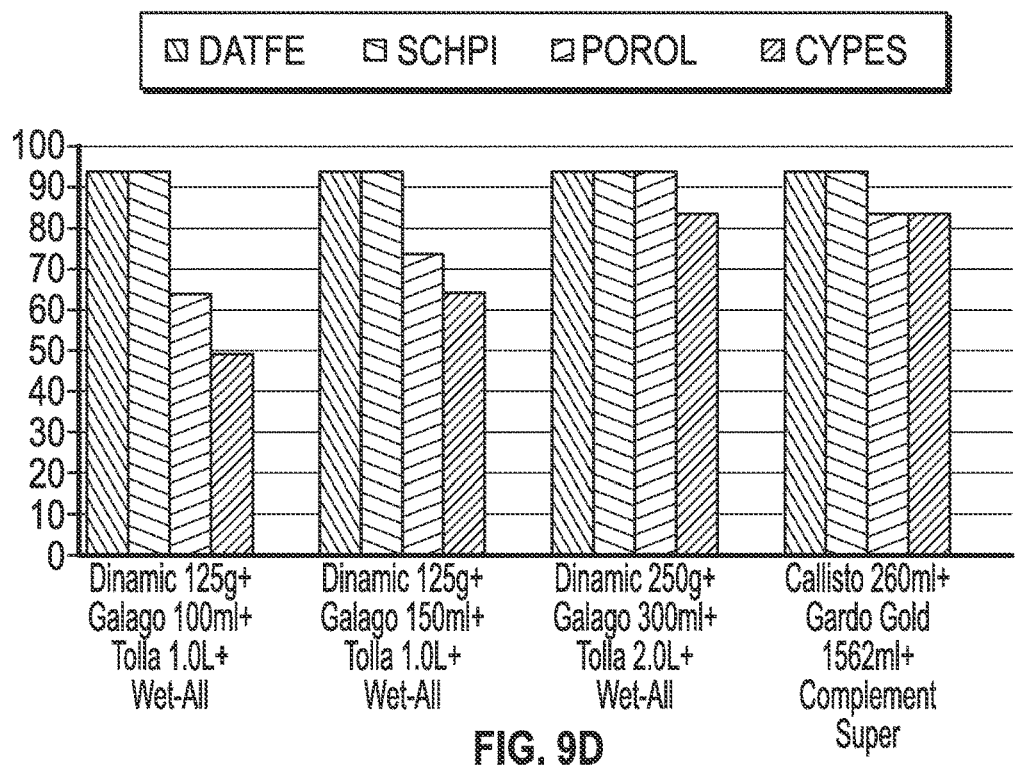
FIG. 9D shows another comparative weed control chart with tank mixtures of DINAMIC® 700 WDG with Galago plus TOLLA 960 plus Wet-All versus a standard tank mixture of CALLISTO® plus GARDO® Gold (S-metolachlor plus terbuthylazine (N-tert-butyl-6-chloro-N-ethyl-1,3,5-triazine-2,4-diamine)) plus COMPLEMENT® Super (Polyether-polymethylsiloxane copolymer, 1000 g/L). Weed species are the same as in FIG. 9A.
Figure 9E:
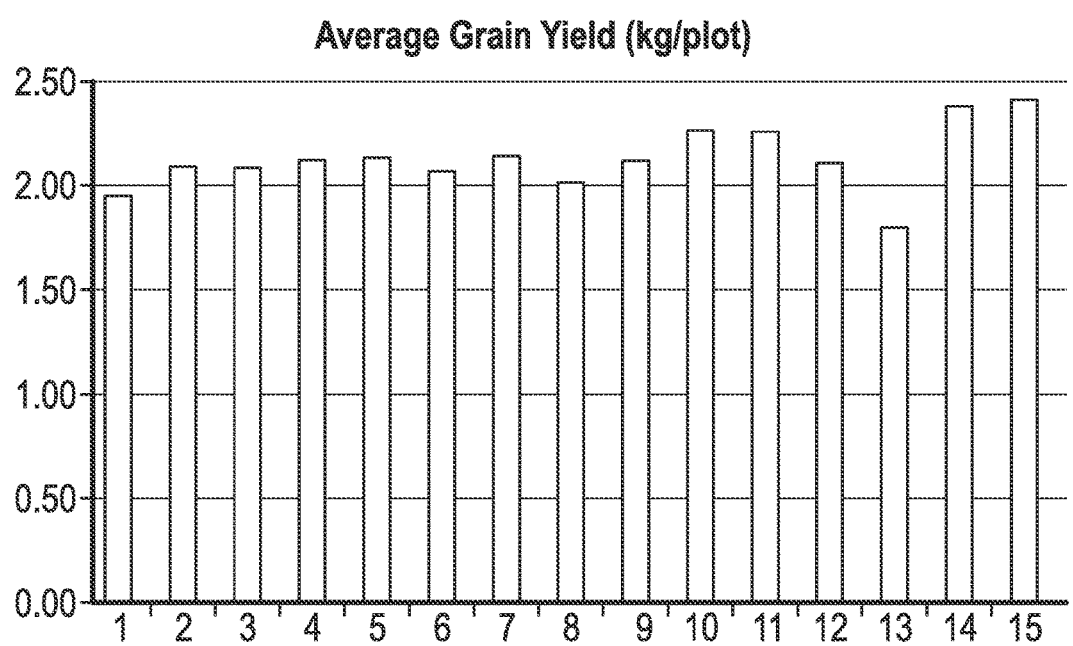
FIG. 9E shows another comparative grain yield chart of 13 different tank mixture combinations employing DINAMIC® 700 WDG (Lanes 1-13). Lane 14 is CALLISTO® plus GARDO® Gold plus COMPLEMENT® Super. Lane 15 is an untreated control.
Figure 10A:
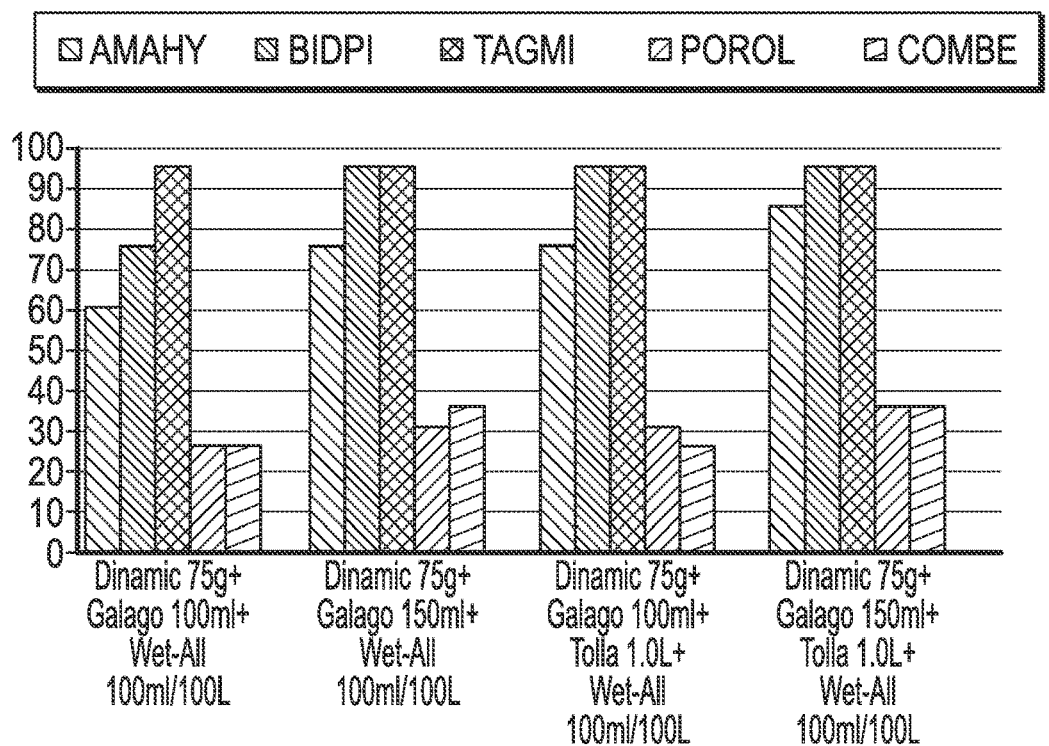
FIG. 10A shows another comparative weed control chart with tank mixtures of DINAMIC® 700 WDG at 75 g/ha with Galago plus Wet-All and with Galago plus TOLLA 960 plus Wet-All. Weed species are *Amaranthus hybridus* (AMAHY), *Bidens pilosa* (BIDPI), *Tagetes minuta* (TAGMI), *Portulaca oleracea* (POROL), and *Commelina benghalensis* (COMBE).
Figure 10B:
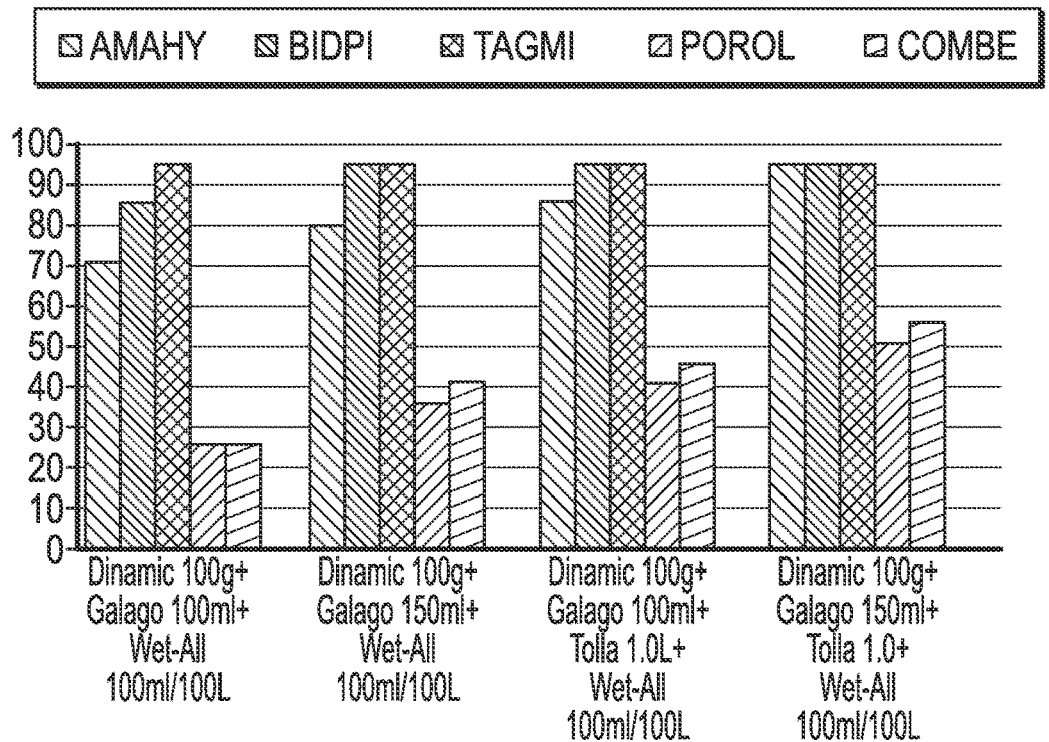
FIG. 10B shows another comparative weed control chart with tank mixtures of DINAMIC® 700 WDG at 100 g/ha with Galago plus Wet-All and with Galago plus TOLLA 960 plus Wet-All. Weed species are the same as in FIG. 10A.
Figure 10C:
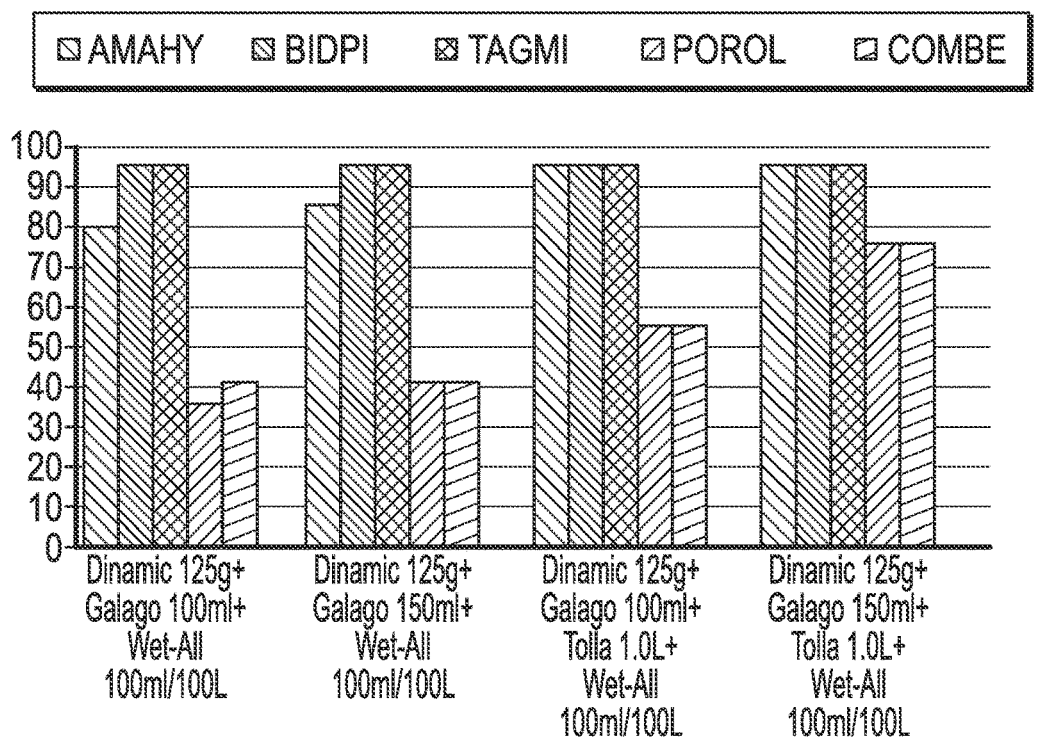
FIG. 10C shows another comparative weed control chart with tank mixtures of DINAMIC® 700 WDG at 125 g/ha with Galago plus Wet-All and with Galago plus TOLLA 960 plus Wet-All. Weed species are the same as in FIG. 10A.
Figure 10D:
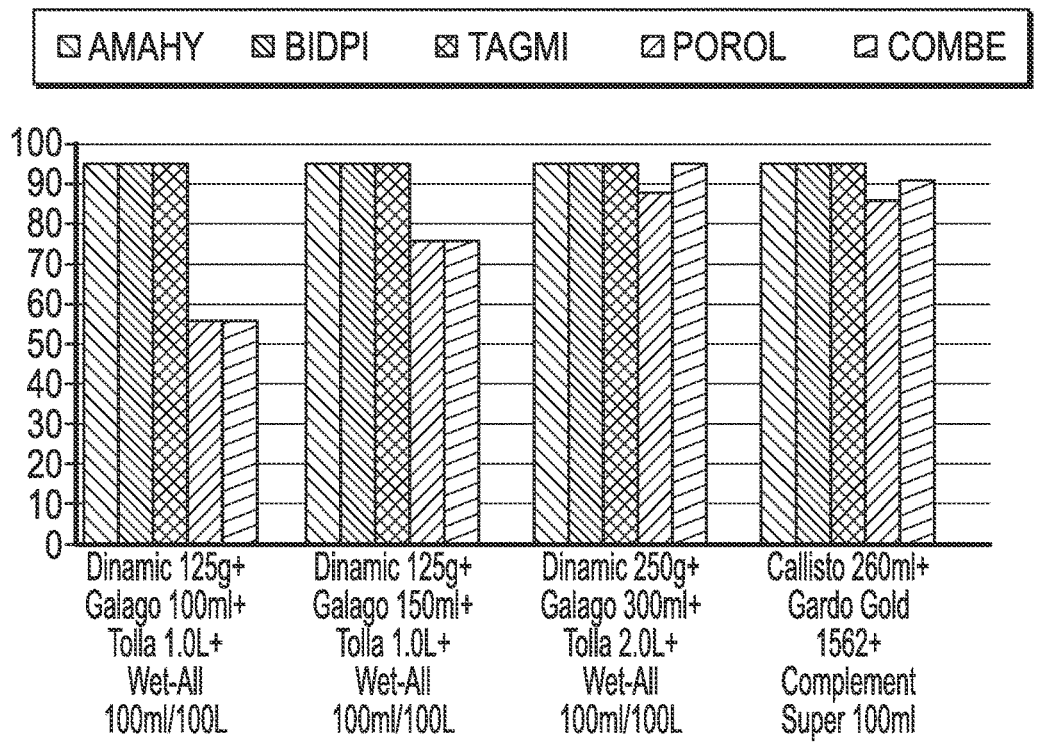
FIG. 10D shows another comparative weed control chart with tank mixtures of DINAMIC® 700 WDG with Galago plus TOLLA 960 plus Wet-All versus a standard tank mixture of CALLISTO® plus GARDO® Gold plus COMPLEMENT® Super. Weed species are the same as in FIG. 10A.
Figure 10E:
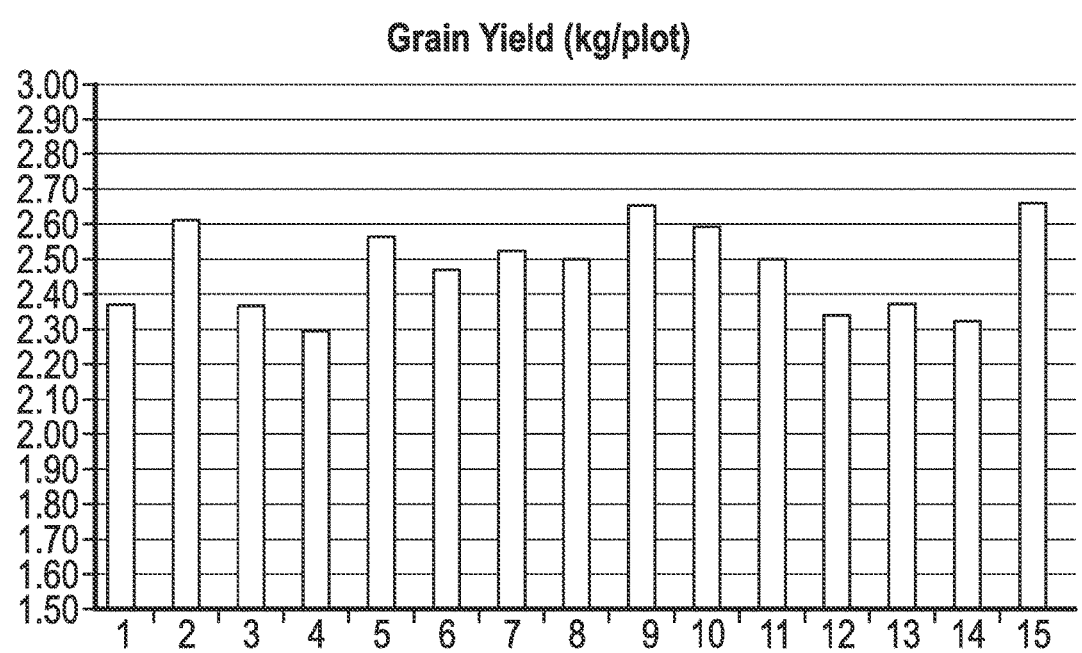
FIG. 10E shows another comparative grain yield chart of 13 different tank mixture combinations employing DINAMIC® 700 WDG (1-13). Lane 14 is CALLISTO® plus GARDO® Gold plus COMPLEMENT® Super. Lane 15 is an untreated control.
Figure 11A:
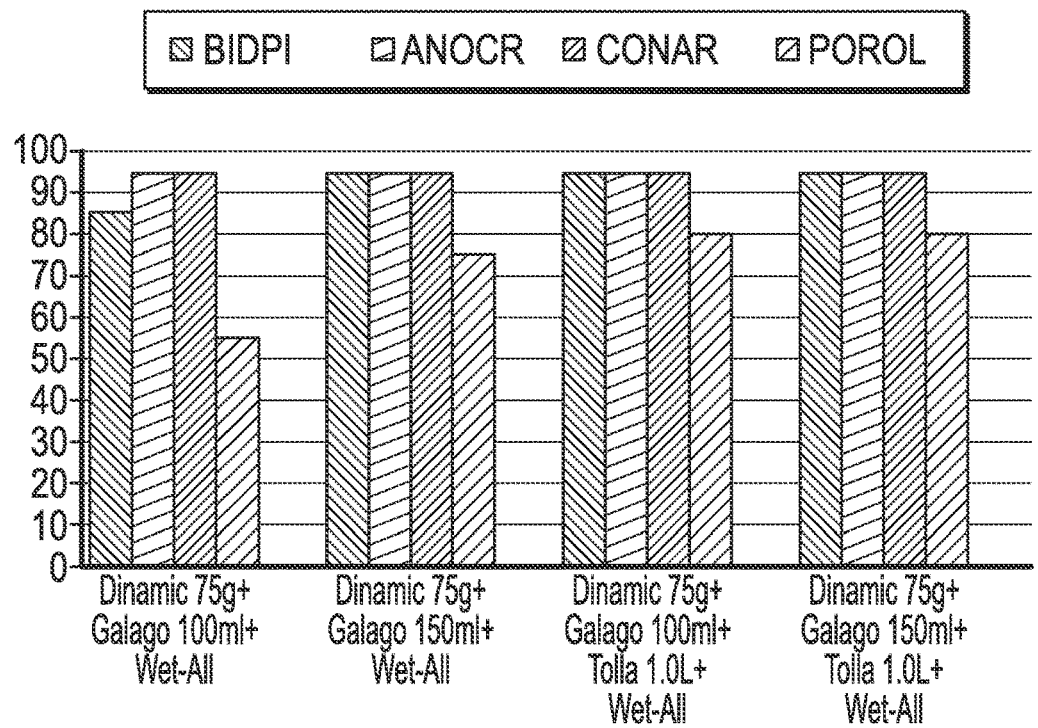
FIG. 11A shows another comparative weed control chart with tank mixtures of DINAMIC® 700 WDG at 75 g/ha with Galago plus Wet-All and with Galago plus TOLLA 960 plus Wet-All. Weed species are *Bidens pilosa* (BIDPI), *Portulaca oleracea* (POROL), *Convolvulus arvensis* (CONAR), and *Anoda cristata* (ANOCR).
Figure 11B:
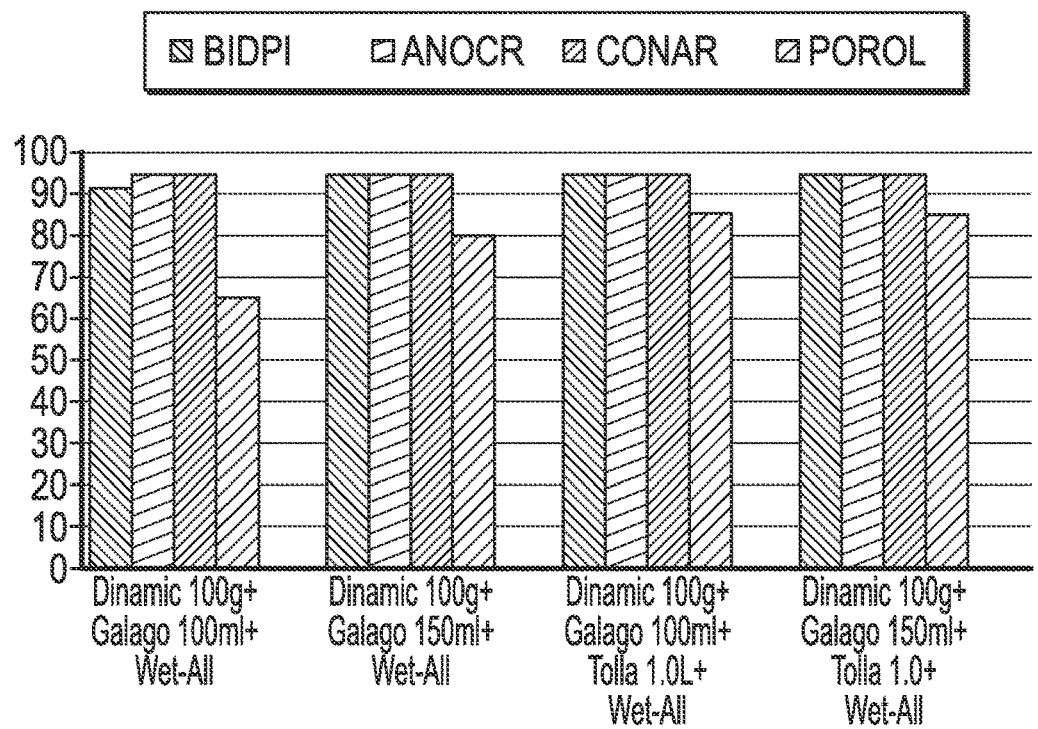
FIG. 11B shows another comparative weed control chart with tank mixtures of DINAMIC® 700 WDG at 100 g/ha with Galago plus Wet-All and with Galago plus TOLLA 960 plus Wet-All. Weed species are the same as FIG. 11A.
Figure 11C:
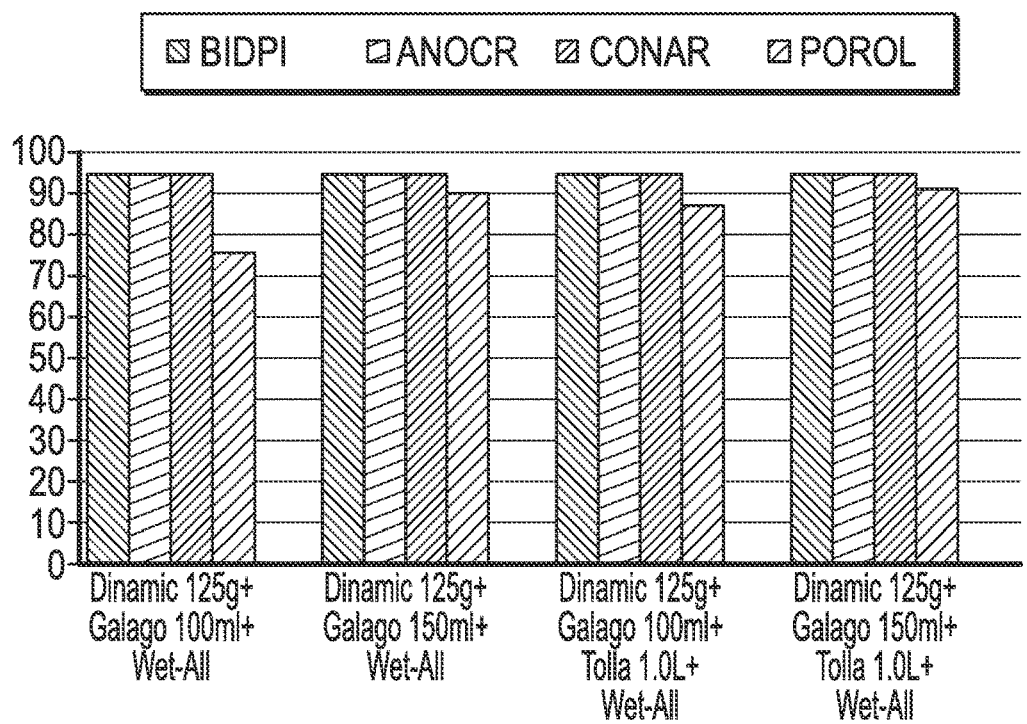
FIG. 11C shows another comparative weed control chart with tank mixtures of DINAMIC® 700 WDG at 125 g/ha with Galago plus Wet-All and with Galago plus TOLLA 960 plus Wet-All. Weed species are the same as FIG. 11A.
Figure 11D:
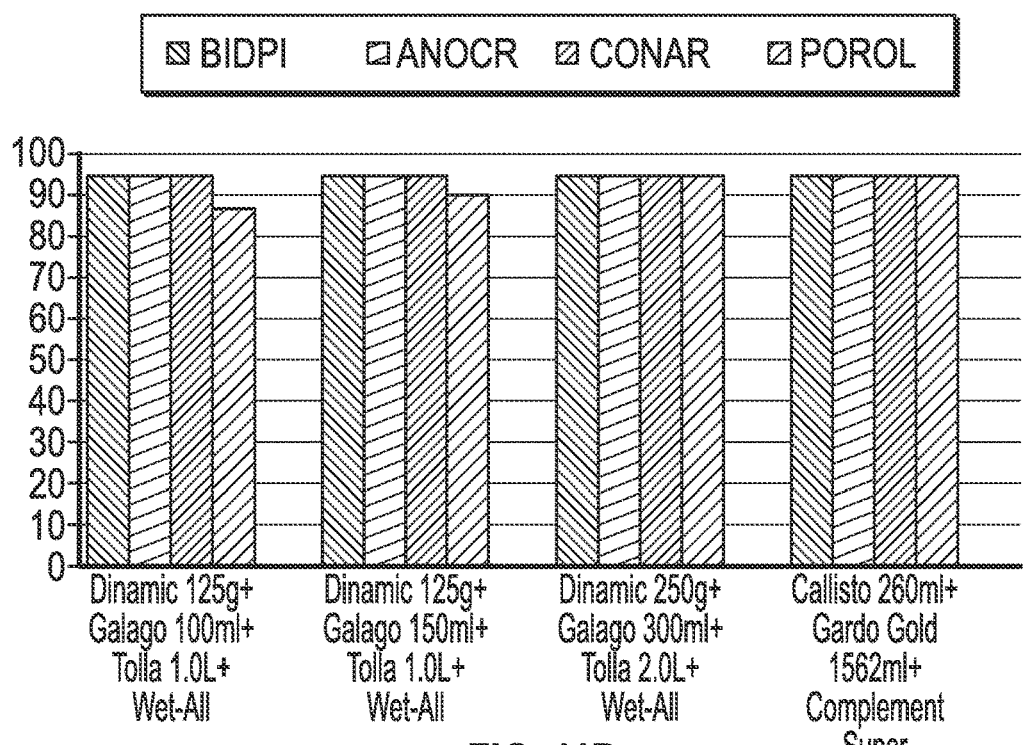
FIG. 11D shows another comparative weed control chart with tank mixtures of DINAMIC® 700 WDG with Galago plus TOLLA 960 plus Wet-All versus a standard tank mixture of CALLISTO® plus GARDO® Gold plus COMPLEMENT® Super. Weed species are the same as in FIG. 11A.
Figure 11E:
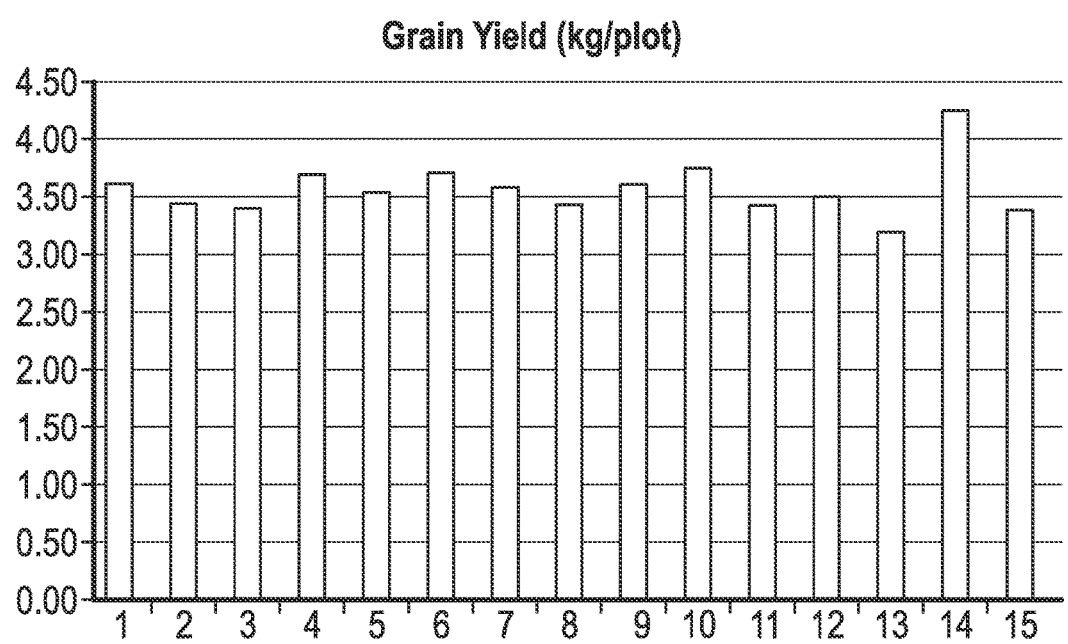
FIG. 11E shows another comparative grain yield chart of 13 different tank mixture combinations employing DINAMIC® 700 WDG (Lanes 1-13). Lane 14 is CALLISTO® plus GARDO® Gold plus COMPLEMENT® Super. Lane 15 is an untreated control.

Referring to FIGS. 2A-B, 3A-C, 4A-C, and 5A-D, all ratings of injury or bleaching are based on a scale from 1 to 9. In bleaching measurements, 1 indicates no bleaching while 9 indicates that the entire plant is white. Any bleaching measurement 4 and above was considered unacceptable for desirable turf species. In injury measurements, 1 indicates no injury while 9 indicates a dead plant. Any injury measurement 4 and above was considered unacceptable for desirable turf species). Density correlates with percent cover where 1 indicates no grass while 9 indicates a full pot.

In general, as evidenced in FIGS. 2A-B, 3A-C, 4A-C, and 5A-D, combinations of amicarbazone with mesotrione resulted in greater efficacy and less bleaching of weeds. Mustard (FIGS. 2A-B), green foxtail (FIGS. 4A-C), and crabgrass (FIGS. 5A-D) control was enhanced with the combination of amicarbazone and mesotrione compared to the application of each product alone. Decreased bleaching appeared to be due, in part, to the increased rate of weed desiccation. Mesotrione alone bleached weeds plants for an extended period of time before turning brown, while the treatments including amicarbazone caused almost immediate desiccation without going through the bleaching phase. *Poa annua* (FIGS. 3A-C) control was enhanced with the combination treatments. The light-colored leaves of the *Poa* plants made bleaching and general desiccation somewhat challenging to distinguish.

Bleaching of St. Augustine (Saphire or Floratam) was minimal regardless of treatment. Decreased bleaching, faster activity and greater control were related to the rate of amicarbazone and mesotrione. The higher rate of control by each product the more complete control and faster control of weeds sensitive to either amicarbazone or mesotrione. The decrease in the degree of bleaching was also dependent on the rate of each product; the higher the rate of amicarbazone, the less bleaching occurred.

The results of this Example demonstrate that combinations of amicarbazone and mesotrione are synergistic in decreasing the bleaching of sensitive weeds. The combination treatments also increased the speed and completeness of kill of sensitive weeds without causing increased phytotoxicity to desirable turf species. The data further tabulated below, along with FIGS. 2A-B, 3A-C, 4A-C, and 5A-D clearly demonstrate the synergistic activity of the combination of amicarbazone and mesotrione.

Concerning the optimum rate of each herbicide product for best control and least bleaching, 1 oz/acre of Xonerate 70 WDG (amicarbazone) plus 4 fl. oz/Acre Tenacity 4 SC (mesotrione) (0.044 lb. active ingredient per acre amicarbazone plus 0.125 lb. active ingredient per acre mesotrione) combined with 4 fl oz/acre Tenacity (40% mesotrione) can provide commercially viable benefits over the use of each herbicide alone. Likewise, 2 oz/Acre Xonerate (0.088 lb. active ingredient per acre amicarbazone) in combination with 4 fl. oz/Acre Tenacity (0.125 lb. active ingredient per acre mesotrione) can provide benefits over the individual use of each product alone. The specific combination for optimum synergy and control without undue bleaching depends on the exact turf type and the species of weeds being targeted.

Table 5-3 below summarizes the treatment parameters for Treatment numbers 1-9 in Tables 5-4 through 5-11 that follow.

TABLE 5-3

Treatment Parameters

| Trt No. | Type | Treatment Name | Form Conc | Form Type | Rate | Rate Unit | Other Rate | Other Rate Unit | Appl Code |
|---|---|---|---|---|---|---|---|---|---|
| 1 | CHK | Untreated Check | | | | | | | |
| 2 | HERB | Amicarbazone | 70 | WG | 0.0219 | lb ai/a | 0.5 | oz/a | A |
| 3 | HERB | Amicarbazone | 70 | WG | 0.131 | lb ai/a | 3.0 | oz/a | A |
| 4 | HERB | Tenacity | 4 | SC | 0.125 | lb ai/a | 4.0 | oz/a | A |
| 5 | HERB | Tenacity | 4 | SC | 0.25 | lb ai/a | 8.0 | oz/a | A |
| 6 | HERB | Tenacity | 4 | SC | 0.125 | lb ai/a | 4.0 | oz/a | A |
| | HERB | Amicarbazone | 70 | WG | 0.0219 | lb ai/a | 0.5 | oz/a | A |
| 7 | HERB | Tenacity | 4 | SC | 0.125 | lb ai/a | 4.0 | oz/a | A |
| | HERB | Amicarbazone | 70 | WG | 0.131 | lb ai/a | 3.0 | oz/a | A |

TABLE 5-3-continued

| | | | | | | | | | |
|---|---|---|---|---|---|---|---|---|---|
| | | | Treatment Parameters | | | | | | |
| Trt No. | Type | Treatment Name | Form Conc | Form Type | Rate | Rate Unit | Other Rate | Other Rate Unit | Appl Code |
| 8 | HERB | Tenacity | 4 | SC | 0.25 | lb ai/a | 8.0 | oz/a | A |
|   | HERB | Amicarbazone | 70 | WG | 0.0219 | lb ai/a | 0.5 | oz/a | A |
| 9 | HERB | Tenacity | 4 | SC | 0.25 | lb ai/a | 8.0 | oz/a | A |
|   | HERB | Amicarbazone | 70 | WG | 0.131 | lb ai/a | 3.0 | oz/a | A |

Type CHK = Check or Untreated (control);
HERB = Herbicide
Treatment Name: Untreated Check is not treated|
Form Type:
WG = Water dispersible granules (a formulation consisting of granules to be applied after disintegration and dispersion in water);
SC = Suspension concentrate (flowable concentrate); a stable suspension of active ingredient(s) in water, intended for dilution with water before use;
Rate Unit: lb ai/a = pounds active ingredient per acre (Metric = Kg ai/ha (hectare)) A
Other Rate Unit: oz/a = ounces product per acre Replications employed include 4, Untreated treatments: 1, Design: Randomized Complete Block, Treatment units: US standard, Treated plot size Width: 4 feet, Treated plot size Length: 4 feet, Application volume: 50 gal/ac, Mix size: 0.5562 liters, Mix overage: 100%, Format definitions: G-All7.DEF, G-All7.FRM. The results of these treatments are summarized below in Tables 5-4 to 5-11.

TABLE 5-4

| | | | | | | |
|---|---|---|---|---|---|---|
| | Kentucky Bluegrass Seedling | | | | | |
| Crop Code | POAPR | POAPR | POAPR | POAPR | POAPR | POAPR |
| BBCH Scale | BGRM | BGRM | BGRM | BGRM | BGRM | BGRM |
| Crop Name | Kentucky bl> | Kentucky bl> | Kentucky bl> | Kentucky bl> | Kentucky bl> | Kentucky bl> |
| Crop Variety | — | — | — | — | — | — |
| Description | Seedling | Seedling | Seedling | Seedling | Seedling | Seedling |
| Rating Data Type | Bleaching | Bleaching | Injury | Bleaching | Bleaching | Injury |
| Days After First/Last Applic. | 6 6 | 7 7 | 10 10 | 10 10 | 14 14 | 14 14 |
| Trt-Eval Interval | 6 DA-A | 7 DA-A | 10 DA-A | 10 DA-A | 14 DA-A | 14 DA-A |
| Trt No. | Treatment Name | 1 | 2 | 3 | 4 | 5 | 6 |
| 1 | Untreated Check | 1.0 a | 1.0 a | 1.0 c | 1.0 a | 1.0 a | 1.3 c |
| 2 | Amicarbazone | 1.0 a | 1.0 a | 1.0 c | 1.0 a | 1.0 a | 1.3 c |
| 3 | Amicarbazone | 1.0 a | 1.0 a | 1.8 c | 1.0 a | 1.5 a | 2.5 c |
| 4 | Tenacity | 1.0 a | 1.0 a | 1.0 c | 1.0 a | 1.0 a | 1.3 c |
| 5 | Tenacity | 1.0 a | 1.0 a | 1.5 c | 1.8 a | 1.8 a | 2.0 c |
| 6 | Tenacity Amicarbazone | 1.0 a | 1.0 a | 1.3 c | 1.0 a | 1.0 a | 1.8 c |
| 7 | Tenacity Amicarbazone | 1.0 a | 1.0 a | 4.0 b | 1.0 a | 1.3 a | 4.5 b |
| 8 | Tenacity Amicarbazone | 1.0 a | 1.0 a | 2.3 c | 1.0 a | 1.3 a | 2.8 c |
| 9 | Tenacity Amicarbazone | 1.0 a | 1.0 a | 8.0 a | 1.0 a | 1.3 a | 8.5 a |
| LSD (P = .10) | 0.00 | 0.00 | 1.29 | 0.60 | 0.48 | 1.45 |
| Standard Deviation | 0.00 | 0.00 | 1.07 | 0.50 | 0.40 | 1.20 |
| CV | 0.0 | 0.0 | 44.2 | 46.15 | 32.46 | 42.01 |
| Bartlett's X2 | 0.0 | 0.0 | 11.088 | 0.0 | 0.099 | 17.602 |
| P(Bartlett's X2) | — | — | 0.05* | — | 0.999 | 0.024* |
| Replicate F | 0.000 | 0.000 | 1.128 | 1.000 | 0.471 | 0.942 |
| Replicate Prob(F) | 1.0000 | 1.0000 | 0.3576 | 0.4098 | 0.7056 | 0.4357 |
| Treatment F | 0.000 | 0.000 | 18.566 | 1.000 | 1.765 | 15.365 |
| Treatment Prob(F) | 1.0000 | 1.0000 | 0.0001 | 0.4613 | 0.1345 | 0.0001 |

| | | | | |
|---|---|---|---|---|
| Crop Code | POAPR | POAPR | POAPR | POAPR |
| BBCH Scale | BGRM | BGRM | BGRM | BGRM |
| Crop Name | Kentucky bl> | Kentucky bl> | Kentucky bl> | Kentucky bl> |
| Crop Variety | — | — | | |

TABLE 5-4-continued

| | | Kentucky Bluegrass Seedling | | | |
|---|---|---|---|---|---|
| Description | | Seedling | Seedling | Seedling | Seedling |
| Rating Data Type | | Bleaching | % Cover | % Cover | % Cover |
| Days After First/Last Applic. | | 20 20 | 20 20 | 24 24 | 31 31 |
| Trt-Eval Interval | | 20 DA-A | 20 DA-A | 24 DA-A | 31 DA-A |
| Trt No. | Treatment Name | 7 | 8 | 9 | 10 |
| 1 | Untreated Check | 1.0 b | 7.8 a | 8.0 a | 8.8 a |
| 2 | Amicarbazone | 1.0 b | 6.5 ab | 6.8 ab | 8.8 a |
| 3 | Amicarbazone | 1.5 a | 4.8 b | 4.8 bc | 7.5 a |
| 4 | Tenacity | 1.0 b | 5.5 b | 5.5 bc | 8.0 a |
| 5 | Tenacity | 1.0 b | 6.3 ab | 6.8 ab | 8.0 a |
| 6 | Tenacity Amicarbazone | 1.0 b | 5.8 b | 6.0 b | 8.5 a |
| 7 | Tenacity Amicarbazone | 1.0 b | 3.0 c | 3.8 c | 5.3 b |
| 8 | Tenacity Amicarbazone | 1.0 b | 5.3 b | 5.3 bc | 7.8 a |
| 9 | Tenacity Amicarbazone | 1.0 b | 1.3 d | 1.5 d | 1.3 c |
| LSD (P = .10) | | 0.23 | 1.31 | 1.30 | 1.56 |
| Standard Deviation | | 0.19 | 1.09 | 1.08 | 1.29 |
| CV | | 18.23 | 21.24 | 20.11 | 18.2 |
| Bartlett's X2 | | 0.0 | 7.214 | 7.444 | 15.439 |
| P(Bartlett's X2) | | — | 0.514 | 0.49 | 0.051 |
| Replicate F | | 1.000 | 3.458 | 2.829 | 3.181 |
| Replicate Prob(F) | | 0.4098 | 0.0322 | 0.0599 | 0.0422 |
| Treatment F | | 3.000 | 12.843 | 12.538 | 14.214 |
| Treatment Prob(F) | | 0.0176 | 0.0001 | 0.0001 | 0.0001 |

Means followed by same letter do not significantly differ (P = .10, Student-Newman-Keuls)
Mean comparisons performed only when AOV Treatment P(F) is significant at mean comparison OSL.

TABLE 5-5

| | | Kentucky Bluegrass Tillering | | | | | |
|---|---|---|---|---|---|---|---|
| Crop Code | | POAPR | POAPR | POAPR | POAPR | POAPR | POAPR |
| BBCH Scale | | BGRM | BGRM | BGRM | BGRM | BGRM | BGRM |
| Crop Name | | Kentucky | Kentucky | Kentucky | Kentucky | Kentucky | Kentucky |
| Crop Variety | | bl> | bl> | bl> | bl> | bl> | bl> |
| Description | | Tillering | Tillering | Tillering | Tillering | Tillering | Tillering |
| Rating Data Type | | Bleaching | Bleaching | Bleaching | Bleaching | Bleaching | Bleaching |
| Days After First/Last Applic. | | 6 6 | 7 7 | 10 10 | 14 14 | 20 20 | 31 31 |
| Trt-Eval Interval | | 6 DA-A | 7 DA-A | 10 DA-A | 14 DA-A | 20 DA-A | 31 DA-A |
| Trt No. | Treatment Name | 11 | 12 | 13 | 14 | 15 | 16 |
| 1 | Untreated Check | 1.0 a | 1.0 a | 1.0 a | 1.0 a | 1.0 a | 1.0 a |
| 2 | Amicarbazone | 1.0 a | 1.0 a | 1.0 a | 1.0 a | 1.3 a | 1.0 a |
| 3 | Amicarbazone | 1.3 a | 1.3 a | 1.3 a | 1.0 a | 1.0 a | 1.0 a |
| 4 | Tenacity | 1.5 a | 1.5 a | 1.0 a | 1.0 a | 1.5 a | 1.0 a |
| 5 | Tenacity | 1.3 a | 1.3 a | 1.3 a | 1.3 a | 1.0 a | 1.0 a |
| 6 | Tenacity Amicarbazone | 1.3 a | 1.3 a | 1.5 a | 1.0 a | 1.5 a | 1.0 a |
| 7 | Tenacity Amicarbazone | 1.3 a | 1.3 a | 1.3 a | 1.5 a | 1.3 a | 1.0 a |
| 8 | Tenacity Amicarbazone | 1.8 a | 1.8 a | 1.5 a | 1.5 a | 1.5 a | 1.0 a |
| 9 | Tenacity Amicarbazone | 1.3 a | 1.3 a | 1.5 a | 1.8 a | 1.5 a | 1.0 a |
| LSD (P = .10) | | 0.55 | 0.55 | 0.65 | 0.56 | 0.73 | 0.00 |
| Standard Deviation | | 0.45 | 0.45 | 0.54 | 0.46 | 0.60 | 0.00 |
| CV | | 35.52 | 35.52 | 43.03 | 37.55 | 47.18 | 0.0 |
| Bartlett's X2 | | 0.105 | 0.105 | 2.518 | 1.577 | 3.311 | 0.0 |
| P(Bartlett's X2) | | 1.00 | 1.00 | 0.774 | 0.665 | 0.652 | . |

TABLE 5-5-continued

Kentucky Bluegrass Tillering

| Replicate F | 0.899 | 0.899 | 0.352 | 0.703 | 2.548 | 0.000 |
|---|---|---|---|---|---|---|
| Replicate Prob(F) | 0.4562 | 0.4562 | 0.7881 | 0.5594 | 0.0797 | 1.0000 |
| Treatment F | 1.045 | 1.045 | 0.648 | 1.615 | 0.592 | 0.000 |
| Treatment Prob(F) | 0.4316 | 0.4316 | 0.7303 | 0.1727 | 0.7745 | 1.0000 |

TABLE 5-6

Mustard

| Crop Code | | POAPR | | SINSS | SINSS | SINSS | SINSS | SINSS |
|---|---|---|---|---|---|---|---|---|
| BBCH Scale | | BRAP | BRAP | BRAP | BRAP | BRAP | BRAP | BRAP |
| Crop Name | | Mustard | Mustard | Mustard | Mustard | Mustard | Mustard | Mustard |
| Crop Variety Description | | | | | | | | |
| Rating Data Type | | Injury | Bleaching | Injury | Bleaching | Injury | Injury | Injury |
| Days After First/Last Applic. | | 3 3 | 6 6 | 6 6 | 7 7 | 7 7 | 10 10 | 14 14 |
| Trt-Eval Interval | | 3 DA-A | 6 DA-A | 6 DA-A | 7 DA-A | 7 DA-A | 10 DA-A | 14 DA-A |
| Trt No. | Treatment Name | 20 | 21 | 22 | 23 | 24 | 25 | 26 |
| 1 | Untreated Check | 1.0 c | 2.8 b | 1.0 c | 1.5 c | 1.3 d | 1.8 c | 1.5 c |
| 2 | Amicarbazone | 2.8 b | 2.0 bc | 2.8 c | 2.0 bc | 4.3 c | 6.0 b | 5.8 b |
| 3 | Amicarbazone | 6.8 a | 1.3 c | 6.5 ab | 2.0 bc | 7.0 b | 8.8 a | 8.8 a |
| 4 | Tenacity | 3.3 b | 5.3 a | 2.8 c | 5.0 a | 4.3 c | 7.3 ab | 8.3 a |
| 5 | Tenacity | 2.3 bc | 5.8 a | 2.5 c | 5.0 a | 4.3 c | 6.8 ab | 7.8 a |
| 6 | Tenacity Amicarbazone | 5.5 a | 2.0 bc | 5.5 b | 2.0 bc | 6.0 bc | 8.5 a | 9.0 a |
| 7 | Tenacity Amicarbazone | 6.5 a | 1.3 c | 6.8 ab | 2.0 bc | 7.0 b | 8.8 a | 9.0 a |
| 8 | Tenacity Amicarbazone | 5.8 a | 2.3 bc | 5.5 b | 2.3 b | 6.0 bc | 8.5 a | 9.0 a |
| 9 | Tenacity Amicarbazone | 7.5 a | 1.3 c | 8.0 a | 2.0 bc | 8.8 a | 9.0 a | 9.0 a |
| LSD (P = .10) | | 1.35 | 0.89 | 1.30 | 0.41 | 1.21 | 1.35 | 1.36 |
| Standard Deviation | | 1.11 | 0.73 | 1.07 | 0.34 | 1.00 | 1.11 | 1.13 |
| CV | | 24.3 | 27.83 | 23.45 | 12.89 | 18.5 | 15.34 | 14.91 |
| Bartlett's X2 | | 8.347 | 8.64 | 0.714 | 0.767 | 6.826 | 16.312 | 20.518 |
| P(Bartlett's X2) | | 0.303 | 0.28 | 0.994 | 0.682 | 0.556 | 0.022* | 0.001* |
| Replicate F | | 0.261 | 0.189 | 0.152 | 2.800 | 0.544 | 1.101 | 1.460 |
| Replicate Prob(F) | | 0.8526 | 0.9030 | 0.9272 | 0.0616 | 0.6570 | 0.3680 | 0.2505 |
| Treatment F | | 17.127 | 21.567 | 19.750 | 63.240 | 19.037 | 17.292 | 19.796 |
| Treatment Prob(F) | | 0.0001 | 0.0001 | 0.0001 | 0.0001 | 0.0001 | 0.0001 | 0.0001 |

Means followed by same letter do not significantly differ (P = .10, Student-Newman-Keuls)
Mean comparisons performed only when AOV Treatment P(F) is significant at mean comparison OSL.

TABLE 5-7

Poa

| Crop Code | | | | | | | | |
|---|---|---|---|---|---|---|---|---|
| BBCH Scale | | | | | | | | |
| Crop Name | | Poa | Poa | Poa | Poa | Poa | Poa | Poa |
| Crop Variety Description | | | | | | | | |
| Rating Data Type | | Bleaching | Bleaching | Injury | Bleaching | Injury | Bleaching | Injury |
| Days After First/Last Applic. | | 6 6 | 7 7 | 10 10 | 14 14 | 14 14 | 16 16 | 16 16 |
| Trt-Eval Interval | | 6 DA-A | 7 DA-A | 10 DA-A | 14 DA-A | 14 DA-A | 16 DA-A | 16 DA-A |
| Trt No. | Treatment Name | 31 | 32 | 33 | 34 | 35 | 36 | 37 |
| 1 | Untreated Check | 1.0 a | 1.0 a | 1.3 de | 1.0 b | 2.0 d | 1.5 ab | 3.0 d |
| 2 | Amicarbazone | 1.0 a | 1.0 a | 1.0 e | 1.0 b | 1.8 d | 1.0 b | 2.5 d |
| 3 | Amicarbazone | 1.0 a | 1.0 a | 3.5 bc | 1.8 b | 4.8 b | 2.0 ab | 5.0 bc |
| 4 | Tenacity | 1.0 a | 1.0 a | 1.3 de | 1.3 b | 1.8 d | 2.3 ab | 2.3 d |
| 5 | Tenacity | 1.3 a | 1.3 a | 2.3 cde | 1.8 b | 2.8 cd | 2.8 ab | 2.8 d |

TABLE 5-7-continued

| | | Poa | | | | | | |
|---|---|---|---|---|---|---|---|---|
| 6 | Tenacity Amicarbazone | 1.3 a | 1.5 a | 2.5 cde | 2.8 b | 4.0 bc | 2.8 ab | 4.0 cd |
| 7 | Tenacity Amicarbazone | 1.0 a | 1.0 a | 4.3 b | 2.3 b | 5.5 b | 2.5 ab | 6.3 b |
| 8 | Tenacity Amicarbazone | 1.0 a | 1.0 a | 2.8 cd | 1.8 b | 4.3 bc | 2.0 ab | 4.8 bc |
| 9 | Tenacity Amicarbazone | 1.3 a | 1.0 a | 6.0 a | 4.5 a | 7.0 a | 3.8 a | 7.8 a |
| LSD (P = .10) | | 0.34 | 0.30 | 1.02 | 1.64 | 1.29 | 1.33 | 1.26 |
| Standard Deviation | | 0.28 | 0.25 | 0.84 | 1.36 | 1.07 | 1.10 | 1.05 |
| CV | | 26.27 | 22.65 | 30.6 | 67.83 | 28.46 | 48.35 | 24.59 |
| Bartlett's X2 | | 0.0 | 0.061 | 11.9 | 10.892 | 13.605 | 13.55 | 11.159 |
| P(Bartlett's X2) | | — | 0.805 | 0.104 | 0.092 | 0.034* | 0.06 | 0.132 |
| Replicate F | | 1.257 | 1.692 | 2.235 | 0.242 | 1.000 | 0.519 | 0.771 |
| Replicate Prob(F) | | 0.3113 | 0.1953 | 0.1101 | 0.8665 | 0.4098 | 0.6732 | 0.5215 |
| Treatment F | | 0.771 | 2.077 | 15.000 | 2.615 | 11.854 | 2.084 | 12.814 |
| Treatment Prob(F) | | 0.6311 | 0.0795 | 0.0001 | 0.0326 | 0.0001 | 0.0786 | 0.0001 |

| Crop Code | | | | | | |
|---|---|---|---|---|---|---|
| BBCH Scale | | | | | | |
| Crop Name | | Poa | Poa | Poa | Poa | Poa |
| Crop Variety | | | | | | |
| Description | | | | | | |
| Rating Data Type | | Bleaching | Injury | Injury | Injury | Injury |
| Days After First/Last Applic. | | 20 20 | 20 20 | 24 24 | 31 31 | 41 41 |
| Trt-Eval Interval | | 20 DA-A | 20 DA-A | 24 DA-A | 31 DA-A | 31 DA-A |

| Trt No. | Treatment Name | 38 | 39 | 40 | 41 | 42 |
|---|---|---|---|---|---|---|
| 1 | Untreated Check | 1.0 a | 2.3 d | 1.8 d | 2.3 c | 2.8 c |
| 2 | Amicarbazone | 1.0 a | 2.5 d | 2.5 cd | 3.3 c | 3.8 c |
| 3 | Amicarbazone | 2.0 a | 5.5 c | 5.3 b | 7.0 ab | 7.5 ab |
| 4 | Tenacity | 1.5 a | 2.0 d | 2.0 d | 2.8 c | 2.8 c |
| 5 | Tenacity | 1.8 a | 2.8 d | 2.8 cd | 2.8 c | 2.8 c |
| 6 | Tenacity Amicarbazone | 2.0 a | 4.8 c | 4.0 bc | 6.3 b | 6.5 ab |
| 7 | Tenacity Amicarbazone | 2.3 a | 6.8 b | 7.0 a | 8.3 a | 8.3 a |
| 8 | Tenacity Amicarbazone | 1.5 a | 5.0 c | 4.8 b | 6.0 b | 6.3 b |
| 9 | Tenacity Amicarbazone | 2.3 a | 8.3 a | 8.0 a | 8.5 a | 8.3 a |
| LSD (P = .10) | | 0.76 | 1.07 | 1.31 | 1.46 | 1.25 |
| Standard Deviation | | 0.63 | 0.88 | 1.08 | 1.20 | 1.03 |
| CV | | 37.13 | 20.03 | 25.58 | 23.07 | 19.07 |
| Bartlett's X2 | | 6.349 | 5.253 | 6.542 | 6.997 | 9.142 |
| P(Bartlett's X2) | | 0.385 | 0.629 | 0.478 | 0.537 | 0.33 |
| Replicate F | | 2.316 | 0.414 | 0.571 | 0.153 | 0.512 |
| Replicate Prob(F) | | 0.1012 | 0.7443 | 0.6393 | 0.9267 | 0.6779 |
| Treatment F | | 2.333 | 24.763 | 16.952 | 17.115 | 21.729 |
| Treatment Prob(F) | | 0.0518 | 0.0001 | 0.0001 | 0.0001 | 0.0001 |

Means followed by same letter do not significantly differ (P = .10, Student-Newman-Keuls)
Mean comparisons performed only when AOV Treatment P(F) is significant at mean comparison OSL.

TABLE 5-8

| | Green Foxtail | | | | | | |
|---|---|---|---|---|---|---|---|
| Crop Code | | | | | | | |
| BBCH Scale | | | | | | | |
| Crop Name | Green Foxta> | Green Foxta> | Green Foxta> | Green Foxta> | Green Foxta> | Green Foxta> | Green Foxta> |
| Crop Variety | | | | | | | |
| Description | | | | | | | |
| Rating Data Type | Bleaching | Injury | Bleaching | Injury | Injury | Injury | Bleaching |
| Days After First/Last Applic. | 16 16 | 16 16 | 20 20 | 20 20 | 24 24 | 31 31 | 31 31 |
| Trt-Eval Interval | 16 DA-A | 16 DA-A | 20 DA-A | 20 DA-A | 24 DA-A | 31 DA-A | 31 DA-A |

TABLE 5-8-continued

| | | Green Foxtail | | | | | | | |
|---|---|---|---|---|---|---|---|---|---|
| Trt No. | Treatment Name | 49 | 50 | 51 | 52 | 53 | 54 | 55 | 56 |
| 1 | Untreated Check | 1.3 d | 1.5 d | 1.5 c | 1.8 d | 1.8 d | 4.0 cd | 3.5 a | |
| 2 | Amicarbazone | 1.0 d | 1.8 d | 1.3 c | 1.8 d | 2.0 d | 2.8 d | 3.0 a | |
| 3 | Amicarbazone | 1.0 d | 2.8 cd | 1.3 c | 3.5 cd | 3.8 c | 5.3 bc | 3.3 a | |
| 4 | Tenacity | 4.0 b | 3.8 c | 3.0 ab | 3.8 cd | 4.0 c | 5.0 bc | 3.3 a | |
| 5 | Tenacity | 5.3 a | 6.0 b | 3.8 a | 5.5 bc | 5.8 b | 6.3 abc | 2.5 a | |
| 6 | Tenacity Amicarbazone | 2.8 c | 5.5 b | 2.0 bc | 5.5 bc | 6.3 b | 6.5 abc | 2.3 a | |
| 7 | Tenacity Amicarbazone | 1.3 d | 7.5 a | 1.5 c | 7.5 ab | 7.5 ab | 8.0 a | 3.0 a | |
| 8 | Tenacity Amicarbazone | 3.0 c | 7.8 a | 2.3 bc | 7.5 ab | 7.3 ab | 7.5 ab | 1.8 a | |
| 9 | Tenacity Amicarbazone | 1.5 d | 8.5 a | 1.3 c | 8.3 a | 8.8 a | 8.3 a | 1.3 a | |
| LSD (P = .10) | | 0.74 | 1.25 | 0.84 | 1.56 | 1.42 | 1.71 | 2.03 | — |
| Standard Deviation | | 0.61 | 1.03 | 0.70 | 1.29 | 1.18 | 1.41 | 1.68 | — |
| CV | | 26.08 | 20.59 | 35.35 | 25.75 | 22.55 | 23.79 | 63.73 | — |
| Bartlett's X2 | | 2.66 | 10.181 | 4.884 | 15.792 | 17.483 | 11.091 | 17.093 | — |
| P(Bartlett's X2) | | 0.85 | 0.253 | 0.674 | 0.045* | 0.025* | 0.135 | 0.029* | — |
| Replicate F | | 1.000 | 1.747 | 1.429 | 1.251 | 1.977 | 1.833 | 1.869 | |
| Replicate Prob(F) | | 0.4098 | 0.1843 | 0.2590 | 0.3132 | 0.1444 | 0.1680 | 0.1618 | |
| Treatment F | | 24.975 | 26.764 | 6.486 | 14.631 | 17.735 | 6.931 | 0.820 | |
| Treatment Prob(F) | | 0.0001 | 0.0001 | 0.0002 | 0.0001 | 0.0001 | 0.0001 | 0.5929 | |

| | | | | | | |
|---|---|---|---|---|---|---|
| Crop Code | | | | | | |
| BBCH Scale | | | | | | |
| Crop Name | | Green Foxta> | Green Foxta> | Green Foxta> | Green Foxta> | Green Foxta> |
| Crop Variety | | | | | | |
| Description | | | | | | |
| Rating Data Type | | Injury | Injury | Bleaching | Bleaching | Injury |
| Days After First/Last Applic. | | 6 6 | 7 7 | 10 10 | 14 14 | 14 14 |
| Trt-Eval Interval | | 6 DA-A | 7 DA-A | 10 DA-A | 14 DA-A | 14 DA-A |

| Trt No. | Treatment Name | 44 | 45 | 46 | 47 | 48 |
|---|---|---|---|---|---|---|
| 1 | Untreated Check | 1.3 f | 1.0 c | 1.0 c | 1.3 d | 1.0 g |
| 2 | Amicarbazone | 1.5 f | 1.5 c | 1.0 c | 1.0 d | 1.3 g |
| 3 | Amicarbazone | 3.8 de | 3.5 b | 1.0 c | 1.0 d | 2.5 f |
| 4 | Tenacity | 3.3 e | 3.8 b | 5.0 a | 5.0 b | 4.3 e |
| 5 | Tenacity | 4.0 de | 4.5 b | 5.8 a | 6.0 a | 5.8 d |
| 6 | Tenacity Amicarbazone | 5.3 cd | 6.0 a | 2.8 b | 2.8 c | 6.5 cd |
| 7 | Tenacity Amicarbazone | 7.5 ab | 8.0 a | 1.0 c | 1.0 d | 7.8 ab |
| 8 | Tenacity Amicarbazone | 6.5 bc | 7.0 a | 2.8 b | 2.5 c | 7.0 bc |
| 9 | Tenacity Amicarbazone | 8.3 a | 8.0 a | 1.3 c | 1.5 d | 8.5 a |
| LSD (P = .10) | | 1.34 | 1.46 | 0.97 | 0.83 | 0.95 |
| Standard Deviation | | 1.11 | 1.20 | 0.80 | 0.69 | 0.78 |
| CV | | 24.21 | 25.05 | 33.46 | 28.04 | 15.87 |
| Bartlett's X2 | | 14.914 | 7.631 | 2.954 | 1.944 | 9.714 |
| P(Bartlett's X2) | | 0.061 | 0.266 | 0.566 | 0.857 | 0.205 |
| Replicate F | | 1.406 | 1.604 | 1.913 | 0.158 | 4.992 |
| Replicate Prob(F) | | 0.2653 | 0.2146 | 0.1544 | 0.9237 | 0.0079 |
| Treatment F | | 20.098 | 18.968 | 21.435 | 29.631 | 51.541 |
| Treatment Prob(F) | | 0.0001 | 0.0001 | 0.0001 | 0.0001 | 0.0001 |

Means followed by same letter do not significantly differ (P = .10, Student-Newman-Keuls)

Mean comparisons performed only when AOV Treatment P(F) is significant at mean comparison OSL.

TABLE 5-9

| | | Crabgrass | | | | | | | | |
|---|---|---|---|---|---|---|---|---|---|---|
| Crop Code | | | | | | | | | | |
| BBCH Scale | | | | | | | | | | |
| Crop Name | | Crabgrass | Crabgrass | Crabgrass | Crabgrass | Crabgrass | Crabgrass | Crabgrass | Crabgrass | Crabgrass |
| Crop Variety Description | | | | | | | | | | |
| Rating Data Type | | Bleaching | Injury | Bleaching | Injury | Bleaching | Bleaching | Injury | Bleaching | Injury |
| Days After First/ Last Applic. | | 6  6 | 6  6 | 7  7 | 7  7 | 10  10 | 14  14 | 14  14 | 16  16 | 16  16 |
| Trt-Eval Interval | | 6 DA-A | 6 DA-A | 7 DA-A | 7 DA-A | 10 DA-A | 14 DA-A | 14 DA-A | 16 DA-A | 16 DA-A |
| Trt No. | Treatment Name | 57 | 58 | 59 | 60 | 61 | 62 | 63 | 64 | 65 |
| 1 | Untreated Check | 1.0 f | 1.0 d | 1.0 c | 1.0 e | 1.0 c | 1.0 c | 1.0 d | 1.0 c | 1.0 d |
| 2 | Amicarbazone | 1.3 f | 1.5 d | 1.0 c | 1.0 e | 1.0 c | 1.0 c | 1.0 d | 1.3 c | 1.3 d |
| 3 | Amicarbazone | 1.0 f | 1.0 d | 1.0 c | 1.0 e | 1.0 c | 1.0 c | 1.0 d | 1.0 c | 1.5 d |
| 4 | Tenacity | 6.0 a | 5.3 c | 6.5 a | 5.3 d | 7.3 a | 7.0 a | 5.8 c | 7.3 a | 7.5 bc |
| 5 | Tenacity | 5.3 b | 5.8 c | 6.0 a | 6.0 cd | 6.8 a | 6.5 a | 6.3 c | 6.5 a | 7.5 bc |
| 6 | Tenacity Amicarbazone | 3.0 d | 5.0 c | 4.3 b | 6.8 bc | 5.0 b | 4.3 b | 7.0 b | 3.5 b | 7.3 c |
| 7 | Tenacity Amicarbazone | 2.3 e | 6.8 b | 2.5 c | 7.3 b | 1.8 c | 2.0 c | 8.5 a | 2.3 c | 8.5 a |
| 8 | Tenacity Amicarbazone | 3.8 c | 5.5 c | 4.5 b | 6.0 cd | 4.3 b | 3.5 b | 7.3 b | 3.8 b | 8.3 ab |
| 9 | Tenacity Amicarbazone | 1.5 f | 8.3 a | 1.3 c | 8.3 a | 1.0 c | 1.0 c | 9.0 a | 1.3 c | 9.0 a |
| LSD (P = .10) | | 0.69 | 0.87 | 1.04 | 0.78 | 1.11 | 1.09 | 0.55 | 1.09 | 0.70 |
| Standard Deviation | | 0.57 | 0.72 | 0.86 | 0.65 | 0.92 | 0.90 | 0.45 | 0.90 | 0.58 |
| CV | | 20.49 | 16.13 | 27.53 | 13.67 | 28.57 | 29.81 | 8.74 | 29.19 | 10.01 |
| Bartlett's X2 | | 2.475 | 4.552 | 7.441 | 3.943 | 6.356 | 1.5 | 1.172 | 8.404 | 2.53 |
| P(Bartlett's X2) | | 0.78 | 0.602 | 0.19 | 0.558 | 0.174 | 0.827 | 0.883 | 0.21 | 0.865 |
| Replicate F | | 0.229 | 0.432 | 1.312 | 0.800 | 1.049 | 2.125 | 0.494 | 1.771 | 0.308 |
| Replicate Prob(F) | | 0.8756 | 0.7317 | 0.2934 | 0.5061 | 0.3889 | 0.1235 | 0.6896 | 0.1795 | 0.8196 |
| Treatment F | | 43.286 | 54.459 | 27.435 | 81.667 | 32.344 | 28.875 | 211.382 | 28.234 | 141.420 |
| Treatment Prob(F) | | 0.0001 | 0.0001 | 0.0001 | 0.0001 | 0.0001 | 0.0001 | 0.0001 | 0.0001 | 0.0001 |
| Crop Code | | | | | | | | | | |
| BBCH Scale | | | | | | | | | | |
| Crop Name | | Crabgrass | Crabgrass | Crabgrass | Crabgrass | Crabgrass | Crabgrass | Crabgrass | Crabgrass | |
| Crop Variety Description | | | | | | | | | | |
| Rating Data Type | | Bleaching | Injury | Injury | % Crab Cvr | % Crab Cvr | Bleaching | % Crab Cvr | Bleaching | |
| Days After First/ Last Applic. | | 20  20 | 20  20 | 24  24 | 24  24 | 31  31 | 31  31 | 41  41 | 41  41 | |
| Trt-Eval Interval | | 20 DA-A | 20 DA-A | 24 DA-A | 24 DA-A | 31 DA-A | 31 DA-A | 41 DA-A | 41 DA-A | |
| Trt No. | Treatment Name | 66 | 67 | 68 | 69 | 70 | 71 | 72 | 73 | |
| 1 | Untreated Check | 1.0 d | 1.0 c | 1.0 c | 8.8 a | 8.8 a | 1.0 b | 9.0 a | 1.0 a | |
| 2 | Amicarbazone | 1.3 d | 1.3 c | 1.5 c | 7.8 a | 8.3 a | 1.0 b | 9.0 a | 1.0 a | |
| 3 | Amicarbazone | 1.0 d | 1.5 c | 1.5 c | 6.3 b | 6.3 b | 1.0 b | 6.8 b | 1.0 a | |
| 4 | Tenacity | 7.3 a | 7.8 b | 7.0 b | 2.8 c | 3.3 c | 2.3 a | 2.0 c | 1.0 a | |
| 5 | Tenacity | 5.5 b | 7.5 b | 7.0 b | 1.8 cd | 2.0 d | 2.5 a | 1.5 c | 1.0 a | |
| 6 | Tenacity Amicarbazone | 3.8 bc | 8.0 ab | 7.8 ab | 1.3 d | 1.0 d | 1.3 b | 1.3 c | 1.0 a | |
| 7 | Tenacity Amicarbazone | 2.8 cd | 8.5 ab | 8.3 ab | 1.0 d | 1.0 d | 1.3 b | 1.3 c | 1.0 a | |
| 8 | Tenacity Amicarbazone | 4.3 bc | 8.5 ab | 8.0 ab | 1.5 cd | 1.0 d | 1.3 b | 1.3 c | 1.0 a | |
| 9 | Tenacity Amicarbazone | 1.5 d | 9.0 a | 9.0 a | 1.0 d | 1.0 d | 1.0 b | 1.8 c | 1.0 a | |
| LSD (P = .10) | | 1.62 | 0.72 | 0.95 | 1.04 | 1.13 | 0.61 | 0.92 | 0.00 | |
| Standard Deviation | | 1.34 | 0.59 | 0.79 | 0.86 | 0.94 | 0.50 | 0.76 | 0.00 | |
| CV | | 42.53 | 10.04 | 13.87 | 24.17 | 25.97 | 36.33 | 20.37 | 0.0 | |
| Bartlett's X2 | | 14.194 | 2.548 | 0.246 | 10.589 | 10.672 | 3.123 | 13.048 | 0.0 | |
| P(Bartlett's X2) | | 0.028* | 0.863 | 0.999 | 0.102 | 0.031* | 0.537 | 0.042* | — | |
| Replicate F | | 3.922 | 1.060 | 0.360 | 1.705 | 3.747 | 2.473 | 5.000 | 0.000 | |

TABLE 5-9-continued

| | Crabgrass | | | | | | | |
|---|---|---|---|---|---|---|---|---|
| Replicate Prob(F) | 0.0207 | 0.3846 | 0.7827 | 0.1926 | 0.0244 | 0.0861 | 0.0078 | 1.0000 |
| Treatment F | 11.119 | 140.921 | 70.888 | 53.050 | 48.253 | 5.182 | 81.429 | 0.000 |
| Treatment Prob(F) | 0.0001 | 0.0001 | 0.0001 | 0.0001 | 0.0001 | 0.0008 | 0.0001 | 1.0000 |

Means followed by same letter do not significantly differ (P = .10, Student-Newman-Keuls)
Mean comparisons performed only when AOV Treatment P(F) is significant at mean comparison OSL.

TABLE 5-10

| | St. Augustine-Sapphire | | | | | | | | |
|---|---|---|---|---|---|---|---|---|---|
| Crop Code BBCH Scale | | | | | | | | | |
| Crop Name Crop Variety | St. Augusti> Sapphire | St. Augusti> Sapphire | St. Augusti> Sapphire | St. Augusti> Sapphire | St. Augusti> Sapphire | St. Augusti> Sapphire | St. Augusti> Sapphire | St. Augusti> Sapphire | St. Augusti> Sapphire |
| Description Rating Data Type | Bleaching | Bleaching | Bleaching | Bleaching | Bleaching | Bleaching | Bleaching | Bleaching | TurfQuality |
| Days After First/Last Applic. | 6  6 | 7  7 | 10  10 | 14  14 | 16  16 | 20  20 | 31  31 | 41  41 | 41  41 |
| Trt-Eval Interval | 6 DA-A | 7 DA-A | 10 DA-A | 14 DA-A | 16 DA-A | 20 DA-A | 31 DA-A | 31 DA-A | 31 DA-A |
| Trt No. | Treatment Name | 75 | 76 | 77 | 78 | 79 | 80 | 81 | 82 | 83 |

| Trt No. | Treatment Name | 75 | 76 | 77 | 78 | 79 | 80 | 81 | 82 | 83 |
|---|---|---|---|---|---|---|---|---|---|---|
| 1 | Untreated Check | 1.0 a | 1.0 b | 1.0 d | 1.0 c | 1.0 d | 1.0 c | 1.0 a | 1.0 a | 7.0 a |
| 2 | Amicarbazone | 1.0 a | 1.0 b | 1.0 d | 1.0 c | 1.0 d | 1.5 c | 1.0 a | 1.0 a | 7.0 a |
| 3 | Amicarbazone | 1.5 a | 1.0 b | 1.0 d | 1.0 c | 1.0 d | 1.0 c | 1.0 a | 1.0 a | 7.5 a |
| 4 | Tenacity | 2.0 a | 2.0 a | 1.5 cd | 1.0 c | 1.0 d | 1.0 c | 1.5 a | 1.0 a | 7.0 a |
| 5 | Tenacity | 2.0 a | 2.0 a | 3.5 a | 2.5 ab | 3.0 b | 3.0 ab | 2.5 a | 1.0 a | 7.0 a |
| 6 | Tenacity Amicarbazone | 2.0 a | 2.0 a | 2.5 abc | 2.0 abc | 2.0 c | 2.5 abc | 2.5 a | 1.0 a | 7.0 a |
| 7 | Tenacity Amicarbazone | 1.5 a | 1.5 ab | 2.0 bcd | 1.5 bc | 2.0 c | 2.0 bc | 1.0 a | 1.0 a | 7.5 a |
| 8 | Tenacity Amicarbazone | 1.5 a | 2.0 a | 2.0 bcd | 1.5 bc | 1.5 cd | 2.5 abc | 2.0 a | 1.0 a | 7.0 a |
| 9 | Tenacity Amicarbazone | 1.0 a | 2.0 a | 3.0 ab | 3.0 a | 4.0 a | 3.5 a | 3.0 a | 1.0 a | 7.5 a |
| LSD (P = .10) | | 0.79 | 0.44 | 0.79 | 0.79 | 0.44 | 0.88 | 1.14 | 0.00 | 0.79 |
| Standard Deviation | | 0.42 | 0.24 | 0.42 | 0.42 | 0.24 | 0.47 | 0.61 | 0.00 | 0.42 |
| CV | | 28.33 | 14.63 | 21.85 | 26.37 | 12.86 | 23.57 | 35.56 | 0.0 | 5.93 |
| Bartlett's X2 | | 0.0 | 0.0 | 0.0 | 0.0 | 0.0 | 0.0 | 0.748 | 0.0 | 0.0 |
| P(Bartlett's X2) | | — | — | — | — | — | — | 0.862 | — | — |
| Replicate F | | 0.308 | 1.000 | 0.308 | 0.308 | 1.000 | 1.000 | 1.333 | 0.000 | 0.308 |
| Replicate Prob(F) | | 0.5943 | 0.3466 | 0.5943 | 0.5943 | 0.3466 | 0.3466 | 0.2815 | 1.0000 | 0.5943 |
| Treatment F | | 2.077 | 8.500 | 9.308 | 6.077 | 40.500 | 7.875 | 3.370 | 0.000 | 0.692 |
| Treatment Prob(F) | | 0.1607 | 0.0033 | 0.0024 | 0.0098 | 0.0001 | 0.0043 | 0.0526 | 1.0000 | 0.6924 |

Means followed by same letter do not significantly differ (P = .10, Student-Newman-Keuls)
Mean comparisons performed only when AOV Treatment P(F) is significant at mean comparison OSL.

TABLE 5-11

| | St. Augustine-Floratum | | | | | | | | |
|---|---|---|---|---|---|---|---|---|---|
| Crop Code BBCH Scale | | | | | | | | | |
| Crop Name Crop Variety | St. Augusti> Floratam | St. Augusti> Floratam | St. Augusti> Floratam | St. Augusti> Floratam | St. Augusti> Floratam | St. Augusti> Floratam | St. Augusti> Floratam | St. Augusti> Floratam | St. Augusti> Floratam |
| Description Rating Data Type | Bleaching | Bleaching | Bleaching | Bleaching | Bleaching | Bleaching | Bleaching | Bleaching | TurfQuality |
| Days After First/Last Applic. | 6  6 | 7  7 | 10  10 | 14  14 | 16  16 | 20  20 | 31  31 | 41  41 | 41  41 |
| Trt-Eval Interval | 6 DA-A | 7 DA-A | 10 DA-A | 14 DA-A | 16 DA-A | 20 DA-A | 31 DA-A | 31 DA-A | 31 DA-A |

TABLE 5-11-continued

St. Augustine-Floratum

| Trt No. | Treatment Name | 85 | 86 | 87 | 88 | 89 | 90 | 91 | 92 | 93 |
|---|---|---|---|---|---|---|---|---|---|---|
| 1 | Untreated Check | 1.0 a | 1.0 c | 1.0 c | 1.0 c | 1.0 e | 1.0 b | 1.0 c | 1.0 a | 6.0 c |
| 2 | Amicarbazone | 1.0 a | 1.0 c | 1.0 c | 1.0 c | 1.0 e | 1.0 b | 1.0 c | 1.0 a | 6.8 bc |
| 3 | Amicarbazone | 1.0 a | 1.0 c | 1.0 c | 1.0 c | 1.3 e | 1.3 b | 1.0 c | 1.0 a | 7.3 ab |
| 4 | Tenacity | 1.3 a | 2.0 bc | 3.0 ab | 2.8 ab | 2.8 cd | 3.3 a | 2.5 abc | 1.0 a | 6.5 bc |
| 5 | Tenacity | 2.0 a | 2.8 ab | 4.0 ab | 3.8 a | 4.8 a | 4.5 a | 4.0 a | 1.0 a | 6.5 bc |
| 6 | Tenacity Amicarbazone | 2.0 a | 2.3 ab | 3.5 ab | 2.8 ab | 4.0 ab | 4.3 a | 3.8 a | 1.0 a | 7.0 ab |
| 7 | Tenacity Amicarbazone | 1.3 a | 1.8 bc | 2.5 b | 2.0 bc | 2.3 d | 2.8 a | 1.8 bc | 1.0 a | 7.8 a |
| 8 | Tenacity Amicarbazone | 2.0 a | 3.3 a | 4.5 a | 3.5 a | 3.5 bc | 3.3 a | 2.8 ab | 1.0 a | 6.5 bc |
| 9 | Tenacity Amicarbazone | 2.0 a | 2.5 ab | 3.8 ab | 3.3 a | 4.5 ab | 4.5 a | 4.0 a | 1.0 a | 7.0 ab |
| LSD (P = .10) | | 0.65 | 0.77 | 1.00 | 0.73 | 0.85 | 1.13 | 1.05 | 0.00 | 0.55 |
| Standard Deviation | | 0.54 | 0.63 | 0.82 | 0.60 | 0.70 | 0.93 | 0.87 | 0.00 | 0.45 |
| CV | | 35.86 | 32.64 | 30.62 | 25.75 | 25.34 | 32.52 | 35.89 | 0.0 | 6.67 |
| Bartlett's X2 | | 1.482 | 4.118 | 1.836 | 0.131 | 4.28 | 6.623 | 4.477 | 0.0 | 0.173 |
| P(Bartlett's X2) | | 0.83 | 0.533 | 0.871 | 1.00 | 0.639 | 0.357 | 0.483 | — | 0.999 |
| Replicate F | | 0.640 | 1.931 | 1.673 | 6.769 | 6.131 | 3.455 | 4.074 | 0.000 | 0.494 |
| Replicate Prob(F) | | 0.5967 | 0.1515 | 0.1992 | 0.0018 | 0.0030 | 0.0323 | 0.0180 | 1.0000 | 0.6896 |
| Treatment F | | 3.240 | 6.793 | 11.367 | 13.846 | 17.972 | 9.898 | 8.889 | 0.000 | 5.090 |
| Treatment Prob(F) | | 0.0121 | 0.0001 | 0.0001 | 0.0001 | 0.0001 | 0.0001 | 0.0001 | 1.0000 | 0.0009 |

Means followed by same letter do not significantly differ (P = .10, Student-Newman-Keuls)
Mean comparisons performed only when AOV Treatment P(F) is significant at mean comparison OSL.

Example 6

A. Pre Emergence Application Against Weed in Maize

In this part of the Example the efficacy of DINAMIC® (amicarbazone 700WDG, 700 grams active/kg, available from Arysta LifeScience North America, Cary, N.C.) mixtures with Galago (mesotrione 480SC, 480 grams active/L, available from Arysta LifeScience North America, Cary, N.C.) as a pre emergence application against weeds in maize (variety PHI 2369W) was determined.

Three trials were conducted at a site with a history of weeds. The trials were executed under moderate weather conditions. Efficacy and visual phytotoxicity assessments were performed in triplicate. Normal practices were carried out to control insects and fungi. Crops were provided in 55 cm row width, at a sowing rate of 65,000 plants/ha, and at a sowing depth of five to eight cm. Soil class was clay with a clay content of about 40%. The site in this Example had been previously used for maize. Trial design was randomized blocks with a plot size of 20 m² replicated four times. Municipal water was used for all applications (pH=7.2).

Application of the treatments shown in Table 6-1 was conducted at pre emergence stage 1 day after planting seed. Application of the treatments was conducted over a 24 hour period. Over this time period, dry bulb temperature was about 30° C., wet bulb temperature was about 26° C., relative humidity was about 70%, cloud cover was about 100%, wind speed was about 1 m/s, and the wind was out of the east. Treatments were administered with a multi-spray gas sprayer with a 4× flat fan 03F80 nozzle. Spacing was 50 cm, with a height of 50 cm, pressure 2.8 Bar, at a ground speed of 1 m/s, and a calibration mean output of 330 L/ha. The soil temperature over the application period averaged to about 28° C. and the soil remained moist and fine.

TABLE 6-1

| | Treatments | | |
|---|---|---|---|
| No | Treatments | Dosage rate (gai/ha) | Dosage rate (g/ha or mL/ha) |
| | Untreated control | — | — |
| 1 | DINAMIC ® 700WDG | 52.5 | 75 |
| 2 | DINAMIC ® 700WDG | 70 | 100 |
| 3 | DINAMIC ® 700WDG | 87.5 | 125 |
| 4 | DINAMIC ® 700WDG | 105 | 150 |
| 5 | DINAMIC ® 700WDG | 210 | 300 |
| 6 | Galago 480SC | 48 | 100 |
| 7 | Galago 480SC | 96 | 200 |
| 8 | DINAMIC ® 700WDG + Galago 480SC | 52.5 48 | 75 100 |
| 9 | DINAMIC ® 700WDG + Galago 480SC | 52.5 72 | 75 150 |
| 10 | DINAMIC ® 700WDG + Galago 480SC | 70 48 | 100 100 |
| 11 | DINAMIC ® 700WDG + Galago 480SC | 70 72 | 100 150 |
| 12 | DINAMIC ® 700WDG + Galago 480SC | 87.5 48 | 125 100 |
| 13 | DINAMIC ® 700WDG + Galago 480SC | 87.5 72 | 125 150 |
| 14 | DINAMIC ® 700WDG + Galago 480SC | 175 144 | 250 300 |

Assessments of the treated crops at 2, 4, and 6 weeks are summarized in Tables 6-2 to 6-4 below. No visual signs of phytotoxicity were noticed over the 6 weeks.

TABLE 6-2

| 2 Week Assessment | |
|---|---|
| Crop condition | Actively growing |
| Crop stage | 4 Leaves |
| BBCH scale | 14 |
| Soil moisture | Moist |
| Rain since last visit | 28 mm |

TABLE 6-3

| 4 Week Assessment | |
|---|---|
| Crop condition | Actively growing |
| Crop stage | 6 Leaves |
| BBCH scale | 16 |
| Soil moisture | Wet |
| Rain since last visit | 6 mm |

TABLE 6-4

| 6 Week Assessment | |
|---|---|
| Crop condition | Actively growing |
| Crop stage | 8 leaves |
| BBCH scale: | 18 |
| Soil moisture | Moist |
| Rain since last visit | 23 mm |

Control and weed cover at 2, 4, and 6 weeks for the indicated species are summarized below in Tables 6-5 through 6-7. 80% is considered acceptable control.

TABLE 6-5

% Control and weed cover (2 weeks after application)

| | Treatments (product/ha) | Rep | ROTTE | IPOPU | AMAHY |
|---|---|---|---|---|---|
| | Untreated control | I | 30 | 40 | 30 |
| | % soil cover | ii | 40 | 30 | 30 |
| | | iii | 40 | 40 | 20 |
| | | iv | 30 | 40 | 30 |
| | Mean | | 35 | 38 | 28 |
| 1 | DINAMIC ® at 75 g | I | 20 | 80 | 90 |
| | | ii | 30 | 80 | 80 |
| | | iii | 20 | 70 | 80 |
| | | iv | 20 | 80 | 80 |
| | Mean | | 23 | 78 | 83 |
| 2 | DINAMIC ® at 100 g | I | 20 | 80 | 90 |
| | | ii | 30 | 70 | 80 |
| | | iii | 30 | 80 | 80 |
| | | iv | 30 | 70 | 80 |
| | Mean | | 28 | 75 | 83 |
| 3 | DINAMIC ® at 125 g | I | 30 | 90 | 95 |
| | | ii | 30 | 70 | 90 |
| | | iii | 30 | 80 | 90 |
| | | iv | 30 | 80 | 90 |
| | Mean | | 30 | 80 | 91 |
| 4 | DINAMIC ® at 150 g | I | 50 | 90 | 80 |
| | | ii | 30 | 80 | 90 |
| | | iii | 40 | 80 | 90 |
| | | iv | 30 | 80 | 90 |
| | Mean | | 38 | 83 | 88 |
| 5 | DINAMIC ® at 300 g | I | 50 | 90 | 100 |
| | | ii | 50 | 95 | 100 |
| | | iii | 60 | 100 | 90 |
| | | iv | 50 | 90 | 95 |
| | Mean | | 53 | 94 | 96 |
| 6 | Galago at 100 ml | I | 60 | 90 | 80 |
| | | ii | 60 | 90 | 90 |
| | | iii | 70 | 90 | 80 |
| | | iv | 60 | 90 | 90 |
| | Mean | | 63 | 90 | 85 |
| 7 | Galago at 200 ml | I | 80 | 90 | 90 |
| | | ii | 70 | 95 | 90 |
| | | iii | 70 | 100 | 95 |
| | | iv | 80 | 95 | 95 |
| | Mean | | 75 | 95 | 93 |
| 8 | DINAMIC ® at 75 g Galago at 100 ml | I | 60 | 90 | 90 |
| | | ii | 60 | 80 | 90 |
| | | iii | 60 | 90 | 80 |
| | | iv | 60 | 90 | 80 |
| | Mean | | 60 | 88 | 85 |

TABLE 6-5-continued

% Control and weed cover (2 weeks after application)

| | Treatments (product/ha) | Rep | ROTTE | IPOPU | AMAHY |
|---|---|---|---|---|---|
| 9 | DINAMIC ® at 75 g Galago at 150 ml | I | 70 | 90 | 100 |
| | | ii | 80 | 90 | 95 |
| | | iii | 80 | 95 | 90 |
| | | iv | 80 | 95 | 95 |
| | Mean | | 78 | 93 | 95 |
| 10 | DINAMIC ® at 100 g Galago at 100 ml | I | 50 | 90 | 90 |
| | | ii | 60 | 90 | 90 |
| | | iii | 70 | 90 | 90 |
| | | iv | 70 | 95 | 90 |
| | Mean | | 63 | 91 | 90 |
| 11 | DINAMIC ® at 100 g Galago at 150 ml | I | 70 | 90 | 100 |
| | | ii | 70 | 90 | 95 |
| | | iii | 80 | 90 | 100 |
| | | iv | 70 | 90 | 95 |
| | Mean | | 73 | 90 | 98 |
| 12 | DINAMIC ® at 125 g Galago at 100 ml | I | 70 | 90 | 95 |
| | | ii | 70 | 80 | 95 |
| | | iii | 60 | 90 | 100 |
| | | iv | 70 | 90 | 90 |
| | Mean | | 68 | 88 | 95 |
| 13 | DINAMIC ® at 125 g Galago at 150 ml | I | 90 | 100 | 100 |
| | | ii | 80 | 100 | 100 |
| | | iii | 80 | 90 | 100 |
| | | iv | 80 | 95 | 100 |
| | Mean | | 83 | 96 | 100 |
| 14 | DINAMIC ® at 250 g Galago at 300 ml | I | 90 | 100 | 100 |
| | | ii | 90 | 100 | 100 |
| | | iii | 95 | 95 | 100 |
| | | iv | 95 | 95 | 100 |
| | Mean | | 93 | 98 | 100 |

ROTTE = *Rottboelia exaltata*; IPOPU = *Ipomoea purpurea*; AMAHY = *Amaranthus hybridus*

TABLE 6-6

% Control and weed cover (4 weeks after application)

| | Treatments (product/ha) | Rep | ROTTE | IPOPU | AMAHY |
|---|---|---|---|---|---|
| | Untreated control | I | 30 | 40 | 30 |
| | % soil cover | ii | 30 | 30 | 40 |
| | | iii | 30 | 40 | 30 |
| | | iv | 20 | 40 | 40 |
| | Mean | | 28 | 38 | 35 |
| 1 | DINAMIC ® at 75 g | I | 20 | 70 | 80 |
| | | ii | 20 | 70 | 80 |
| | | iii | 20 | 70 | 70 |
| | | iv | 20 | 70 | 80 |
| | Mean | | 20 | 70 | 78 |
| 2 | DINAMIC ® at 100 g | I | 20 | 80 | 80 |
| | | ii | 30 | 70 | 80 |
| | | iii | 20 | 70 | 80 |
| | | iv | 20 | 70 | 80 |
| | Mean | | 23 | 73 | 80 |
| 3 | DINAMIC ® at 125 g | I | 30 | 80 | 90 |
| | | ii | 30 | 70 | 90 |
| | | iii | 20 | 70 | 90 |
| | | iv | 30 | 80 | 90 |
| | Mean | | 28 | 75 | 90 |
| 4 | DINAMIC ® at 150 g | I | 40 | 80 | 80 |
| | | ii | 30 | 80 | 90 |
| | | iii | 40 | 80 | 80 |
| | | iv | 20 | 80 | 90 |
| | Mean | | 33 | 80 | 85 |
| 5 | DINAMIC ® at 300 g | I | 40 | 90 | 100 |
| | | ii | 50 | 90 | 100 |
| | | iii | 50 | 100 | 90 |
| | | iv | 50 | 90 | 90 |
| | Mean | | 48 | 93 | 95 |

TABLE 6-6-continued

% Control and weed cover (4 weeks after application)

| | Treatments (product/ha) | Rep | ROTTE | IPOPU | AMAHY |
|---|---|---|---|---|---|
| 6 | Galago at 100 ml | I | 50 | 90 | 80 |
| | | ii | 60 | 80 | 80 |
| | | iii | 60 | 80 | 80 |
| | | iv | 60 | 90 | 80 |
| | Mean | | 58 | 85 | 80 |
| 7 | Galago at 200 ml | I | 80 | 90 | 90 |
| | | ii | 60 | 90 | 90 |
| | | iii | 70 | 100 | 90 |
| | | iv | 70 | 95 | 90 |
| | Mean | | 70 | 94 | 90 |
| 8 | DINAMIC® at 75 g Galago at 100 ml | I | 60 | 90 | 90 |
| | | ii | 60 | 80 | 90 |
| | | iii | 50 | 80 | 80 |
| | | iv | 60 | 80 | 80 |
| | Mean | | 58 | 83 | 85 |
| 9 | DINAMIC® at 75 g Galago at 150 ml | I | 70 | 90 | 100 |
| | | ii | 70 | 90 | 90 |
| | | iii | 70 | 90 | 90 |
| | | iv | 80 | 95 | 95 |
| | Mean | | 73 | 91 | 94 |
| 10 | DINAMIC® at 100 g Galago at 100 ml | I | 50 | 90 | 90 |
| | | ii | 50 | 80 | 80 |
| | | iii | 70 | 80 | 90 |
| | | iv | 60 | 90 | 90 |
| | Mean | | 58 | 85 | 88 |
| 11 | DINAMIC® at 100 g Galago at 150 ml | I | 70 | 90 | 100 |
| | | ii | 70 | 80 | 95 |
| | | iii | 70 | 90 | 98 |
| | | iv | 70 | 90 | 95 |
| | Mean | | 70 | 88 | 97 |
| 12 | DINAMIC® at 125 g Galago at 100 ml | I | 70 | 90 | 95 |
| | | ii | 70 | 80 | 90 |
| | | iii | 60 | 90 | 100 |
| | | iv | 60 | 90 | 90 |
| | Mean | | 65 | 88 | 94 |
| 13 | DINAMIC® at 125 g Galago at 150 ml | I | 90 | 100 | 100 |
| | | ii | 80 | 100 | 100 |
| | | iii | 70 | 90 | 100 |
| | | iv | 80 | 98 | 100 |
| | Mean | | 80 | 97 | 100 |
| 14 | DINAMIC® at 250 g Galago at 300 ml | I | 90 | 100 | 100 |
| | | ii | 90 | 100 | 100 |
| | | iii | 90 | 95 | 100 |
| | | iv | 90 | 95 | 100 |
| | Mean | | 90 | 98 | 100 |

ROTTE = *Rottboelia exaltata*; IPOPU = *Ipomoea purpurea*; AMAHY = *Amaranthus hybridus*

TABLE 6-7

% Control and weed cover (6 weeks after application)

| | Treatments (product/ha) | Rep | ROTTE | IPOPU | AMAHY |
|---|---|---|---|---|---|
| | Untreated control % soil cover | I | 20 | 40 | 40 |
| | | ii | 30 | 30 | 40 |
| | | iii | 20 | 50 | 30 |
| | | iv | 20 | 40 | 40 |
| | Mean | | 23 | 40 | 38 |
| 1 | DINAMIC® at 75 g | I | 20 | 70 | 80 |
| | | ii | 20 | 70 | 80 |
| | | iii | 10 | 70 | 80 |
| | | iv | 20 | 70 | 80 |
| | Mean | | 18 | 70 | 80 |
| 2 | DINAMIC® at 100 g | I | 20 | 70 | 80 |
| | | ii | 20 | 70 | 80 |
| | | iii | 20 | 70 | 80 |
| | | iv | 10 | 70 | 80 |
| | Mean | | 18 | 70 | 80 |
| 3 | DINAMIC® at 125 g | I | 20 | 80 | 90 |
| | | ii | 30 | 70 | 90 |
| | | iii | 20 | 70 | 90 |
| | | iv | 30 | 70 | 90 |
| | Mean | | 25 | 73 | 90 |
| 4 | DINAMIC® at 150 g | I | 30 | 70 | 90 |
| | | ii | 30 | 80 | 90 |
| | | iii | 30 | 80 | 90 |
| | | iv | 20 | 70 | 90 |
| | Mean | | 28 | 75 | 90 |
| 5 | DINAMIC® at 300 g | I | 30 | 80 | 100 |
| | | ii | 40 | 90 | 100 |
| | | iii | 50 | 98 | 90 |
| | | iv | 40 | 90 | 90 |
| | Mean | | 40 | 90 | 95 |
| 6 | Galago at 100 ml | I | 50 | 80 | 90 |
| | | ii | 50 | 80 | 80 |
| | | iii | 50 | 80 | 70 |
| | | iv | 50 | 80 | 80 |
| | Mean | | 50 | 80 | 80 |
| 7 | Galago at 200 ml | I | 70 | 90 | 90 |
| | | ii | 60 | 90 | 90 |
| | | iii | 60 | 98 | 90 |
| | | iv | 60 | 90 | 90 |
| | Mean | | 63 | 92 | 90 |
| 8 | DINAMIC® at 75 g Galago at 100 ml | I | 50 | 80 | 80 |
| | | ii | 60 | 80 | 80 |
| | | iii | 50 | 80 | 80 |
| | | iv | 60 | 80 | 80 |
| | Mean | | 55 | 80 | 80 |
| 9 | DINAMIC® at 75 g Galago at 150 ml | I | 70 | 90 | 100 |
| | | ii | 70 | 90 | 90 |
| | | iii | 70 | 90 | 90 |
| | | iv | 70 | 90 | 90 |
| | Mean | | 70 | 90 | 93 |
| 10 | DINAMIC® at 100 g Galago at 100 ml | I | 60 | 80 | 80 |
| | | ii | 50 | 80 | 80 |
| | | iii | 70 | 80 | 90 |
| | | iv | 70 | 90 | 90 |
| | Mean | | 63 | 83 | 85 |
| 11 | DINAMIC® at 100 g Galago at 150 ml | I | 70 | 90 | 100 |
| | | ii | 70 | 80 | 95 |
| | | iii | 60 | 80 | 95 |
| | | iv | 70 | 90 | 95 |
| | Mean | | 68 | 85 | 96 |
| 12 | DINAMIC® at 125 g Galago at 100 ml | I | 60 | 80 | 90 |
| | | ii | 70 | 80 | 90 |
| | | iii | 60 | 80 | 100 |
| | | iv | 60 | 90 | 90 |
| | Mean | | 63 | 83 | 93 |
| 13 | DINAMIC® at 125 g Galago at 150 ml | I | 80 | 100 | 100 |
| | | ii | 80 | 100 | 100 |
| | | iii | 70 | 90 | 100 |
| | | iv | 80 | 95 | 100 |
| | Mean | | 78 | 96 | 100 |
| 14 | DINAMIC® at 250 g Galago at 300 ml | I | 80 | 100 | 100 |
| | | ii | 90 | 100 | 100 |
| | | iii | 90 | 90 | 100 |
| | | iv | 90 | 95 | 100 |
| | Mean | | 88 | 96 | 100 |

ROTTE = *Rottboelia exaltata*; IPOPU = *Ipomoea purpurea*; AMAHY = *Amaranthus hybridus*

DINAMIC® 700WDG at 100 g/ha alone showed marginal control of *Amaranthus hybridus*, but the rest of the spectrum was insufficiently controlled by rates up to 300 g/ha. DINAMIC® 700WDG at 300 mL/ha controlled *Ipomoea purpurea*, but *Rottboellia exaltata* was still too tough to be controlled. Galago 480SC at 100 mL/ha showed marginal control of *Ipomoea purpurea* and *Amaranthus hybridus*, but could also not control *Rottboellia exaltata*. The combination (DINAMIC® at 75 g/ha+Galago at 100 mL/ha) resulted in marginal control of *Amaranthus hybridus* and *Ipomoea purpurea*. DINAMIC® at 250 g/ha+Galago at 300 mL/ha was the only treatment which could control *Rottboellia exaltata* with satisfactory results. There were no visual signs of phytotoxicity were noticed throughout the growing season. DINAMIC® at 300 g/ha can be used to control *Amaranthus hybridus* and *Ipomoea purpurea*. Galago at 200 mL/ha can be used to control *Amaranthus hybridus* and *Ipomoea purpurea*. DINAMIC® at 75 g/ha+ Galago at 100 mL/ha can be used to control *Amaranthus hybridus* and *Ipomoea purpurea*. DINAMIC® at 250 g/ha+ Galago at 300 mL/ha can be used to control *Amaranthus hybridus*, *Ipomoea purpurea* and *Rottboellia exaltata*.

B. Pre Emergence Application Against Weed in Maize

In this part of the Example the efficacy of DINAMIC® (amicarbazone 700WDG, 700 grams active/kg, available from Arysta LifeScience North America, Cary, N.C.) mixtures with Galago (mesotrione 480SC, 480 grams active/L, available from Arysta LifeScience North America, Cary, N.C.) as a pre emergence application against weeds in maize (variety PHI 32Y85) was determined.

Trials were conducted at a site with a history of weeds. The trials were executed under moderate weather conditions. Efficacy and visual phytotoxicity assessments were performed in triplicate. Normal practices were carried out to control insects and fungi. Crops were provided in 76 cm row width, at a sowing rate of 65,000 plants/ha, and at a sowing depth of five to eight cm. Soil class was clay with a clay content of about 35%. The site in this Example had been previously used for soya beans. Trial design was randomized blocks with a plot size of 20 m$^2$ replicated four times. Municipal water was used for all applications (pH=7.2).

Application of the treatments shown in Table 6-8 was conducted at pre emergence stage 1 day after planting seed. Application of the treatments was conducted over a 24 hour period. Over this time period, dry bulb temperature was about 26° C., wet bulb temperature was about 23° C., relative humidity was about 70%, cloud cover was about 50%, wind speed was about 0 m/s. Treatments were administered with a multi-spray gas sprayer with a 4× flat fan 03F80 nozzle. Spacing was 50 cm, with a height of 50 cm, pressure 2.8 Bar, at a ground speed of 1 m/s, and a calibration mean output of 330 L/ha. The soil temperature over the application period averaged to about 24° C. and the soil remained moist and fine.

TABLE 6-8

Treatments

| No | Treatments | Dosage rate (gai/ha) | Dosage rate (g/ha or mL/ha) |
|---|---|---|---|
|  | Untreated control | — | — |
| 1 | DINAMIC ® 700WDG | 52.5 | 75 |
| 2 | DINAMIC ® 700WDG | 70 | 100 |
| 3 | DINAMIC ® 700WDG | 87.5 | 125 |
| 4 | DINAMIC ® 700WDG | 105 | 150 |
| 5 | DINAMIC ® 700WDG | 210 | 300 |
| 6 | Galago 480SC | 48 | 100 |
| 7 | Galago 480SC | 96 | 200 |
| 8 | DINAMIC ® 700WDG + | 52.5 | 75 |
|  | Galago 480SC | 48 | 100 |
| 9 | DINAMIC ® 700WDG + | 52.5 | 75 |
|  | Galago 480SC | 72 | 150 |
| 10 | DINAMIC ® 700WDG + | 70 | 100 |
|  | Galago 480SC | 48 | 100 |
| 11 | DINAMIC ® 700WDG + | 70 | 100 |
|  | Galago 480SC | 72 | 150 |
| 12 | DINAMIC ® 700WDG + | 87.5 | 125 |
|  | Galago 480SC | 48 | 100 |
| 13 | DINAMIC ® 700WDG + | 87.5 | 125 |
|  | Galago 480SC | 72 | 150 |
| 14 | DINAMIC ® 700WDG + | 175 | 250 |
|  | Galago 480SC | 144 | 300 |

Assessments of the treated crops at 2, 4, and 6 weeks are summarized in Tables 6-9 to 6-11 below. No visual signs of phytotoxicity were noticed over the 6 weeks.

TABLE 6-9

2 Week Assessment

| | |
|---|---|
| Crop condition | Actively growing |
| Crop stage | 3-4 Leaves |
| BBCH scale | 13 |
| Soil moisture | Moist |
| Rain since last visit | 0 mm |

TABLE 6-10

4 Week Assessment

| | |
|---|---|
| Crop condition | Actively growing |
| Crop stage | 6 Leaves |
| BBCH scale | 16 |
| Soil moisture | Wet |
| Rain since last visit | 18 mm |

TABLE 6-11

6 Week Assessment

| | |
|---|---|
| Crop condition | Actively growing |
| Crop stage | 8 leaves |
| BBCH scale: | 18 |
| Soil moisture | Moist |
| Rain since last visit | 12 mm |

Control and weed cover at 2, 4, and 6 weeks for the indicated species are summarized below in Tables 6-12 through 6-14. 80% is considered acceptable control.

TABLE 6-12

% Control and weed cover (2 weeks after application)

| Treatments (product/ha) | | Rep | DIGSA | POROL | AMAHY | COMBE |
|---|---|---|---|---|---|---|
| Untreated control | | i | 30 | 20 | 30 | 20 |
| % soil cover | | ii | 40 | 10 | 20 | 30 |
| | | iii | 40 | 20 | 30 | 10 |
| | | iv | 30 | 20 | 30 | 20 |
| Mean | | | 35 | 18 | 28 | 20 |
| 1 | DINAMIC ® at 75 g | i | 60 | 50 | 70 | 50 |
| | | ii | 70 | 40 | 90 | 60 |
| | | iii | 60 | 40 | 80 | 60 |
| | | iv | 70 | 50 | 70 | 60 |
| Mean | | | 65 | 45 | 78 | 58 |
| 2 | DINAMIC ® at 100 g | i | 70 | 50 | 70 | 50 |
| | | ii | 70 | 40 | 70 | 50 |
| | | iii | 70 | 50 | 80 | 60 |
| | | iv | 70 | 50 | 80 | 60 |
| Mean | | | 70 | 48 | 75 | 55 |

TABLE 6-12-continued

% Control and weed cover (2 weeks after application)

| Treatments (product/ha) | Rep | DIGSA | POROL | AMAHY | COMBE |
|---|---|---|---|---|---|
| 3 DINAMIC ® at 125 g | I | 70 | 50 | 80 | 60 |
| | ii | 70 | 50 | 90 | 70 |
| | iii | 80 | 40 | 80 | 70 |
| | iv | 70 | 40 | 80 | 70 |
| Mean | | 73 | 45 | 83 | 68 |
| 4 DINAMIC ® at 150 g | I | 80 | 60 | 100 | 70 |
| | ii | 90 | 70 | 100 | 80 |
| | iii | 80 | 80 | 95 | 80 |
| | iv | 80 | 60 | 100 | 80 |
| Mean | | 83 | 68 | 99 | 78 |
| 5 DINAMIC ® at 300 g | I | 90 | 90 | 100 | 80 |
| | ii | 80 | 80 | 95 | 95 |
| | iii | 80 | 80 | 100 | 90 |
| | iv | 90 | 90 | 100 | 90 |
| Mean | | 84 | 77 | 99 | 89 |
| 6 Galago at 100 ml | I | 70 | 70 | 80 | 70 |
| | ii | 70 | 70 | 70 | 80 |
| | iii | 60 | 60 | 80 | 70 |
| | iv | 70 | 70 | 90 | 80 |
| Mean | | 68 | 68 | 80 | 75 |
| 7 Galago at 200 ml | I | 70 | 80 | 80 | 80 |
| | ii | 90 | 90 | 90 | 90 |
| | iii | 80 | 90 | 90 | 90 |
| | iv | 80 | 80 | 90 | 80 |
| Mean | | 80 | 85 | 88 | 85 |
| 8 DINAMIC ® at 75 g Galago at 100 ml | I | 70 | 60 | 70 | 70 |
| | ii | 80 | 70 | 90 | 90 |
| | iii | 80 | 70 | 90 | 80 |
| | iv | 70 | 60 | 80 | 80 |
| Mean | | 75 | 65 | 83 | 80 |
| 9 DINAMIC ® at 75 g Galago at 150 ml | I | 80 | 70 | 70 | 70 |
| | ii | 80 | 70 | 90 | 70 |
| | iii | 70 | 80 | 90 | 80 |
| | iv | 70 | 70 | 90 | 80 |
| Mean | | 75 | 73 | 85 | 75 |
| 10 DINAMIC ® at 100 g Galago at 100 ml | I | 70 | 70 | 80 | 80 |
| | ii | 80 | 80 | 90 | 90 |
| | iii | 80 | 70 | 95 | 80 |
| | iv | 80 | 70 | 90 | 80 |
| Mean | | 78 | 73 | 89 | 83 |
| 11 DINAMIC ® at 100 g Galago at 150 ml | I | 80 | 80 | 95 | 95 |
| | ii | 90 | 80 | 90 | 95 |
| | iii | 80 | 80 | 95 | 90 |
| | iv | 90 | 70 | 95 | 95 |
| Mean | | 85 | 78 | 94 | 94 |
| 12 DINAMIC ® at 125 g Galago at 100 ml | I | 80 | 70 | 90 | 90 |
| | ii | 80 | 80 | 90 | 80 |
| | iii | 80 | 70 | 98 | 90 |
| | iv | 80 | 70 | 95 | 95 |
| Mean | | 80 | 73 | 93 | 89 |
| 13 DINAMIC ® at 125 g Galago at 150 ml | I | 90 | 90 | 95 | 90 |
| | ii | 80 | 90 | 100 | 70 |
| | iii | 90 | 90 | 95 | 80 |
| | iv | 80 | 80 | 100 | 90 |
| Mean | | 85 | 88 | 98 | 83 |
| 14 DINAMIC ® at 250 g Galago at 300 ml | I | 90 | 100 | 100 | 100 |
| | ii | 100 | 100 | 100 | 100 |
| | iii | 95 | 100 | 100 | 100 |
| | iv | 95 | 100 | 100 | 100 |
| Mean | | 95 | 100 | 100 | 100 |

DIGSA = *Digitaria sanguinalis*;
POROL = *Portulaca oleracea*;
AMAHY = *Amaranthus hybridus*;
COMBE = *Commelina benghalensis*

TABLE 6-13

% Control and weed cover (4 weeks after application)

| Treatments (product/ha) | Rep | DIGSA | POROL | AMAHY | COMBE |
|---|---|---|---|---|---|
| Untreated control % soil cover | I | 30 | 20 | 30 | 20 |
| | ii | 40 | 10 | 20 | 30 |
| | iii | 40 | 20 | 30 | 10 |
| | iv | 30 | 20 | 30 | 20 |
| Mean | | 35 | 18 | 28 | 20 |
| 1 DINAMIC ® at 75 g | I | 50 | 40 | 70 | 50 |
| | ii | 60 | 40 | 80 | 50 |
| | iii | 60 | 40 | 80 | 50 |
| | iv | 70 | 50 | 80 | 50 |
| Mean | | 60 | 43 | 78 | 50 |
| 2 DINAMIC ® at 100 g | I | 70 | 40 | 70 | 50 |
| | ii | 60 | 40 | 70 | 50 |
| | iii | 60 | 50 | 80 | 60 |
| | iv | 70 | 40 | 80 | 60 |
| Mean | | 65 | 43 | 75 | 55 |
| 3 DINAMIC ® at 125 g | I | 70 | 40 | 80 | 60 |
| | ii | 70 | 50 | 80 | 70 |
| | iii | 70 | 40 | 80 | 60 |
| | iv | 70 | 40 | 80 | 70 |
| Mean | | 70 | 43 | 80 | 65 |
| 4 DINAMIC ® at 150 g | I | 80 | 60 | 100 | 70 |
| | ii | 80 | 60 | 98 | 70 |
| | iii | 70 | 80 | 90 | 70 |
| | iv | 80 | 50 | 100 | 80 |
| Mean | | 78 | 63 | 97 | 73 |
| 5 DINAMIC ® at 300 g | I | 80 | 90 | 100 | 80 |
| | ii | 80 | 70 | 95 | 90 |
| | iii | 80 | 80 | 100 | 80 |
| | iv | 90 | 80 | 100 | 90 |
| Mean | | 80 | 72 | 98 | 79 |
| 6 Galago at 100 ml | I | 70 | 70 | 80 | 70 |
| | ii | 60 | 70 | 70 | 70 |
| | iii | 60 | 60 | 70 | 70 |
| | iv | 60 | 70 | 80 | 80 |
| Mean | | 63 | 68 | 75 | 73 |
| 7 Galago at 200 ml | I | 70 | 80 | 80 | 80 |
| | ii | 80 | 80 | 90 | 80 |
| | iii | 80 | 80 | 80 | 80 |
| | iv | 80 | 80 | 90 | 80 |
| Mean | | 78 | 80 | 85 | 80 |
| 8 DINAMIC ® at 75 g Galago at 100 ml | I | 70 | 60 | 70 | 70 |
| | ii | 70 | 60 | 90 | 80 |
| | iii | 70 | 70 | 80 | 80 |
| | iv | 70 | 60 | 70 | 70 |
| Mean | | 70 | 63 | 78 | 75 |
| 9 DINAMIC ® at 75 g Galago at 150 ml | I | 70 | 70 | 70 | 70 |
| | ii | 70 | 60 | 90 | 70 |
| | iii | 60 | 70 | 80 | 70 |
| | iv | 70 | 70 | 90 | 70 |
| Mean | | 68 | 68 | 83 | 70 |
| 10 DINAMIC ® at 100 g Galago at 100 ml | I | 70 | 70 | 80 | 80 |
| | ii | 80 | 70 | 80 | 80 |
| | iii | 70 | 70 | 90 | 70 |
| | iv | 80 | 70 | 90 | 80 |
| Mean | | 75 | 70 | 85 | 78 |
| 11 DINAMIC ® at 100 g Galago at 150 ml | I | 80 | 80 | 90 | 90 |
| | ii | 80 | 70 | 90 | 90 |
| | iii | 70 | 80 | 90 | 90 |
| | iv | 90 | 70 | 90 | 90 |
| Mean | | 80 | 75 | 90 | 90 |
| 12 DINAMIC ® at 125 g Galago at 100 ml | I | 70 | 70 | 90 | 80 |
| | ii | 80 | 70 | 90 | 80 |
| | iii | 80 | 70 | 95 | 90 |
| | iv | 70 | 70 | 90 | 90 |
| Mean | | 75 | 70 | 91 | 85 |
| 13 DINAMIC ® at 125 g Galago at 150 ml | I | 80 | 80 | 90 | 80 |
| | ii | 80 | 90 | 100 | 70 |
| | iii | 80 | 90 | 95 | 80 |
| | iv | 70 | 80 | 100 | 80 |
| Mean | | 78 | 85 | 96 | 78 |

TABLE 6-13-continued

% Control and weed cover (4 weeks after application)

| Treatments (product/ha) | Rep | DIGSA | POROL | AMAHY | COMBE |
|---|---|---|---|---|---|
| 14 DINAMIC ® at 250 g | I | 90 | 100 | 100 | 100 |
| Galago at 300 ml | ii | 98 | 100 | 100 | 100 |
| | iii | 90 | 100 | 100 | 100 |
| | iv | 95 | 100 | 100 | 100 |
| Mean | | 93 | 100 | 100 | 100 |

DIGSA = *Digitaria sanguinalis*;
POROL = *Portulaca oleracea*;
AMAHY = *Amaranthus hybridus*;
COMBE = *Commelina benghalensis*

TABLE 6-14

% Control and weed cover (6 weeks after application)

| Treatments (product/ha) | Rep | DIGSA | POROL | AMAHY | COMBE |
|---|---|---|---|---|---|
| Untreated control | I | 20 | 30 | 30 | 20 |
| % soil cover | ii | 30 | 20 | 20 | 30 |
| | iii | 30 | 30 | 30 | 10 |
| | iv | 20 | 20 | 40 | 20 |
| Mean | | 25 | 25 | 30 | 20 |
| 1 DINAMIC ® at 75 g | I | 50 | 40 | 70 | 50 |
| | ii | 60 | 40 | 80 | 50 |
| | iii | 50 | 30 | 70 | 50 |
| | iv | 60 | 40 | 80 | 50 |
| Mean | | 55 | 38 | 75 | 50 |
| 2 DINAMIC ® at 100 g | I | 60 | 40 | 70 | 50 |
| | ii | 60 | 40 | 70 | 50 |
| | iii | 60 | 40 | 80 | 50 |
| | iv | 60 | 40 | 80 | 60 |
| Mean | | 60 | 40 | 75 | 53 |
| 3 DINAMIC ® at 125 g | I | 70 | 40 | 80 | 60 |
| | ii | 70 | 50 | 80 | 60 |
| | iii | 60 | 40 | 80 | 60 |
| | iv | 70 | 40 | 80 | 70 |
| Mean | | 68 | 43 | 80 | 63 |
| 4 DINAMIC ® at 150 g | I | 70 | 60 | 95 | 70 |
| | ii | 70 | 50 | 95 | 60 |
| | iii | 70 | 70 | 90 | 70 |
| | iv | 80 | 50 | 100 | 70 |
| Mean | | 73 | 58 | 95 | 68 |
| 5 DINAMIC ® at 300 g | I | 80 | 80 | 100 | 80 |
| | ii | 70 | 70 | 95 | 90 |
| | iii | 80 | 70 | 95 | 80 |
| | iv | 90 | 80 | 100 | 80 |
| Mean | | 77 | 66 | 96 | 75 |
| 6 Galago at 100 ml | I | 70 | 70 | 70 | 70 |
| | ii | 60 | 70 | 70 | 70 |
| | iii | 60 | 60 | 70 | 70 |
| | iv | 50 | 60 | 80 | 70 |
| Mean | | 60 | 65 | 73 | 70 |
| 7 Galago at 200 ml | I | 60 | 70 | 80 | 80 |
| | ii | 70 | 70 | 90 | 80 |
| | iii | 80 | 80 | 80 | 80 |
| | iv | 80 | 80 | 90 | 80 |
| Mean | | 73 | 75 | 85 | 80 |
| 8 DINAMIC ® at 75 g | I | 70 | 60 | 70 | 70 |
| Galago at 100 ml | ii | 70 | 50 | 80 | 70 |
| | iii | 60 | 60 | 70 | 70 |
| | iv | 60 | 60 | 70 | 70 |
| Mean | | 65 | 58 | 73 | 70 |
| 9 DINAMIC ® at 75 g | I | 60 | 70 | 80 | 70 |
| Galago at 150 ml | ii | 70 | 60 | 90 | 70 |
| | iii | 60 | 60 | 80 | 80 |
| | iv | 70 | 70 | 90 | 70 |
| Mean | | 65 | 65 | 85 | 73 |
| 10 DINAMIC ® at 100 g | I | 70 | 70 | 80 | 80 |
| Galago at 100 ml | ii | 70 | 60 | 80 | 70 |
| | iii | 70 | 70 | 80 | 70 |
| | iv | 80 | 70 | 80 | 80 |
| Mean | | 73 | 68 | 80 | 75 |

TABLE 6-14-continued

% Control and weed cover (6 weeks after application)

| Treatments (product/ha) | Rep | DIGSA | POROL | AMAHY | COMBE |
|---|---|---|---|---|---|
| 11 DINAMIC ® at 100 g | I | 80 | 80 | 90 | 80 |
| Galago at 150 ml | ii | 80 | 70 | 90 | 80 |
| | iii | 70 | 70 | 90 | 80 |
| | iv | 80 | 70 | 90 | 90 |
| Mean | | 78 | 73 | 90 | 83 |
| 12 DINAMIC ® at 125 g | I | 70 | 70 | 90 | 80 |
| Galago at 100 ml | ii | 80 | 70 | 95 | 80 |
| | iii | 80 | 60 | 95 | 80 |
| | iv | 70 | 70 | 90 | 80 |
| Mean | | 75 | 68 | 93 | 80 |
| 13 DINAMIC ® at 125 g | I | 80 | 80 | 90 | 90 |
| Galago at 150 ml | ii | 80 | 90 | 98 | 80 |
| | iii | 80 | 90 | 90 | 80 |
| | iv | 70 | 90 | 100 | 90 |
| Mean | | 78 | 88 | 95 | 85 |
| 14 DINAMIC ® at 250 g | I | 90 | 100 | 100 | 100 |
| Galago at 300 ml | ii | 95 | 100 | 100 | 100 |
| | iii | 90 | 100 | 100 | 100 |
| | iv | 90 | 100 | 100 | 100 |
| Mean | | 91 | 100 | 100 | 100 |

DIGSA = *Digitaria sanguinalis*;
POROL = *Portulaca oleracea*;
AMAHY = *Amaranthus hybridus*;
COMBE = *Commelina benghalensis*

DINAMIC® 700WDG at 125 g/ha alone showed marginal control of *Amaranthus hybridus*, but the rest of the spectrum was insufficiently controlled by rates as high as 300 g/ha. Galago 480SC at 200 mL/ha controlled *Amaranthus hybridus* and showed marginal control of *Commilina benghalensis*. The combination (DINAMIC® at 75 g/ha+ Galago at 150 mL/ha) resulted in satisfactory control of *Amaranthus hybridus* only. However, when the DINAMIC® rate of this combination was increased to 100 g/ha *Commilina benghalensis* was also controlled satisfactorily. Should the DINAMIC® rate of the combination be increased further to 125 g/ha, *Portulaca oleracea* was added to the controlled spectrum. *Digitaria sanguinalis* could be controlled by the high rate (DINAMIC® at 250 g/ha+ Galago at 300 mL/ha). No visual signs of phytotoxicity were noticed throughout the growing season. DINAMIC® can be applied in combination with Galago to give the following control: DINAMIC® at 100 g/ha+Galago at 150 mL/ha to control *Amaranthus hybridus* and *Commilina benghalensis*. DINAMIC® at 125 g/ha+Galago at 150 mL/ha to control *Amaranthus hybridus, Commilina Benghalensis* and *Portulaca oleracea*. The higher dosage rate (DINAMIC® at 250 g/ha+Galago at 300 mL/ha can be used to control the entire spectrum.

C. Pre Emergence Application Against Weed in Maize

In this part of the Example the efficacy of DINAMIC® (amicarbazone 700WDG, 700 grams active/kg, available from Arysta LifeScience North America, Cary, N.C.) mixtures with Galago (mesotrione 480SC, 480 grams active/L, available from Arysta LifeScience North America, Cary, N.C.) as a pre emergence application against weeds in maize (variety PAN60-445B) was determined.

Trials were conducted at a site with a history of weeds. The trials were executed under moderate weather conditions. Efficacy and visual phytotoxicity assessments were performed in triplicate. Normal practices were carried out to control insects and fungi. Crops were provided in 76 cm row width, at a sowing rate of 65,000 plants/ha, and at a sowing depth of five to eight cm. Soil class was clay with a clay content of about 28%. The site in this Example had been previously used for soya beans. Trial design was randomized blocks with a plot size of 20 m² replicated four times. Municipal water was used for all applications (pH=7.2).

Application of the treatments shown in Table 6-15 was conducted at pre emergence stage 3 days after planting seed. Application of the treatments was conducted over a 24 hour period. Over this time period, dry bulb temperature was about 20° C., wet bulb temperature was about 16° C., relative humidity was about 65%, cloud cover was about 10%, wind speed was about 0 m/s. Treatments were administered with a multi-spray gas sprayer with a 4× flat fan 03F80 nozzle. Spacing was 50 cm, with a height of 50 cm, pressure 2.8 Bar, at a ground speed of 1 m/s, and a calibration mean output of 330 L/ha. The soil temperature over the application period averaged to about 20° C. and the soil remained moist and fine.

TABLE 6-15

Treatments

| No | Treatments | Dosage rate (gai/ha) | Dosage rate (g/ha or mL/ha) |
|---|---|---|---|
|  | Untreated control | — | — |
| 1 | DINAMIC ® 700WDG | 52.5 | 75 |
| 2 | DINAMIC ® 700WDG | 70 | 100 |
| 3 | DINAMIC ® 700WDG | 87.5 | 125 |
| 4 | DINAMIC ® 700WDG | 105 | 150 |
| 5 | DINAMIC ® 700WDG | 210 | 300 |
| 6 | Galago 480SC | 48 | 100 |
| 7 | Galago 480SC | 96 | 200 |
| 8 | DINAMIC ® 700WDG + | 52.5 | 75 |
|  | Galago 480SC | 48 | 100 |
| 9 | DINAMIC ® 700WDG + | 52.5 | 75 |
|  | Galago 480SC | 72 | 150 |
| 10 | DINAMIC ® 700WDG + | 70 | 100 |
|  | Galago 480SC | 48 | 100 |
| 11 | DINAMIC ® 700WDG + | 70 | 100 |
|  | Galago 480SC | 72 | 150 |
| 12 | DINAMIC ® 700WDG + | 87.5 | 125 |
|  | Galago 480SC | 48 | 100 |
| 13 | DINAMIC ® 700WDG + | 87.5 | 125 |
|  | Galago 480SC | 72 | 150 |
| 14 | DINAMIC ® 700WDG + | 175 | 250 |
|  | Galago 480SC | 144 | 300 |

Assessments of the treated crops at 2, 4, and 6 weeks are summarized in Tables 6-16 to 6-18 below. No visual signs of phytotoxicity were noticed over the 6 weeks.

TABLE 6-16

2 Week Assessment

| Crop condition | Actively growing |
|---|---|
| Crop stage | 3 Leaves |
| BBCH scale | 13 |
| Soil moisture | Moist |
| Rain since last visit | 16 mm |

TABLE 6-17

4 Week Assessment

| Crop condition | Actively growing |
|---|---|
| Crop stage | 5 Leaves |
| BBCH scale | 15 |
| Soil moisture | Wet |
| Rain since last visit | 30 mm |

TABLE 6-18

6 Week Assessment

| Crop condition | Actively growing |
|---|---|
| Crop stage | 8 leaves |
| BBCH scale: | 18 |
| Soil moisture | Moist |
| Rain since last visit | 22 mm |

Control and weed cover at 2, 4, and 6 weeks for the indicated species are summarized below in Tables 6-19 through 6-21. 80% is considered acceptable control.

TABLE 6-19

% Control and weed cover (2 weeks after application)

| Treatments (product/ha) | Rep | AMASP | ELEIN | IPOPU | COMBE |
|---|---|---|---|---|---|
| Untreated control | I | 30 | 20 | 30 | 20 |
| % soil cover | ii | 40 | 10 | 20 | 30 |
|  | iii | 40 | 20 | 30 | 10 |
|  | iv | 30 | 20 | 30 | 20 |
|  | Mean | 35 | 18 | 28 | 20 |
| 1 DINAMIC ® at 75 g | I | 70 | 70 | 60 | 70 |
|  | ii | 70 | 70 | 60 | 60 |
|  | iii | 70 | 70 | 60 | 60 |
|  | iv | 70 | 60 | 50 | 70 |
|  | Mean | 70 | 68 | 58 | 65 |
| 2 DINAMIC ® at 100 g | I | 70 | 70 | 70 | 70 |
|  | ii | 70 | 70 | 60 | 70 |
|  | iii | 70 | 70 | 60 | 70 |
|  | iv | 70 | 70 | 60 | 70 |
|  | Mean | 70 | 70 | 63 | 70 |
| 3 DINAMIC ® at 125 g | I | 80 | 70 | 70 | 70 |
|  | ii | 70 | 80 | 60 | 70 |
|  | iii | 80 | 80 | 70 | 70 |
|  | iv | 70 | 70 | 60 | 70 |
|  | Mean | 75 | 75 | 65 | 70 |
| 4 DINAMIC ® at 150 g | I | 80 | 80 | 70 | 80 |
|  | ii | 80 | 70 | 70 | 70 |
|  | iii | 80 | 70 | 60 | 80 |
|  | iv | 80 | 70 | 70 | 70 |
|  | Mean | 80 | 73 | 68 | 75 |
| 5 DINAMIC ® at 300 g | I | 90 | 80 | 90 | 80 |
|  | ii | 80 | 80 | 80 | 80 |
|  | iii | 80 | 90 | 90 | 80 |
|  | iv | 90 | 90 | 90 | 80 |
|  | Mean | 85 | 85 | 88 | 80 |
| 6 Galago at 100 ml | I | 90 | 80 | 80 | 80 |
|  | ii | 80 | 80 | 80 | 80 |
|  | iii | 80 | 70 | 80 | 70 |
|  | iv | 90 | 70 | 80 | 80 |
|  | Mean | 85 | 75 | 80 | 78 |
| 7 Galago at 200 ml | I | 100 | 90 | 95 | 90 |
|  | ii | 100 | 90 | 95 | 90 |
|  | iii | 100 | 95 | 98 | 90 |
|  | iv | 100 | 95 | 98 | 90 |
|  | Mean | 100 | 93 | 97 | 90 |
| 8 DINAMIC ® at 75 g | I | 80 | 80 | 70 | 80 |
| Galago at 100 ml | ii | 80 | 80 | 70 | 70 |
|  | iii | 80 | 80 | 70 | 70 |
|  | iv | 80 | 70 | 60 | 80 |
|  | Mean | 80 | 78 | 68 | 75 |
| 9 DINAMIC ® at 75 g | I | 80 | 80 | 80 | 80 |
| Galago at 150 ml | ii | 80 | 80 | 70 | 80 |
|  | iii | 80 | 80 | 70 | 80 |
|  | iv | 80 | 80 | 70 | 80 |
|  | Mean | 80 | 80 | 73 | 80 |
| 10 DINAMIC ® at 100 g | I | 90 | 80 | 80 | 80 |
| Galago at 100 ml | ii | 80 | 90 | 70 | 80 |
|  | iii | 90 | 90 | 80 | 80 |
|  | iv | 80 | 80 | 70 | 80 |
|  | Mean | 85 | 85 | 75 | 80 |

TABLE 6-19-continued

% Control and weed cover (2 weeks after application)

| Treatments (product/ha) | Rep | AMASP | ELEIN | IPOPU | COMBE |
|---|---|---|---|---|---|
| 11 DINAMIC ® at 100 g Galago at 150 ml | I | 95 | 90 | 80 | 90 |
| | ii | 95 | 80 | 80 | 80 |
| | iii | 95 | 80 | 70 | 90 |
| | iv | 90 | 80 | 80 | 90 |
| Mean | | 94 | 83 | 78 | 88 |
| 12 DINAMIC ® at 125 g Galago at 100 ml | I | 100 | 95 | 100 | 95 |
| | ii | 95 | 95 | 98 | 90 |
| | iii | 95 | 100 | 100 | 90 |
| | iv | 100 | 100 | 100 | 90 |
| Mean | | 98 | 98 | 100 | 91 |
| 13 DINAMIC ® at 125 g Galago at 150 ml | I | 100 | 90 | 95 | 90 |
| | ii | 95 | 90 | 90 | 90 |
| | iii | 95 | 80 | 90 | 80 |
| | iv | 100 | 80 | 95 | 90 |
| Mean | | 98 | 85 | 93 | 88 |
| 14 DINAMIC ® at 250 g Galago at 300 ml | I | 100 | 100 | 100 | 100 |
| | ii | 100 | 100 | 100 | 95 |
| | iii | 100 | 100 | 98 | 95 |
| | iv | 100 | 100 | 95 | 90 |
| Mean | | 100 | 100 | 98 | 95 |

AMASP = *Amaranthus spinosus*;
COMBE = *Commelina benghalensis*;
IPOPU= *Ipomoea purpurea*;
ELEIN = *Eleusine indica*

TABLE 6-20

% Control and weed cover (4 weeks after application)

| Treatments (product/ha) | Rep | AMASP | ELEIN | IPOPU | COMBE |
|---|---|---|---|---|---|
| Untreated control % soil cover | I | 30 | 20 | 30 | 20 |
| | ii | 40 | 10 | 20 | 30 |
| | iii | 40 | 20 | 30 | 10 |
| | iv | 30 | 20 | 30 | 20 |
| Mean | | 35 | 18 | 28 | 20 |
| 1 DINAMIC ® at 75 g | I | 60 | 60 | 50 | 60 |
| | ii | 70 | 60 | 60 | 60 |
| | iii | 60 | 70 | 60 | 50 |
| | iv | 70 | 60 | 50 | 70 |
| Mean | | 65 | 63 | 55 | 60 |
| 2 DINAMIC ® at 100 g | I | 60 | 60 | 60 | 70 |
| | ii | 60 | 70 | 50 | 60 |
| | iii | 60 | 60 | 60 | 70 |
| | iv | 70 | 60 | 60 | 60 |
| Mean | | 63 | 63 | 58 | 65 |
| 3 DINAMIC ® at 125 g | I | 70 | 70 | 70 | 60 |
| | ii | 70 | 80 | 60 | 70 |
| | iii | 70 | 70 | 60 | 70 |
| | iv | 60 | 70 | 60 | 60 |
| Mean | | 68 | 73 | 63 | 65 |
| 4 DINAMIC ® at 150 g | I | 80 | 70 | 60 | 70 |
| | ii | 80 | 70 | 70 | 70 |
| | iii | 80 | 60 | 60 | 80 |
| | iv | 80 | 70 | 60 | 70 |
| Mean | | 80 | 68 | 63 | 73 |
| 5 DINAMIC ® at 300 g | I | 90 | 80 | 90 | 80 |
| | ii | 80 | 80 | 80 | 80 |
| | iii | 80 | 90 | 90 | 70 |
| | iv | 90 | 90 | 90 | 80 |
| Mean | | 85 | 85 | 88 | 78 |
| 6 Galago at 100 ml | I | 80 | 70 | 70 | 70 |
| | ii | 70 | 60 | 70 | 70 |
| | iii | 70 | 60 | 70 | 60 |
| | iv | 70 | 60 | 70 | 70 |
| Mean | | 73 | 63 | 70 | 68 |
| 7 Galago at 200 ml | I | 90 | 80 | 80 | 80 |
| | ii | 90 | 80 | 80 | 80 |
| | iii | 90 | 90 | 90 | 80 |
| | iv | 90 | 80 | 90 | 80 |
| Mean | | 90 | 83 | 85 | 80 |

TABLE 6-20-continued

% Control and weed cover (4 weeks after application)

| Treatments (product/ha) | Rep | AMASP | ELEIN | IPOPU | COMBE |
|---|---|---|---|---|---|
| 8 DINAMIC ® at 75 g Galago at 100 ml | I | 70 | 70 | 60 | 70 |
| | ii | 70 | 70 | 60 | 70 |
| | iii | 70 | 70 | 70 | 70 |
| | iv | 80 | 70 | 60 | 80 |
| Mean | | 73 | 70 | 63 | 73 |
| 9 DINAMIC ® at 75 g Galago at 150 ml | I | 70 | 70 | 70 | 80 |
| | ii | 70 | 80 | 70 | 70 |
| | iii | 80 | 80 | 60 | 70 |
| | iv | 70 | 70 | 70 | 80 |
| Mean | | 73 | 75 | 68 | 75 |
| 10 DINAMIC ® at 100 g Galago at 100 ml | I | 80 | 70 | 70 | 70 |
| | ii | 80 | 80 | 70 | 80 |
| | iii | 80 | 80 | 70 | 80 |
| | iv | 80 | 80 | 70 | 80 |
| Mean | | 80 | 78 | 70 | 78 |
| 11 DINAMIC ® at 100 g Galago at 150 ml | I | 90 | 80 | 70 | 80 |
| | ii | 90 | 80 | 80 | 70 |
| | iii | 95 | 70 | 70 | 80 |
| | iv | 90 | 80 | 70 | 90 |
| Mean | | 91 | 78 | 73 | 80 |
| 12 DINAMIC ® at 125 g Galago at 100 ml | I | 100 | 90 | 100 | 90 |
| | ii | 90 | 95 | 95 | 90 |
| | iii | 95 | 100 | 100 | 90 |
| | iv | 100 | 100 | 100 | 90 |
| Mean | | 96 | 96 | 99 | 90 |
| 13 DINAMIC ® at 125 g Galago at 150 ml | I | 100 | 80 | 90 | 90 |
| | ii | 95 | 90 | 90 | 80 |
| | iii | 90 | 80 | 90 | 80 |
| | iv | 100 | 80 | 90 | 90 |
| Mean | | 96 | 83 | 90 | 85 |
| 14 DINAMIC ® at 250 g Galago at 300 ml | I | 100 | 100 | 100 | 100 |
| | ii | 100 | 100 | 100 | 95 |
| | iii | 100 | 100 | 95 | 90 |
| | iv | 100 | 100 | 95 | 90 |
| Mean | | 100 | 100 | 98 | 94 |

AMASP = *Amaranthus spinosus*;
COMBE = *Commelina benghalensis*;
IPOPU= *Ipomoea purpurea*;
ELEIN = *Eleusine indica*

TABLE 6-21

% Control and weed cover (6 weeks after application)

| Treatments (product/ha) | Rep | AMASP | ELEIN | IPOPU | COMBE |
|---|---|---|---|---|---|
| Untreated control % soil cover | I | 30 | 10 | 30 | 30 |
| | ii | 40 | 10 | 20 | 30 |
| | iii | 40 | 20 | 30 | 10 |
| | iv | 30 | 10 | 30 | 30 |
| Mean | | 35 | 13 | 28 | 25 |
| 1 DINAMIC ® at 75 g | I | 50 | 60 | 50 | 50 |
| | ii | 60 | 60 | 60 | 60 |
| | iii | 60 | 60 | 50 | 50 |
| | iv | 60 | 50 | 50 | 60 |
| Mean | | 58 | 58 | 53 | 55 |
| 2 DINAMIC ® at 100 g | I | 60 | 60 | 60 | 70 |
| | ii | 60 | 60 | 50 | 60 |
| | iii | 60 | 60 | 60 | 60 |
| | iv | 60 | 60 | 60 | 60 |
| Mean | | 60 | 60 | 58 | 63 |
| 3 DINAMIC ® at 125 g | I | 60 | 60 | 70 | 60 |
| | ii | 70 | 70 | 60 | 60 |
| | iii | 60 | 70 | 50 | 60 |
| | iv | 60 | 70 | 60 | 60 |
| Mean | | 63 | 68 | 60 | 63 |
| 4 DINAMIC ® at 150 g | I | 80 | 60 | 60 | 70 |
| | ii | 70 | 70 | 60 | 70 |
| | iii | 70 | 60 | 60 | 80 |
| | iv | 80 | 60 | 50 | 70 |
| Mean | | 75 | 63 | 58 | 73 |

TABLE 6-21-continued

% Control and weed cover (6 weeks after application)

| Treatments (product/ha) | Rep | AMASP | ELEIN | IPOPU | COMBE |
|---|---|---|---|---|---|
| 5 DINAMIC ® at 300 g | I | 80 | 70 | 80 | 70 |
| | ii | 80 | 80 | 80 | 80 |
| | iii | 80 | 80 | 90 | 70 |
| | iv | 90 | 90 | 80 | 80 |
| Mean | | 83 | 80 | 83 | 75 |
| 6 Galago at 100 ml | I | 70 | 60 | 70 | 70 |
| | ii | 60 | 60 | 60 | 60 |
| | iii | 70 | 60 | 70 | 60 |
| | iv | 70 | 60 | 70 | 70 |
| Mean | | 68 | 60 | 68 | 65 |
| 7 Galago at 200 ml | I | 80 | 80 | 80 | 80 |
| | ii | 90 | 80 | 80 | 80 |
| | iii | 80 | 90 | 80 | 90 |
| | iv | 90 | 80 | 90 | 80 |
| Mean | | 85 | 83 | 83 | 83 |
| 8 DINAMIC ® at 75 g Galago at 100 ml | I | 70 | 60 | 60 | 70 |
| | ii | 60 | 70 | 50 | 70 |
| | iii | 60 | 70 | 60 | 60 |
| | iv | 70 | 60 | 60 | 70 |
| Mean | | 65 | 65 | 58 | 68 |
| 9 DINAMIC ® at 75 g Galago at 150 ml | I | 60 | 70 | 70 | 70 |
| | ii | 70 | 70 | 60 | 70 |
| | iii | 70 | 70 | 50 | 70 |
| | iv | 60 | 60 | 70 | 80 |
| Mean | | 65 | 68 | 63 | 73 |
| 10 DINAMIC ® at 100 g Galago at 100 ml | I | 70 | 70 | 60 | 70 |
| | ii | 70 | 70 | 70 | 70 |
| | iii | 80 | 80 | 70 | 80 |
| | iv | 70 | 70 | 60 | 80 |
| Mean | | 73 | 73 | 65 | 75 |
| 11 DINAMIC ® at 100 g Galago at 150 ml | I | 80 | 70 | 70 | 80 |
| | ii | 90 | 80 | 70 | 70 |
| | iii | 90 | 70 | 60 | 80 |
| | iv | 90 | 80 | 70 | 80 |
| Mean | | 88 | 75 | 68 | 78 |
| 12 DINAMIC ® at 125 g Galago at 100 ml | I | 98 | 90 | 100 | 90 |
| | ii | 90 | 90 | 95 | 80 |
| | iii | 90 | 100 | 98 | 90 |
| | iv | 100 | 98 | 98 | 90 |
| Mean | | 95 | 95 | 98 | 88 |
| 13 DINAMIC ® at 125 g Galago at 150 ml | I | 98 | 80 | 90 | 90 |
| | ii | 95 | 90 | 95 | 80 |
| | iii | 90 | 80 | 95 | 80 |
| | iv | 98 | 90 | 90 | 90 |
| Mean | | 95 | 85 | 93 | 85 |
| 14 DINAMIC ® at 250 g Galago at 300 ml | I | 100 | 100 | 100 | 100 |
| | ii | 100 | 100 | 100 | 98 |
| | iii | 100 | 100 | 95 | 90 |
| | iv | 100 | 100 | 90 | 80 |
| Mean | | 100 | 100 | 96 | 92 |

AMASP = *Amaranthus spinosus*;
COMBE = *Commelina benghalensis*;
IPOPU= *Ipomoea purpurea*;
ELEIN = *Eleusine indica*

DINAMIC® 700WDG at 300 g/ha showed satisfactory control of *Amaranthus spinosus*, *Eleusine indica* and *Ipomoea purpurea* but could not control *Commilina benghalensis*. Galago 480SC at 200 mL/ha showed sufficient of the entire weed spectrum. The combinations at the higher dosage rates resulted in excellent control. DINAMIC® at 125 g/ha+Galago at 100 mL/ha showed good control over the entire weed spectrum. No visual signs of phytotoxicity were noticed throughout the growing season. DINAMIC® at 300 g/ha alone or Galago 480SC at 200 mL/ha can be used to control *Amaranthus spinosus*, *Eleusine indica* and *Ipomoea purpurea*. DINAMIC® at 125 g/ha+Galago at 100 mL/ha can be used to control *Amaranthus spinosus*, *Eleusine indica*, *Ipomoea purpurea* and *Commilina benghalensis*.

D. Pre Emergence Application Against Weed in Maize

In this part of the Example the efficacy of DINAMIC® (amicarbazone 700WDG, 700 grams active/kg, available from Arysta LifeScience North America, Cary, N.C.) mixtures with Galago (mesotrione 480SC, 480 grams active/L, available from Arysta LifeScience North America, Cary, N.C.) or TOLLA 840 S (available from Volanco Agroscience, Mt. Edgecombe, South Africa) as a pre emergence application against weeds in maize (variety PHI 2369W) was determined.

Trials were conducted at a site with a history of weeds. The trials were executed under moderate weather conditions. Efficacy and visual phytotoxicity assessments were performed in triplicate. Normal practices were carried out to control insects and fungi. Crops were provided in 55 cm row width, at a sowing rate of 65,000 plants/ha, and at a sowing depth of five to eight cm. Soil class was clay with a clay content of about 40%. The site in this Example had been previously used for maize. Trial design was randomized blocks with a plot size of 20 m² replicated four times. Municipal water was used for all applications (pH=7.2).

Application of the treatments shown in Table 6-22 was conducted at pre emergence stage 1 day after planting seed. Application of the treatments was conducted over a 24 hour period. Over this time period, dry bulb temperature was about 26° C., wet bulb temperature was about 16° C., relative humidity was about 65%-70%, cloud cover was about 100%, and wind speed was about 1 m/s out of the east. Treatments were administered with a multi-spray gas sprayer with a 4× flat fan 03F80 nozzle. Spacing was 50 cm, with a height of 50 cm, pressure 2.8 Bar, at a ground speed of 1 m/s, and a calibration mean output of 330 L/ha. The soil temperature over the application period averaged to about 28° C. and the soil remained moist and fine.

TABLE 6-22

Treatments

| No | Treatments | Dosage rate (gai/ha) | Dosage rate (g/ha or mL/ha) |
|---|---|---|---|
| | Untreated control | — | — |
| 1 | DINAMIC ® 700WDG + Galago 480SC | 52.5 48 | 75 100 |
| 2 | DINAMIC ® 700WDG + Galago 480SC | 52.5 72 | 75 150 |
| 3 | DINAMIC ® 700WDG + Galago 480SC | 70 48 | 100 100 |
| 4 | DINAMIC ® 700WDG + Galago 480SC | 70 72 | 100 150 |
| 5 | DINAMIC ® 700WDG + Galago 480SC | 87.5 48 | 125 100 |
| 6 | DINAMIC ® 700WDG + Galago 480SC | 87.5 72 | 125 150 |
| 7 | DINAMIC ® 700WDG + Galago 480SC + TOLLA 840S | 52.5 48 840 | 75 100 1000 |
| 8 | DINAMIC ® 700WDG + Galago 480SC + TOLLA 840S | 52.5 72 840 | 75 150 1000 |
| 9 | DINAMIC ® 700WDG + Galago 480SC + TOLLA 840S | 70 48 840 | 100 100 1000 |
| 10 | DINAMIC ® 700WDG + Galago 480SC + TOLLA 840S | 70 72 840 | 100 150 1000 |
| 11 | DINAMIC ® 700WDG + Galago 480SC + TOLLA 840S | 87.5 48 840 | 125 100 1000 |
| 12 | DINAMIC ® 700WDG + Galago 480SC + TOLLA 840S | 87.5 72 840 | 125 150 1000 |
| 13 | DINAMIC ® 700WDG + Galago 480SC + TOLLA 840S | 175 144 840 | 250 300 2000 |

TABLE 6-22-continued

| No | Treatments | Dosage rate (gai/ha) | Dosage rate (g/ha or mL/ha) |
|---|---|---|---|
| 14 | CALLISTO ® 480SC + | 124.8 | 260 |
|  | DUAL S GOLD ® 915EC | 649.7 | 710 |

Assessments of the treated crops at 2, 4, and 6 weeks are summarized in Tables 6-23 to 6-25 below. No visual signs of phytotoxicity were noticed over the 6 weeks.

TABLE 6-23

2 Week Assessment

| Crop condition | Actively growing |
|---|---|
| Crop stage | 4 Leaves |
| BBCH scale | 14 |
| Soil moisture | Moist |
| Rain since last visit | 28 mm |

TABLE 6-24

4 Week Assessment

| Crop condition | Actively growing |
|---|---|
| Crop stage | 6 Leaves |
| BBCH scale | 16 |
| Soil moisture | Wet |
| Rain since last visit | 6 mm |

TABLE 6-25

6 Week Assessment

| Crop condition | Actively growing |
|---|---|
| Crop stage | 8 leaves |
| BBCH scale: | 18 |
| Soil moisture | Moist |
| Rain since last visit | 23 mm |

Control and weed cover at 2, 4, and 6 weeks for the indicated species are summarized below in Tables 6-26 through 6-28. 80% is considered acceptable control.

TABLE 6-26

% Control and weed cover (2 weeks after application)

| Treatments (product/ha) | Rep | ROTEX | IPOPU | AMAHY |
|---|---|---|---|---|
| Untreated control | I | 30 | 40 | 30 |
| % soil cover | ii | 40 | 30 | 30 |
|  | iii | 40 | 40 | 20 |
|  | iv | 30 | 40 | 30 |
| Mean |  | 35 | 38 | 28 |
| 1 DINAMIC ® at 75 g | I | 60 | 80 | 80 |
| Galago at 100 ml | ii | 60 | 70 | 80 |
|  | iii | 60 | 80 | 70 |
|  | iv | 60 | 80 | 70 |
| Mean |  | 60 | 78 | 75 |
| 2 DINAMIC ® at 75 g | I | 70 | 80 | 90 |
| Galago at 150 ml | ii | 80 | 80 | 80 |
|  | iii | 80 | 90 | 80 |
|  | iv | 80 | 80 | 90 |
| Mean |  | 78 | 83 | 85 |

TABLE 6-26-continued

% Control and weed cover (2 weeks after application)

| Treatments (product/ha) | Rep | ROTEX | IPOPU | AMAHY |
|---|---|---|---|---|
| 3 DINAMIC ® at 100 g | I | 50 | 80 | 80 |
| Galago at 100 ml | ii | 60 | 90 | 80 |
|  | iii | 70 | 80 | 80 |
|  | iv | 70 | 80 | 80 |
| Mean |  | 63 | 83 | 80 |
| 4 DINAMIC ® at 100 g | I | 70 | 80 | 90 |
| Galago at 150 ml | ii | 70 | 90 | 80 |
|  | iii | 80 | 90 | 90 |
|  | iv | 70 | 80 | 90 |
| Mean |  | 73 | 85 | 88 |
| 5 DINAMIC ® at 125 g | I | 70 | 90 | 95 |
| Galago at 100 ml | ii | 70 | 80 | 95 |
|  | iii | 60 | 90 | 100 |
|  | iv | 70 | 90 | 90 |
| Mean |  | 68 | 88 | 95 |
| 6 DINAMIC ® at 125 g | I | 90 | 100 | 100 |
| Galago at 150 ml | ii | 80 | 100 | 100 |
|  | iii | 80 | 90 | 100 |
|  | iv | 80 | 95 | 100 |
| Mean |  | 83 | 96 | 100 |
| 7 DINAMIC ® at 75 g | I | 80 | 90 | 95 |
| Galago at 100 ml | ii | 80 | 90 | 95 |
| TOLLA at 1000 ml | iii | 80 | 80 | 95 |
|  | iv | 70 | 90 | 98 |
| Mean |  | 78 | 88 | 96 |
| 8 DINAMIC ® at 75 g | I | 80 | 90 | 100 |
| Galago at 150 ml | ii | 80 | 90 | 100 |
| TOLLA at 1000 ml | iii | 80 | 90 | 100 |
|  | iv | 80 | 95 | 100 |
| Mean |  | 80 | 91 | 100 |
| 9 DINAMIC ® at 100 g | I | 90 | 95 | 100 |
| Galago at 100 ml | ii | 80 | 95 | 100 |
| TOLLA at 1000 ml | iii | 80 | 95 | 100 |
|  | iv | 90 | 90 | 100 |
| Mean |  | 85 | 94 | 100 |
| 10 DINAMIC ® at 100 g | I | 90 | 95 | 100 |
| Galago at 150 ml | ii | 90 | 95 | 100 |
| TOLLA at 1000 ml | iii | 90 | 98 | 100 |
|  | iv | 80 | 95 | 100 |
| Mean |  | 88 | 96 | 100 |
| 11 DINAMIC ® at125 g | I | 80 | 98 | 100 |
| Galago at 100 ml | ii | 90 | 95 | 100 |
| TOLLA at 1000 ml | iii | 80 | 95 | 100 |
|  | iv | 90 | 98 | 100 |
| Mean |  | 85 | 97 | 100 |
| 12 DINAMIC ® at 125 g | I | 90 | 100 | 100 |
| Galago at 150 ml | ii | 90 | 95 | 100 |
| TOLLA at 1000 ml | iii | 80 | 100 | 100 |
|  | iv | 90 | 98 | 100 |
| Mean |  | 88 | 98 | 100 |
| 13 DINAMIC ® at 250 g | I | 95 | 100 | 100 |
| Galago at 300 ml | ii | 100 | 100 | 100 |
| TOLLA at 2000 ml | iii | 100 | 100 | 100 |
|  | iv | 98 | 100 | 100 |
| Mean |  | 98 | 100 | 100 |
| 14 Calisto at 260 ml | I | 80 | 95 | 100 |
| DUAL S GOLD ® at 710 ml | ii | 80 | 95 | 100 |
|  | iii | 80 | 100 | 100 |
|  | iv | 70 | 95 | 100 |
| Mean |  | 78 | 96 | 100 |

ROTTE = *Rottboelia exaltata*; IPOPU = *Ipomoea purpurea*; AMAHY = *Amaranthus hybridus*

TABLE 6-27

% Control and weed cover (4 weeks after application)

| Treatments (product/ha) | Rep | ROTEX | IPOPU | AMAHY |
|---|---|---|---|---|
| Untreated control % soil cover | I | 30 | 40 | 30 |
| | ii | 40 | 30 | 30 |
| | iii | 40 | 40 | 20 |
| | iv | 30 | 40 | 30 |
| Mean | | 35 | 38 | 28 |
| 1 DINAMIC ® at 75 g Galago at 100 ml | I | 50 | 70 | 70 |
| | ii | 50 | 60 | 70 |
| | iii | 50 | 70 | 60 |
| | iv | 50 | 70 | 60 |
| Mean | | 50 | 68 | 65 |
| 2 DINAMIC ® at 75 g Galago at 150 ml | I | 70 | 70 | 80 |
| | ii | 70 | 70 | 70 |
| | iii | 80 | 80 | 70 |
| | iv | 70 | 70 | 80 |
| Mean | | 73 | 73 | 75 |
| 3 DINAMIC ® at 100 g Galago at 100 ml | I | 50 | 70 | 70 |
| | ii | 60 | 80 | 70 |
| | iii | 60 | 70 | 70 |
| | iv | 60 | 70 | 70 |
| Mean | | 58 | 73 | 70 |
| 4 DINAMIC ® at 100 g Galago at 150 ml | I | 60 | 70 | 80 |
| | ii | 70 | 80 | 70 |
| | iii | 70 | 80 | 80 |
| | iv | 70 | 70 | 80 |
| Mean | | 68 | 75 | 78 |
| 5 DINAMIC ® at 125 g Galago at 100 ml | I | 70 | 80 | 90 |
| | ii | 60 | 80 | 90 |
| | iii | 60 | 90 | 100 |
| | iv | 70 | 90 | 90 |
| Mean | | 65 | 85 | 93 |
| 6 DINAMIC ® at 125 g Galago at 150 ml | I | 90 | 100 | 100 |
| | ii | 70 | 98 | 100 |
| | iii | 70 | 90 | 100 |
| | iv | 80 | 95 | 100 |
| Mean | | 78 | 96 | 100 |
| 7 DINAMIC ® at 75 g Galago at 100 ml TOLLA at 1000 ml | I | 80 | 90 | 95 |
| | ii | 70 | 80 | 90 |
| | iii | 80 | 80 | 95 |
| | iv | 60 | 80 | 98 |
| Mean | | 73 | 83 | 95 |
| 8 DINAMIC ® at 75 g Galago at 150 ml TOLLA at 1000 ml | I | 70 | 90 | 100 |
| | ii | 80 | 90 | 100 |
| | iii | 80 | 90 | 100 |
| | iv | 70 | 90 | 100 |
| Mean | | 75 | 90 | 100 |
| 9 DINAMIC ® at 100 g Galago at 100 ml TOLLA at 1000 ml | I | 80 | 90 | 100 |
| | ii | 80 | 90 | 100 |
| | iii | 80 | 90 | 100 |
| | iv | 80 | 90 | 100 |
| Mean | | 80 | 90 | 100 |
| 10 DINAMIC ® at 100 g Galago at 150 ml TOLLA at 1000 ml | I | 90 | 90 | 100 |
| | ii | 80 | 90 | 100 |
| | iii | 90 | 95 | 100 |
| | iv | 80 | 95 | 100 |
| Mean | | 85 | 93 | 100 |
| 11 DINAMIC ® at 125 g Galago at 100 ml TOLLA at 1000 ml | I | 80 | 95 | 100 |
| | ii | 80 | 90 | 100 |
| | iii | 70 | 90 | 100 |
| | iv | 90 | 95 | 100 |
| Mean | | 80 | 93 | 100 |
| 12 DINAMIC ® at 125 g Galago at 150 ml TOLLA at 1000 ml | I | 90 | 98 | 100 |
| | ii | 80 | 95 | 100 |
| | iii | 80 | 98 | 100 |
| | iv | 90 | 98 | 100 |
| Mean | | 85 | 97 | 100 |
| 13 DINAMIC ® at 250 g Galago at 300 ml TOLLA at 2000 ml | I | 95 | 100 | 100 |
| | ii | 98 | 100 | 100 |
| | iii | 100 | 100 | 100 |
| | iv | 95 | 100 | 100 |
| Mean | | 97 | 100 | 100 |
| 14 Calisto at 260 ml DUAL S GOLD ® at 710 ml | I | 80 | 95 | 100 |
| | ii | 70 | 90 | 100 |
| | iii | 80 | 98 | 100 |
| | iv | 70 | 95 | 100 |
| Mean | | 75 | 95 | 100 |

ROTTE = *Rottboelia exaltata*; IPOPU = *Ipomoea purpurea*; AMAHY = *Amaranthus hybridus*

TABLE 6-28

% Control and weed cover (6 weeks after application)

| Treatments (product/ha) | Rep | ROTEX | IPOPU | AMAHY |
|---|---|---|---|---|
| Untreated control % soil cover | I | 30 | 40 | 30 |
| | ii | 40 | 30 | 30 |
| | iii | 40 | 40 | 20 |
| | iv | 30 | 40 | 30 |
| Mean | | 35 | 38 | 28 |
| 1 DINAMIC ® at 75 g Galago at 100 ml | I | 50 | 70 | 60 |
| | ii | 50 | 60 | 70 |
| | iii | 50 | 60 | 60 |
| | iv | 50 | 70 | 60 |
| Mean | | 50 | 65 | 63 |
| 2 DINAMIC ® at 75 g Galago at 150 ml | I | 70 | 70 | 80 |
| | ii | 70 | 70 | 70 |
| | iii | 70 | 80 | 70 |
| | iv | 70 | 70 | 80 |
| Mean | | 70 | 73 | 75 |
| 3 DINAMIC ® at 100 g Galago at 100 ml | I | 50 | 70 | 80 |
| | ii | 50 | 70 | 70 |
| | iii | 50 | 70 | 70 |
| | iv | 60 | 70 | 80 |
| Mean | | 53 | 70 | 75 |
| 4 DINAMIC ® at 100 g Galago at 150 ml | I | 60 | 70 | 80 |
| | ii | 60 | 80 | 70 |
| | iii | 60 | 70 | 80 |
| | iv | 70 | 70 | 70 |
| Mean | | 63 | 73 | 75 |
| 5 DINAMIC ® at 125 g Galago at 100 ml | I | 60 | 70 | 90 |
| | ii | 60 | 80 | 90 |
| | iii | 60 | 90 | 100 |
| | iv | 60 | 80 | 90 |
| Mean | | 60 | 80 | 93 |
| 6 DINAMIC ® at 125 g Galago at 150 ml | I | 80 | 100 | 100 |
| | ii | 70 | 95 | 100 |
| | iii | 70 | 90 | 100 |
| | iv | 80 | 95 | 100 |
| Mean | | 75 | 95 | 100 |
| 7 DINAMIC ® at 75 g Galago at 100 ml TOLLA at 1000 ml | I | 80 | 80 | 90 |
| | ii | 70 | 80 | 90 |
| | iii | 70 | 80 | 95 |
| | iv | 60 | 80 | 98 |
| Mean | | 70 | 80 | 93 |
| 8 DINAMIC ® at 75 g Galago at 150 ml TOLLA at 1000 ml | I | 70 | 90 | 100 |
| | ii | 70 | 90 | 100 |
| | iii | 80 | 90 | 100 |
| | iv | 70 | 80 | 100 |
| Mean | | 73 | 88 | 100 |
| 9 DINAMIC ® at 100 g Galago at 100 ml TOLLA at 1000 ml | I | 70 | 90 | 100 |
| | ii | 80 | 80 | 100 |
| | iii | 80 | 80 | 100 |
| | iv | 70 | 90 | 100 |
| Mean | | 75 | 85 | 100 |
| 10 DINAMIC ® at 100 g Galago at 150 ml TOLLA at 1000 ml | I | 80 | 90 | 100 |
| | ii | 80 | 90 | 100 |
| | iii | 90 | 95 | 100 |
| | iv | 80 | 90 | 100 |
| Mean | | 83 | 91 | 100 |

TABLE 6-28-continued

% Control and weed cover (6 weeks after application)

| Treatments (product/ha) | Rep | ROTEX | IPOPU | AMAHY |
|---|---|---|---|---|
| 11 DINAMIC ® at 125 g | I | 70 | 95 | 100 |
| Galago at 100 ml | ii | 80 | 90 | 100 |
| TOLLA at 1000 ml | iii | 70 | 90 | 100 |
| | iv | 80 | 90 | 100 |
| Mean | | 75 | 91 | 100 |
| 12 DINAMIC ® at 125 g | I | 90 | 95 | 100 |
| Galago at 150 ml | ii | 80 | 95 | 100 |
| TOLLA at 1000 ml | iii | 80 | 95 | 100 |
| | iv | 80 | 98 | 100 |
| Mean | | 83 | 96 | 100 |
| 13 DINAMIC ® at 250 g | I | 95 | 100 | 100 |
| Galago at 300 ml | ii | 95 | 100 | 100 |
| TOLLA at 2000 ml | iii | 100 | 100 | 100 |
| | iv | 95 | 100 | 100 |
| Mean | | 96 | 100 | 100 |
| 14 Calisto at 260 ml | I | 80 | 90 | 100 |
| DUAL S GOLD ® at 710 ml | ii | 70 | 90 | 100 |
| | iii | 80 | 95 | 100 |
| | iv | 70 | 95 | 100 |
| Mean | | 75 | 93 | 100 |

ROTTE = *Rottboelia exaltata*; IPOPU = *Ipomoea purpurea*; AMAHY = *Amaranthus hybridus*

DINAMIC® 700WDG at 125 g/ha+Galago 480SC at 100 mL/ha showed satisfactory control of *Amaranthus hybridus* and marginal control of *Ipomoea purpurea* but *Rottboellia exaltata* was insufficiently controlled even by the higher rate of Galago 480SC (150 mL/ha). The higher rate of this combination (DINAMIC® 700WDG at 125 g/ha+Galago 480SC at 150 mL/ha) performed on par with the standard CALLISTO® at 260 mL/ha+DUAL S GOLD® at 710 mL/ha. The addition of TOLLA showed a significant improvement to efficacy of the DINAMIC®+Galago mixture. DINAMIC® 700WDG at 75 g/ha+Galago 480SC at 100 mL/ha+TOLLA 840S at 1000 mL/ha resulted in satisfactory control of *Amaranthus hybridus* and marginal control of *Ipomoea purpurea*. DINAMIC® 700WDG at 100 g/ha+Galago 480SC at 150 mL/ha+TOLLA 840S at 1000 mL/ha compared with the standard CALLISTO® at 260 mL/ha+DUAL S GOLD® at 710 mL/ha. DINAMIC® 700WDG at 125 g/ha+Galago 480SC at 150 mL/ha+TOLLA 840S at 1000 mL/ha resulted in satisfactory control of *Rottboellia exaltata* which could not be achieved by the standard CALLISTO® at 260 mL/ha+DUAL S GOLD® at 710 mL/ha. DINAMIC® 700WDG at 125 g/ha+Galago 480SC at 150 mL/ha can be used to control *Amaranthus hybridus* and *Ipomoea purpurea*. DINAMIC® 700WDG at 75 g/ha+Galago 480SC at 150 mL/ha+TOLLA 840S at 1000 mL/ha can be used to control *Amaranthus hybridus* and *Ipomoea purpurea*. To control *Rottboellia exaltata* DINAMIC® 700WDG at 125 g/ha+Galago 480SC at 150 mL/ha+TOLLA 840S at 1000 mL/ha can be used.

E. Pre Emergence Application Against Weed in Maize

In this part of the Example the efficacy of DINAMIC® (amicarbazone 700WDG, 700 grams active/kg, available from Arysta LifeScience North America, Cary, N.C.) mixtures with Galago (mesotrione 480SC, 480 grams active/L, available from Arysta LifeScience North America, Cary, N.C.) or TOLLA 840 S (available from Volanco Agroscience, Mt. Edgecombe, South Africa) as a pre emergence application against weeds in maize (variety PHI 32Y85) was determined. A comparison with CALLISTO® 480SC plus DUAL S GOLD® 915EC (both available from Syngenta, Greensboro, N.C.) was performed.

Trials were conducted at a site with a history of weeds. The trials were executed under moderate weather conditions. Efficacy and visual phytotoxicity assessments were performed in triplicate. Normal practices were carried out to control insects and fungi. Crops were provided in 76 cm row width, at a sowing rate of 65,000 plants/ha, and at a sowing depth of five to eight cm. Soil class was clay with a clay content of about 35%. The site in this Example had been previously used for soya beans. Trial design was randomized blocks with a plot size of 20 m² replicated four times. Municipal water was used for all applications (pH=7.2).

Application of the treatments shown in Table 6-29 was conducted at pre emergence stage 1 day after planting seed. Application of the treatments was conducted over a 24 hour period. Over this time period, dry bulb temperature was about 26° C., wet bulb temperature was about 23° C., relative humidity was about 70%, cloud cover was about 50%, and wind speed was about 0 m/s. Treatments were administered with a multi-spray gas sprayer with a 4× flat fan 03F80 nozzle. Spacing was 50 cm, with a height of 50 cm, pressure 2.8 Bar, at a ground speed of 1 m/s, and a calibration mean output of 330 L/ha. The soil temperature over the application period averaged to about 24° C. and the soil remained moist and fine.

TABLE 6-29

Treatments

| No | Treatments | Dosage rate (gai/ha) | Dosage rate (g/ha or mL/ha) |
|---|---|---|---|
| | Untreated control | — | — |
| 1 | DINAMIC ® 700WDG + | 52.5 | 75 |
| | Galago 480SC | 48 | 100 |
| 2 | DINAMIC ® 700WDG + | 52.5 | 75 |
| | Galago 480SC | 72 | 150 |
| 3 | DINAMIC ® 700WDG + | 70 | 100 |
| | Galago 480SC | 48 | 100 |
| 4 | DINAMIC ® 700WDG + | 70 | 100 |
| | Galago 480SC | 72 | 150 |
| 5 | DINAMIC ® 700WDG + | 87.5 | 125 |
| | Galago 480SC | 48 | 100 |
| 6 | DINAMIC ® 700WDG + | 87.5 | 125 |
| | Galago 480SC | 72 | 150 |
| 7 | DINAMIC ® 700WDG + | 52.5 | 75 |
| | Galago 480SC + | 48 | 100 |
| | TOLLA 840S | 840 | 1000 |
| 8 | DINAMIC ® 700WDG + | 52.5 | 75 |
| | Galago 480SC + | 72 | 150 |
| | TOLLA 840S | 840 | 1000 |
| 9 | DINAMIC ® 700WDG + | 70 | 100 |
| | Galago 480SC + | 48 | 100 |
| | TOLLA 840S | 840 | 1000 |
| 10 | DINAMIC ® 700WDG + | 70 | 100 |
| | Galago 480SC + | 72 | 150 |
| | TOLLA 840S | 840 | 1000 |
| 11 | DINAMIC ® 700WDG + | 87.5 | 125 |
| | Galago 480SC + | 48 | 100 |
| | TOLLA 840S | 840 | 1000 |
| 12 | DINAMIC ® 700WDG + | 87.5 | 125 |
| | Galago 480SC + | 72 | 150 |
| | TOLLA 840S | 840 | 1000 |
| 13 | DINAMIC ® 700WDG + | 175 | 250 |
| | Galago 480SC + | 144 | 300 |
| | TOLLA 840S | 840 | 2000 |
| 14 | CALLISTO ® 480SC + | 124.8 | 260 |
| | DUAL S GOLD ® 915EC | 649.7 | 710 |

Assessments of the treated crops at 2, 4, and 6 weeks are summarized in Tables 6-23 to 6-25 below. No visual signs of phytotoxicity were noticed over the 6 weeks.

TABLE 6-30

2 Week Assessment

| | |
|---|---|
| Crop condition | Actively growing |
| Crop stage | 3-4 Leaves |
| BBCH scale | 13 |
| Soil moisture | Moist |
| Rain since last visit | 0 mm |

TABLE 6-31

4 Week Assessment

| | |
|---|---|
| Crop condition | Actively growing |
| Crop stage | 6 Leaves |
| BBCH scale | 16 |
| Soil moisture | Wet |
| Rain since last visit | 18 mm |

TABLE 6-32

6 Week Assessment

| | |
|---|---|
| Crop condition | Actively growing |
| Crop stage | 8 leaves |
| BBCH scale: | 18 |
| Soil moisture | Moist |
| Rain since last visit | 12 mm |

Control and weed cover at 2, 4, and 6 weeks for the indicated species are summarized below in Tables 6-33 through 6-35. 80% is considered acceptable control.

TABLE 6-33

% Control and weed cover (2 weeks after application)

| Treatments (product/ha) | | Rep | DIGSA | POROL | AMAHY | COMBE |
|---|---|---|---|---|---|---|
| | Untreated control | I | 30 | 20 | 30 | 20 |
| | % soil cover | ii | 40 | 10 | 20 | 30 |
| | | iii | 40 | 20 | 30 | 10 |
| | | iv | 30 | 20 | 30 | 20 |
| | Mean | | 35 | 18 | 28 | 20 |
| 1 | DINAMIC ® at 75 g | I | 70 | 60 | 70 | 70 |
| | Galago at 100 ml | ii | 80 | 70 | 90 | 90 |
| | | iii | 80 | 70 | 90 | 80 |
| | | iv | 70 | 60 | 80 | 80 |
| | Mean | | 75 | 65 | 83 | 80 |
| 2 | DINAMIC ® at 75 g | I | 80 | 70 | 70 | 70 |
| | Galago at 150 ml | ii | 80 | 70 | 90 | 70 |
| | | iii | 70 | 80 | 90 | 80 |
| | | iv | 70 | 70 | 90 | 80 |
| | Mean | | 75 | 73 | 85 | 75 |
| 3 | DINAMIC ® at 100 g | I | 70 | 70 | 80 | 80 |
| | Galago at 100 ml | ii | 80 | 80 | 90 | 90 |
| | | iii | 80 | 70 | 95 | 80 |
| | | iv | 80 | 70 | 90 | 80 |
| | Mean | | 78 | 73 | 89 | 83 |
| 4 | DINAMIC ® at 100 g | I | 80 | 80 | 95 | 95 |
| | Galago at 150 ml | ii | 90 | 80 | 90 | 95 |
| | | iii | 80 | 80 | 95 | 90 |
| | | iv | 90 | 70 | 95 | 95 |
| | Mean | | 85 | 78 | 94 | 94 |
| 5 | DINAMIC ® at 125 g | I | 80 | 70 | 90 | 90 |
| | Galago at 100 ml | ii | 80 | 80 | 90 | 80 |
| | | iii | 80 | 70 | 98 | 90 |
| | | iv | 80 | 70 | 95 | 95 |
| | Mean | | 80 | 73 | 93 | 89 |

TABLE 6-33-continued

% Control and weed cover (2 weeks after application)

| Treatments (product/ha) | | Rep | DIGSA | POROL | AMAHY | COMBE |
|---|---|---|---|---|---|---|
| 6 | DINAMIC ® at 125 g | I | 90 | 90 | 95 | 90 |
| | Galago at 150 ml | ii | 80 | 90 | 100 | 70 |
| | | iii | 90 | 90 | 95 | 80 |
| | | iv | 80 | 80 | 100 | 90 |
| | Mean | | 85 | 88 | 98 | 83 |
| 7 | DINAMIC ® at 75 g | I | 95 | 70 | 95 | 80 |
| | Galago at 100 ml | ii | 90 | 70 | 90 | 90 |
| | TOLLA at 1000 ml | iii | 90 | 70 | 90 | 95 |
| | | iv | 90 | 70 | 95 | 90 |
| | Mean | | 91 | 70 | 93 | 89 |
| 8 | DINAMIC ® at 75 g | I | 100 | 70 | 80 | 98 |
| | Galago at 150 ml | ii | 95 | 80 | 95 | 90 |
| | TOLLA at 1000 ml | iii | 95 | 70 | 90 | 95 |
| | | iv | 100 | 80 | 90 | 90 |
| | Mean | | 98 | 75 | 89 | 93 |
| 9 | DINAMIC ® at 100 g | I | 95 | 90 | 90 | 95 |
| | Galago at 100 ml | ii | 95 | 80 | 90 | 95 |
| | TOLLA at 1000 ml | iii | 100 | 90 | 100 | 90 |
| | | iv | 100 | 90 | 90 | 100 |
| | Mean | | 98 | 88 | 93 | 95 |
| 10 | DINAMIC ® at 100 g | I | 100 | 100 | 90 | 80 |
| | Galago at 150 ml | ii | 98 | 100 | 100 | 95 |
| | TOLLA at 1000 ml | iii | 100 | 100 | 100 | 90 |
| | | iv | 95 | 100 | 95 | 95 |
| | Mean | | 98 | 100 | 96 | 90 |
| 11 | DINAMIC ® at 125 g | I | 100 | 100 | 90 | 95 |
| | Galago at 100 ml | ii | 100 | 100 | 100 | 98 |
| | TOLLA at 1000 ml | iii | 95 | 100 | 95 | 90 |
| | | iv | 98 | 100 | 100 | 100 |
| | Mean | | 98 | 100 | 96 | 96 |
| 12 | DINAMIC ® at 125 g | I | 100 | 100 | 90 | 80 |
| | Galago at 150 ml | ii | 100 | 100 | 100 | 90 |
| | TOLLA at 1000 ml | iii | 100 | 100 | 100 | 90 |
| | | iv | 100 | 100 | 100 | 90 |
| | Mean | | 100 | 100 | 98 | 88 |
| 13 | DINAMIC ® at 250 g | I | 100 | 100 | 100 | 90 |
| | Galago at 300 ml | ii | 100 | 100 | 100 | 100 |
| | TOLLA at 2000 ml | iii | 100 | 100 | 90 | 100 |
| | | iv | 100 | 100 | 100 | 100 |
| | Mean | | 100 | 100 | 98 | 98 |
| 14 | Calisto at 260 ml | I | 100 | 90 | 90 | 90 |
| | DUAL S GOLD ® | ii | 100 | 90 | 95 | 95 |
| | at 710 ml | iii | 100 | 80 | 100 | 90 |
| | | iv | 100 | 90 | 100 | 95 |
| | Mean | | 100 | 88 | 96 | 93 |

DIGSA = *Digitaria sanguinalis*;
POROL = *Portulaca oleracea*;
AMAHY = *Amaranthus hybridus*;
COMBE = *Commelina benghalensis*

TABLE 6-34

% Control and weed cover (4 weeks after application)

| Treatments (product/ha) | | Rep | DIGSA | POROL | AMAHY | COMBE |
|---|---|---|---|---|---|---|
| | Untreated control | I | 30 | 20 | 30 | 20 |
| | % soil cover | ii | 40 | 10 | 20 | 30 |
| | | iii | 40 | 20 | 30 | 10 |
| | | iv | 30 | 20 | 30 | 20 |
| | Mean | | 35 | 18 | 28 | 20 |
| 1 | DINAMIC ® at 75 g | I | 70 | 70 | 60 | 70 |
| | Galago at 100 ml | ii | 70 | 70 | 60 | 70 |
| | | iii | 70 | 70 | 70 | 70 |
| | | iv | 80 | 70 | 60 | 80 |
| | Mean | | 73 | 70 | 63 | 73 |
| 2 | DINAMIC ® at 75 g | I | 70 | 70 | 70 | 80 |
| | Galago at 150 ml | ii | 70 | 80 | 70 | 70 |
| | | iii | 80 | 80 | 60 | 70 |
| | | iv | 70 | 70 | 70 | 80 |
| | Mean | | 73 | 75 | 68 | 75 |

TABLE 6-34-continued

% Control and weed cover (4 weeks after application)

| Treatments (product/ha) | Rep | DIGSA | POROL | AMAHY | COMBE |
|---|---|---|---|---|---|
| 3 DINAMIC ® at 100 g | I | 80 | 70 | 70 | 70 |
| Galago at 100 ml | ii | 80 | 80 | 70 | 80 |
| | iii | 80 | 80 | 70 | 80 |
| | iv | 80 | 80 | 70 | 80 |
| Mean | | 80 | 78 | 70 | 78 |
| 4 DINAMIC ® at 100 g | I | 90 | 80 | 70 | 80 |
| Galago at 150 ml | ii | 90 | 80 | 80 | 70 |
| | iii | 95 | 70 | 70 | 80 |
| | iv | 90 | 80 | 70 | 90 |
| Mean | | 91 | 78 | 73 | 80 |
| 5 DINAMIC ® at 125 g | I | 100 | 90 | 100 | 90 |
| Galago at 100 ml | ii | 90 | 95 | 95 | 90 |
| | iii | 95 | 100 | 100 | 90 |
| | iv | 100 | 100 | 100 | 90 |
| Mean | | 96 | 96 | 99 | 90 |
| 6 DINAMIC ® at 125 g | I | 100 | 80 | 90 | 90 |
| Galago at 150 ml | ii | 95 | 90 | 90 | 80 |
| | iii | 90 | 80 | 90 | 80 |
| | iv | 100 | 80 | 90 | 90 |
| Mean | | 96 | 83 | 90 | 85 |
| 7 DINAMIC ® at 75 g | I | 100 | 100 | 80 | 95 |
| Galago at 100 ml | ii | 100 | 100 | 70 | 95 |
| TOLLA at 1000 ml | iii | 100 | 100 | 80 | 98 |
| | iv | 100 | 100 | 80 | 95 |
| Mean | | 100 | 100 | 78 | 96 |
| 8 DINAMIC ® at 75 g | I | 100 | 100 | 80 | 100 |
| Galago at 150 ml | ii | 98 | 100 | 80 | 98 |
| TOLLA at 1000 ml | iii | 100 | 100 | 80 | 100 |
| | iv | 100 | 100 | 80 | 98 |
| Mean | | 100 | 100 | 80 | 99 |
| 9 DINAMIC ® at 100 g | I | 100 | 100 | 95 | 98 |
| Galago at 100 ml | ii | 100 | 100 | 80 | 98 |
| TOLLA at 1000 ml | iii | 100 | 100 | 90 | 95 |
| | iv | 100 | 100 | 80 | 100 |
| Mean | | 100 | 100 | 86 | 98 |
| 10 DINAMIC ® at 100 g | I | 100 | 100 | 80 | 95 |
| Galago at 150 ml | ii | 98 | 100 | 90 | 98 |
| TOLLA at 1000 ml | iii | 100 | 100 | 80 | 98 |
| | iv | 100 | 100 | 80 | 100 |
| Mean | | 100 | 100 | 83 | 98 |
| 11 DINAMIC ® at 125 g | I | 100 | 100 | 98 | 100 |
| Galago at 100 ml | ii | 100 | 100 | 100 | 100 |
| TOLLA at 1000 ml | iii | 100 | 100 | 95 | 100 |
| | iv | 100 | 100 | 100 | 100 |
| Mean | | 100 | 100 | 98 | 100 |
| 12 DINAMIC ® at 125 g | I | 100 | 100 | 98 | 100 |
| Galago at 150 ml | ii | 100 | 100 | 100 | 100 |
| TOLLA at 1000 ml | iii | 100 | 100 | 100 | 100 |
| | iv | 100 | 100 | 100 | 100 |
| Mean | | 100 | 100 | 100 | 100 |
| 13 DINAMIC ® at 250 g | I | 100 | 100 | 100 | 100 |
| Galago at 300 ml | ii | 100 | 100 | 100 | 100 |
| TOLLA at 2000 ml | iii | 100 | 100 | 100 | 100 |
| | iv | 100 | 100 | 100 | 100 |
| Mean | | 100 | 100 | 100 | 100 |
| 14 Calisto at 260 ml | I | 100 | 100 | 100 | 100 |
| DUAL S GOLD ® at 710 ml | ii | 100 | 100 | 100 | 100 |
| | iii | 100 | 100 | 95 | 100 |
| | iv | 100 | 100 | 90 | 100 |
| Mean | | 100 | 100 | 96 | 100 |

DIGSA = *Digitaria sanguinalis*; POROL = *Portulaca oleracea*; AMAHY = *Amaranthus hybridus*; COMBE = *Commelina benghalensis*

TABLE 6-35

% Control and weed cover (6 weeks after application)

| Treatments (product/ha) | Rep | DIGSA | POROL | AMAHY | COMBE |
|---|---|---|---|---|---|
| Untreated control | I | 30 | 20 | 30 | 20 |
| % soil cover | ii | 40 | 10 | 20 | 30 |
| | iii | 40 | 20 | 30 | 10 |
| | iv | 30 | 20 | 30 | 20 |
| Mean | | 35 | 18 | 28 | 20 |
| 1 DINAMIC ® at 75 g | I | 70 | 60 | 60 | 70 |
| Galago at 100 ml | ii | 60 | 70 | 50 | 70 |
| | iii | 60 | 70 | 60 | 60 |
| | iv | 70 | 60 | 60 | 70 |
| Mean | | 65 | 65 | 58 | 68 |
| 2 DINAMIC ® at 75 g | I | 60 | 70 | 70 | 70 |
| Galago at 150 ml | ii | 70 | 70 | 60 | 70 |
| | iii | 70 | 70 | 50 | 70 |
| | iv | 60 | 60 | 70 | 80 |
| Mean | | 65 | 68 | 63 | 73 |
| 3 DINAMIC ® at 100 g | I | 70 | 70 | 60 | 70 |
| Galago at 100 ml | ii | 70 | 70 | 70 | 70 |
| | iii | 80 | 80 | 70 | 80 |
| | iv | 70 | 70 | 60 | 80 |
| Mean | | 73 | 73 | 65 | 75 |
| 4 DINAMIC ® at 100 g | I | 80 | 70 | 70 | 80 |
| Galago at 150 ml | ii | 90 | 80 | 70 | 70 |
| | iii | 90 | 70 | 60 | 80 |
| | iv | 90 | 80 | 70 | 80 |
| Mean | | 88 | 75 | 68 | 78 |
| 5 DINAMIC ® at 125 g | I | 98 | 90 | 100 | 90 |
| Galago at 100 ml | ii | 90 | 90 | 95 | 80 |
| | iii | 90 | 100 | 98 | 90 |
| | iv | 100 | 98 | 98 | 90 |
| Mean | | 95 | 95 | 98 | 88 |
| 6 DINAMIC ® at 125 g | I | 98 | 80 | 90 | 90 |
| Galago at 150 ml | ii | 95 | 90 | 95 | 80 |
| | iii | 90 | 80 | 95 | 80 |
| | iv | 98 | 90 | 90 | 90 |
| Mean | | 95 | 85 | 93 | 85 |
| 7 DINAMIC ® at 75 g | I | 100 | 100 | 70 | 95 |
| Galago at 100 ml | ii | 100 | 100 | 60 | 90 |
| TOLLA at 1000 ml | iii | 100 | 100 | 70 | 95 |
| | iv | 100 | 100 | 70 | 95 |
| Mean | | 100 | 100 | 68 | 94 |
| 8 DINAMIC ® at 75 g | I | 100 | 100 | 70 | 100 |
| Galago at 150 ml | ii | 100 | 100 | 80 | 100 |
| TOLLA at 1000 ml | iii | 100 | 100 | 70 | 100 |
| | iv | 100 | 100 | 70 | 98 |
| Mean | | 100 | 100 | 73 | 100 |
| 9 DINAMIC ® at 100 g | I | 100 | 100 | 90 | 100 |
| Galago at 100 ml | ii | 100 | 100 | 80 | 100 |
| TOLLA at 1000 ml | iii | 100 | 100 | 80 | 98 |
| | iv | 100 | 100 | 80 | 100 |
| Mean | | 100 | 100 | 83 | 100 |
| 10 DINAMIC ® at 100 g | I | 100 | 100 | 80 | 98 |
| Galago at 150 ml | ii | 98 | 100 | 90 | 100 |
| TOLLA at 1000 ml | iii | 100 | 100 | 90 | 100 |
| | iv | 100 | 100 | 80 | 100 |
| Mean | | 100 | 100 | 85 | 100 |
| 11 DINAMIC ® at 125 g | I | 100 | 100 | 100 | 100 |
| Galago at 100 ml | ii | 100 | 100 | 100 | 100 |
| TOLLA at 1000 ml | iii | 100 | 100 | 98 | 100 |
| | iv | 100 | 100 | 100 | 100 |
| Mean | | 100 | 100 | 100 | 100 |
| 12 DINAMIC ® at 125 g | I | 100 | 100 | 100 | 100 |
| Galago at 150 ml | ii | 100 | 100 | 100 | 100 |
| TOLLA at 1000 ml | iii | 100 | 100 | 100 | 100 |
| | iv | 100 | 100 | 100 | 100 |
| Mean | | 100 | 100 | 100 | 100 |
| 13 DINAMIC ® at 250 g | I | 100 | 100 | 100 | 100 |
| Galago at 300 ml | ii | 100 | 100 | 100 | 100 |
| TOLLA at 2000 ml | iii | 100 | 100 | 100 | 100 |
| | iv | 100 | 100 | 100 | 100 |
| Mean | | 100 | 100 | 100 | 100 |

TABLE 6-35-continued

% Control and weed cover (6 weeks after application)

| Treatments (product/ha) | Rep | DIGSA | POROL | AMAHY | COMBE |
|---|---|---|---|---|---|
| 14 Calisto at 260 ml DUAL S GOLD ® at 710 ml | I | 100 | 100 | 100 | 100 |
| | ii | 100 | 100 | 100 | 100 |
| | iii | 100 | 100 | 95 | 100 |
| | iv | 100 | 100 | 95 | 100 |
| Mean | | 100 | 100 | 98 | 100 |

DIGSA = *Digitaria sanguinalis*; POROL = *Portulaca oleracea*; AMAHY = *Amaranthus hybridus*; COMBE = *Commelina benghalensis*

DINAMIC® 700WDG at 125 g/ha+Galago 480SC at 100 mL/ha showed satisfactory control of *Digitaria sanguinalis, Portulaca oleracea, Amaranthus hybridus* and *Commilina benghalensis*. This combination compared favorably with the standard CALLISTO® at 260 mL/ha+DUAL S GOLD® at 710 mL/ha. The addition of TOLLA improved the efficacy of the DINAMIC®+Galago mixture. DINAMIC® 700WDG at 100 g/ha+Galago 480SC at 100 mL/ha+TOLLA 840S at 1000 mL/ha resulted in 100% control of *Digitaria sanguinalis, Portulaca oleracea* and *Commilina benghalensis*, and satisfactory control of *Amaranthus hybridus*. This combination compared favorably with the standard CALLISTO® at 260 mL/ha+DUAL S GOLD® at 710 mL/ha. No visual signs of phytotoxicity were noticed throughout the growing season. DINAMIC® 700WDG at 125 g/ha+Galago 480SC at 100 mL/ha can be used to control *Digitaria sanguinalis, Portulaca oleracea, Amaranthus hybridus* and *Commilina benghalensis*. DINAMIC® 700WDG at 100 g/ha+Galago 480SC at 100 mL/ha+TOLLA 840S at 1000 mL/ha can be used to control *Digitaria sanguinalis, Portulaca oleracea, Amaranthus hybridus* and *Commilina benghalensis*.

F. Pre Emergence Application Against Weed in Maize

In this part of the Example the efficacy of DINAMIC® (amicarbazone 700WDG, 700 grams active/kg, available from Arysta LifeScience North America, Cary, N.C.) mixtures with Galago (mesotrione 480SC, 480 grams active/L, available from Arysta LifeScience North America, Cary, N.C.) or TOLLA 840 S (available from Volanco Agroscience, Mt. Edgecombe, South Africa) as a pre emergence application against weeds in maize (variety PAN60-445B) was determined. A comparison with CALLISTO® 480SC plus DUAL S GOLD® 915EC (both available from Syngenta, Greensboro, N.C.) was performed.

Trials were conducted at a site with a history of weeds. The trials were executed under moderate weather conditions. Efficacy and visual phytotoxicity assessments were performed in triplicate. Normal practices were carried out to control insects and fungi. Crops were provided in 76 cm row width, at a sowing rate of 65,000 plants/ha, and at a sowing depth of five to eight cm. Soil class was clay with a clay content of about 28%. The site in this Example had been previously used for soya beans. Trial design was randomized blocks with a plot size of 20 m² replicated four times. Municipal water was used for all applications (pH=7.2).

Application of the treatments shown in Table 6-29 was conducted at pre emergence stage 3 days after planting seed. Application of the treatments was conducted over a 24 hour period. Over this time period, dry bulb temperature was about 22° C., wet bulb temperature was about 18° C., relative humidity was about 65%, cloud cover was about 30%, and wind speed was about 0 m/s. Treatments were administered with a multi-spray gas sprayer with a 4× flat fan 03F80 nozzle. Spacing was 50 cm, with a height of 50 cm, pressure 2.8 Bar, at a ground speed of 1 m/s, and a calibration mean output of 330 L/ha. The soil temperature over the application period averaged to about 22° C. and the soil remained moist and fine.

TABLE 6-36

| No | Treatments | Dosage rate (gai/ha) | Dosage rate (g/ha or mL/ha) |
|---|---|---|---|
| | Untreated control | — | — |
| 1 | DINAMIC ® 700WDG + | 52.5 | 75 |
| | Galago 480SC | 48 | 100 |
| 2 | DINAMIC ® 700WDG + | 52.5 | 75 |
| | Galago 480SC | 72 | 150 |
| 3 | DINAMIC ® 700WDG + | 70 | 100 |
| | Galago 480SC | 48 | 100 |
| 4 | DINAMIC ® 700WDG + | 70 | 100 |
| | Galago 480SC | 72 | 150 |
| 5 | DINAMIC ® 700WDG + | 87.5 | 125 |
| | Galago 480SC | 48 | 100 |
| 6 | DINAMIC ® 700WDG + | 87.5 | 125 |
| | Galago 480SC | 72 | 150 |
| 7 | DINAMIC ® 700WDG + | 52.5 | 75 |
| | Galago 480SC + | 48 | 100 |
| | TOLLA 840S | 840 | 1000 |
| 8 | DINAMIC ® 700WDG + | 52.5 | 75 |
| | Galago 480SC + | 72 | 150 |
| | TOLLA 840S | 840 | 1000 |
| 9 | DINAMIC ® 700WDG + | 70 | 100 |
| | Galago 480SC + | 48 | 100 |
| | TOLLA 840S | 840 | 1000 |
| 10 | DINAMIC ® 700WDG + | 70 | 100 |
| | Galago 480SC + | 72 | 150 |
| | TOLLA 840S | 840 | 1000 |
| 11 | DINAMIC ® 700WDG + | 87.5 | 125 |
| | Galago 480SC + | 48 | 100 |
| | TOLLA 840S | 840 | 1000 |
| 12 | DINAMIC ® 700WDG + | 87.5 | 125 |
| | Galago 480SC + | 72 | 150 |
| | TOLLA 840S | 840 | 1000 |
| 13 | DINAMIC ® 700WDG + | 175 | 250 |
| | Galago 480SC + | 144 | 300 |
| | TOLLA 840S | 840 | 2000 |
| 14 | CALLISTO ® 480SC + | 124.8 | 260 |
| | DUAL S GOLD ® 915EC | 649.7 | 710 |

Assessments of the treated crops at 2, 4, and 6 weeks are summarized in Tables 6-37 to 6-39 below. No visual signs of phytotoxicity were noticed over the 6 weeks.

TABLE 6-37

2 Week Assessment

| | |
|---|---|
| Crop condition | Actively growing |
| Crop stage | 3 Leaves |
| BBCH scale | 13 |
| Soil moisture | Moist |
| Rain since last visit | 16 mm |

TABLE 6-38

4 Week Assessment

| | |
|---|---|
| Crop condition | Actively growing |
| Crop stage | 5 Leaves |
| BBCH scale | 15 |
| Soil moisture | Wet |
| Rain since last visit | 30 mm |

TABLE 6-39

| 6 Week Assessment | |
|---|---|
| Crop condition | Actively growing |
| Crop stage | 8 leaves |
| BBCH scale: | 18 |
| Soil moisture | Moist |
| Rain since last visit | 22 mm |

Control and weed cover at 2, 4, and 6 weeks for the indicated species are summarized below in Tables 6-40 through 6-42. 80% is considered acceptable control.

TABLE 6-40

% Control and weed cover (2 weeks after application)

| Treatments (product/ha) | Rep | AMASP | ELEIN | IPOPU | COMBE |
|---|---|---|---|---|---|
| Untreated control | I | 30 | 20 | 30 | 20 |
| % soil cover | ii | 40 | 10 | 20 | 30 |
| | iii | 40 | 20 | 30 | 10 |
| | iv | 30 | 20 | 30 | 20 |
| Mean | | 35 | 18 | 28 | 20 |
| DINAMIC ® at 75 g | I | 80 | 80 | 70 | 80 |
| Galago at 100 ml | ii | 80 | 80 | 70 | 70 |
| | iii | 80 | 80 | 70 | 70 |
| | iv | 80 | 70 | 60 | 80 |
| Mean | | 80 | 78 | 68 | 75 |
| DINAMIC ® at 75 g | I | 80 | 80 | 80 | 80 |
| Galago at 150 ml | ii | 80 | 80 | 70 | 80 |
| | iii | 80 | 80 | 70 | 80 |
| | iv | 80 | 80 | 70 | 80 |
| Mean | | 80 | 80 | 73 | 80 |
| DINAMIC ® at 100 g | I | 90 | 80 | 80 | 80 |
| Galago at 100 ml | ii | 80 | 90 | 70 | 80 |
| | iii | 90 | 90 | 80 | 80 |
| | iv | 80 | 80 | 70 | 80 |
| Mean | | 85 | 85 | 75 | 80 |
| DINAMIC ® at 100 g | I | 95 | 90 | 80 | 90 |
| Galago at 150 ml | ii | 95 | 80 | 80 | 80 |
| | iii | 95 | 80 | 70 | 90 |
| | iv | 90 | 80 | 80 | 90 |
| Mean | | 94 | 83 | 78 | 88 |
| DINAMIC ® at 125 g | I | 100 | 95 | 100 | 95 |
| Galago at 100 ml | ii | 95 | 95 | 98 | 90 |
| | iii | 95 | 100 | 100 | 90 |
| | iv | 100 | 100 | 100 | 90 |
| Mean | | 98 | 98 | 100 | 91 |
| DINAMIC ® at 125 g | I | 100 | 90 | 95 | 90 |
| Galago at 150 ml | ii | 95 | 90 | 90 | 90 |
| | iii | 95 | 80 | 90 | 80 |
| | iv | 100 | 80 | 95 | 90 |
| Mean | | 98 | 85 | 93 | 88 |
| DINAMIC ® at 75 g | I | 100 | 100 | 90 | 95 |
| Galago at 100 ml | ii | 100 | 100 | 80 | 95 |
| TOLLA at 1000 ml | iii | 100 | 98 | 80 | 100 |
| | iv | 100 | 100 | 90 | 95 |
| Mean | | 100 | 100 | 85 | 96 |
| DINAMIC ® at 75 g | I | 100 | 100 | 90 | 100 |
| Galago at 150 ml | ii | 98 | 100 | 90 | 98 |
| TOLLA at 1000 ml | iii | 100 | 100 | 90 | 98 |
| | iv | 100 | 100 | 90 | 98 |
| Mean | | 100 | 100 | 90 | 99 |
| DINAMIC ® at 100 g | I | 100 | 100 | 100 | 95 |
| Galago at 100 ml | ii | 100 | 100 | 90 | 98 |
| TOLLA at 1000 ml | iii | 100 | 100 | 90 | 98 |
| | iv | 100 | 100 | 95 | 100 |
| Mean | | 100 | 100 | 94 | 98 |
| DINAMIC ® at 100 g | I | 98 | 100 | 90 | 95 |
| Galago at 150 ml | ii | 98 | 100 | 90 | 95 |
| TOLLA at 1000 ml | iii | 100 | 100 | 90 | 100 |
| | iv | 100 | 100 | 90 | 100 |
| Mean | | 99 | 100 | 90 | 98 |

TABLE 6-40-continued

% Control and weed cover (2 weeks after application)

| Treatments (product/ha) | Rep | AMASP | ELEIN | IPOPU | COMBE |
|---|---|---|---|---|---|
| DINAMIC ® at 125 g | I | 100 | 100 | 95 | 100 |
| Galago at 100 ml | ii | 100 | 100 | 98 | 100 |
| TOLLA at 1000 ml | iii | 100 | 100 | 95 | 100 |
| | iv | 100 | 100 | 98 | 100 |
| Mean | | 100 | 100 | 97 | 100 |
| DINAMIC ® at 125 g | I | 100 | 100 | 95 | 100 |
| Galago at 150 ml | ii | 100 | 100 | 98 | 100 |
| TOLLA at 1000 ml | iii | 100 | 100 | 98 | 100 |
| | iv | 100 | 100 | 98 | 100 |
| Mean | | 100 | 100 | 97 | 100 |
| DINAMIC ® at 250 g | I | 100 | 100 | 100 | 100 |
| Galago at 300 ml | ii | 100 | 100 | 100 | 100 |
| TOLLA at 2000 ml | iii | 100 | 100 | 100 | 100 |
| | iv | 100 | 100 | 100 | 100 |
| Mean | | 100 | 100 | 100 | 100 |
| Calisto at 260 ml | I | 100 | 100 | 100 | 100 |
| DUAL S GOLD ® at 710 ml | ii | 100 | 100 | 100 | 100 |
| | iii | 100 | 100 | 90 | 100 |
| | iv | 100 | 100 | 90 | 100 |
| Mean | | 100 | 100 | 95 | 100 |

AMASP = *Amaranthus spinosus*; COMBE = *Commelina benghalensis*; IPOPU = *Ipomoea purpurea*; ELEIN = *Eleusine indica*

TABLE 6-41

% Control and weed cover (4 weeks after application)

| | Treatments (product/ha) | Rep | AMASP | ELEIN | IPOPU | COMBE |
|---|---|---|---|---|---|---|
| | Untreated control | I | 30 | 20 | 30 | 20 |
| | % soil cover | ii | 40 | 10 | 20 | 30 |
| | | iii | 40 | 20 | 30 | 10 |
| | | iv | 30 | 20 | 30 | 20 |
| | Mean | | 35 | 18 | 28 | 20 |
| 1 | DINAMIC ® at 75 g | I | 70 | 70 | 60 | 70 |
| | Galago at 100 ml | ii | 70 | 70 | 60 | 70 |
| | | iii | 70 | 70 | 70 | 70 |
| | | iv | 80 | 70 | 60 | 80 |
| | Mean | | 73 | 70 | 63 | 73 |
| 2 | DINAMIC ® at 75 g | I | 70 | 70 | 70 | 80 |
| | Galago at 150 ml | ii | 70 | 80 | 70 | 70 |
| | | iii | 80 | 80 | 60 | 70 |
| | | iv | 70 | 70 | 70 | 80 |
| | Mean | | 73 | 75 | 68 | 75 |
| 3 | DINAMIC ® at 100 g | I | 80 | 70 | 70 | 70 |
| | Galago at 100 ml | ii | 80 | 80 | 70 | 80 |
| | | iii | 80 | 80 | 70 | 80 |
| | | iv | 80 | 80 | 70 | 80 |
| | Mean | | 80 | 78 | 70 | 78 |
| 4 | DINAMIC ® at 100 g | I | 90 | 80 | 70 | 80 |
| | Galago at 150 ml | ii | 90 | 80 | 80 | 70 |
| | | iii | 95 | 70 | 70 | 80 |
| | | iv | 90 | 80 | 70 | 90 |
| | Mean | | 91 | 78 | 73 | 80 |
| 5 | DINAMIC ® at 125 g | I | 100 | 90 | 100 | 90 |
| | Galago at 100 ml | ii | 90 | 95 | 95 | 90 |
| | | iii | 95 | 100 | 100 | 90 |
| | | iv | 100 | 100 | 100 | 90 |
| | Mean | | 96 | 96 | 99 | 90 |
| 6 | DINAMIC ® at 125 g | I | 100 | 80 | 90 | 90 |
| | Galago at 150 ml | ii | 95 | 90 | 90 | 80 |
| | | iii | 90 | 80 | 90 | 80 |
| | | iv | 100 | 80 | 90 | 90 |
| | Mean | | 96 | 83 | 90 | 85 |
| 7 | DINAMIC ® at 75 g | I | 100 | 100 | 80 | 95 |
| | Galago at 100 ml | ii | 100 | 100 | 70 | 95 |
| | TOLLA at 1000 ml | iii | 100 | 100 | 80 | 98 |
| | | iv | 100 | 100 | 80 | 95 |
| | Mean | | 100 | 100 | 78 | 96 |

TABLE 6-41-continued

% Control and weed cover (4 weeks after application)

| Treatments (product/ha) | | Rep | AMASP | ELEIN | IPOPU | COMBE |
|---|---|---|---|---|---|---|
| 8 | DINAMIC ® at 75 g | I | 100 | 100 | 80 | 100 |
| | Galago at 150 ml | ii | 98 | 100 | 80 | 98 |
| | TOLLA at 1000 ml | iii | 100 | 100 | 80 | 100 |
| | | iv | 100 | 100 | 80 | 98 |
| | Mean | | 100 | 100 | 80 | 99 |
| 9 | DINAMIC ® at 100 g | I | 100 | 100 | 95 | 98 |
| | Galago at 100 ml | ii | 100 | 100 | 80 | 98 |
| | TOLLA at 1000 ml | iii | 100 | 100 | 90 | 95 |
| | | iv | 100 | 100 | 80 | 100 |
| | Mean | | 100 | 100 | 86 | 98 |
| 10 | DINAMIC ® at 100 g | I | 100 | 100 | 80 | 95 |
| | Galago at 150 ml | ii | 98 | 100 | 90 | 98 |
| | TOLLA at 1000 ml | iii | 100 | 100 | 80 | 98 |
| | | iv | 100 | 100 | 80 | 100 |
| | Mean | | 100 | 100 | 83 | 98 |
| 11 | DINAMIC ® at 125 g | I | 100 | 100 | 98 | 100 |
| | Galago at 100 ml | ii | 100 | 100 | 100 | 100 |
| | TOLLA at 1000 ml | iii | 100 | 100 | 95 | 100 |
| | | iv | 100 | 100 | 100 | 100 |
| | Mean | | 100 | 100 | 98 | 100 |
| 12 | DINAMIC ® at 125 g | I | 100 | 100 | 98 | 100 |
| | Galago at 150 ml | ii | 100 | 100 | 100 | 100 |
| | TOLLA at 1000 ml | iii | 100 | 100 | 100 | 100 |
| | | iv | 100 | 100 | 100 | 100 |
| | Mean | | 100 | 100 | 100 | 100 |
| 13 | DINAMIC ® at 250 g | I | 100 | 100 | 100 | 100 |
| | Galago at 300 ml | ii | 100 | 100 | 100 | 100 |
| | TOLLA at 2000 ml | iii | 100 | 100 | 100 | 100 |
| | | iv | 100 | 100 | 100 | 100 |
| | Mean | | 100 | 100 | 100 | 100 |
| 14 | Calisto at 260 ml | I | 100 | 100 | 100 | 100 |
| | DUAL S GOLD ® at 710 ml | ii | 100 | 100 | 100 | 100 |
| | | iii | 100 | 100 | 95 | 100 |
| | | iv | 100 | 100 | 90 | 100 |
| | Mean | | 100 | 100 | 96 | 100 |

AMASP = *Amaranthus spinosus*; COMBE = *Commelina benghalensis*; IPOPU= *Ipomoea purpurea*; ELEIN = *Eleusine indica*

TABLE 6-42

% Control and weed cover (6 weeks after application)

| | | | AMASP | ELEIN | IPOPU | COMBE |
|---|---|---|---|---|---|---|
| | | iii | 40 | 20 | 30 | 10 |
| | | iv | 30 | 20 | 30 | 20 |
| | Mean | | 35 | 18 | 28 | 20 |
| 1 | DINAMIC ® at 75 g | I | 70 | 60 | 60 | 70 |
| | Galago at 100 ml | ii | 60 | 70 | 50 | 70 |
| | | iii | 60 | 70 | 60 | 60 |
| | | iv | 70 | 60 | 60 | 70 |
| | Mean | | 65 | 65 | 58 | 68 |
| 2 | DINAMIC ® at 75 g | I | 60 | 70 | 70 | 70 |
| | Galago at 150 ml | ii | 70 | 70 | 60 | 70 |
| | | iii | 70 | 70 | 50 | 70 |
| | | iv | 60 | 60 | 70 | 80 |
| | Mean | | 65 | 68 | 63 | 73 |
| 3 | DINAMIC ® at 100 g | I | 70 | 70 | 60 | 70 |
| | Galago at 100 ml | ii | 70 | 70 | 70 | 70 |
| | | iii | 80 | 80 | 70 | 80 |
| | | iv | 70 | 70 | 60 | 80 |
| | Mean | | 73 | 73 | 65 | 75 |
| 4 | DINAMIC ® at 100 g | I | 80 | 70 | 70 | 80 |
| | Galago at 150 ml | ii | 90 | 80 | 70 | 70 |
| | | iii | 90 | 70 | 60 | 80 |
| | | iv | 90 | 80 | 70 | 80 |
| | Mean | | 88 | 75 | 68 | 78 |
| 5 | DINAMIC ® at 125 g | I | 98 | 90 | 100 | 90 |
| | Galago at 100 ml | ii | 90 | 90 | 95 | 80 |
| | | iii | 90 | 100 | 98 | 90 |
| | | iv | 100 | 98 | 98 | 90 |
| | Mean | | 95 | 95 | 98 | 88 |
| 6 | DINAMIC ® at 125 g | I | 98 | 80 | 90 | 90 |
| | Galago at 150 ml | ii | 95 | 90 | 95 | 80 |
| | | iii | 90 | 80 | 95 | 80 |
| | | iv | 98 | 90 | 90 | 90 |
| | Mean | | 95 | 85 | 93 | 85 |
| 7 | DINAMIC ® at 75 g | I | 100 | 100 | 70 | 95 |
| | Galago at 100 ml | ii | 100 | 100 | 60 | 90 |
| | TOLLA at 1000 ml | iii | 100 | 100 | 70 | 95 |
| | | iv | 100 | 100 | 70 | 95 |
| | Mean | | 100 | 100 | 68 | 94 |
| 8 | DINAMIC ® at 75 g | I | 100 | 100 | 70 | 100 |
| | Galago at 150 ml | ii | 100 | 100 | 80 | 100 |
| | TOLLA at 1000 ml | iii | 100 | 100 | 70 | 100 |
| | | iv | 100 | 100 | 70 | 98 |
| | Mean | | 100 | 100 | 73 | 100 |
| 9 | DINAMIC ® at 100 g | I | 100 | 100 | 90 | 100 |
| | Galago at 100 ml | ii | 100 | 100 | 80 | 100 |
| | TOLLA at 1000 ml | iii | 100 | 100 | 80 | 98 |
| | | iv | 100 | 100 | 80 | 100 |
| | Mean | | 100 | 100 | 83 | 100 |
| 10 | DINAMIC ® at 100 g | I | 100 | 100 | 80 | 98 |
| | Galago at 150 ml | ii | 98 | 100 | 90 | 100 |
| | TOLLA at 1000 ml | iii | 100 | 100 | 90 | 100 |
| | | iv | 100 | 100 | 80 | 100 |
| | Mean | | 100 | 100 | 85 | 100 |
| 11 | DINAMIC ® at 125 g | I | 100 | 100 | 100 | 100 |
| | Galago at 100 ml | ii | 100 | 100 | 100 | 100 |
| | TOLLA at 1000 ml | iii | 100 | 100 | 98 | 100 |
| | | iv | 100 | 100 | 100 | 100 |
| | Mean | | 100 | 100 | 100 | 100 |
| 12 | DINAMIC ® at 125 g | I | 100 | 100 | 100 | 100 |
| | Galago at 150 ml | ii | 100 | 100 | 100 | 100 |
| | TOLLA at 1000 ml | iii | 100 | 100 | 100 | 100 |
| | | iv | 100 | 100 | 100 | 100 |
| | Mean | | 100 | 100 | 100 | 100 |
| 13 | DINAMIC ® at 250 g | I | 100 | 100 | 100 | 100 |
| | Galago at 300 ml | ii | 100 | 100 | 100 | 100 |
| | TOLLA at 2000 ml | iii | 100 | 100 | 100 | 100 |
| | | iv | 100 | 100 | 100 | 100 |
| | Mean | | 100 | 100 | 100 | 100 |
| 14 | Calisto at 260 ml | I | 100 | 100 | 100 | 100 |
| | DUAL S GOLD ® at 710 ml | ii | 100 | 100 | 100 | 100 |
| | | iii | 100 | 100 | 95 | 100 |
| | | iv | 100 | 100 | 95 | 100 |
| | Mean | | 100 | 100 | 98 | 100 |

AMASP = *Amaranthus spinosus*; COMBE = *Commelina benghalensis*; IPOPU= *Ipomoea purpurea*; ELEIN = *Eleusine indica*

DINAMIC® 700WDG at 125 g/ha+Galago 480SC at 100 mL/ha showed satisfactory control of *Amaranthus spinosus, Eleusine indica, Ipomoea purpurea* and *Commilina benghalensis*. The addition of TOLLA to the above mixture appears to be a good practice. DINAMIC® 700WDG at 75 g/ha+Galago 480SC at 100 mL/ha+TOLLA 840S at 1000 mL/ha performed excellently on *Amaranthus spinosus, Eleusine indica* and *Commilina benghalensis*. However to control *Ipomoea purpurea* the dosage rate of DINAMIC® has to be increased from 75 g/ha to 100 g/ha—this combination compared with the standard CALLISTO® at 260 mL/ha+DUAL S GOLD® at 710 mL/ha. No visual signs of phytotoxicity were noticed throughout the growing season. DINAMIC® 700WDG at 125 g/ha+Galago 480SC at 100 mL/ha can be used to control *Amaranthus spinosus, Eleusine indica, Ipomoea purpurea* and *Commilina benghalensis*. DINAMIC® 700WDG at 75 g/ha+Galago 480SC at 100 mL/ha+TOLLA 840S at 1000 mL/ha can be used to control *Amaranthus spinosus, Eleusine indica, Ipomoea purpurea* and *Commilina benghalensis*.

G. Post Emergence Application Against Weed in Maize

In this part of the Example the efficacy of DINAMIC® (amicarbazone 700WDG, 700 grams active/kg, available from Arysta LifeScience North America, Cary, N.C.) mixtures with Galago (mesotrione 480SC, 480 grams active/L, available from Arysta LifeScience North America, Cary, N.C.) with or without Wet-All (available from Arysta Life-Science North America, Cary, N.C.) as a post emergence application against weeds in maize (variety PHI 2369W) was determined.

Trials were conducted at a site with a history of weeds. The trials were executed under moderate weather conditions. Efficacy and visual phytotoxicity assessments were performed in triplicate. Normal practices were carried out to control insects and fungi. Crops were provided in 55 cm row width, at a sowing rate of 65,000 plants/ha, and at a sowing depth of five to eight cm. Soil class was clay with a clay content of about 40%. The site in this Example had been previously used for maize. Trial design was randomized blocks with a plot size of 20 m$^2$ replicated four times. Municipal water was used for all applications (pH=7.2).

Application of the treatments shown in Table 6-43 was conducted at post emergence stage 15 days after planting. Application of the treatments was conducted over a 24 hour period. Over this time period, dry bulb temperature was about 30° C., wet bulb temperature was about 24° C., relative humidity was about 55%, cloud cover was about 0%, and wind speed was about 0 m/s. Treatments were administered with a multi-spray gas sprayer with a 4× flat fan 03F80 nozzle. Spacing was 50 cm, with a height of 50 cm, pressure 2.8 Bar, at a ground speed of 1 m/s, and a calibration mean output of 330 L/ha. The soil temperature over the application period averaged to about 29° C. and the soil remained moist and fine. Crops stage at the outset was about 4 leaves with a BBCH scale of 14. Crop and weeds were actively growing. Weed stage was about 3-5 leaves.

TABLE 6-43

| | Treatments | | |
|---|---|---|---|
| No | Treatments | Dosage rate (gai/ha) | Dosage rate (g/ha or mL/ha) |
| | Untreated control | — | — |
| 1 | DINAMIC ® 700WDG + | 52.5 | 75 |
| | Galago 480SC | 48 | 100 |
| 2 | DINAMIC ® 700WDG + | 52.5 | 75 |
| | Galago 480SC | 72 | 150 |
| 3 | DINAMIC ® 700WDG + | 70 | 100 |
| | Galago 480SC | 48 | 100 |
| 4 | DINAMIC ® 700WDG + | 70 | 100 |
| | Galago 480SC | 72 | 150 |
| 5 | DINAMIC ® 700WDG + | 87.5 | 125 |
| | Galago 480SC | 48 | 100 |
| 6 | DINAMIC ® 700WDG + | 87.5 | 125 |
| | Galago 480SC | 72 | 150 |
| 7 | DINAMIC ® 700WDG + | 175 | 250 |
| | Galago 480SC + | 144 | 300 |
| | Wet-All | | |
| 8 | DINAMIC ® 700WDG + | 52.5 | 75 |
| | Galago 480SC + | 48 | 100 |
| | Wet-All | — | 0.1% |
| 9 | DINAMIC ® 700WDG + | 52.5 | 75 |
| | Galago 480SC + | 72 | 150 |
| | Wet-All | — | 0.1% |
| 10 | DINAMIC ® 700WDG + | 70 | 100 |
| | Galago 480SC + | 48 | 100 |
| | Wet-All | — | 0.1% |
| 11 | DINAMIC ® 700WDG + | 70 | 100 |
| | Galago 480SC + | 72 | 150 |
| | Wet-All | — | 0.1% |
| 12 | DINAMIC ® 700WDG + | 87.5 | 125 |
| | Galago 480SC + | 48 | 100 |
| | Wet-All | — | 0.1% |
| 13 | DINAMIC ® 700WDG + | 87.5 | 125 |
| | Galago 480SC + | 72 | 150 |
| | Wet-All | — | 0.1% |

TABLE 6-43-continued

| | Treatments | | |
|---|---|---|---|
| No | Treatments | Dosage rate (gai/ha) | Dosage rate (g/ha or mL/ha) |
| 14 | DINAMIC ® 700WDG + | 175 | 250 |
| | Galago 480SC + | 144 | 300 |
| | Wet-All | — | 0.1% |

Assessments of the treated crops at 2, 4, and 6 weeks are summarized in Tables 6-44 to 6-46 below. No visual signs of phytotoxicity were noticed over the first 2 weeks. Signs of phytotoxicity were noticed in treatment 14 at 4 week assessment. Signs of phytotoxicity were noticed in treatment 13 at 6 weeks.

TABLE 6-44

| 2 Week Assessment | |
|---|---|
| Crop condition | Actively growing |
| Crop stage | 5-6 Leaves |
| BBCH scale | 15-16 |
| Soil moisture | Wet |
| Rain since last visit | 18 mm |

TABLE 6-45

| 4 Week Assessment | |
|---|---|
| Crop condition | Actively growing |
| Crop stage | 8 Leaves |
| BBCH scale | 18 |
| Soil moisture | Wet |
| Rain since last visit | 38 mm |

TABLE 6-46

| 6 Week Assessment | |
|---|---|
| Crop condition | Actively growing |
| Crop stage | 10 leaves |
| BBCH scale: | 20 |
| Soil moisture | Moist |
| Rain since last visit | 0 mm |

Control and weed cover at 2, 4, and 6 weeks for the indicated species are summarized below in Tables 6-47 through 6-49. 80% is considered acceptable control.

TABLE 6-47

| % Control and weed cover (2 weeks after application) | | | | |
|---|---|---|---|---|
| Treatments (product/ha) | Rep | ROTEX | IPOPU | AMAHY |
| Untreated control | I | 50 | 20 | 30 |
| % soil cover | ii | 40 | 10 | 50 |
| | iii | 40 | 20 | 40 |
| | iv | 30 | 20 | 50 |
| | Mean | 40 | 18 | 43 |
| 1 DINAMIC ® at 75 g | I | 50 | 60 | 60 |
| Galago at 100 ml | ii | 60 | 60 | 70 |
| | iii | 60 | 70 | 80 |
| | iv | 60 | 60 | 70 |
| | Mean | 58 | 63 | 70 |
| 2 DINAMIC ® at 75 g | I | 70 | 70 | 70 |
| Galago at 150 ml | ii | 80 | 70 | 80 |
| | iii | 80 | 70 | 80 |
| | iv | 70 | 70 | 70 |
| | Mean | 75 | 70 | 75 |

TABLE 6-47-continued

% Control and weed cover (2 weeks after application)

| Treatments (product/ha) | Rep | ROTEX | IPOPU | AMAHY |
|---|---|---|---|---|
| 3 DINAMIC ® at 100 g | I | 50 | 50 | 70 |
| Galago at 100 ml | ii | 60 | 60 | 70 |
|  | iii | 70 | 60 | 70 |
|  | iv | 60 | 70 | 70 |
| Mean |  | 60 | 60 | 70 |
| 4 DINAMIC ® at 100 g | I | 70 | 70 | 90 |
| Galago at 150 ml | ii | 70 | 80 | 90 |
|  | iii | 70 | 80 | 80 |
|  | iv | 70 | 80 | 90 |
| Mean |  | 70 | 78 | 88 |
| 5 DINAMIC ® at 125 g | I | 60 | 70 | 90 |
| Galago at 100 ml | ii | 60 | 80 | 90 |
|  | iii | 70 | 80 | 95 |
|  | iv | 80 | 70 | 90 |
| Mean |  | 68 | 75 | 91 |
| 6 DINAMIC ® at 125 g | I | 80 | 90 | 95 |
| Galago at 150 ml | ii | 60 | 90 | 95 |
|  | iii | 70 | 90 | 95 |
|  | iv | 80 | 90 | 95 |
| Mean |  | 73 | 90 | 95 |
| 7 DINAMIC ® at 250 g | I | 80 | 95 | 100 |
| Galago at 300 ml | ii | 90 | 95 | 100 |
|  | iii | 90 | 98 | 100 |
|  | iv | 90 | 98 | 100 |
| Mean |  | 88 | 97 | 100 |
| 8 DINAMIC ® at 75 g | I | 60 | 80 | 80 |
| Galago at 100 ml | ii | 60 | 70 | 70 |
| Wet-All at 0.1% | iii | 70 | 70 | 80 |
|  | iv | 60 | 70 | 80 |
| Mean |  | 63 | 73 | 78 |
| 9 DINAMIC ® at 75 g | I | 70 | 80 | 80 |
| Galago at 150 ml | ii | 80 | 70 | 80 |
| Wet-All at 0.1% | iii | 80 | 80 | 80 |
|  | iv | 70 | 70 | 80 |
| Mean |  | 75 | 75 | 80 |
| 10 DINAMIC ® at 100 g | I | 60 | 70 | 80 |
| Galago at 100 ml | ii | 70 | 70 | 80 |
| Wet-All at 0.1% | iii | 60 | 70 | 80 |
|  | iv | 70 | 70 | 80 |
| Mean |  | 65 | 70 | 80 |
| 11 DINAMIC ® at 100 g | I | 80 | 80 | 90 |
| Galago at 150 ml | ii | 80 | 80 | 90 |
| Wet-All at 0.1% | iii | 80 | 90 | 95 |
|  | iv | 80 | 80 | 90 |
| Mean |  | 80 | 83 | 91 |
| 12 DINAMIC ® at 125 g | I | 70 | 80 | 95 |
| Galago at 100 ml | ii | 70 | 80 | 95 |
| Wet-All at 0.1% | iii | 80 | 80 | 98 |
|  | iv | 70 | 80 | 95 |
| Mean |  | 73 | 80 | 96 |
| 13 DINAMIC ® at 125 g | I | 70 | 90 | 100 |
| Galago at 150 ml | ii | 80 | 90 | 100 |
| Wet-All at 0.1% | iii | 80 | 90 | 100 |
|  | iv | 80 | 80 | 100 |
| Mean |  | 78 | 88 | 100 |
| 14 DINAMIC ® at 250 g | I | 90 | 100 | 100 |
| Galago at 300 ml | ii | 90 | 95 | 100 |
| Wet-All at 0.2% | iii | 95 | 95 | 100 |
|  | iv | 90 | 95 | 100 |
| Mean |  | 91 | 96 | 100 |

ROTTE = *Rottboelia exaltata*; IPOPU = *Ipomoea purpurea*; AMAHY = *Amaranthus hybridus*

TABLE 6-48

% Control and weed cover (4 weeks after application)

| Treatments (product/ha) | Rep | ROTEX | IPOPU | AMAHY |
|---|---|---|---|---|
| Untreated control | I | 40 | 20 | 40 |
| % soil cover | ii | 40 | 20 | 40 |
|  | iii | 40 | 30 | 30 |
|  | iv | 30 | 20 | 50 |
| Mean |  | 38 | 23 | 40 |
| DINAMIC ® at 75 g | I | 50 | 70 | 60 |
| Galago at 100 ml | ii | 60 | 60 | 70 |
|  | iii | 50 | 70 | 80 |
|  | iv | 60 | 60 | 70 |
| Mean |  | 55 | 65 | 70 |
| DINAMIC ® at 75 g | I | 80 | 70 | 70 |
| Galago at 150 ml | ii | 80 | 70 | 80 |
|  | iii | 80 | 70 | 80 |
|  | iv | 70 | 70 | 70 |
| Mean |  | 78 | 70 | 75 |
| DINAMIC ® at 100 g | I | 60 | 60 | 70 |
| Galago at 100 ml | ii | 70 | 70 | 70 |
|  | iii | 70 | 60 | 70 |
|  | iv | 60 | 70 | 70 |
| Mean |  | 65 | 65 | 70 |
| DINAMIC ® at 100 g | I | 80 | 80 | 90 |
| Galago at 150 ml | ii | 70 | 90 | 90 |
|  | iii | 70 | 80 | 80 |
|  | iv | 80 | 80 | 90 |
| Mean |  | 75 | 83 | 88 |
| DINAMIC ® at 125 g | I | 60 | 80 | 90 |
| Galago at 100 ml | ii | 70 | 80 | 90 |
|  | iii | 70 | 80 | 95 |
|  | iv | 80 | 80 | 90 |
| Mean |  | 70 | 80 | 91 |
| DINAMIC ® at 125 g | I | 80 | 90 | 95 |
| Galago at 150 ml | ii | 70 | 95 | 95 |
|  | iii | 80 | 95 | 95 |
|  | iv | 80 | 90 | 95 |
| Mean |  | 78 | 93 | 95 |
| DINAMIC ® at 250 g | I | 90 | 98 | 100 |
| Galago at 300 ml | ii | 90 | 100 | 100 |
|  | iii | 95 | 100 | 100 |
|  | iv | 90 | 100 | 100 |
| Mean |  | 91 | 100 | 100 |
| DINAMIC ® at 75 g | I | 60 | 80 | 80 |
| Galago at 100 ml | ii | 60 | 70 | 70 |
| Wet-All at 0.1% | iii | 70 | 80 | 80 |
|  | iv | 60 | 70 | 80 |
| Mean |  | 63 | 75 | 78 |
| DINAMIC ® at 75 g | I | 80 | 80 | 80 |
| Galago at 150 ml | ii | 80 | 80 | 80 |
| Wet-All at 0.1% | iii | 80 | 80 | 80 |
|  | iv | 80 | 80 | 80 |
| Mean |  | 80 | 80 | 80 |
| DINAMIC ® at 100 g | I | 70 | 70 | 80 |
| Galago at 100 ml | ii | 70 | 80 | 80 |
| Wet-All at 0.1% | iii | 70 | 70 | 80 |
|  | iv | 70 | 70 | 80 |
| Mean |  | 70 | 75 | 80 |
| DINAMIC ® at 100 g | I | 80 | 90 | 90 |
| Galago at 150 ml | ii | 80 | 90 | 90 |
| Wet-All at 0.1% | iii | 80 | 90 | 95 |
|  | iv | 80 | 90 | 90 |
| Mean |  | 80 | 90 | 91 |
| DINAMIC ® at 125 g | I | 70 | 80 | 95 |
| Galago at 100 ml | ii | 80 | 90 | 95 |
| Wet-All at 0.1% | iii | 80 | 90 | 98 |
|  | iv | 70 | 90 | 95 |
| Mean |  | 75 | 88 | 96 |
| DINAMIC ® at 125 g | I | 80 | 100 | 100 |
| Galago at 150 ml | ii | 90 | 100 | 100 |
| Wet-All at 0.1% | iii | 90 | 100 | 100 |
|  | iv | 80 | 95 | 100 |
| Mean |  | 85 | 99 | 100 |

TABLE 6-48-continued

% Control and weed cover (4 weeks after application)

| Treatments (product/ha) | Rep | ROTEX | IPOPU | AMAHY |
|---|---|---|---|---|
| DINAMIC ® at 250 g | I | 95 | 100 | 100 |
| Galago at 300 ml | ii | 95 | 100 | 100 |
| Wet-All at 0.2% | iii | 98 | 100 | 100 |
| | iv | 95 | 100 | 100 |
| Mean | | 96 | 100 | 100 |

ROTTE = *Rottboelia exaltata*; IPOPU = *Ipomoea purpurea*; AMAHY = *Amaranthus hybridus*

TABLE 6-49

% Control and weed cover (6 weeks after application)

| Treatments (product/ha) | Rep | ROTEX | IPOPU | AMAHY |
|---|---|---|---|---|
| Untreated control | I | 40 | 20 | 40 |
| % soil cover | ii | 40 | 20 | 40 |
| | iii | 40 | 30 | 30 |
| | iv | 30 | 20 | 50 |
| Mean | | 38 | 23 | 40 |
| DINAMIC ® at 75 g | I | 50 | 70 | 60 |
| Galago at 100 ml | ii | 50 | 70 | 70 |
| | iii | 50 | 70 | 70 |
| | iv | 60 | 70 | 70 |
| Mean | | 53 | 70 | 68 |
| DINAMIC ® at 75 g | I | 80 | 70 | 70 |
| Galago at 150 ml | ii | 70 | 70 | 80 |
| | iii | 80 | 80 | 80 |
| | iv | 70 | 80 | 70 |
| Mean | | 75 | 75 | 75 |
| DINAMIC ® at 100 g | I | 70 | 70 | 70 |
| Galago at 100 ml | ii | 70 | 70 | 95 |
| | iii | 70 | 70 | 70 |
| | iv | 60 | 80 | 70 |
| Mean | | 68 | 73 | 76 |
| DINAMIC ® at 100 g | I | 80 | 90 | 90 |
| Galago at 150 ml | ii | 80 | 90 | 90 |
| | iii | 70 | 90 | 95 |
| | iv | 80 | 80 | 90 |
| Mean | | 78 | 88 | 91 |
| DINAMIC ® at 125 g | I | 70 | 80 | 90 |
| Galago at 100 ml | ii | 70 | 80 | 90 |
| | iii | 70 | 80 | 90 |
| | iv | 70 | 80 | 90 |
| Mean | | 70 | 80 | 90 |
| DINAMIC ® at 125 g | I | 80 | 90 | 95 |
| Galago at 150 ml | ii | 80 | 98 | 98 |
| | iii | 80 | 95 | 95 |
| | iv | 80 | 95 | 100 |
| Mean | | 80 | 95 | 97 |
| DINAMIC ® at 250 g | I | 90 | 100 | 100 |
| Galago at 300 ml | ii | 95 | 100 | 100 |
| | iii | 95 | 100 | 100 |
| | iv | 90 | 100 | 100 |
| Mean | | 93 | 100 | 100 |
| DINAMIC ® at 75 g | I | 60 | 80 | 80 |
| Galago at 100 ml | ii | 60 | 70 | 70 |
| Wet-All at 0.1% | iii | 60 | 80 | 80 |
| | iv | 60 | 70 | 80 |
| Mean | | 60 | 75 | 78 |
| DINAMIC ® at 75 g | I | 70 | 80 | 80 |
| Galago at 150 ml | ii | 80 | 90 | 90 |
| Wet-All at 0.1% | iii | 80 | 80 | 80 |
| | iv | 70 | 80 | 90 |
| Mean | | 75 | 83 | 85 |
| DINAMIC ® at 100 g | I | 70 | 70 | 90 |
| Galago at 100 ml | ii | 75 | 80 | 80 |
| Wet-All at 0.1% | iii | 75 | 80 | 90 |
| | iv | 70 | 70 | 90 |
| Mean | | 73 | 75 | 88 |

TABLE 6-49-continued

% Control and weed cover (6 weeks after application)

| Treatments (product/ha) | Rep | ROTEX | IPOPU | AMAHY |
|---|---|---|---|---|
| DINAMIC ® at 100 g | I | 80 | 90 | 95 |
| Galago at 150 ml | ii | 90 | 95 | 95 |
| Wet-All at 0.1% | iii | 80 | 90 | 100 |
| | iv | 80 | 90 | 100 |
| Mean | | 83 | 91 | 98 |
| DINAMIC ® at 125 g | I | 70 | 90 | 95 |
| Galago at 100 ml | ii | 80 | 90 | 95 |
| Wet-All at 0.1% | iii | 80 | 90 | 100 |
| | iv | 70 | 90 | 98 |
| Mean | | 75 | 90 | 97 |
| DINAMIC ® at 125 g | I | 80 | 100 | 100 |
| Galago at 150 ml | ii | 90 | 100 | 100 |
| Wet-All at 0.1% | iii | 90 | 100 | 100 |
| | iv | 80 | 100 | 100 |
| Mean | | 85 | 100 | 100 |
| DINAMIC ® at 250 g | I | 95 | 100 | 100 |
| Galago at 300 ml | ii | 95 | 100 | 100 |
| Wet-All at 0.2% | iii | 100 | 100 | 100 |
| | iv | 95 | 100 | 100 |
| Mean | | 96 | 100 | 100 |

ROTTE = *Rottboelia exaltata*; IPOPU = *Ipomoea purpurea*; AMAHY = *Amaranthus hybridus*

DINAMIC®+Galago without a wetter: DINAMIC® 700WDG at 100 g/ha+Galago 480SC at 150 mL/ha showed satisfactory control of *Amaranthus hybridus* and *Ipomoea purpurea*. *Rottboellia exaltata* was insufficiently controlled by this mixture. It was however marginally controlled by DINAMIC® 700WDG at 125 g/ha+Galago 480SC at 150 mL/ha. DINAMIC®+Galago with a wetter: It is clear that a wetter improved efficacy. DINAMIC® 700WDG at 75 g/ha+Galago 480SC at 150 mL/ha+Wet-All at 0.1% resulted in satisfactory control of *Amaranthus hybridus* and *Ipomoea purpurea* in comparison to the equivalent treatment without a wetter (treatment 2). *Rottboellia exaltata* could still not be controlled by this mixture and needed higher rates (DINAMIC® 700WDG at 100 g/ha+Galago 480SC at 150 mL/ha+Wet-All at 0.1%) to be controlled satisfactory. Signs of phytotoxicity were noticed in the plots were DINAMIC® 700WDG at 250 g/ha+Galago 480SC at 300 mL/ha+Wet-All at 0.1% was sprayed. DINAMIC® 700WDG at 75 g/ha+Galago 480SC at 100 mL/ha+Wet-All at 0.1% can be used to control *Amaranthus hybridus* and *Ipomoea purpurea*. To control *Rottboellia exaltata* DINAMIC® 700WDG at 100 g/ha+Galago 480SC at 150 mL/ha+Wet-All at 0.1% can be used.

H. Post Emergence Application Against Weed in Maize

In this part of the Example the efficacy of DINAMIC® (amicarbazone 700WDG, 700 grams active/kg, available from Arysta LifeScience North America, Cary, N.C.) mixtures with Galago (mesotrione 480SC, 480 grams active/L, available from Arysta LifeScience North America, Cary, N.C.) with or without Wet-All (available from Arysta LifeScience North America, Cary, N.C.) as a post emergence application against weeds in maize (variety PHI 32Y85) was determined.

Trials were conducted at a site with a history of weeds. The trials were executed under moderate weather conditions. Efficacy and visual phytotoxicity assessments were performed in triplicate. Normal practices were carried out to control insects and fungi. Crops were provided in 76 cm row width, at a sowing rate of 65,000 plants/ha, and at a sowing depth of five to eight cm. Soil class was clay with a clay content of about 35%. The site in this Example had been previously used for soya beans. Trial design was randomized blocks with a plot size of 20 m² replicated four times. Municipal water was used for all applications (pH=7.2).

Application of the treatments shown in Table 6-50 was conducted at post emergence stage 14 days after planting. Application of the treatments was conducted over a 24 hour period. Over this time period, dry bulb temperature was about 24-26° C., wet bulb temperature was about 20° C., relative humidity was about 60%, cloud cover was about 70%, and wind speed was about 0 m/s. Treatments were administered with a multi-spray gas sprayer with a 4× flat fan 03F80 nozzle. Spacing was 50 cm, with a height of 50 cm, pressure 2.8 Bar, at a ground speed of 1 m/s, and a calibration mean output of 330 L/ha. The soil temperature over the application period averaged to about 23° C. and the soil remained moist and fine. Crops stage at the outset was about 4 leaves with a BBCH scale of 14. Crop and weeds were actively growing. Weed stage was about 2-5 leaves.

TABLE 6-50

Treatments

| No | Treatments | Dosage rate (gai/ha) | Dosage rate (g/ha or mL/ha) |
|---|---|---|---|
| | Untreated control | — | — |
| 1 | DINAMIC ® 700WDG + | 52.5 | 75 |
| | Galago 480SC | 48 | 100 |
| 2 | DINAMIC ® 700WDG + | 52.5 | 75 |
| | Galago 480SC | 72 | 150 |
| 3 | DINAMIC ® 700WDG + | 70 | 100 |
| | Galago 480SC | 48 | 100 |
| 4 | DINAMIC ® 700WDG + | 70 | 100 |
| | Galago 480SC | 72 | 150 |
| 5 | DINAMIC ® 700WDG + | 87.5 | 125 |
| | Galago 480SC | 48 | 100 |
| 6 | DINAMIC ® 700WDG + | 87.5 | 125 |
| | Galago 480SC | 72 | 150 |
| 7 | DINAMIC ® 700WDG + | 175 | 250 |
| | Galago 480SC + | 144 | 300 |
| 8 | DINAMIC ® 700WDG + | 52.5 | 75 |
| | Galago 480SC + | 48 | 100 |
| | Wet-All | — | 0.1% |
| 9 | DINAMIC ® 700WDG + | 52.5 | 75 |
| | Galago 480SC + | 72 | 150 |
| | Wet-All | — | 0.1% |
| 10 | DINAMIC ® 700WDG + | 70 | 100 |
| | Galago 480SC + | 48 | 100 |
| | Wet-All | — | 0.1% |
| 11 | DINAMIC ® 700WDG + | 70 | 100 |
| | Galago 480SC + | 72 | 150 |
| | Wet-All | — | 0.1% |
| 12 | DINAMIC ® 700WDG + | 87.5 | 125 |
| | Galago 480SC + | 48 | 100 |
| | Wet-All | — | 0.1% |
| 13 | DINAMIC ® 700WDG + | 87.5 | 125 |
| | Galago 480SC + | 72 | 150 |
| | Wet-All | — | 0.1% |
| 14 | DINAMIC ® 700WDG + | 175 | 250 |
| | Galago 480SC + | 144 | 300 |
| | Wet-All | — | 0.1% |

Assessments of the treated crops at 2, 4, and 6 weeks are summarized in Tables 6-51 to 6-53 below. No visual signs of phytotoxicity were noticed over the 6 weeks.

TABLE 6-51

2 Week Assessment

| | |
|---|---|
| Crop condition | Actively growing |
| Crop stage | 6 Leaves |
| BBCH scale | 16 |
| Soil moisture | Moist |
| Rain since last visit | 8 mm |

TABLE 6-52

4 Week Assessment

| | |
|---|---|
| Crop condition | Actively growing |
| Crop stage | 7 Leaves |
| BBCH scale | 17 |
| Soil moisture | Wet |
| Rain since last visit | 44 mm |

TABLE 6-53

6 Week Assessment

| | |
|---|---|
| Crop condition | Actively growing |
| Crop stage | 9 leaves |
| BBCH scale: | 19 |
| Soil moisture | Moist |
| Rain since last visit | 0 mm |

Control and weed cover at 2, 4, and 6 weeks for the indicated species are summarized below in Tables 6-54 through 6-56. 80% is considered acceptable control.

TABLE 6-54

% Control and weed cover (2 weeks after application)

| Treatments (product/ha) | Rep | DIGSA | POROL | AMAHY | COMBE |
|---|---|---|---|---|---|
| Untreated control | I | 30 | 20 | 30 | 20 |
| % soil cover | ii | 40 | 10 | 20 | 30 |
| | iii | 40 | 20 | 30 | 10 |
| | iv | 30 | 20 | 30 | 20 |
| | Mean | 35 | 18 | 28 | 20 |
| 1 DINAMIC ® at 75 g | I | 80 | 80 | 70 | 60 |
| Galago at 100 ml | ii | 80 | 80 | 70 | 60 |
| | iii | 80 | 80 | 70 | 50 |
| | iv | 80 | 70 | 60 | 70 |
| | Mean | 80 | 78 | 68 | 60 |
| 2 DINAMIC ® at 75 g | I | 90 | 80 | 80 | 70 |
| Galago at 150 ml | ii | 90 | 80 | 70 | 80 |
| | iii | 90 | 80 | 70 | 80 |
| | iv | 90 | 80 | 70 | 80 |
| | Mean | 90 | 80 | 73 | 78 |
| 3 DINAMIC ® at 100 g | I | 80 | 70 | 80 | 70 |
| Galago at 100 ml | ii | 80 | 80 | 70 | 80 |
| | iii | 90 | 70 | 80 | 70 |
| | iv | 80 | 80 | 70 | 70 |
| | Mean | 83 | 75 | 75 | 73 |
| 4 DINAMIC ® at 100 g | I | 95 | 90 | 80 | 90 |
| Galago at 150 ml | ii | 95 | 80 | 80 | 80 |
| | iii | 95 | 80 | 70 | 90 |
| | iv | 90 | 80 | 80 | 80 |
| | Mean | 94 | 83 | 78 | 85 |
| 5 DINAMIC ® at 125 g | I | 80 | 80 | 80 | 80 |
| Galago at 100 ml | ii | 70 | 80 | 80 | 80 |
| | iii | 80 | 80 | 80 | 70 |
| | iv | 80 | 80 | 80 | 70 |
| | Mean | 78 | 80 | 80 | 75 |
| 6 DINAMIC ® at 125 g | I | 100 | 90 | 95 | 90 |
| Galago at 150 ml | ii | 95 | 90 | 90 | 90 |
| | iii | 95 | 80 | 90 | 80 |
| | iv | 100 | 80 | 95 | 90 |
| | Mean | 98 | 85 | 93 | 88 |
| 7 DINAMIC ® at 250 g | I | 100 | 100 | 95 | 95 |
| Galago at 300 ml | ii | 100 | 100 | 95 | 95 |
| | iii | 100 | 98 | 98 | 100 |
| | iv | 100 | 100 | 98 | 95 |
| | Mean | 100 | 100 | 97 | 96 |
| 8 DINAMIC ® at 75 g | I | 100 | 100 | 80 | 70 |
| Galago at 100 ml | ii | 98 | 100 | 90 | 80 |
| Wet-All at 0.1% | iii | 100 | 100 | 80 | 70 |
| | iv | 100 | 100 | 80 | 70 |
| | Mean | 100 | 100 | 83 | 73 |

TABLE 6-54-continued

% Control and weed cover (2 weeks after application)

| Treatments (product/ha) | Rep | DIGSA | POROL | AMAHY | COMBE |
|---|---|---|---|---|---|
| 9 DINAMIC ® at 75 g | I | 100 | 100 | 80 | 80 |
| Galago at 150 ml | ii | 100 | 100 | 80 | 80 |
| Wet-All at 0.1% | iii | 100 | 100 | 90 | 80 |
|  | iv | 100 | 100 | 90 | 80 |
| Mean |  | 100 | 100 | 85 | 80 |
| 10 DINAMIC ® at 100 g | I | 98 | 100 | 90 | 70 |
| Galago at 100 ml | ii | 98 | 100 | 80 | 70 |
| Wet-All at 0.1% | iii | 100 | 100 | 90 | 80 |
|  | iv | 100 | 100 | 90 | 80 |
| Mean |  | 99 | 100 | 88 | 75 |
| 11 DINAMIC ® at 100 g | I | 100 | 100 | 90 | 90 |
| Galago at 150 ml | ii | 100 | 100 | 90 | 90 |
| Wet-All at 0.1% | iii | 100 | 100 | 95 | 90 |
|  | iv | 100 | 100 | 80 | 90 |
| Mean |  | 100 | 100 | 89 | 90 |
| 12 DINAMIC ® at 125 g | I | 100 | 100 | 90 | 80 |
| Galago at 100 ml | ii | 100 | 100 | 95 | 70 |
| Wet-All at 0.1% | iii | 100 | 100 | 95 | 80 |
|  | iv | 100 | 100 | 90 | 90 |
| Mean |  | 100 | 100 | 93 | 80 |
| 13 DINAMIC ® at 125 g | I | 100 | 100 | 100 | 100 |
| Galago at 150 ml | ii | 100 | 100 | 100 | 95 |
| Wet-All at 0.1% | iii | 100 | 100 | 100 | 95 |
|  | iv | 100 | 100 | 100 | 95 |
| Mean |  | 100 | 100 | 100 | 96 |
| 14 DINAMIC ® at 250 g | I | 100 | 100 | 100 | 100 |
| Galago at 300 ml | ii | 100 | 100 | 100 | 100 |
| Wet-All at 0.2% | iii | 100 | 100 | 100 | 100 |
|  | iv | 100 | 100 | 100 | 100 |
| Mean |  | 100 | 100 | 100 | 100 |

DIGSA = *Digitaria sanguinalis*; POROL = *Portulaca oleracea*; AMAHY = *Amaranthus hybridus*; COMBE = *Commelina benghalensis*

TABLE 6-55

% Control and weed cover (4 weeks after application)

| Treatments (product/ha) | Rep | DIGSA | POROL | AMAHY | COMBE |
|---|---|---|---|---|---|
| Untreated control | I | 40 | 10 | 30 | 20 |
| % soil cover | ii | 40 | 10 | 20 | 30 |
|  | iii | 50 | 10 | 30 | 10 |
|  | iv | 30 | 20 | 30 | 20 |
| Mean |  | 40 | 13 | 28 | 20 |
| 1 DINAMIC ® at 75 g | I | 70 | 70 | 60 | 50 |
| Galago at 100 ml | ii | 70 | 70 | 60 | 50 |
|  | iii | 70 | 70 | 60 | 50 |
|  | iv | 70 | 70 | 50 | 60 |
| Mean |  | 70 | 70 | 58 | 53 |
| 2 DINAMIC ® at 75 g | I | 80 | 80 | 80 | 60 |
| Galago at 150 ml | ii | 70 | 80 | 60 | 60 |
|  | iii | 70 | 70 | 70 | 70 |
|  | iv | 70 | 80 | 70 | 70 |
| Mean |  | 73 | 78 | 70 | 65 |
| 3 DINAMIC ® at 100 g | I | 80 | 70 | 60 | 60 |
| Galago at 100 ml | ii | 80 | 80 | 60 | 70 |
|  | iii | 80 | 80 | 60 | 70 |
|  | iv | 70 | 70 | 60 | 70 |
| Mean |  | 78 | 75 | 60 | 68 |
| 4 DINAMIC ® at 100 g | I | 90 | 90 | 80 | 90 |
| Galago at 150 ml | ii | 95 | 70 | 70 | 70 |
|  | iii | 95 | 80 | 70 | 70 |
|  | iv | 90 | 80 | 80 | 80 |
| Mean |  | 93 | 80 | 75 | 78 |
| 5 DINAMIC ® at 125 g | I | 80 | 70 | 70 | 70 |
| Galago at 100 ml | ii | 70 | 70 | 70 | 70 |
|  | iii | 70 | 70 | 70 | 60 |
|  | iv | 70 | 70 | 70 | 70 |
| Mean |  | 73 | 70 | 70 | 68 |
| 6 DINAMIC ® at 125 g | I | 98 | 90 | 90 | 80 |
| Galago at 150 ml | ii | 90 | 80 | 90 | 80 |
|  | iii | 90 | 80 | 90 | 90 |
|  | iv | 100 | 80 | 90 | 80 |
| Mean |  | 95 | 83 | 90 | 83 |
| 7 DINAMIC ® at 250 g | I | 100 | 100 | 95 | 95 |
| Galago at 300 ml | ii | 100 | 100 | 90 | 95 |
|  | iii | 100 | 98 | 95 | 100 |
|  | iv | 100 | 100 | 95 | 90 |
| Mean |  | 100 | 100 | 94 | 95 |
| 8 DINAMIC ® at 75 g | I | 100 | 100 | 80 | 60 |
| Galago at 100 ml | ii | 98 | 100 | 90 | 70 |
| Wet-All at 0.1% | iii | 100 | 100 | 90 | 60 |
|  | iv | 100 | 100 | 80 | 60 |
| Mean |  | 100 | 100 | 85 | 63 |
| 9 DINAMIC ® at 75 g | I | 100 | 100 | 80 | 70 |
| Galago at 150 ml | ii | 100 | 100 | 80 | 70 |
| Wet-All at 0.1% | iii | 100 | 100 | 90 | 80 |
|  | iv | 100 | 100 | 90 | 80 |
| Mean |  | 100 | 100 | 85 | 75 |
| 10 DINAMIC ® at 100 g | I | 98 | 100 | 90 | 60 |
| Galago at 100 ml | ii | 95 | 100 | 90 | 60 |
| Wet-All at 0.1% | iii | 100 | 100 | 90 | 70 |
|  | iv | 100 | 100 | 90 | 80 |
| Mean |  | 98 | 100 | 90 | 68 |
| 11 DINAMIC ® at 100 g | I | 100 | 100 | 90 | 80 |
| Galago at 150 ml | ii | 100 | 100 | 90 | 80 |
| Wet-All at 0.1% | iii | 100 | 100 | 95 | 80 |
|  | iv | 100 | 100 | 90 | 80 |
| Mean |  | 100 | 100 | 91 | 80 |
| 12 DINAMIC ® at 125 g | I | 100 | 100 | 95 | 70 |
| Galago at 100 ml | ii | 100 | 100 | 95 | 90 |
| Wet-All at 0.1% | iii | 100 | 100 | 95 | 70 |
|  | iv | 100 | 100 | 90 | 80 |
| Mean |  | 100 | 100 | 94 | 78 |
| 13 DINAMIC ® at 125 g | I | 100 | 100 | 100 | 100 |
| Galago at 150 ml | ii | 100 | 100 | 100 | 90 |
| Wet-All at 0.1% | iii | 100 | 100 | 100 | 90 |
|  | iv | 100 | 100 | 100 | 90 |
| Mean |  | 100 | 100 | 100 | 93 |
| 14 DINAMIC ® at 250 g | I | 100 | 100 | 100 | 100 |
| Galago at 300 ml | ii | 100 | 100 | 100 | 100 |
| Wet-All at 0.2% | iii | 100 | 100 | 100 | 100 |
|  | iv | 100 | 100 | 100 | 100 |
| Mean |  | 100 | 100 | 100 | 100 |

DIGSA = *Digitaria sanguinalis*; POROL = *Portulaca oleracea*; AMAHY = *Amaranthus hybridus*; COMBE = *Commelina benghalensis*

TABLE 6-56

% Control and weed cover (6 weeks after application)

| Treatments (product/ha) | Rep | DIGSA | POROL | AMAHY | COMBE |
|---|---|---|---|---|---|
| Untreated control | I | 40 | 10 | 30 | 20 |
| % soil cover | ii | 40 | 10 | 20 | 30 |
|  | iii | 50 | 10 | 30 | 10 |
|  | iv | 30 | 10 | 40 | 20 |
| Mean |  | 40 | 10 | 30 | 20 |
| DINAMIC ® at 75 g | I | 60 | 60 | 50 | 50 |
| Galago at 100 ml | ii | 70 | 60 | 60 | 50 |
|  | iii | 60 | 60 | 60 | 50 |
|  | iv | 70 | 60 | 50 | 50 |
| Mean |  | 65 | 60 | 55 | 50 |
| DINAMIC ® at 75 g | I | 80 | 80 | 70 | 60 |
| Galago at 150 ml | ii | 70 | 80 | 60 | 60 |
|  | iii | 70 | 70 | 70 | 60 |
|  | iv | 60 | 80 | 70 | 60 |
| Mean |  | 70 | 78 | 68 | 60 |

TABLE 6-56-continued

% Control and weed cover (6 weeks after application)

| Treatments (product/ha) | Rep | DIGSA | POROL | AMAHY | COMBE |
|---|---|---|---|---|---|
| DINAMIC ® at 100 g | i | 70 | 70 | 60 | 60 |
| Galago at 100 ml | ii | 70 | 70 | 60 | 60 |
|  | iii | 70 | 80 | 50 | 60 |
|  | iv | 60 | 60 | 60 | 60 |
| Mean |  | 68 | 70 | 58 | 60 |
| DINAMIC ® at 100 g | i | 90 | 90 | 80 | 80 |
| Galago at 150 ml | ii | 90 | 70 | 70 | 70 |
|  | iii | 90 | 70 | 70 | 60 |
|  | iv | 80 | 80 | 70 | 70 |
| Mean |  | 88 | 78 | 73 | 70 |
| DINAMIC ® at 125 g | i | 70 | 70 | 60 | 60 |
| Galago at 100 ml | ii | 70 | 70 | 60 | 60 |
|  | iii | 70 | 70 | 70 | 60 |
|  | iv | 70 | 70 | 70 | 60 |
| Mean |  | 70 | 70 | 65 | 60 |
| DINAMIC ® at 125 g | i | 90 | 90 | 80 | 70 |
| Galago at 150 ml | ii | 90 | 90 | 80 | 70 |
|  | iii | 90 | 80 | 80 | 80 |
|  | iv | 100 | 80 | 80 | 80 |
| Mean |  | 93 | 85 | 80 | 75 |
| DINAMIC ® at 250 g | i | 100 | 100 | 95 | 90 |
| Galago at 300 ml | ii | 100 | 100 | 95 | 95 |
|  | iii | 100 | 95 | 95 | 100 |
|  | iv | 100 | 100 | 95 | 90 |
| Mean |  | 100 | 99 | 95 | 94 |
| DINAMIC ® at 75 g | i | 100 | 100 | 80 | 60 |
| Galago at 100 ml | ii | 100 | 100 | 90 | 60 |
| Wet-All at 0.1% | iii | 100 | 100 | 80 | 50 |
|  | iv | 100 | 100 | 80 | 60 |
| Mean |  | 100 | 100 | 83 | 58 |
| DINAMIC ® at 75 g | i | 100 | 100 | 80 | 60 |
| Galago at 150 ml | ii | 100 | 100 | 80 | 60 |
| Wet-All at 0.1% | iii | 100 | 100 | 90 | 70 |
|  | iv | 100 | 100 | 90 | 80 |
| Mean |  | 100 | 100 | 85 | 68 |
| DINAMIC ® at 100 g | i | 95 | 100 | 90 | 50 |
| Galago at 100 ml | ii | 95 | 100 | 90 | 60 |
| Wet-All at 0.1% | iii | 100 | 100 | 90 | 60 |
|  | iv | 100 | 100 | 90 | 80 |
| Mean |  | 98 | 100 | 90 | 63 |
| DINAMIC ® at 100 g | i | 100 | 100 | 95 | 80 |
| Galago at 150 ml | ii | 100 | 100 | 95 | 80 |
| Wet-All at 0.1% | iii | 100 | 100 | 95 | 80 |
|  | iv | 100 | 100 | 95 | 80 |
| Mean |  | 100 | 100 | 95 | 80 |
| DINAMIC ® at 125 g | i | 100 | 100 | 95 | 70 |
| Galago at 100 ml | ii | 100 | 100 | 95 | 80 |
| Wet-All at 0.1% | iii | 100 | 100 | 95 | 80 |
|  | iv | 100 | 100 | 95 | 80 |
| Mean |  | 100 | 100 | 95 | 78 |
| DINAMIC ® at 125 g | i | 100 | 100 | 100 | 95 |
| Galago at 150 ml | ii | 100 | 100 | 100 | 90 |
| Wet-All at 0.1% | iii | 100 | 100 | 100 | 80 |
|  | iv | 100 | 100 | 100 | 90 |
| Mean |  | 100 | 100 | 100 | 89 |
| DINAMIC ® at 250 g | i | 100 | 100 | 100 | 100 |
| Galago at 300 ml | ii | 100 | 100 | 100 | 100 |
| Wet-All at 0.2% | iii | 100 | 100 | 100 | 100 |
|  | iv | 100 | 100 | 100 | 100 |
| Mean |  | 100 | 100 | 100 | 100 |

DIGSA = *Digitaria sanguinalis*; POROL = *Portulaca oleracea*; AMAHY = *Amaranthus hybridus*; COMBE = *Commelina benghalensis*

The higher Galago rate (150 mL/ha) improves control when used as a mixing partner for DINAMIC®. DINAMIC®+Galago without a wetter: DINAMIC® 700WDG at 125 g/ha+Galago 480SC at 150 mL/ha showed satisfactory control of *Digitaria sanguinalis* and *Portulaca oleracea* and marginal control of *Amaranthus hybridus*. It could however not control Commilina benghalensis except with higher rates. DINAMIC®+Galago with a wetter: A wetter should be used with these mixtures (see treatment 1 vs. treatment 8). DINAMIC® 700WDG at 75 g/ha+Galago 480SC at 100 mL/ha+Wet-All at 0.1% resulted in 100% control of *Amaranthus spinosus* and *Portulaca oleracea* in comparison to 65% and 60% respectively without a wetter (treatment1). *Commilina benghalensis* could not be controlled by this mixture and needed higher rates (DINAMIC® 700WDG at 100 g/ha+Galago 480SC at 150 mL/ha+Wet-All at 0.1%) to be controlled satisfactory. No visual signs of phytotoxicity were noticed throughout the growing season. DINAMIC® 700WDG at 75 g/ha+Galago 480SC at 100 mL/ha+Wet-All at 0.1% can be used to control *Digitaria sanguinalis, Portulaca oleracea* and *Amaranthus hybridus*. To control *Commilina benghalensis* DINAMIC® 700WDG at 100 g/ha+Galago 480SC at 150 mL/ha+Wet-All at 0.1% can be used.

I. Post Emergence Application Against Weed in Maize

In this part of the Example the efficacy of DINAMIC® (amicarbazone 700WDG, 700 grams active/kg, available from Arysta LifeScience North America, Cary, N.C.) mixtures with Galago (mesotrione 480SC, 480 grams active/L, available from Arysta LifeScience North America, Cary, N.C.) with or without Wet-All (available from Arysta LifeScience North America, Cary, N.C.) as a post emergence application against weeds in maize (variety PAN60-445B) was determined.

Trials were conducted at a site with a history of broad leaf weeds and grasses. The trials were executed under moderate weather conditions. Efficacy and visual phytotoxicity assessments were performed in triplicate. Normal practices were carried out to control insects and fungi. Crops were provided in 76 cm row width, at a sowing rate of 65,000 plants/ha, and at a sowing depth of five to eight cm. Soil class was clay with a clay content of about 28%. The site in this Example had been previously used for soya beans. Trial design was randomized blocks with a plot size of 20 m² replicated four times. Municipal water was used for all applications (pH=7.2).

Application of the treatments shown in Table 6-57 was conducted at post emergence stage 18 days after planting. Application of the treatments was conducted over a 24 hour period. Over this time period, dry bulb temperature was about 31° C., wet bulb temperature was about 28° C., relative humidity was about 80%, cloud cover was about 100%, and wind speed was about 0 m/s. Treatments were administered with a multi-spray gas sprayer with a 4× flat fan 03F80 nozzle. Spacing was 50 cm, with a height of 50 cm, pressure 2.8 Bar, at a ground speed of 1 m/s, and a calibration mean output of 330 L/ha. The soil temperature over the application period averaged to about 29° C. and the soil remained moist and fine. Crops stage at the outset was about 4 leaves with a BBCH scale of 14. Crop and weeds were actively growing. Weed stage was about 2-6 leaves.

TABLE 6-57

Treatments

| No | Treatments | Dosage rate (gai/ha) | Dosage rate (g/ha or mL/ha) |
|---|---|---|---|
|  | Untreated control | — | — |
| 1 | DINAMIC ® 700WDG + | 52.5 | 75 |
|  | Galago 480SC | 48 | 100 |
| 2 | DINAMIC ® 700WDG + | 52.5 | 75 |
|  | Galago 480SC | 72 | 150 |
| 3 | DINAMIC ® 700WDG + | 70 | 100 |
|  | Galago 480SC | 48 | 100 |
| 4 | DINAMIC ® 700WDG + | 70 | 100 |
|  | Galago 480SC | 72 | 150 |

TABLE 6-57-continued

Treatments

| No | Treatments | Dosage rate (gai/ha) | Dosage rate (g/ha or mL/ha) |
|---|---|---|---|
| 5 | DINAMIC ® 700WDG + | 87.5 | 125 |
|  | Galago 480SC | 48 | 100 |
| 6 | DINAMIC ® 700WDG + | 87.5 | 125 |
|  | Galago 480SC | 72 | 150 |
| 7 | DINAMIC ® 700WDG + | 175 | 250 |
|  | Galago 480SC + | 144 | 300 |
| 8 | DINAMIC ® 700WDG + | 52.5 | 75 |
|  | Galago 480SC + | 48 | 100 |
|  | Wet-All | — | 0.1% |
| 9 | DINAMIC ® 700WDG + | 52.5 | 75 |
|  | Galago 480SC + | 72 | 150 |
|  | Wet-All | — | 0.1% |
| 10 | DINAMIC ® 700WDG + | 70 | 100 |
|  | Galago 480SC + | 48 | 100 |
|  | Wet-All | — | 0.1% |
| 11 | DINAMIC ® 700WDG + | 70 | 100 |
|  | Galago 480SC + | 72 | 150 |
|  | Wet-All | — | 0.1% |
| 12 | DINAMIC ® 700WDG + | 87.5 | 125 |
|  | Galago 480SC + | 48 | 100 |
|  | Wet-All | — | 0.1% |
| 13 | DINAMIC ® 700WDG + | 87.5 | 125 |
|  | Galago 480SC + | 72 | 150 |
|  | Wet-All | — | 0.1% |
| 14 | DINAMIC ® 700WDG + | 175 | 250 |
|  | Galago 480SC + | 144 | 300 |
|  | Wet-All | — | 0.1% |

Assessments of the treated crops at 2, 4, and 6 weeks are summarized in Tables 6-58 to 6-60 below. No visual signs of phytotoxicity were noticed over 4 weeks. Signs of phytotoxicity were noticed in treatment 13 at 6 weeks.

TABLE 6-58

2 Week Assessment

| | |
|---|---|
| Crop condition | Actively growing |
| Crop stage | 6 Leaves |
| BBCH scale | 16 |
| Soil moisture | Moist |
| Rain since last visit | 16 mm |

TABLE 6-59

4 Week Assessment

| | |
|---|---|
| Crop condition | Actively growing |
| Crop stage | 8 Leaves |
| BBCH scale | 18 |
| Soil moisture | Wet |
| Rain since last visit | 30 mm |

TABLE 6-60

6 Week Assessment

| | |
|---|---|
| Crop condition | Actively growing |
| Crop stage | 10 leaves |
| BBCH scale: | 18 |
| Soil moisture | Moist |
| Rain since last visit | 0 mm |

Control and weed cover at 2, 4, and 6 weeks for the indicated species are summarized below in Tables 6-61 through 6-63. 80% is considered acceptable control.

TABLE 6-61

% Control and weed cover (2 weeks after application)

| Treatments (product/ha) | DAA | AMASP | ELEIN | IPOPU | COMBE |
|---|---|---|---|---|---|
| Untreated control | 2 | 35 | 18 | 28 | 20 |
| % soil cover | 4 | 35 | 13 | 30 | 23 |
|  | 6 | 33 | 13 | 30 | 25 |
| 1 DINAMIC ® at 75 g | 2 | 80 | 78 | 68 | 75 |
| Galago at 100 ml | 4 | 73 | 70 | 60 | 75 |
|  | 6 | 65 | 63 | 50 | 70 |
| 2 DINAMIC ® at 75 g | 2 | 80 | 80 | 73 | 80 |
| Galago at 150 ml | 4 | 73 | 75 | 68 | 80 |
|  | 6 | 68 | 73 | 63 | 80 |
| 3 DINAMIC ® at 100 g | 2 | 85 | 85 | 75 | 80 |
| Galago at 100 ml | 4 | 78 | 78 | 68 | 80 |
|  | 6 | 73 | 75 | 63 | 75 |
| 4 DINAMIC ® at 100 g | 2 | 94 | 83 | 78 | 88 |
| Galago at 150 ml | 4 | 90 | 80 | 70 | 88 |
|  | 6 | 85 | 75 | 63 | 83 |
| 5 DINAMIC ® at 125 g | 2 | 98 | 85 | 80 | 91 |
| Galago at 100 ml | 4 | 96 | 80 | 70 | 91 |
|  | 6 | 95 | 78 | 65 | 85 |
| 6 DINAMIC ® at 125 g | 2 | 98 | 90 | 93 | 88 |
| Galago at 150 ml | 4 | 96 | 90 | 90 | 88 |
|  | 6 | 94 | 83 | 83 | 90 |
| 7 DINAMIC ® at 250 g | 2 | 100 | 100 | 100 | 96 |
| Galago at 300 ml | 4 | 100 | 100 | 100 | 96 |
|  | 6 | 100 | 100 | 100 | 95 |
| 8 DINAMIC ® at 75 g | 2 | 100 | 100 | 90 | 99 |
| Galago at 100 ml | 4 | 100 | 100 | 83 | 99 |
| Wet-All at 0.1% | 6 | 100 | 100 | 80 | 90 |
| 9 DINAMIC ® at 75 g | 2 | 100 | 100 | 100 | 98 |
| Galago at 150 ml | 4 | 100 | 100 | 90 | 98 |
| Wet-All at 0.1% | 6 | 100 | 100 | 84 | 93 |
| 10 DINAMIC ® at 100 g | 2 | 99 | 100 | 90 | 98 |
| Galago at 100 ml | 4 | 100 | 100 | 83 | 98 |
| Wet-All at 0.1% | 6 | 100 | 100 | 78 | 93 |
| 11 DINAMIC ® at 100 g | 2 | 100 | 100 | 97 | 100 |
| Galago at 150 ml | 4 | 100 | 100 | 95 | 100 |
| Wet-All at 0.1% | 6 | 100 | 100 | 90 | 100 |
| 12 DINAMIC ® at 125 g | 2 | 100 | 100 | 97 | 100 |
| Galago at 100 ml | 4 | 100 | 100 | 93 | 100 |
| Wet-All at 0.1% | 6 | 100 | 100 | 88 | 100 |
| 13 DINAMIC ® at 125 g | 2 | 100 | 100 | 100 | 100 |
| Galago at 150 ml | 4 | 100 | 100 | 100 | 100 |
| Wet-All at 0.1% | 6 | 100 | 100 | 100 | 100 |
| 14 DINAMIC ® at 250 g | 2 | 100 | 100 | 95 | 100 |
| Galago at 300 ml | 4 | 100 | 100 | 99 | 100 |
| Wet-All at 0.2% | 6 | 100 | 100 | 99 | 100 |

AMASP = *Amaranthus spinosus*; COMBE = *Commelina benghalensis*; IPOPU = *Ipomoea purpurea*; ELEIN = *Eleusine indica*

TABLE 6-62

% Control and weed cover (4 weeks after application)

| Treatments (product/ha) | Rep | AMASP | ELEIN | IPOPU | COMBE |
|---|---|---|---|---|---|
| Untreated control % soil cover | I | 30 | 10 | 40 | 20 |
| | ii | 40 | 10 | 20 | 30 |
| | iii | 40 | 20 | 30 | 10 |
| | iv | 30 | 10 | 30 | 30 |
| Mean | | 35 | 13 | 30 | 23 |
| 1 DINAMIC ® at 75 g Galago at 100 ml | I | 70 | 70 | 60 | 80 |
| | ii | 70 | 70 | 60 | 70 |
| | iii | 80 | 70 | 60 | 70 |
| | iv | 70 | 70 | 60 | 80 |
| Mean | | 73 | 70 | 60 | 75 |
| 2 DINAMIC ® at 75 g Galago at 150 ml | I | 70 | 80 | 70 | 80 |
| | ii | 80 | 70 | 70 | 80 |
| | iii | 70 | 70 | 60 | 80 |
| | iv | 70 | 80 | 70 | 80 |
| Mean | | 73 | 75 | 68 | 80 |
| 3 DINAMIC ® at 100 g Galago at 100 ml | I | 80 | 70 | 70 | 80 |
| | ii | 70 | 80 | 70 | 80 |
| | iii | 80 | 80 | 70 | 80 |
| | iv | 80 | 80 | 60 | 80 |
| Mean | | 78 | 78 | 68 | 80 |
| 4 DINAMIC ® at 100 g Galago at 150 ml | I | 90 | 80 | 70 | 90 |
| | ii | 90 | 80 | 70 | 80 |
| | iii | 90 | 80 | 70 | 90 |
| | iv | 90 | 80 | 70 | 90 |
| Mean | | 90 | 80 | 70 | 88 |
| 5 DINAMIC ® at 125 g Galago at 100 ml | I | 100 | 80 | 70 | 95 |
| | ii | 90 | 80 | 70 | 90 |
| | iii | 95 | 80 | 70 | 90 |
| | iv | 100 | 80 | 70 | 90 |
| Mean | | 96 | 80 | 70 | 91 |
| 6 DINAMIC ® at 125 g Galago at 150 ml | I | 100 | 90 | 90 | 90 |
| | ii | 95 | 90 | 90 | 90 |
| | iii | 90 | 90 | 90 | 80 |
| | iv | 100 | 90 | 90 | 90 |
| Mean | | 96 | 90 | 90 | 88 |
| 7 DINAMIC ® at 250 g Galago at 300 ml | I | 100 | 100 | 100 | 95 |
| | ii | 100 | 100 | 100 | 95 |
| | iii | 100 | 100 | 100 | 100 |
| | iv | 100 | 100 | 100 | 95 |
| Mean | | 100 | 100 | 100 | 96 |
| 8 DINAMIC ® at 75 g Galago at 100 ml Wet-All at 0.1% | I | 100 | 100 | 80 | 100 |
| | ii | 100 | 100 | 80 | 98 |
| | iii | 100 | 100 | 90 | 98 |
| | iv | 100 | 100 | 80 | 98 |
| Mean | | 100 | 100 | 83 | 99 |
| 9 DINAMIC ® at 75 g Galago at 150 ml Wet-All at 0.1% | I | 100 | 100 | 98 | 95 |
| | ii | 100 | 100 | 90 | 98 |
| | iii | 100 | 100 | 80 | 98 |
| | iv | 100 | 100 | 90 | 100 |
| Mean | | 100 | 100 | 90 | 98 |
| 10 DINAMIC ® at 100 g Galago at 100 ml Wet-All at 0.1% | I | 100 | 100 | 80 | 95 |
| | ii | 98 | 100 | 90 | 95 |
| | iii | 100 | 100 | 80 | 100 |
| | iv | 100 | 100 | 80 | 100 |
| Mean | | 100 | 100 | 83 | 98 |
| 11 DINAMIC ® at 100 g Galago at 150 ml Wet-All at 0.1% | I | 100 | 100 | 95 | 100 |
| | ii | 100 | 100 | 95 | 100 |
| | iii | 100 | 100 | 95 | 100 |
| | iv | 100 | 100 | 95 | 100 |
| Mean | | 100 | 100 | 95 | 100 |
| 12 DINAMIC ® at 125 g Galago at 100 ml Wet-All at 0.1% | I | 100 | 100 | 90 | 100 |
| | ii | 100 | 100 | 95 | 100 |
| | iii | 100 | 100 | 95 | 100 |
| | iv | 100 | 100 | 90 | 100 |
| Mean | | 100 | 100 | 93 | 100 |
| 13 DINAMIC ® at 125 g Galago at 150 ml Wet-All at 0.1% | I | 100 | 100 | 100 | 100 |
| | ii | 100 | 100 | 100 | 100 |
| | iii | 100 | 100 | 100 | 100 |
| | iv | 100 | 100 | 100 | 100 |
| Mean | | 100 | 100 | 100 | 100 |
| 14 DINAMIC ® at 250 g Galago at 300 ml Wet-All at 0.2% | I | 100 | 100 | 100 | 100 |
| | ii | 100 | 100 | 100 | 100 |
| | iii | 100 | 100 | 95 | 100 |
| | iv | 100 | 100 | 100 | 100 |
| Mean | | 100 | 100 | 99 | 100 |

AMASP = *Amaranthus spinosus*; COMBE = *Commelina benghalensis*; IPOPU= *Ipomoea purpurea*; ELEIN = *Eleusine indica*

TABLE 6-63

% Control and weed cover (6 weeks after application)

| Treatments (product/ha) | Rep | AMASP | ELEIN | IPOPU | COMBE |
|---|---|---|---|---|---|
| Untreated control % soil cover | I | 30 | 10 | 40 | 20 |
| | ii | 40 | 10 | 20 | 30 |
| | iii | 30 | 20 | 30 | 20 |
| | iv | 30 | 10 | 30 | 30 |
| Mean | | 33 | 13 | 30 | 25 |
| 1 DINAMIC ® at 75 g Galago at 100 ml | I | 60 | 60 | 50 | 70 |
| | ii | 70 | 60 | 50 | 70 |
| | iii | 70 | 70 | 50 | 70 |
| | iv | 60 | 60 | 50 | 70 |
| Mean | | 65 | 63 | 50 | 70 |
| 2 DINAMIC ® at 75 g Galago at 150 ml | I | 70 | 70 | 60 | 80 |
| | ii | 70 | 70 | 70 | 80 |
| | iii | 60 | 70 | 60 | 80 |
| | iv | 70 | 80 | 60 | 80 |
| Mean | | 68 | 73 | 63 | 80 |
| 3 DINAMIC ® at 100 g Galago at 100 ml | I | 80 | 70 | 70 | 80 |
| | ii | 70 | 80 | 60 | 70 |
| | iii | 70 | 70 | 60 | 70 |
| | iv | 70 | 80 | 60 | 80 |
| Mean | | 73 | 75 | 63 | 75 |
| 4 DINAMIC ® at 100 g Galago at 150 ml | I | 90 | 70 | 60 | 80 |
| | ii | 90 | 80 | 60 | 80 |
| | iii | 80 | 80 | 60 | 90 |
| | iv | 80 | 70 | 70 | 80 |
| Mean | | 85 | 75 | 63 | 83 |
| 5 DINAMIC ® at 125 g Galago at 100 ml | I | 100 | 80 | 60 | 90 |
| | ii | 90 | 80 | 60 | 90 |
| | iii | 90 | 70 | 70 | 80 |
| | iv | 100 | 80 | 70 | 80 |
| Mean | | 95 | 78 | 65 | 85 |
| 6 DINAMIC ® at 125 g Galago at 150 ml | I | 100 | 80 | 80 | 90 |
| | ii | 90 | 90 | 80 | 90 |
| | iii | 90 | 80 | 80 | 90 |
| | iv | 95 | 80 | 90 | 90 |
| Mean | | 94 | 83 | 83 | 90 |
| 7 DINAMIC ® at 250 g Galago at 300 ml | I | 100 | 100 | 100 | 95 |
| | ii | 100 | 100 | 100 | 90 |
| | iii | 100 | 100 | 100 | 98 |
| | iv | 100 | 100 | 100 | 95 |
| Mean | | 100 | 100 | 100 | 95 |
| 8 DINAMIC ® at 75 g Galago at 100 ml Wet-All at 0.1% | I | 100 | 100 | 80 | 90 |
| | ii | 100 | 100 | 80 | 90 |
| | iii | 100 | 100 | 80 | 90 |
| | iv | 100 | 100 | 80 | 90 |
| Mean | | 100 | 100 | 80 | 90 |
| 9 DINAMIC ® at 75 g Galago at 150 ml Wet-All at 0.1% | I | 100 | 100 | 95 | 90 |
| | ii | 100 | 100 | 80 | 95 |
| | iii | 100 | 100 | 80 | 90 |
| | iv | 100 | 100 | 80 | 95 |
| Mean | | 100 | 100 | 84 | 93 |
| 10 DINAMIC ® at 100 g Galago at 100 ml Wet-All at 0.1% | I | 100 | 100 | 80 | 90 |
| | ii | 100 | 100 | 80 | 90 |
| | iii | 100 | 100 | 70 | 98 |
| | iv | 100 | 100 | 80 | 95 |
| Mean | | 100 | 100 | 78 | 93 |

TABLE 6-63-continued

% Control and weed cover (6 weeks after application)

| Treatments (product/ha) | Rep | AMASP | ELEIN | IPOPU | COMBE |
|---|---|---|---|---|---|
| 11 DINAMIC® at 100 g | i | 100 | 100 | 90 | 100 |
| Galago at 150 ml | ii | 100 | 100 | 90 | 100 |
| Wet-All at 0.1% | iii | 100 | 100 | 90 | 100 |
|  | iv | 100 | 100 | 90 | 100 |
| Mean |  | 100 | 100 | 90 | 100 |
| 12 DINAMIC® at 125 g | i | 100 | 100 | 80 | 100 |
| Galago at 100 ml | ii | 100 | 100 | 90 | 100 |
| Wet-All at 0.1% | iii | 100 | 100 | 90 | 100 |
|  | iv | 100 | 100 | 90 | 100 |
| Mean |  | 100 | 100 | 88 | 100 |
| 13 DINAMIC® at 125 g | i | 100 | 100 | 100 | 100 |
| Galago at 150 ml | ii | 100 | 100 | 100 | 100 |
| Wet-All at 0.1% | iii | 100 | 100 | 100 | 100 |
|  | iv | 100 | 100 | 100 | 100 |
| Mean |  | 100 | 100 | 100 | 100 |
| 14 DINAMIC® at 250 g | i | 100 | 100 | 100 | 100 |
| Galago at 300 ml | ii | 100 | 100 | 100 | 100 |
| Wet-All at 0.2% | iii | 100 | 100 | 95 | 100 |
|  | iv | 100 | 100 | 100 | 100 |
| Mean |  | 100 | 100 | 99 | 100 |

AMASP = *Amaranthus spinosus*; COMBE = *Commelina benghalensis*; IPOPU = *Ipomoea purpurea*; ELEIN = *Eleusine indica*

The higher Galago rate (150 mL/ha) improves control when used as a mixing partner for DINAMIC®. A wetter is beneficially used with this mixture. DINAMIC®+Galago without a wetter: DINAMIC® 700WDG at 125 g/ha+Galago 480SC at 100 mL/ha showed satisfactory control of *Amaranthus spinosus* and *Commilina benghalensis*, and as soon as the Galago rate increases to 150 mL/ha *Eleusine indica* and *Ipomoea purpurea* are also controlled. DINAMIC®+Galago with a wetter: DINAMIC® 700WDG at 75 g/ha+Galago 480SC at 100 mL/ha+Wet-All at 0.1% resulted in excellent control of *Amaranthus spinosus, Commilina benghalensis* and *Eleusine indica*, but *Ipomoea purpurea* was marginally controlled. Signs of phytotoxicity were noticed in the plots were DINAMIC® 700WDG at 250 g/ha+Galago 480SC at 300 mL/ha+Wet-All at 0.1% was sprayed. DINAMIC® 700WDG at 125 g/ha+Galago 480SC at 150 mL/ha can be used to control *Amaranthus spinosus, Eleusine indica, Ipomoea purpurea* and *Commilina benghalensis*. DINAMIC® 700WDG at 75 g/ha+Galago 480SC at 100 mL/ha+Wet-All at 0.1% can be used to control *Amaranthus spinosus, Eleusine indica, Ipomoea purpurea* and *Commilina benghalensis*.

J. Post Emergence Application Against Weed in Maize

In this part of the Example the efficacy of DINAMIC® (amicarbazone 700WDG, 700 grams active/kg, available from Arysta LifeScience North America, Cary, N.C.) mixtures with Galago (mesotrione 480SC, 480 grams active/L, available from Arysta LifeScience North America, Cary, N.C.) or TOLLA 960 (available from Arysta LifeScience North America, Cary, N.C.) with or without Wet-All (available from Arysta LifeScience North America, Cary, N.C.) as a post emergence application against weeds in maize (variety PHI 2369W) was determined. A comparison with CALLISTO® 480SC plus GARDOGOLD® 500SC plus COMPLEMENT® Super (each available from Syngenta, Greensboro, N.C.) was performed.

Trials were conducted at a site with a history of weeds. The trials were executed under moderate weather conditions. Efficacy and visual phytotoxicity assessments were performed in triplicate. Normal practices were carried out to control insects and fungi. Crops were provided in 55 cm row width, at a sowing rate of 65,000 plants/ha, and at a sowing depth of five to eight cm. Soil class was clay with a clay content of about 40%. The site in this Example had been previously used for maize. Trial design was randomized blocks with a plot size of 20 m² replicated four times. Municipal water was used for all applications (pH=7.2).

Application of the treatments shown in Table 6-64 was conducted at post emergence stage 15 days after planting. Application of the treatments was conducted over a 24 hour period. Over this time period, dry bulb temperature was about 32° C., wet bulb temperature was about 25° C., relative humidity was about 50%, cloud cover was about 0%, and wind speed was about 0 m/s. Treatments were administered with a multi-spray gas sprayer with a 4× flat fan 03F80 nozzle. Spacing was 50 cm, with a height of 50 cm, pressure 2.8 Bar, at a ground speed of 1 m/s, and a calibration mean output of 330 L/ha. The soil temperature over the application period averaged to about 29° C. and the soil remained moist and fine. Crops stage at the outset was about 4 leaves with a BBCH scale of 14. Crop and weeds were actively growing. Weed stage was about 3-5 leaves.

TABLE 6-64

Treatments

| No | Treatments | Dosage rate (gai/ha) | Dosage rate (g/ha or mL/ha) |
|---|---|---|---|
|  | Untreated control | — | — |
| 1 | DINAMIC® 700WDG + | 52.5 | 75 |
|  | Galago 480SC + | 48 | 100 |
|  | Wet-All | — | 0.1% |
| 2 | DINAMIC® 700WDG + | 52.5 | 75 |
|  | Galago 480SC + | 72 | 150 |
|  | Wet-All | — | 0.1% |
| 3 | DINAMIC® 700WDG + | 70 | 100 |
|  | Galago 480SC + | 48 | 100 |
|  | Wet-All | — | 0.1% |
| 4 | DINAMIC® 700WDG + | 70 | 100 |
|  | Galago 480SC + | 72 | 150 |
|  | Wet-All | — | 0.1% |
| 5 | DINAMIC® 700WDG + | 87.5 | 125 |
|  | Galago 480SC + | 48 | 100 |
|  | Wet-All | — | 0.1% |
| 6 | DINAMIC® 700WDG + | 87.5 | 125 |
|  | Galago 480SC + | 72 | 150 |
|  | Wet-All | — | 0.1% |
| 7 | DINAMIC® 700WDG + | 52.5 | 75 |
|  | Galago 480SC + | 48 | 100 |
|  | TOLLA 960 | 960 | 1000 |
|  | Wet-All | — | 0.1% |
| 8 | DINAMIC® 700WDG + | 52.5 | 75 |
|  | Galago 480SC + | 72 | 150 |
|  | TOLLA 960 | 960 | 1000 |
|  | Wet-All | — | 0.1% |
| 9 | DINAMIC® 700WDG + | 70 | 100 |
|  | Galago 480SC + | 48 | 100 |
|  | TOLLA 960 | 960 | 1000 |
|  | Wet-All | — | 0.1% |
| 10 | DINAMIC® 700WDG + | 70 | 100 |
|  | Galago 480SC + | 72 | 150 |
|  | TOLLA 960 | 960 | 1000 |
|  | Wet-All | — | 0.1% |
| 11 | DINAMIC® 700WDG + | 87.5 | 125 |
|  | Galago 480SC + | 48 | 100 |
|  | TOLLA 960 | 960 | 1000 |
|  | Wet-All | — | 0.1% |
| 12 | DINAMIC® 700WDG + | 87.5 | 125 |
|  | Galago 480SC + | 72 | 150 |
|  | TOLLA 960 | 960 | 1000 |
|  | Wet-All | — | 0.1% |
| 13 | DINAMIC® 700WDG + | 175 | 250 |
|  | Galago 480SC + | 144 | 300 |
|  | TOLLA 960 | 960 | 1000 |
|  | Wet-All | — | 0.1% |

TABLE 6-64-continued

| No | Treatments | Dosage rate (gai/ha) | Dosage rate (g/ha or mL/ha) |
|---|---|---|---|
| 14 | CALLISTO ® 480SC + | 52.5 | 260 |
|  | GardoGold 500SC + | 48 | 1562 |
|  | Compliment Super | 960 | 0.1% |

Assessments of the treated crops at 2, 4, and 6 weeks are summarized in Tables 6-65 to 6-67 below. No visual signs of phytotoxicity were noticed over 2 weeks. Signs of phytotoxicity were noticed in treatment 13 at 4 and 6 weeks.

TABLE 6-65

| 2 Week Assessment | |
|---|---|
| Crop condition | Actively growing |
| Crop stage | 5-6 Leaves |
| BBCH scale | 15-16 |
| Soil moisture | Wet |
| Rain since last visit | 18 mm |

TABLE 6-66

| 4 Week Assessment | |
|---|---|
| Crop condition | Actively growing |
| Crop stage | 8 Leaves |
| BBCH scale | 18 |
| Soil moisture | Wet |
| Rain since last visit | 38 mm |

TABLE 6-67

| 6 Week Assessment | |
|---|---|
| Crop condition | Actively growing |
| Crop stage | 10 leaves |
| BBCH scale: | 20 |
| Soil moisture | Moist |
| Rain since last visit | 0 mm |

Control and weed cover at 2, 4, and 6 weeks for the indicated species are summarized below in Tables 6-68 through 6-70. 80% is considered acceptable control.

TABLE 6-68

| % Control and weed cover (2 weeks after application) | | | | | |
|---|---|---|---|---|---|
| Treatments (product/ha) | | Rep | ROTEX | AMAHY | COMBE |
|  | Untreated control | I | 30 | 40 | 30 |
|  | % soil cover | ii | 40 | 30 | 30 |
|  |  | iii | 40 | 50 | 10 |
|  |  | iv | 30 | 40 | 30 |
|  | Mean |  | 35 | 40 | 25 |
| 1 | DINAMIC ® at 75 g | I | 30 | 80 | 90 |
|  | Galago at 100 ml | ii | 40 | 70 | 90 |
|  | Wet-All at 0.1% | iii | 30 | 80 | 90 |
|  |  | iv | 20 | 80 | 90 |
|  | Mean |  | 30 | 78 | 90 |
| 2 | DINAMIC ® at 75 g | I | 50 | 80 | 100 |
|  | Galago at 150 ml | ii | 40 | 80 | 100 |
|  | Wet-All at 0.1% | iii | 40 | 90 | 95 |
|  |  | iv | 50 | 80 | 100 |
|  | Mean |  | 45 | 83 | 99 |

TABLE 6-68-continued

| % Control and weed cover (2 weeks after application) | | | | | |
|---|---|---|---|---|---|
| Treatments (product/ha) | | Rep | ROTEX | AMAHY | COMBE |
| 3 | DINAMIC ® at 100 g | I | 40 | 80 | 95 |
|  | Galago at 100 ml | ii | 40 | 90 | 95 |
|  | Wet-All at 0.1% | iii | 40 | 80 | 100 |
|  |  | iv | 50 | 90 | 90 |
|  | Mean |  | 43 | 85 | 95 |
| 4 | DINAMIC ® at 100 g | I | 60 | 90 | 100 |
|  | Galago at 150 ml | ii | 40 | 90 | 100 |
|  | Wet-All at 0.1% | iii | 50 | 90 | 100 |
|  |  | iv | 60 | 90 | 100 |
|  | Mean |  | 53 | 90 | 100 |
| 5 | DINAMIC ® at 125 g | I | 50 | 90 | 95 |
|  | Galago at 100 ml | ii | 40 | 80 | 95 |
|  | Wet-All at 0.1% | iii | 50 | 90 | 100 |
|  |  | iv | 50 | 95 | 95 |
|  | Mean |  | 48 | 89 | 96 |
| 6 | DINAMIC ® at 125 g | I | 70 | 100 | 100 |
|  | Galago at 150 ml | ii | 50 | 100 | 100 |
|  | Wet-All at 0.1% | iii | 60 | 95 | 100 |
|  |  | iv | 60 | 100 | 100 |
|  | Mean |  | 60 | 99 | 100 |
| 7 | DINAMIC ® at 75 g | I | 70 | 80 | 90 |
|  | Galago at 100 ml | ii | 80 | 80 | 95 |
|  | TOLLA 960 at 1000 ml | iii | 80 | 80 | 95 |
|  | Wet-All at 0.1% | iv | 80 | 80 | 90 |
|  | Mean |  | 78 | 80 | 93 |
| 8 | DINAMIC ® at 75 g | I | 70 | 100 | 100 |
|  | Galago at 150 ml | ii | 80 | 90 | 100 |
|  | TOLLA 960 at 1000 ml | iii | 80 | 80 | 100 |
|  | Wet-All at 0.1% | iv | 90 | 90 | 100 |
|  | Mean |  | 80 | 90 | 100 |
| 9 | DINAMIC ® at 100 g | I | 80 | 100 | 98 |
|  | Galago at 100 ml | ii | 90 | 100 | 98 |
|  | TOLLA 960 at 1000 ml | iii | 80 | 90 | 100 |
|  | Wet-All at 0.1% | iv | 80 | 90 | 95 |
|  | Mean |  | 83 | 95 | 98 |
| 10 | DINAMIC ® at 100 g | I | 90 | 90 | 100 |
|  | Galago at 150 ml | ii | 80 | 90 | 100 |
|  | TOLLA 960 at 1000 ml | iii | 80 | 90 | 100 |
|  | Wet-All at 0.1% | iv | 90 | 90 | 100 |
|  | Mean |  | 85 | 90 | 100 |
| 11 | DINAMIC ® at 125 g | I | 95 | 95 | 100 |
|  | Galago at 100 ml | ii | 80 | 100 | 100 |
|  | TOLLA 960 at 1000 ml | iii | 90 | 90 | 98 |
|  | Wet-All at 0.1% | iv | 90 | 90 | 95 |
|  | Mean |  | 89 | 94 | 98 |
| 12 | DINAMIC ® at 125 g | I | 90 | 100 | 100 |
|  | Galago at 150 ml | ii | 100 | 100 | 100 |
|  | TOLLA 960 at 1000 ml | iii | 95 | 100 | 100 |
|  | Wet-All at 0.1% | iv | 95 | 100 | 100 |
|  | Mean |  | 95 | 100 | 100 |
| 13 | DINAMIC ® at 250 g | I | 100 | 100 | 100 |
|  | Galago at 300 ml | ii | 95 | 100 | 100 |
|  | TOLLA 960 at 1000 ml | iii | 100 | 100 | 100 |
|  | Wet-All at 0.1% | iv | 95 | 100 | 100 |
|  | Mean |  | 98 | 100 | 100 |
| 14 | CALLISTO ® 480SC at 260 ml | I | 100 | 95 | 100 |
|  | GardoGOLD at 1562 ml | ii | 95 | 100 | 100 |
|  | Compliment at 0.1% | iii | 95 | 95 | 100 |
|  |  | iv | 95 | 100 | 100 |
|  | Mean |  | 96 | 98 | 100 |

ROTTE = *Rottboelia exaltata*; IPOPU = *Ipomoea purpurea*; AMAHY = *Amaranthus hybridus*

TABLE 6-69

% Control and weed cover (4 weeks after application)

| | Treatments (product/ha) | Rep | ROTEX | AMAHY | COMBE |
|---|---|---|---|---|---|
| | Untreated control | I | 30 | 40 | 30 |
| | % soil cover | ii | 40 | 30 | 30 |
| | | iii | 40 | 50 | 10 |
| | | iv | 30 | 40 | 30 |
| | Mean | | 35 | 40 | 25 |
| 1 | DINAMIC ® at 75 g | I | 40 | 80 | 90 |
| | Galago at 100 ml | ii | 40 | 80 | 90 |
| | Wet-All at 0.1% | iii | 30 | 90 | 95 |
| | | iv | 30 | 80 | 90 |
| | Mean | | 35 | 83 | 91 |
| 2 | DINAMIC ® at 75 g | I | 50 | 90 | 100 |
| | Galago at 150 ml | ii | 40 | 80 | 100 |
| | Wet-All at 0.1% | iii | 50 | 95 | 95 |
| | | iv | 50 | 90 | 100 |
| | Mean | | 48 | 89 | 99 |
| 3 | DINAMIC ® at 100 g | I | 40 | 90 | 95 |
| | Galago at 100 ml | ii | 50 | 90 | 98 |
| | Wet-All at 0.1% | iii | 40 | 90 | 100 |
| | | iv | 50 | 90 | 95 |
| | Mean | | 45 | 90 | 97 |
| 4 | DINAMIC ® at 100 g | I | 60 | 100 | 100 |
| | Galago at 150 ml | ii | 50 | 100 | 100 |
| | Wet-All at 0.1% | iii | 50 | 95 | 100 |
| | | iv | 60 | 95 | 100 |
| | Mean | | 55 | 98 | 100 |
| 5 | DINAMIC ® at 125 g | I | 50 | 95 | 95 |
| | Galago at 100 ml | ii | 50 | 90 | 100 |
| | Wet-All at 0.1% | iii | 60 | 95 | 100 |
| | | iv | 50 | 95 | 98 |
| | Mean | | 53 | 94 | 98 |
| 6 | DINAMIC ® at 125 g | I | 70 | 100 | 100 |
| | Galago at 150 ml | ii | 60 | 100 | 100 |
| | Wet-All at 0.1% | iii | 70 | 98 | 100 |
| | | iv | 60 | 100 | 100 |
| | Mean | | 65 | 100 | 100 |
| 7 | DINAMIC ® at 75 g | I | 70 | 90 | 90 |
| | Galago at 100 ml | ii | 80 | 90 | 98 |
| | TOLLA 960 at 1000 ml | iii | 80 | 80 | 95 |
| | Wet-All at 0.1% | iv | 80 | 90 | 95 |
| | Mean | | 78 | 88 | 95 |
| 8 | DINAMIC ® at 75 g | I | 80 | 100 | 100 |
| | Galago at 150 ml | ii | 80 | 90 | 100 |
| | TOLLA 960 at 1000 ml | iii | 80 | 90 | 100 |
| | Wet-All at 0.1% | iv | 90 | 95 | 100 |
| | Mean | | 83 | 94 | 100 |
| 9 | DINAMIC ® at 100 g | I | 80 | 100 | 100 |
| | Galago at 100 ml | ii | 90 | 100 | 98 |
| | TOLLA 960 at 1000 ml | iii | 90 | 95 | 100 |
| | Wet-All at 0.1% | iv | 90 | 95 | 98 |
| | Mean | | 88 | 98 | 99 |
| 10 | DINAMIC ® at 100 g | I | 90 | 95 | 100 |
| | Galago at 150 ml | ii | 80 | 95 | 100 |
| | TOLLA 960 at 1000 ml | iii | 90 | 90 | 100 |
| | Wet-All at 0.1% | iv | 90 | 95 | 100 |
| | Mean | | 88 | 94 | 100 |
| 11 | DINAMIC ® at 125 g | I | 95 | 98 | 100 |
| | Galago at 100 ml | ii | 90 | 100 | 100 |
| | TOLLA 960 at 1000 ml | iii | 95 | 95 | 100 |
| | Wet-All at 0.1% | iv | 90 | 95 | 98 |
| | Mean | | 93 | 97 | 100 |
| 12 | DINAMIC ® at 125 g | I | 90 | 100 | 100 |
| | Galago at 150 ml | ii | 100 | 100 | 100 |
| | TOLLA 960 at 1000 ml | iii | 98 | 100 | 100 |
| | Wet-All at 0.1% | iv | 98 | 100 | 100 |
| | Mean | | 97 | 100 | 100 |
| 13 | DINAMIC ® at 250 g | I | 100 | 100 | 100 |
| | Galago at 300 ml | ii | 95 | 100 | 100 |
| | TOLLA 960 at 1000 ml | iii | 100 | 100 | 100 |
| | Wet-All at 0.1% | iv | 100 | 100 | 100 |
| | Mean | | 99 | 100 | 100 |
| 14 | CALLISTO ® 480SC at 260 ml | I | 100 | 100 | 100 |
| | GardoGOLD at 1562 ml | ii | 95 | 100 | 100 |
| | Compliment at 0.1% | iii | 98 | 95 | 100 |
| | | iv | 100 | 100 | 100 |
| | Mean | | 98 | 99 | 100 |

ROTTE = *Rottboelia exaltata*; IPOPU = *Ipomoea purpurea*; AMAHY = *Amaranthus hybridus*

TABLE 6-70

% Control and weed cover (6 weeks after application)

| | Treatments (product/ha) | Rep | ROTEX | AMAHY | COMBE |
|---|---|---|---|---|---|
| | Untreated control | I | 30 | 40 | 30 |
| | % soil cover | ii | 30 | 30 | 40 |
| | | iii | 40 | 50 | 10 |
| | | iv | 20 | 40 | 40 |
| | Mean | | 30 | 40 | 30 |
| 1 | DINAMIC ® at 75 g | I | 40 | 80 | 90 |
| | Galago at 100 ml | ii | 40 | 80 | 95 |
| | Wet-All at 0.1% | iii | 30 | 90 | 95 |
| | | iv | 40 | 90 | 95 |
| | Mean | | 38 | 85 | 94 |
| 2 | DINAMIC ® at 75 g | I | 50 | 90 | 100 |
| | Galago at 150 ml | ii | 50 | 90 | 100 |
| | Wet-All at 0.1% | iii | 50 | 98 | 98 |
| | | iv | 50 | 90 | 100 |
| | Mean | | 50 | 92 | 100 |
| 3 | DINAMIC ® at 100 g | I | 50 | 90 | 95 |
| | Galago at 100 ml | ii | 50 | 95 | 100 |
| | Wet-All at 0.1% | iii | 50 | 95 | 100 |
| | | iv | 50 | 90 | 98 |
| | Mean | | 50 | 93 | 98 |
| 4 | DINAMIC ® at 100 g | I | 60 | 100 | 100 |
| | Galago at 150 ml | ii | 50 | 100 | 100 |
| | Wet-All at 0.1% | iii | 60 | 100 | 100 |
| | | iv | 70 | 98 | 100 |
| | Mean | | 60 | 100 | 100 |
| 5 | DINAMIC ® at 125 g | I | 50 | 98 | 95 |
| | Galago at 100 ml | ii | 60 | 95 | 100 |
| | Wet-All at 0.1% | iii | 60 | 95 | 100 |
| | | iv | 50 | 95 | 100 |
| | Mean | | 55 | 96 | 99 |
| 6 | DINAMIC ® at 125 g | I | 70 | 100 | 100 |
| | Galago at 150 ml | ii | 70 | 100 | 100 |
| | Wet-All at 0.1% | iii | 70 | 100 | 100 |
| | | iv | 70 | 100 | 100 |
| | Mean | | 70 | 100 | 100 |
| 7 | DINAMIC ® at 75 g | I | 80 | 90 | 95 |
| | Galago at 100 ml | ii | 80 | 90 | 100 |
| | TOLLA 960 at 1000 ml | iii | 80 | 90 | 95 |
| | Wet-All at 0.1% | iv | 90 | 95 | 98 |
| | Mean | | 83 | 91 | 97 |
| 8 | DINAMIC ® at 75 g | I | 90 | 100 | 100 |
| | Galago at 150 ml | ii | 80 | 95 | 100 |
| | TOLLA 960 at 1000 ml | iii | 80 | 95 | 100 |
| | Wet-All at 0.1% | iv | 90 | 95 | 100 |
| | Mean | | 85 | 96 | 100 |
| 9 | DINAMIC ® at 100 g | I | 80 | 100 | 100 |
| | Galago at 100 ml | ii | 95 | 100 | 100 |
| | TOLLA 960 at 1000 ml | iii | 95 | 100 | 100 |
| | Wet-All at 0.1% | iv | 90 | 95 | 100 |
| | Mean | | 90 | 99 | 100 |
| 10 | DINAMIC ® at 100 g | I | 90 | 98 | 100 |
| | Galago at 150 ml | ii | 90 | 95 | 100 |
| | TOLLA 960 at 1000 ml | iii | 90 | 95 | 100 |
| | Wet-All at 0.1% | iv | 95 | 95 | 100 |
| | Mean | | 91 | 96 | 100 |

TABLE 6-70-continued

% Control and weed cover (6 weeks after application)

| Treatments (product/ha) | | Rep | ROTEX | AMAHY | COMBE |
|---|---|---|---|---|---|
| 11 | DINAMIC ® at 125 g | I | 95 | 100 | 100 |
| | Galago at 100 ml | ii | 95 | 100 | 100 |
| | TOLLA 960 at 1000 ml | iii | 95 | 95 | 100 |
| | Wet-All at 0.1% | iv | 95 | 100 | 100 |
| | Mean | | 95 | 99 | 100 |
| 12 | DINAMIC ® at 125 g | I | 98 | 100 | 100 |
| | Galago at 150 ml | ii | 100 | 100 | 100 |
| | TOLLA 960 at 1000 ml | iii | 98 | 100 | 100 |
| | Wet-All at 0.1% | iv | 100 | 100 | 100 |
| | Mean | | 99 | 100 | 100 |
| 13 | DINAMIC ® at 250 g | I | 100 | 100 | 100 |
| | Galago at 300 ml | ii | 98 | 100 | 100 |
| | TOLLA 960 at 1000 ml | iii | 100 | 100 | 100 |
| | Wet-All at 0.1% | iv | 100 | 100 | 100 |
| | Mean | | 100 | 100 | 100 |
| 14 | CALLISTO ® 480SC at 260 ml | I | 100 | 100 | 100 |
| | GardoGOLD at 1562 ml | ii | 98 | 100 | 100 |
| | Compliment at 0.1% | iii | 100 | 98 | 100 |
| | | iv | 100 | 100 | 100 |
| | Mean | | 100 | 100 | 100 |

ROTTE = *Rottboelia exaltata*; IPOPU = *Ipomoea purpurea*; AMAHY = *Amaranthus hybridus*

DINAMIC®+Galago+Wet-All: Rottboellia exaltata could not be controlled by any dosage rates of this mixture. DINAMIC® 700WDG at 75 g/ha+Galago 480SC at 100 mL/ha+Wet-All at 0.1% resulted in satisfactory control of *Amaranthus hybridus* and *Ipomoea purpurea*. With the exception of Rottboellia exaltata DINAMIC® 700WDG at 125 g/ha+Galago 480SC at 150 mL/ha+Wet-All at 0.1% compared with the standard CALLISTO® 480 SC at 260 mL/ha+Gardo Gold at 1562 mL/ha+Compliment at 0.1%. Rottboellia exaltata was 100% controlled by the standard treatment. DINAMIC®+Galago+TOLLA+Wet-All: DINAMIC® 700WDG at 75 g/ha+Galago 480SC at 100 mL/ha+TOLLA 960EC at 1000 mL/ha+Wet-All at 0.1% showed acceptable control of the entire weed spectrum after 6 weeks. DINAMIC® 700WDG at 125 g/ha+Galago 480SC at 150 mL/ha+TOLLA 960EC at 1000 mL/ha+Wet-All at 0.1% showed similar results to the standard CALLISTO® 480 SC at 260 mL/ha+Gardo Gold at 1562 mL/ha+Compliment at 0.1%. Signs of phytotoxicity were noticed in the plots were DINAMIC® 700WDG at 250 g/ha+Galago 480SC at 300 mL/ha+TOLLA 960EC at 1000 mL/ha+Wet-All at 0.1% was sprayed. DINAMIC® 700WDG at 75 g/ha+Galago 480SC at 150 mL/ha+TOLLA 960EC at 1000 mL/ha+Wet-All at 0.1% can safely be used to control of *Amaranthus hybridus, Ipomoea purpurea* and *Rottboellia exaltata*.

K. Post Emergence Application Against Weed in Maize

In this part of the Example the efficacy of DINAMIC® (amicarbazone 700WDG, 700 grams active/kg, available from Arysta LifeScience North America, Cary, N.C.) mixtures with Galago (mesotrione 480SC, 480 grams active/L, available from Arysta LifeScience North America, Cary, N.C.) or TOLLA 840S (available from Arysta LifeScience North America, Cary, N.C.) with or without Wet-All (available from Arysta LifeScience North America, Cary, N.C.) as a post emergence application against weeds in maize (variety PHI 32Y85) was determined. A comparison with CALLISTO® 480SC plus GARDOGOLD® 500SC plus COMPLEMENT® Super (each available from Syngenta, Greensboro, N.C.) was performed.

Trials were conducted at a site with a history of weeds. The trials were executed under moderate weather conditions. Efficacy and visual phytotoxicity assessments were performed in triplicate. Normal practices were carried out to control insects and fungi. Crops were provided in 76 cm row width, at a sowing rate of 65,000 plants/ha, and at a sowing depth of five to eight cm. Soil class was clay with a clay content of about 35%. The site in this Example had been previously used for soya beans. Trial design was randomized blocks with a plot size of 20 m² replicated four times. Municipal water was used for all applications (pH=7.2).

Application of the treatments shown in Table 6-71 was conducted at post emergence stage 14 days after planting. Application of the treatments was conducted over a 24 hour period. Over this time period, dry bulb temperature was about 26° C., wet bulb temperature was about 21° C., relative humidity was about 65%, cloud cover was about 50%, and wind speed was about 0 m/s. Treatments were administered with a multi-spray gas sprayer with a 4x flat fan 03F80 nozzle. Spacing was 50 cm, with a height of 50 cm, pressure 2.8 Bar, at a ground speed of 1 m/s, and a calibration mean output of 330 L/ha. The soil temperature over the application period averaged to about 23° C. and the soil remained moist and fine. Crops stage at the outset was about 4 leaves with a BBCH scale of 14. Crop and weeds were actively growing. Weed stage was about 2-5 leaves.

TABLE 6-71

Treatments

| No | Treatments | Dosage rate (gai/ha) | Dosage rate (g/ha or mL/ha) |
|---|---|---|---|
| | Untreated control | — | — |
| 1 | DINAMIC ® 700WDG + | 52.5 | 75 |
| | Galago 480SC + | 48 | 100 |
| | Wet-All | — | 0.1% |
| 2 | DINAMIC ® 700WDG + | 52.5 | 75 |
| | Galago 480SC + | 72 | 150 |
| | Wet-All | — | 0.1% |
| 3 | DINAMIC ® 700WDG + | 70 | 100 |
| | Galago 480SC + | 48 | 100 |
| | Wet-All | — | 0.1% |
| 4 | DINAMIC ® 700WDG + | 70 | 100 |
| | Galago 480SC + | 72 | 150 |
| | Wet-All | — | 0.1% |
| 5 | DINAMIC ® 700WDG + | 87.5 | 125 |
| | Galago 480SC + | 48 | 100 |
| | Wet-All | — | 0.1% |
| 6 | DINAMIC ® 700WDG + | 87.5 | 125 |
| | Galago 480SC + | 72 | 150 |
| | Wet-All | — | 0.1% |
| 7 | DINAMIC ® 700WDG + | 52.5 | 75 |
| | Galago 480SC + | 48 | 100 |
| | TOLLA 960 | 960 | 1000 |
| | Wet-All | — | 0.1% |
| 8 | DINAMIC ® 700WDG + | 52.5 | 75 |
| | Galago 480SC + | 72 | 150 |
| | TOLLA 960 | 960 | 1000 |
| | Wet-All | — | 0.1% |
| 9 | DINAMIC ® 700WDG + | 70 | 100 |
| | Galago 480SC + | 48 | 100 |
| | TOLLA 960 | 960 | 1000 |
| | Wet-All | — | 0.1% |
| 10 | DINAMIC ® 700WDG + | 70 | 100 |
| | Galago 480SC + | 72 | 150 |
| | TOLLA 960 | 960 | 1000 |
| | Wet-All | — | 0.1% |
| 11 | DINAMIC ® 700WDG + | 87.5 | 125 |
| | Galago 480SC + | 48 | 100 |
| | TOLLA 960 | 960 | 1000 |
| | Wet-All | — | 0.1% |

TABLE 6-71-continued

| No | Treatments | Dosage rate (gai/ha) | Dosage rate (g/ha or mL/ha) |
|---|---|---|---|
| 12 | DINAMIC ® 700WDG + | 87.5 | 125 |
|  | Galago 480SC + | 72 | 150 |
|  | TOLLA 960 | 960 | 1000 |
|  | Wet-All | — | 0.1% |
| 13 | DINAMIC ® 700WDG + | 175 | 250 |
|  | Galago 480SC + | 144 | 300 |
|  | TOLLA 960 | 960 | 1000 |
|  | Wet-All | — | 0.1% |
| 14 | CALLISTO ® 480SC + | 52.5 | 260 |
|  | GardoGold 500SC + | 48 | 1562 |
|  | Compliment | 960 | 0.1% |

Assessments of the treated crops at 2, 4, and 6 weeks are summarized in Tables 6-72 to 6-74 below. No visual signs of phytotoxicity were noticed over 6 weeks.

TABLE 6-72

| 2 Week Assessment | |
|---|---|
| Crop condition | Actively growing |
| Crop stage | 6 Leaves |
| BBCH scale | 16 |
| Soil moisture | Moist |
| Rain since last visit | 8 mm |

TABLE 6-73

| 4 Week Assessment | |
|---|---|
| Crop condition | Actively growing |
| Crop stage | 7 Leaves |
| BBCH scale | 17 |
| Soil moisture | Wet |
| Rain since last visit | 44 mm |

TABLE 6-74

| 6 Week Assessment | |
|---|---|
| Crop condition | Actively growing |
| Crop stage | 9 leaves |
| BBCH scale: | 19 |
| Soil moisture | Moist |
| Rain since last visit | 0 mm |

Control and weed cover at 2, 4, and 6 weeks for the indicated species are summarized below in Tables 6-75 through 6-77. 80% is considered acceptable control.

TABLE 6-75

| % Control and weed cover (2 weeks after application) | | | | | |
|---|---|---|---|---|---|
| Treatments (product/ha) | Rep | DIGSA | POROL | AMAHY | COMBE |
| Untreated control | I | 30 | 20 | 20 | 30 |
| % soil cover | ii | 40 | 10 | 30 | 20 |
|  | iii | 40 | 20 | 10 | 30 |
|  | iv | 30 | 20 | 20 | 30 |
| Mean |  | 35 | 18 | 20 | 28 |
| 1 DINAMIC ® at 75 g | I | 80 | 80 | 70 | 70 |
| Galago at 100 ml | ii | 70 | 80 | 70 | 80 |
| Wet-All at 0.1% | iii | 80 | 70 | 60 | 70 |
|  | iv | 80 | 70 | 70 | 70 |
| Mean |  | 78 | 75 | 68 | 73 |
| 2 DINAMIC ® at 75 g | I | 80 | 80 | 70 | 60 |
| Galago at 150 ml | ii | 90 | 80 | 80 | 70 |
| Wet-All at 0.1% | iii | 90 | 70 | 70 | 70 |
|  | iv | 90 | 70 | 70 | 70 |
| Mean |  | 88 | 75 | 73 | 68 |
| 3 DINAMIC ® at 100 g | I | 70 | 90 | 90 | 80 |
| Galago at 100 ml | ii | 80 | 90 | 80 | 80 |
| Wet-All at 0.1% | iii | 80 | 80 | 90 | 80 |
|  | iv | 70 | 90 | 90 | 70 |
| Mean |  | 75 | 88 | 88 | 78 |
| 4 DINAMIC ® at 100 g | I | 90 | 90 | 90 | 80 |
| Galago at 150 ml | ii | 100 | 100 | 90 | 80 |
| Wet-All at 0.1% | iii | 95 | 90 | 90 | 80 |
|  | iv | 90 | 90 | 90 | 80 |
| Mean |  | 94 | 93 | 90 | 80 |
| 5 DINAMIC ® at 125 g | I | 90 | 100 | 98 | 95 |
| Galago at 100 ml | ii | 95 | 100 | 100 | 95 |
| Wet-All at 0.1% | iii | 90 | 100 | 95 | 95 |
|  | iv | 90 | 100 | 95 | 95 |
| Mean |  | 91 | 100 | 97 | 95 |
| 6 DINAMIC ® at 125 g | I | 95 | 100 | 95 | 100 |
| Galago at 150 ml | ii | 100 | 100 | 100 | 100 |
| Wet-All at 0.1% | iii | 98 | 100 | 98 | 100 |
|  | iv | 95 | 100 | 100 | 100 |
| Mean |  | 97 | 100 | 98 | 100 |
| 7 DINAMIC ® at 75 g | I | 90 | 100 | 85 | 90 |
| Galago at 100 ml | ii | 90 | 100 | 90 | 90 |
| TOLLA 960 at 1000 ml | iii | 95 | 100 | 90 | 95 |
| Wet-All at 0.1% | iv | 95 | 100 | 80 | 90 |
| Mean |  | 93 | 100 | 86 | 91 |
| 8 DINAMIC ® at 75 g | I | 95 | 100 | 90 | 100 |
| Galago at 150 ml | ii | 100 | 100 | 100 | 100 |
| TOLLA 960 at 1000 ml | iii | 100 | 100 | 95 | 95 |
| Wet-All at 0.1% | iv | 100 | 100 | 95 | 100 |
| Mean |  | 99 | 100 | 95 | 99 |
| 9 DINAMIC ® at 100 g | I | 95 | 100 | 100 | 100 |
| Galago at 100 ml | ii | 100 | 100 | 100 | 95 |
| TOLLA 960 at 1000 ml | iii | 98 | 100 | 100 | 100 |
| Wet-All at 0.1% | iv | 95 | 100 | 100 | 100 |
| Mean |  | 97 | 100 | 100 | 99 |
| 10 DINAMIC ® at 100 g | I | 90 | 100 | 95 | 95 |
| Galago at 150 ml | ii | 100 | 100 | 100 | 100 |
| TOLLA 960 at 1000 ml | iii | 100 | 100 | 100 | 100 |
| Wet-All at 0.1% | iv | 100 | 100 | 98 | 100 |
| Mean |  | 98 | 100 | 98 | 99 |
| 11 DINAMIC ® at 125 g | I | 90 | 100 | 100 | 100 |
| Galago at 100 ml | ii | 90 | 100 | 98 | 100 |
| TOLLA 960 at 1000 ml | iii | 95 | 100 | 98 | 95 |
| Wet-All at 0.1% | iv | 95 | 100 | 100 | 98 |
| Mean |  | 93 | 100 | 99 | 98 |
| 12 DINAMIC ® at 125 g | I | 100 | 100 | 90 | 100 |
| Galago at 150 ml | ii | 100 | 100 | 100 | 100 |
| TOLLA 960 at 1000 ml | iii | 100 | 100 | 95 | 98 |
| Wet-All at 0.1% | iv | 100 | 100 | 95 | 100 |
| Mean |  | 100 | 100 | 95 | 100 |
| 13 DINAMIC ® at 250 g | I | 100 | 100 | 100 | 100 |
| Galago at 300 ml | ii | 100 | 100 | 100 | 100 |
| TOLLA 960 at 1000 ml | iii | 100 | 100 | 100 | 100 |
| Wet-All at 0.1% | iv | 100 | 100 | 100 | 100 |
| Mean |  | 100 | 100 | 100 | 100 |
| 14 CALLISTO ® 480SC at 260 ml | I | 95 | 90 | 98 | 100 |
| GardoGOLD at 1562 ml | ii | 90 | 95 | 100 | 100 |
| Compliment at 0.1% | iii | 95 | 100 | 98 | 100 |
|  | iv | 95 | 95 | 98 | 100 |
| Mean |  | 94 | 95 | 99 | 100 |

DIGSA = *Digitaria sanguinalis*; POROL = *Portulaca oleracea*; AMAHY = *Amaranthus hybridus*; COMBE = *Commelina benghalensis*

TABLE 6-76

% Control and weed cover (4 weeks after application)

| Treatments (product/ha) | Rep | DIGSA | POROL | AMAHY | COMBE |
|---|---|---|---|---|---|
| Untreated control % soil cover | I | 30 | 20 | 20 | 30 |
| | ii | 40 | 10 | 30 | 20 |
| | iii | 40 | 20 | 10 | 30 |
| | iv | 30 | 20 | 20 | 30 |
| Mean | | 35 | 18 | 20 | 28 |
| DINAMIC ® at 75 g Galago at 100 ml Wet-All at 0.1% | I | 80 | 80 | 70 | 80 |
| | ii | 80 | 80 | 70 | 80 |
| | iii | 80 | 70 | 70 | 70 |
| | iv | 90 | 80 | 80 | 70 |
| Mean | | 83 | 78 | 73 | 75 |
| DINAMIC ® at 75 g Galago at 150 ml Wet-All at 0.1% | I | 90 | 80 | 70 | 70 |
| | ii | 90 | 80 | 80 | 80 |
| | iii | 90 | 70 | 80 | 80 |
| | iv | 98 | 80 | 80 | 70 |
| Mean | | 92 | 78 | 78 | 75 |
| DINAMIC ® at 100 g Galago at 100 ml Wet-All at 0.1% | I | 80 | 90 | 90 | 80 |
| | ii | 90 | 90 | 90 | 80 |
| | iii | 80 | 90 | 90 | 70 |
| | iv | 80 | 90 | 90 | 80 |
| Mean | | 83 | 90 | 90 | 78 |
| DINAMIC ® at 100 g Galago at 150 ml Wet-All at 0.1% | I | 95 | 95 | 90 | 80 |
| | ii | 100 | 100 | 90 | 80 |
| | iii | 98 | 90 | 95 | 90 |
| | iv | 90 | 95 | 90 | 90 |
| Mean | | 96 | 95 | 91 | 85 |
| DINAMIC ® at 125 g Galago at 100 ml Wet-All at 0.1% | I | 95 | 100 | 98 | 95 |
| | ii | 98 | 100 | 100 | 95 |
| | iii | 90 | 100 | 95 | 95 |
| | iv | 95 | 100 | 95 | 95 |
| Mean | | 95 | 100 | 97 | 95 |
| DINAMIC ® at 125 g Galago at 150 ml Wet-All at 0.1% | I | 98 | 100 | 95 | 100 |
| | ii | 100 | 100 | 100 | 100 |
| | iii | 100 | 100 | 98 | 100 |
| | iv | 98 | 100 | 100 | 100 |
| Mean | | 99 | 100 | 98 | 100 |
| DINAMIC ® at 75 g Galago at 100 ml TOLLA 960 at 1000 ml Wet-All at 0.1% | I | 90 | 100 | 85 | 90 |
| | ii | 95 | 100 | 90 | 90 |
| | iii | 100 | 100 | 90 | 95 |
| | iv | 98 | 100 | 80 | 90 |
| Mean | | 96 | 100 | 86 | 91 |
| DINAMIC ® at 75 g Galago at 150 ml TOLLA 960 at 1000 ml Wet-All at 0.1% | I | 100 | 100 | 90 | 100 |
| | ii | 100 | 100 | 100 | 100 |
| | iii | 100 | 100 | 95 | 95 |
| | iv | 100 | 100 | 95 | 100 |
| Mean | | 100 | 100 | 95 | 99 |
| DINAMIC ® at 100 g Galago at 100 ml TOLLA 960 at 1000 ml Wet-All at 0.1% | I | 98 | 100 | 100 | 100 |
| | ii | 100 | 100 | 100 | 95 |
| | iii | 100 | 100 | 100 | 100 |
| | iv | 95 | 100 | 100 | 100 |
| Mean | | 98 | 100 | 100 | 99 |
| DINAMIC ® at 100 g Galago at 150 ml TOLLA 960 at 1000 ml Wet-All at 0.1% | I | 95 | 100 | 95 | 95 |
| | ii | 100 | 100 | 100 | 100 |
| | iii | 100 | 100 | 100 | 100 |
| | iv | 100 | 100 | 98 | 100 |
| Mean | | 99 | 100 | 98 | 99 |
| DINAMIC ® at 125 g Galago at 100 ml TOLLA 960 at 1000 ml Wet-All at 0.1% | I | 95 | 100 | 100 | 100 |
| | ii | 90 | 100 | 98 | 100 |
| | iii | 98 | 100 | 98 | 95 |
| | iv | 95 | 100 | 100 | 98 |
| Mean | | 95 | 100 | 99 | 98 |
| DINAMIC ® at 125 g Galago at 150 ml TOLLA 960 at 1000 ml Wet-All at 0.1% | I | 100 | 100 | 90 | 100 |
| | ii | 100 | 100 | 100 | 100 |
| | iii | 100 | 100 | 95 | 98 |
| | iv | 100 | 100 | 95 | 100 |
| Mean | | 100 | 100 | 95 | 100 |
| DINAMIC ® at 250 g Galago at 300 ml TOLLA 960 at 1000 ml Wet-All at 0.1% | I | 100 | 100 | 100 | 100 |
| | ii | 100 | 100 | 100 | 100 |
| | iii | 100 | 100 | 100 | 100 |
| | iv | 100 | 100 | 100 | 100 |
| Mean | | 100 | 100 | 100 | 100 |
| CALLISTO ® 480SC at 260 ml GardoGOLD at 1562 ml Compliment at 0.1% | I | 95 | 90 | 98 | 100 |
| | ii | 95 | 95 | 100 | 100 |
| | iii | 98 | 100 | 98 | 100 |
| | iv | 95 | 95 | 98 | 100 |
| Mean | | 96 | 95 | 99 | 100 |

DIGSA = *Digitaria sanguinalis*; POROL = *Portulaca oleracea*; AMAHY = *Amaranthus hybridus*; COMBE = *Commelina benghalensis*

TABLE 6-77

% Control and weed cover (6 weeks after application)

| | Treatments (product/ha) | Rep | DIGSA | POROL | AMAHY | COMBE |
|---|---|---|---|---|---|---|
| | Untreated control % soil cover | I | 20 | 20 | 30 | 30 |
| | | ii | 20 | 20 | 40 | 20 |
| | | iii | 30 | 20 | 20 | 30 |
| | | iv | 20 | 30 | 20 | 30 |
| | Mean | | 23 | 23 | 28 | 28 |
| 1 | DINAMIC ® at 75 g Galago at 100 ml Wet-All at 0.1% | I | 80 | 80 | 70 | 80 |
| | | ii | 90 | 70 | 80 | 70 |
| | | iii | 90 | 70 | 70 | 70 |
| | | iv | 90 | 80 | 80 | 70 |
| | Mean | | 88 | 75 | 75 | 73 |
| 2 | DINAMIC ® at 75 g Galago at 150 ml Wet-All at 0.1% | I | 95 | 70 | 70 | 70 |
| | | ii | 90 | 80 | 80 | 80 |
| | | iii | 95 | 70 | 80 | 70 |
| | | iv | 100 | 70 | 70 | 70 |
| | Mean | | 95 | 73 | 75 | 73 |
| 3 | DINAMIC ® at 100 g Galago at 100 ml Wet-All at 0.1% | I | 80 | 80 | 90 | 80 |
| | | ii | 90 | 80 | 90 | 80 |
| | | iii | 80 | 80 | 90 | 70 |
| | | iv | 90 | 80 | 90 | 70 |
| | Mean | | 85 | 80 | 90 | 75 |
| 4 | DINAMIC ® at 100 g Galago at 150 ml Wet-All at 0.1% | I | 100 | 90 | 95 | 80 |
| | | ii | 100 | 95 | 90 | 70 |
| | | iii | 100 | 90 | 95 | 80 |
| | | iv | 95 | 90 | 90 | 90 |
| | Mean | | 99 | 91 | 93 | 80 |
| 5 | DINAMIC ® at 125 g Galago at 100 ml Wet-All at 0.1% | I | 98 | 100 | 100 | 90 |
| | | ii | 100 | 100 | 100 | 95 |
| | | iii | 95 | 100 | 95 | 95 |
| | | iv | 95 | 100 | 95 | 90 |
| | Mean | | 97 | 100 | 98 | 93 |
| 6 | DINAMIC ® at 125 g Galago at 150 ml Wet-All at 0.1% | I | 100 | 100 | 95 | 100 |
| | | ii | 100 | 100 | 100 | 100 |
| | | iii | 100 | 100 | 100 | 100 |
| | | iv | 100 | 100 | 100 | 100 |
| | Mean | | 100 | 100 | 99 | 100 |

TABLE 6-77-continued

% Control and weed cover (6 weeks after application)

| Treatments (product/ha) | Rep | DIGSA | POROL | AMAHY | COMBE |
|---|---|---|---|---|---|
| 7  DINAMIC ® at 75 g | i | 95 | 100 | 90 | 90 |
| Galago at 100 ml | ii | 95 | 100 | 90 | 95 |
| TOLLA 960 at 1000 ml | iii | 100 | 100 | 95 | 98 |
| Wet-All at 0.1% | iv | 100 | 100 | 90 | 90 |
| Mean | | 98 | 100 | 91 | 93 |
| 8  DINAMIC ® at 75 g | i | 100 | 100 | 90 | 100 |
| Galago at 150 ml | ii | 100 | 100 | 100 | 100 |
| TOLLA 960 at 1000 ml | iii | 100 | 100 | 98 | 95 |
| Wet-All at 0.1% | iv | 100 | 100 | 95 | 100 |
| Mean | | 100 | 100 | 96 | 99 |
| 9  DINAMIC ® at 100 g | i | 100 | 100 | 100 | 100 |
| Galago at 100 ml | ii | 100 | 100 | 100 | 98 |
| TOLLA 960 at 1000 ml | iii | 100 | 100 | 100 | 100 |
| Wet-All at 0.1% | iv | 98 | 100 | 100 | 100 |
| Mean | | 100 | 100 | 100 | 100 |
| 10 DINAMIC ® at 100 g | i | 95 | 100 | 95 | 95 |
| Galago at 150 ml | ii | 100 | 100 | 100 | 100 |
| TOLLA 960 at 1000 ml | iii | 100 | 100 | 100 | 100 |
| Wet-All at 0.1% | iv | 100 | 100 | 100 | 100 |
| Mean | | 99 | 100 | 99 | 99 |
| 11 DINAMIC ® at 125 g | i | 95 | 100 | 100 | 100 |
| Galago at 100 ml | ii | 95 | 100 | 100 | 100 |
| TOLLA 960 at 1000 ml | iii | 100 | 100 | 98 | 95 |
| Wet-All at 0.1% | iv | 95 | 100 | 100 | 100 |
| Mean | | 96 | 100 | 100 | 99 |
| 12 DINAMIC ® at 125 g | i | 100 | 100 | 95 | 100 |
| Galago at 150 ml | ii | 100 | 100 | 100 | 100 |
| TOLLA 960 at 1000 ml | iii | 100 | 100 | 100 | 100 |
| Wet-All at 0.1% | iv | 100 | 100 | 98 | 100 |
| Mean | | 100 | 100 | 98 | 100 |
| 13 DINAMIC ® at 250 g | i | 100 | 100 | 100 | 100 |
| Galago at 300 ml | ii | 100 | 100 | 100 | 100 |
| TOLLA 960 at 1000 ml | iii | 100 | 100 | 100 | 100 |
| Wet-All at 0.1% | iv | 100 | 100 | 100 | 100 |
| Mean | | 100 | 100 | 100 | 100 |
| 14 CALLISTO ® 480SC at 260 ml | i | 95 | 95 | 100 | 100 |
| GardoGOLD at 1562 ml | ii | 95 | 95 | 100 | 100 |
| Compliment at 0.1% | iii | 98 | 100 | 98 | 100 |
|  | iv | 95 | 95 | 100 | 100 |
| Mean | | 96 | 96 | 100 | 100 |

DIGSA = *Digitaria sanguinalis*; POROL = *Portulaca oleracea*; AMAHY = *Amaranthus hybridus*; COMBE = *Commelina benghalensis*

DINAMIC®+Galago+Wet-All: DINAMIC® 700WDG at 100 g/ha+Galago 480SC at 100 mL/ha+Wet-All at 0.1% resulted in satisfactory control of *Digitaria sanguinalis, Portulaca oleracea* and *Amaranthus hybridus. Commilina benghalensis* was insufficiently controlled but as soon as the Galago rate was increased to 100 mL/ha satisfactory control was achieved. DINAMIC®+Galago+TOLLA+Wet-All: The addition of TOLLA showed a drastic improvement on control. DINAMIC® 700WDG at 75 g/ha+Galago 480SC at 100 mL/ha+TOLLA 960EC at 1000 mL/ha+Wet-All at 0.1% showed excellent control of the entire weed spectrum after 6 weeks. This mixture performed on par with the standard CALLISTO® 480 SC at 260 mL/ha+Gardo Gold at 1562 mL/ha+Compliment at 0.1%. No visual signs of phytotoxicity were noticed throughout the growing season. DINAMIC® 700WDG at 75 g/ha+Galago 480SC at 100 mL/ha+TOLLA 960EC at 1000 mL/ha+Wet-All at 0.1% can be used for to control *Digitaria sanguinalis, Portulaca oleracea, Amaranthus hybridus* and *Commilina benghalensis*.

L. Post Emergence Application Against Weed in Maize

In this part of the Example the efficacy of DINAMIC® (amicarbazone 700WDG, 700 grams active/kg, available from Arysta LifeScience North America, Cary, N.C.) mixtures with Galago (mesotrione 480SC, 480 grams active/L, available from Arysta LifeScience North America, Cary, N.C.) or TOLLA 840S (available from Arysta LifeScience North America, Cary, N.C.) with or without Wet-All (available from Arysta LifeScience North America, Cary, N.C.) as a post emergence application against weeds in maize (variety PAN60-445B) was determined. A comparison with CALLISTO® 480SC plus GARDOGOLD® 500SC plus COMPLEMENT® Super (each available from Syngenta, Greensboro, N.C.) was performed.

Trials were conducted at a site with a history of broad leaf weeds and grasses. The trials were executed under moderate weather conditions. Efficacy and visual phytotoxicity assessments were performed in triplicate. Normal practices were carried out to control insects and fungi. Crops were provided in 76 cm row width, at a sowing rate of 65,000 plants/ha, and at a sowing depth of five to eight cm. Soil class was clay with a clay content of about 28%. The site in this Example had been previously used for soya beans. Trial design was randomized blocks with a plot size of 20 m² replicated four times. Municipal water was used for all applications (pH=7.2).

Application of the treatments shown in Table 6-78 was conducted at post emergence stage 18 days after planting. Application of the treatments was conducted over a 24 hour period. Over this time period, dry bulb temperature was about 31° C., wet bulb temperature was about 28° C., relative humidity was about 80%, cloud cover was about 100%, and wind speed was about 0 m/s. Treatments were administered with a multi-spray gas sprayer with a 4× flat fan 03F80 nozzle. Spacing was 50 cm, with a height of 50 cm, pressure 2.8 Bar, at a ground speed of 1 m/s, and a calibration mean output of 330 L/ha. The soil temperature over the application period averaged to about 29° C. and the soil remained moist and fine. Crops stage at the outset was about 4 leaves with a BBCH scale of 14. Crop and weeds were actively growing. Weed stage was about 2-6 leaves.

TABLE 6-78

Treatments

| No | Treatments | Dosage rate (gai/ha) | Dosage rate (g/ha or mL/ha) |
|---|---|---|---|
|   | Untreated control | — | — |
| 1 | DINAMIC ® 700WDG + | 52.5 | 75 |
|   | Galago 480SC + | 48 | 100 |
|   | Wet-All | — | 0.1% |
| 2 | DINAMIC ® 700WDG + | 52.5 | 75 |
|   | Galago 480SC + | 72 | 150 |
|   | Wet-All | — | 0.1% |
| 3 | DINAMIC ® 700WDG + | 70 | 100 |
|   | Galago 480SC + | 48 | 100 |
|   | Wet-All | — | 0.1% |
| 4 | DINAMIC ® 700WDG + | 70 | 100 |
|   | Galago 480SC + | 72 | 150 |
|   | Wet-All | — | 0.1% |
| 5 | DINAMIC ® 700WDG + | 87.5 | 125 |
|   | Galago 480SC + | 48 | 100 |
|   | Wet-All | — | 0.1% |
| 6 | DINAMIC ® 700WDG + | 87.5 | 125 |
|   | Galago 480SC + | 72 | 150 |
|   | Wet-All | — | 0.1% |
| 7 | DINAMIC ® 700WDG + | 52.5 | 75 |
|   | Galago 480SC + | 48 | 100 |
|   | TOLLA 960 | 960 | 1000 |
|   | Wet-All | — | 0.1% |
| 8 | DINAMIC ® 700WDG + | 52.5 | 75 |
|   | Galago 480SC + | 72 | 150 |
|   | TOLLA 960 | 960 | 1000 |
|   | Wet-All | — | 0.1% |

TABLE 6-78-continued

Treatments

| No | Treatments | Dosage rate (gai/ha) | Dosage rate (g/ha or mL/ha) |
|---|---|---|---|
| 9 | DINAMIC ® 700WDG + | 70 | 100 |
|   | Galago 480SC + | 48 | 100 |
|   | TOLLA 960 | 960 | 1000 |
|   | Wet-All | — | 0.1% |
| 10 | DINAMIC ® 700WDG + | 70 | 100 |
|   | Galago 480SC + | 72 | 150 |
|   | TOLLA 960 | 960 | 1000 |
|   | Wet-All | — | 0.1% |
| 11 | DINAMIC ® 700WDG + | 87.5 | 125 |
|   | Galago 480SC + | 48 | 100 |
|   | TOLLA 960 | 960 | 1000 |
|   | Wet-All | — | 0.1% |
| 12 | DINAMIC ® 700WDG + | 87.5 | 125 |
|   | Galago 480SC + | 72 | 150 |
|   | TOLLA 960 | 960 | 1000 |
|   | Wet-All | — | 0.1% |
| 13 | DINAMIC ® 700WDG + | 175 | 250 |
|   | Galago 480SC + | 144 | 300 |
|   | TOLLA 960 | 960 | 1000 |
|   | Wet-All | — | 0.1% |
| 14 | CALLISTO ® 480SC + | 52.5 | 260 |
|   | GardoGold 500SC + | 48 | 1562 |
|   | Compliment | 960 | 0.1% |

Assessments of the treated crops at 2, 4, and 6 weeks are summarized in Tables 6-79 to 6-81 below. No visual signs of phytotoxicity were noticed over 4 weeks. Signs of phytotoxicity were noticed in treatment 13 at 6 weeks.

TABLE 6-79

2 Week Assessment

| | |
|---|---|
| Crop condition | Actively growing |
| Crop stage | 6 Leaves |
| BBCH scale | 16 |
| Soil moisture | Moist |
| Rain since last visit | 16 mm |

TABLE 6-80

4 Week Assessment

| | |
|---|---|
| Crop condition | Actively growing |
| Crop stage | 8 Leaves |
| BBCH scale | 18 |
| Soil moisture | Wet |
| Rain since last visit | 30 mm |

TABLE 6-81

6 Week Assessment

| | |
|---|---|
| Crop condition | Actively growing |
| Crop stage | 10 leaves |
| BBCH scale: | 18 |
| Soil moisture | Moist |
| Rain since last visit | 0 mm |

Control and weed cover at 2, 4, and 6 weeks for the indicated species are summarized below in Tables 6-82 through 6-84. 80% is considered acceptable control.

TABLE 6-82

% Control and weed cover (2 weeks after application)

| | Treatments (product/ha) | Rep | AMASP | ELEIN | IPOPI | COMBI |
|---|---|---|---|---|---|---|
| | Untreated control | I | 30 | 30 | 20 | 20 |
| | % soil cover | ii | 20 | 40 | 10 | 30 |
| | | iii | 30 | 40 | 20 | 10 |
| | | iv | 30 | 30 | 20 | 20 |
| | Mean | | 28 | 35 | 18 | 20 |
| 1 | DINAMIC ® at 75 g | I | 100 | 100 | 90 | 100 |
| | Galago at 100 ml | ii | 98 | 100 | 90 | 98 |
| | Wet-All at 0.1% | iii | 100 | 100 | 90 | 98 |
| | | iv | 100 | 100 | 90 | 98 |
| | Mean | | 100 | 100 | 90 | 99 |
| 2 | DINAMIC ® at 75 g | I | 100 | 100 | 100 | 95 |
| | Galago at 150 ml | ii | 100 | 100 | 100 | 98 |
| | Wet-All at 0.1% | iii | 100 | 100 | 100 | 98 |
| | | iv | 100 | 100 | 100 | 100 |
| | Mean | | 100 | 100 | 100 | 98 |
| 3 | DINAMIC ® at 100 g | I | 98 | 100 | 90 | 95 |
| | Galago at 100 ml | ii | 98 | 100 | 90 | 95 |
| | Wet-All at 0.1% | iii | 100 | 100 | 90 | 100 |
| | | iv | 100 | 100 | 90 | 100 |
| | Mean | | 99 | 100 | 90 | 98 |
| 4 | DINAMIC ® at 100 g | I | 100 | 100 | 95 | 100 |
| | Galago at 150 ml | ii | 100 | 100 | 98 | 100 |
| | Wet-All at 0.1% | iii | 100 | 100 | 95 | 100 |
| | | iv | 100 | 100 | 98 | 100 |
| | Mean | | 100 | 100 | 97 | 100 |
| 5 | DINAMIC ® at 125 g | I | 100 | 100 | 95 | 100 |
| | Galago at 100 ml | ii | 100 | 100 | 98 | 100 |
| | Wet-All at 0.1% | iii | 100 | 100 | 98 | 100 |
| | | iv | 100 | 100 | 98 | 100 |
| | Mean | | 100 | 100 | 97 | 100 |
| 6 | DINAMIC ® at 125 g | I | 100 | 100 | 100 | 100 |
| | Galago at 150 ml | ii | 100 | 100 | 100 | 100 |
| | Wet-All at 0.1% | iii | 100 | 100 | 100 | 100 |
| | | iv | 100 | 100 | 100 | 100 |
| | Mean | | 100 | 100 | 100 | 100 |
| 7 | DINAMIC ® at 75 g | I | 90 | 95 | 100 | 90 |
| | Galago at 100 ml | ii | 90 | 90 | 100 | 95 |
| | TOLLA 960 at 1000 ml | iii | 95 | 90 | 100 | 95 |
| | Wet-All at 0.1% | iv | 90 | 95 | 100 | 95 |
| | Mean | | 91 | 93 | 100 | 100 |
| 8 | DINAMIC ® at 75 g | I | 95 | 90 | 100 | 95 |
| | Galago at 150 ml | ii | 95 | 90 | 100 | 95 |
| | TOLLA 960 at 1000 ml | iii | 95 | 90 | 100 | 98 |
| | Wet-All at 0.1% | iv | 98 | 90 | 100 | 95 |
| | Mean | | 96 | 90 | 100 | 96 |
| 9 | DINAMIC ® at 100 g | I | 90 | 95 | 100 | 98 |
| | Galago at 100 ml | ii | 90 | 90 | 100 | 100 |
| | TOLLA 960 at 1000 ml | iii | 90 | 90 | 100 | 95 |
| | Wet-All at 0.1% | iv | 90 | 90 | 100 | 100 |
| | Mean | | 90 | 91 | 100 | 98 |
| 10 | DINAMIC ® at 100 g | I | 98 | 98 | 100 | 100 |
| | Galago at 150 ml | ii | 98 | 95 | 100 | 100 |
| | TOLLA 960 at 1000 ml | iii | 98 | 98 | 100 | 100 |
| | Wet-All at 0.1% | iv | 90 | 95 | 100 | 100 |
| | Mean | | 96 | 97 | 100 | 100 |

TABLE 6-82-continued

% Control and weed cover (2 weeks after application)

| Treatments (product/ha) | Rep | AMASP | ELEIN | IPOPI | COMBI |
|---|---|---|---|---|---|
| 11 DINAMIC ® at 125 g | I | 95 | 100 | 100 | 95 |
| Galago at 100 ml | ii | 95 | 98 | 100 | 95 |
| TOLLA 960 at 1000 ml | iii | 90 | 95 | 100 | 95 |
| Wet-All at 0.1% | iv | 95 | 95 | 100 | 98 |
| Mean | | 94 | 97 | 100 | 96 |
| 12 DINAMIC ® at 125 g | I | 98 | 98 | 100 | 98 |
| Galago at 150 ml | ii | 100 | 95 | 100 | 100 |
| TOLLA 960 at 1000 ml | iii | 100 | 98 | 100 | 100 |
| Wet-All at 0.1% | iv | 95 | 95 | 100 | 100 |
| Mean | | 98 | 97 | 100 | 100 |
| 13 DINAMIC ® at 250 g | I | 100 | 98 | 100 | 100 |
| Galago at 300 ml | ii | 100 | 100 | 100 | 100 |
| TOLLA 960 at 1000 ml | iii | 100 | 100 | 100 | 100 |
| Wet-All at 0.1% | iv | 100 | 98 | 100 | 100 |
| Mean | | 100 | 99 | 100 | 100 |
| 14 CALLISTO ® 480SC at 260 ml | I | 90 | 98 | 100 | 90 |
| GardoGOLD at 1562 ml | ii | 90 | 95 | 100 | 95 |
| Compliment at 0.1% | iii | 95 | 90 | 100 | 90 |
| | iv | 95 | 90 | 100 | 90 |
| Mean | | 93 | 93 | 100 | 91 |

AMASP = *Amaranthus spinosus*; COMBE = *Commelina benghalensis*; IPOPU = *Ipomoea purpurea*; ELEIN = *Eleusine indica*

TABLE 6-83

% Control and weed cover (4 weeks after application)

| Treatments (product/ha) | Rep | AMASP | ELEIN | IPOPI | COMBI |
|---|---|---|---|---|---|
| Untreated control % soil cover | I | 30 | 30 | 20 | 20 |
| | ii | 20 | 30 | 20 | 30 |
| | iii | 30 | 30 | 20 | 20 |
| | iv | 30 | 20 | 30 | 20 |
| Mean | | 28 | 28 | 23 | 23 |
| 1 DINAMIC ® at 75 g | I | 100 | 100 | 80 | 100 |
| Galago at 100 ml | ii | 100 | 100 | 80 | 98 |
| Wet-All at 0.1% | iii | 100 | 100 | 90 | 98 |
| | iv | 100 | 100 | 80 | 98 |
| Mean | | 100 | 100 | 83 | 99 |
| 2 DINAMIC ® at 75 g | I | 100 | 100 | 98 | 95 |
| Galago at 150 ml | ii | 100 | 100 | 90 | 98 |
| Wet-All at 0.1% | iii | 100 | 100 | 80 | 98 |
| | iv | 100 | 100 | 90 | 100 |
| Mean | | 100 | 100 | 90 | 98 |
| 3 DINAMIC ® at 100 g | I | 100 | 100 | 80 | 95 |
| Galago at 100 ml | ii | 98 | 100 | 90 | 95 |
| Wet-All at 0.1% | iii | 100 | 100 | 80 | 100 |
| | iv | 100 | 100 | 80 | 100 |
| Mean | | 100 | 100 | 83 | 98 |
| 4 DINAMIC ® at 100 g | I | 100 | 100 | 95 | 100 |
| Galago at 150 ml | ii | 100 | 100 | 95 | 100 |
| Wet-All at 0.1% | iii | 100 | 100 | 95 | 100 |
| | iv | 100 | 100 | 95 | 100 |
| Mean | | 100 | 100 | 95 | 100 |
| 5 DINAMIC ® at 125 g | I | 100 | 100 | 90 | 100 |
| Galago at 100 ml | ii | 100 | 100 | 95 | 100 |
| Wet-All at 0.1% | iii | 100 | 100 | 95 | 100 |
| | iv | 100 | 100 | 90 | 100 |
| Mean | | 100 | 100 | 93 | 100 |
| 6 DINAMIC ® at 125 g | I | 100 | 100 | 100 | 100 |
| Galago at 150 ml | ii | 100 | 100 | 100 | 100 |
| Wet-All at 0.1% | iii | 100 | 100 | 100 | 100 |
| | iv | 100 | 100 | 100 | 100 |
| Mean | | 100 | 100 | 100 | 100 |
| 7 DINAMIC ® at 75 g | I | 100 | 98 | 100 | 90 |
| Galago at 100 ml | ii | 100 | 95 | 100 | 95 |
| TOLLA 960 at 1000 ml | iii | 100 | 98 | 100 | 95 |
| Wet-All at 0.1% | iv | 100 | 100 | 100 | 95 |
| Mean | | 100 | 98 | 100 | 100 |
| 8 DINAMIC ® at 75 g | I | 100 | 100 | 100 | 95 |
| Galago at 150 ml | ii | 100 | 100 | 100 | 95 |
| TOLLA 960 at 1000 ml | iii | 100 | 100 | 100 | 98 |
| Wet-All at 0.1% | iv | 100 | 100 | 100 | 95 |
| Mean | | 100 | 100 | 100 | 96 |
| 9 DINAMIC ® at 100 g | I | 100 | 100 | 100 | 98 |
| Galago at 100 ml | ii | 100 | 98 | 100 | 100 |
| TOLLA 960 at 1000 ml | iii | 100 | 95 | 100 | 95 |
| Wet-All at 0.1% | iv | 100 | 100 | 100 | 100 |
| Mean | | 100 | 98 | 100 | 98 |
| 10 DINAMIC ® at 100 g | I | 100 | 100 | 100 | 100 |
| Galago at 150 ml | ii | 100 | 100 | 100 | 100 |
| TOLLA 960 at 1000 ml | iii | 100 | 100 | 100 | 100 |
| Wet-All at 0.1% | iv | 100 | 100 | 100 | 100 |
| Mean | | 100 | 100 | 100 | 100 |
| 11 DINAMIC ® at 125 g | I | 100 | 100 | 100 | 95 |
| Galago at 100 ml | ii | 100 | 100 | 100 | 95 |
| TOLLA 960 at 1000 ml | iii | 100 | 95 | 100 | 95 |
| Wet-All at 0.1% | iv | 100 | 98 | 100 | 98 |
| Mean | | 100 | 98 | 100 | 96 |
| 12 DINAMIC ® at 125 g | I | 100 | 100 | 100 | 98 |
| Galago at 150 ml | ii | 100 | 100 | 100 | 100 |
| TOLLA 960 at 1000 ml | iii | 100 | 100 | 100 | 100 |
| Wet-All at 0.1% | iv | 100 | 100 | 100 | 100 |
| Mean | | 100 | 100 | 100 | 100 |
| 13 DINAMIC ® at 250 g | I | 100 | 100 | 100 | 100 |
| Galago at 300 ml | ii | 100 | 100 | 100 | 100 |
| TOLLA 960 at 1000 ml | iii | 100 | 100 | 100 | 100 |
| Wet-All at 0.1% | iv | 100 | 100 | 100 | 100 |
| Mean | | 100 | 100 | 100 | 100 |
| 14 CALLISTO ® 480SC at 260 ml | I | 100 | 100 | 100 | 90 |
| GardoGOLD at 1562 ml | ii | 100 | 100 | 100 | 95 |
| Compliment at 0.1% | iii | 100 | 100 | 100 | 90 |
| | iv | 100 | 100 | 100 | 90 |
| Mean | | 100 | 100 | 100 | 91 |

AMASP = *Amaranthus spinosu*; COMBE = *Commelina benghalensis*; IPOPU = *Ipomoea purpurea*; ELEIN = *Eleusine indica*

TABLE 6-84

% Control and weed cover (6 weeks after application)

| | Treatments (product/ha) | Rep | AMASP | ELEIN | IPOPI | COMBI |
|---|---|---|---|---|---|---|
| | Untreated control % soil cover | I | 30 | 20 | 20 | 30 |
| | | ii | 30 | 20 | 20 | 30 |
| | | iii | 40 | 20 | 20 | 20 |
| | | iv | 30 | 20 | 30 | 20 |
| | Mean | | 33 | 20 | 23 | 25 |
| 1 | DINAMIC ® at 75 g | I | 100 | 100 | 80 | 90 |
| | Galago at 100 ml | ii | 100 | 100 | 80 | 90 |
| | Wet-All at 0.1% | iii | 100 | 100 | 80 | 90 |
| | | iv | 100 | 100 | 80 | 90 |
| | Mean | | 100 | 100 | 80 | 90 |
| 2 | DINAMIC ® at 75 g | I | 100 | 100 | 95 | 90 |
| | Galago at 150 ml | ii | 100 | 100 | 80 | 95 |
| | Wet-All at 0.1% | iii | 100 | 100 | 80 | 90 |
| | | iv | 100 | 100 | 80 | 95 |
| | Mean | | 100 | 100 | 84 | 93 |
| 3 | DINAMIC ® at 100 g | I | 100 | 100 | 80 | 90 |
| | Galago at 100 ml | ii | 100 | 100 | 80 | 90 |
| | Wet-All at 0.1% | iii | 100 | 100 | 70 | 98 |
| | | iv | 100 | 100 | 80 | 95 |
| | Mean | | 100 | 100 | 78 | 93 |
| 4 | DINAMIC ® at 100 g | I | 100 | 100 | 90 | 100 |
| | Galago at 150 ml | ii | 100 | 100 | 90 | 100 |
| | Wet-All at 0.1% | iii | 100 | 100 | 90 | 100 |
| | | iv | 100 | 100 | 90 | 100 |
| | Mean | | 100 | 100 | 90 | 100 |
| 5 | DINAMIC ® at 125 g | I | 100 | 100 | 80 | 100 |
| | Galago at 100 ml | ii | 100 | 100 | 90 | 100 |
| | Wet-All at 0.1% | iii | 100 | 100 | 90 | 100 |
| | | iv | 100 | 100 | 90 | 100 |
| | Mean | | 100 | 100 | 88 | 100 |
| 6 | DINAMIC ® at 125 g | I | 100 | 100 | 100 | 100 |
| | Galago at 150 ml | ii | 100 | 100 | 100 | 100 |
| | Wet-All at 0.1% | iii | 100 | 100 | 100 | 100 |
| | | iv | 100 | 100 | 100 | 100 |
| | Mean | | 100 | 100 | 100 | 100 |
| 7 | DINAMIC ® at 75 g | I | 100 | 100 | 100 | 95 |
| | Galago at 100 ml | ii | 100 | 98 | 100 | 95 |
| | TOLLA 960 at 1000 ml | iii | 100 | 100 | 100 | 98 |
| | Wet-All at 0.1% | iv | 100 | 100 | 100 | 98 |
| | Mean | | 100 | 100 | 100 | 100 |
| 8 | DINAMIC ® at 75 g | I | 100 | 100 | 100 | 95 |
| | Galago at 150 ml | ii | 100 | 100 | 100 | 98 |
| | TOLLA 960 at 1000 ml | iii | 100 | 100 | 100 | 100 |
| | Wet-All at 0.1% | iv | 100 | 100 | 100 | 95 |
| | Mean | | 100 | 100 | 100 | 97 |
| 9 | DINAMIC ® at 100 g | I | 100 | 100 | 100 | 100 |
| | Galago at 100 ml | ii | 100 | 100 | 100 | 100 |
| | TOLLA 960 at 1000 ml | iii | 100 | 95 | 100 | 95 |
| | Wet-All at 0.1% | iv | 100 | 100 | 100 | 100 |
| | Mean | | 100 | 99 | 100 | 99 |
| 10 | DINAMIC ® at 100 g | I | 100 | 100 | 100 | 100 |
| | Galago at 150 ml | ii | 100 | 100 | 100 | 100 |
| | TOLLA 960 at 1000 ml | iii | 100 | 100 | 100 | 100 |
| | Wet-All at 0.1% | iv | 100 | 100 | 100 | 100 |
| | Mean | | 100 | 100 | 100 | 100 |
| 11 | DINAMIC ® at 125 g | I | 100 | 100 | 100 | 98 |
| | Galago at 100 ml | ii | 100 | 100 | 100 | 98 |
| | TOLLA 960 at 1000 ml | iii | 100 | 95 | 100 | 95 |
| | Wet-All at 0.1% | iv | 100 | 100 | 100 | 100 |
| | Mean | | 100 | 99 | 100 | 98 |
| 12 | DINAMIC ® at 125 g | I | 100 | 100 | 100 | 100 |
| | Galago at 150 ml | ii | 100 | 100 | 100 | 100 |
| | TOLLA 960 at 1000 ml | iii | 100 | 100 | 100 | 100 |
| | Wet-All at 0.1% | iv | 100 | 100 | 100 | 100 |
| | Mean | | 100 | 100 | 100 | 100 |
| 13 | DINAMIC ® at 250 g | I | 100 | 100 | 100 | 100 |
| | Galago at 300 ml | ii | 100 | 100 | 100 | 100 |
| | TOLLA 960 at 1000 ml | iii | 100 | 100 | 100 | 100 |
| | Wet-All at 0.1% | iv | 100 | 100 | 100 | 100 |
| | Mean | | 100 | 100 | 100 | 100 |
| 14 | CALLISTO ® 480SC at 260 ml | I | 100 | 100 | 100 | 95 |
| | GardoGOLD at 1562 ml | ii | 100 | 100 | 100 | 95 |
| | Compliment at 0.1% | iii | 100 | 100 | 100 | 90 |
| | | iv | 100 | 100 | 100 | 95 |
| | Mean | | 100 | 100 | 100 | 94 |

AMASP = *Amaranthus spinosus*; COMBE = *Commelina benghalensis*; IPOPU = *Ipomoea purpurea*; ELEIN = *Eleusine indica*

The results indicate that TOLLA was unnecessarily added to the DINAMIC®+Galago+Wet-All mixture as the mixture gave sufficient control without TOLLA. DINAMIC®+Galago+Wet-All: DINAMIC® 700WDG at 75 g/ha+Galago 480SC at 100 mL/ha+Wet-All at 0.1% resulted in excellent control of *Amaranthus spinosus* and satisfactory control of *Commilina benghalensis* and *Ipomoea purpurea*. With the exception of *Ipomoea purpurea* this mixture compared with the standard CALLISTO® 480 SC at 260 mL/ha+Gardo Gold at 1562 mL/ha+Compliment at 0.1%. DINAMIC®+Galago+TOLLA+Wet-All: DINAMIC® 700WDG at 75 g/ha+Galago 480SC at 100 mL/ha+TOLLA 960EC at 1000 mL/ha+Wet-All at 0.1% showed 100% control of the entire weed spectrum after 6 weeks. This mixture outperformed the standard CALLISTO® 480 SC at 260 mL/ha+Gardo Gold at 1562 mL/ha+Compliment at 0.1%. Signs of phytotoxicity were noticed in the plots were DINAMIC® 700WDG at 250 g/ha+Galago 480SC at 300 mL/ha+TOLLA 960EC at 1000 mL/ha+Wet-All at 0.1% was sprayed. DINAMIC® 700WDG at 75 g/ha+Galago 480SC at 100 mL/ha+TOLLA 960EC at 1000 mL/ha+Wet-All at 0.1% can be used to control of *Amaranthus spinosus, Eleusine indica, Ipomoea purpurea* and *Commilina benghalensis*.

M. Pre Emergence Application Against Weed in Maize

This Example compares the herbicidal selectivity and efficacy of DINAMIC® 700WDG applied in combination with Galago and TOLLA 840S as a pre-emergence application with regards to both crop and weeds in dry land maize. Treatments and conditions are tabulated below.

TABLE 6-85

Treatments

| TREATMENT | Rate/ha Product (l) | a.i. (g) |
|---|---|---|
| 1 DINAMIC ® + Galago | 75 g + 100 ml | 52.5 + 48 |
| 2 DINAMIC ® + Galago | 75 g + 150 ml | 52.5 + 72 |
| 3 DINAMIC ® + Galago | 100 g + 100 ml | 70 + 48 |
| 4 DINAMIC ® + Galago | 100 g + 150 ml | 70 + 72 |
| 5 DINAMIC ® + Galago | 125 g + 100 ml | 87.5 + 48 |
| 6 DINAMIC ® + Galago | 125 g + 150 ml | 87.5 + 72 |
| 7 DINAMIC ® + Galago + TOLLA 840S | 75 g + 100 ml + 1.0 l | 52.5 + 48 + 840 |
| 8 DINAMIC ® + Galago + TOLLA 840S | 75 g + 150 ml + 1.0 l | 52.5 + 72 + 840 |
| 9 DINAMIC ® + Galago + TOLLA 840S | 100 g + 100 ml + 1.0 l | 70 + 48 + 840 |
| 10 DINAMIC ® + Galago + TOLLA 840S | 100 g + 150 ml + 1.0 l | 70 + 72 + 840 |
| 11 DINAMIC ® + Galago + TOLLA 840S | 125 g + 100 ml + 1.0 l | 87.5 + 48 + 840 |
| 12 DINAMIC ® + Galago + TOLLA 840S | 125 g + 150 ml + 1.0 l | 87.5 + 72 + 840 |
| 13 DINAMIC ® + Galago + TOLLA 840S | 250 g + 300 ml + 2.0 l | 175 + 144 + 1680 |
| 14 CALLISTO ® + Dual Gold | 260 ml + 710 ml | 125 + 650 |
| 15 Untreated control | — | — |

TABLE 6-86

Test products

| | Product | Active Ingredient | Form | Manufacturer/ Supplier | Reg. No. |
|---|---|---|---|---|---|
| 1 | DINAMIC ® 700WDG | Amicarbazone 700 g/kg | WDG | Arysta Lifescience | |
| 2 | Galago | Mesotrione 480 g/l | SC | Arysta Lifescience | L. 8089 |
| 3 | TOLLA 840 S | Metolachlor 840 g/l + Safener | EC | Arysta Lifescience | L. 7374 |
| 4 | CALLISTO ® | Mesotrione 480 g/l | SC | Syngenta | L. 6795 |
| 5 | DUAL S GOLD ® | S-Metolachlor 915 g/l + Safener | EC | Syngenta | L. 5749 |

TABLE 6-87

TRIAL DESIGN:

| | |
|---|---|
| Design | Completely randomized design |
| Replicates | Five |
| Plot size | 5 m × 2.5 m = Nett/plot |

TABLE 6-88

SPRAYER

| | |
|---|---|
| Sprayer | CO$_2$ Precision Sprayer |
| Boom | 2.5 m aluminium |
| Nozzle | 5 × 11002 flat fan nozzles (Teejet 11002 DG) |
| Pressure | 2.7 Bar |
| Application | 200 l/ha |

Spray Water Quality
pH: 6.62
EC: 0.85 mS/m
Spray Volume
200 l/ha at 2.7 Bar

TABLE 6-89

WEATHER INFORMATION AT APPLICATION

| | |
|---|---|
| Temperature (max) | 21.9° C. |
| RH: | 48% |
| Wind: | 0-10 km/h, N |
| Cloud | 6/8 |

TABLE 6-90

SOIL PROPERTIES AT APPLICATION:

| | |
|---|---|
| Clay Fraction | 16.0% |
| Silt Fraction | 3.5% |
| Sand Fraction | 80.5% |
| pH (KCl) | 5.1 |
| Moisture | Surface dry, subsurface moist at 6 cm |
| Seedbed condition | Medium to cloddy |

Irrigation

None (rain-fed)

Crop

Crop: Maize

Variety: Phb 31 G 54 BR

Growth stage: Pre-emergence (BBCH growth stage 00)

Sowing depth: 5 cm

Sowing density: 45000 plants/ha

TABLE 6-91

WEED INFORMATION

| SPECIES | COMMON NAME | ABBREVIATION |
|---|---|---|
| *Bidens pilosa* | Blackjack | BIDPI |
| *Amaranthus hybridus* | Pigweed | AMAHY |
| *Tagetes minuta* | Khaki weed | TAGMI |
| *Digitaria sanquinalis* | Crab-finger grass | DIGSA |

TABLE 6-92

ASSESSMENT DETAILS:

| | |
|---|---|
| Method | Comparative Efficacy |
| Herbicide | Efficacy:<br>Number of weeds in treated versus untreated plots<br>Selectivity:<br>1. Visual phytotoxicity: BBA 1-9 scale (refer to appendix for details)<br>2. Yield: 20 cobs harvested at random from each plot. Average grain weight per plot determined using a precision 2 decimal scale. Statistical evaluation: |

TABLE 6-92-continued

ASSESSMENT DETAILS:

| | |
|---|---|
| | ANOVA at the 95% probability using Tukeys LSD formulae |
| Assessment Times-Days After Application (DAA) | 14 DAA - Efficacy/Selectivity<br>28 DAA - Efficacy/Selectivity<br>42 DAA - Efficacy/Selectivity<br>56 DAA - Efficacy<br>Harvest - Selectivity |

TABLE 6-93

Comparative yield of DINAMIC ® 700WDG programs

| | YIELD (Kg/plot) | | | | |
|---|---|---|---|---|---|
| | Replicate | | | | |
| TREATMENT | I | II | III | IV | Mean |
| 1 DINAMIC ® + Galago<br>75 g + 100 ml | 2.77 | 2.45 | 3.07 | 3.25 | 2.89 b |
| 2 DINAMIC ® + Galago<br>75 g + 150 ml 0 | 2.14 | 2.11 | 3.03 | 2.65 | 2.34 ab |
| 3 DINAMIC ® + Galago<br>100 g + 100 ml | 2.45 | 3.12 | 2.33 | 2.50 | 2.70 ab |
| 4 DINAMIC ® + Galago<br>100 g + 150 ml | 2.35 | 2.33 | 2.50 | 2.32 | 2.72 ab |
| 5 DINAMIC ® + Galago<br>125 g + 100 ml | 3.00 | 3.13 | 2.97 | 2.42 | 2.44 b |
| 6 DINAMIC ® + Galago<br>125 g + 150 ml | 2.67 | 2.17 | 2.06 | 2.06 | 2.75 a |
| 7 DINAMIC ® + Galago + TOLLA 840S<br>75 g + 100 ml + 1.0 l | 2.64 | 2.56 | 2.76 | 3.00 | 2.16 ab |
| 8 DINAMIC ® + Galago + TOLLA 840S<br>75 g + 150 ml + 1.0 l | 2.73 | 2.90 | 2.98 | 3.06 | 2.30 b |
| 9 DINAMIC ® + Galago + TOLLA 840S<br>100 g + 100 ml + 1.0 l | 2.70 | 2.86 | 2.94 | 3.02 | 2.39 b |
| 10 DINAMIC ® + Galago + TOLLA 840S<br>100 g + 150 ml + 1.0 l | 2.73 | 2.90 | 2.98 | 3.06 | 2.47 b |
| 11 DINAMIC ® + Galago + TOLLA 840S<br>125 g + 100 ml + 1.0 l | 2.71 | 2.87 | 2.96 | 3.04 | 2.92 b |
| 12 DINAMIC ® + Galago + TOLLA 840S<br>125 g + 150 ml + 1.0 l | 2.70 | 2.87 | 2.95 | 3.03 | 2.88 b |
| 13 DINAMIC ® + Galago + TOLLA 840S<br>250 g + 300 ml + 2.0 l | 2.72 | 2.88 | 2.96 | 3.05 | 2.67 b |
| 14 CALLISTO ® + Dual Gold<br>260 ml + 710 ml | 2.68 | 2.85 | 2.93 | 3.01 | 2.99 b |
| 15 Untreated control | 2.68 | 2.84 | 2.92 | 3.00 | 2.89 b |

Note:
Treatment means sharing the same letter do not differ significantly by LSD test at the 5% ($\alpha = 0.05$) level of probability

TABLE 6-94

Comparative visual phytotoxicity of DINAMIC ® 700WDG pre-emergence programs

| | | BBA VISUAL PHYTOTOXICITY SCALE<br>(1 - no damage; 9 - dead) | | | | |
|---|---|---|---|---|---|---|
| | | Replicate | | | | |
| TREATMENT | Timing | I | II | III | IV | Mean |
| 1 DINAMIC ® + Galago<br>75 g + 100 ml | 14<br>28<br>42 | 1<br>1<br>1 | 1<br>1<br>1 | 1<br>1<br>1 | 1<br>1<br>1 | 1.0<br>1.0<br>1.0 |
| 2 DINAMIC ® + Galago<br>75 g + 150 ml | 14<br>28<br>42 | 1<br>1<br>1 | 1<br>1<br>1 | 1<br>1<br>1 | 1<br>1<br>1 | 1.0<br>1.0<br>1.0 |
| 3 DINAMIC ® + Galago<br>100 g + 100 ml | 14<br>28<br>42 | 1<br>1<br>1 | 1<br>1<br>1 | 1<br>1<br>1 | 1<br>1<br>1 | 1.0<br>1.0<br>1.0 |

TABLE 6-94-continued

Comparative visual phytotoxicity of DINAMIC ® 700WDG pre-emergence programs

|  |  | BBA VISUAL PHYTOTOXICITY SCALE (1 - no damage; 9 - dead) | | | | |
|---|---|---|---|---|---|---|
|  |  | Replicate | | | | |
| TREATMENT | Timing | I | II | III | IV | Mean |
| 4 DINAMIC ® + Galago<br>100 g + 150 ml | 14<br>28<br>42 | 1<br>1<br>1 | 1<br>1<br>1 | 1<br>1<br>1 | 1<br>1<br>1 | 1.0<br>1.0<br>1.0 |
| 5 DINAMIC ® + Galago<br>125 g + 100 ml | 14<br>28<br>42 | 1<br>1<br>1 | 1<br>1<br>1 | 1<br>1<br>1 | 1<br>1<br>1 | 1.0<br>1.0<br>1.0 |
| 6 DINAMIC ® + Galago<br>125 g + 150 ml | 14<br>28<br>42 | 1<br>1<br>1 | 1<br>1<br>1 | 1<br>1<br>1 | 1<br>1<br>1 | 1.0<br>1.0<br>1.0 |
| 7 DINAMIC ® + Galago + TOLLA 840S<br>75 g + 100 ml + 1.0 l | 14<br>28<br>42 | 1<br>1<br>1 | 1<br>1<br>1 | 1<br>1<br>1 | 1<br>1<br>1 | 1.0<br>1.0<br>1.0 |
| 8 DINAMIC ® + Galago + TOLLA 840S<br>75 g + 150 ml + 1.0 l | 14<br>28<br>42 | 1<br>1<br>1 | 1<br>1<br>1 | 1<br>1<br>1 | 1<br>1<br>1 | 1.0<br>1.0<br>1.0 |
| 9 DINAMIC ® + Galago + TOLLA 840S<br>100 g + 100 ml + 1.0 l | 14<br>28<br>42 | 1<br>1<br>1 | 1<br>1<br>1 | 1<br>1<br>1 | 1<br>1<br>1 | 1.0<br>1.0<br>1.0 |
| 10 DINAMIC ® + Galago + TOLLA 840S<br>100 g + 150 ml + 1.0 l | 14<br>28<br>42 | 1<br>1<br>1 | 1<br>1<br>1 | 1<br>1<br>1 | 1<br>1<br>1 | 1.0<br>1.0<br>1.0 |
| 11 DINAMIC ® + Galago + TOLLA 840S<br>125 g + 100 ml + 1.0 l | 14<br>28<br>42 | 1<br>1<br>1 | 1<br>1<br>1 | 1<br>1<br>1 | 1<br>1<br>1 | 1.0<br>1.0<br>1.0 |
| 12 DINAMIC ® + Galago + TOLLA 840S<br>125 g + 150 ml + 1.0 l | 14<br>28<br>42 | 1<br>1<br>1 | 1<br>1<br>1 | 1<br>1<br>1 | 1<br>1<br>1 | 1.0<br>1.0<br>1.0 |
| 13 DINAMIC ® + Galago + TOLLA 840S<br>250 g + 300 ml + 2.0 l | 14<br>28<br>42 | 1<br>1<br>1 | 1<br>1<br>1 | 1<br>1<br>1 | 1<br>1<br>1 | 1.0<br>1.0<br>1.0 |
| 14 CALLISTO ® + Dual Gold<br>260 ml + 710 ml | 14<br>28<br>42 | 1<br>1<br>1 | 1<br>1<br>1 | 1<br>1<br>1 | 1<br>1<br>1 | 1.0<br>1.0<br>1.0 |
| 15 Untreated control | 14<br>28<br>42 | 1<br>1<br>1 | 1<br>1<br>1 | 1<br>1<br>1 | 1<br>1<br>1 | 1.0<br>1.0<br>1.0 |

TABLE 6-95

Comparative herbicidal activity of DINAMIC ® 700WDG pre-emergence programs

|  |  | AVERAGE % WEED CONTROL BY SPECIES<br>% C = Visual % weed control<br>% P = Visual % weed pressure | | | | | | | |
|---|---|---|---|---|---|---|---|---|---|
|  |  | BIDPI | | AMAHY | | TAGMI | | DIGSA | |
| TREATMENT | Timing | % C | % P | % C | % P | % C | % P | % C | % P |
| 1 DINAMIC ® + Galago<br>75 g + 100 ml | 14<br>28<br>42<br>56 | 95<br>90<br>80<br>60 | 5<br>10<br>12<br>15 | 85<br>75<br>65<br>55 | 3<br>10<br>15<br>20 | 100<br>100<br>80<br>70 | 3<br>5<br>10<br>12 | 45<br>40<br>20<br>10 | 3<br>5<br>10<br>15 |
| 2 DINAMIC ® + Galago<br>75 g + 150 ml | 14<br>28<br>42<br>56 | 98<br>96<br>80<br>70 | 5<br>10<br>15<br>20 | 96<br>90<br>85<br>80 | 3<br>5<br>10<br>20 | 100<br>100<br>94<br>90 | 1<br>3<br>5<br>10 | 50<br>50<br>30<br>20 | 1<br>3<br>10<br>15 |
| 3 DINAMIC ® + Galago<br>100 g + 100 ml | 14<br>28<br>42<br>56 | 96<br>92<br>75<br>65 | 3<br>5<br>10<br>12 | 95<br>93<br>85<br>70 | 3<br>5<br>10<br>20 | 100<br>100<br>90<br>80 | 1<br>3<br>5<br>10 | 45<br>40<br>20<br>10 | 5<br>10<br>15<br>25 |
| 4 DINAMIC ® + Galago<br>100 g + 150 ml | 14<br>28<br>42<br>56 | 96<br>92<br>85<br>70 | 3<br>5<br>10<br>10 | 98<br>96<br>92<br>90 | 3<br>5<br>15<br>25 | 100<br>100<br>95<br>90 | 1<br>5<br>10<br>12 | 55<br>50<br>40<br>35 | 3<br>5<br>10<br>15 |

TABLE 6-95-continued

Comparative herbicidal activity of DINAMIC ® 700WDG pre-emergence programs

AVERAGE % WEED CONTROL BY SPECIES
% C = Visual % weed control
% P = Visual % weed pressure

| TREATMENT | Timing | BIDPI % C | BIDPI % P | AMAHY % C | AMAHY % P | TAGMI % C | TAGMI % P | DIGSA % C | DIGSA % P |
|---|---|---|---|---|---|---|---|---|---|
| 5 DINAMIC ® + Galago | 14 | 99 | 3 | 98 | 3 | 100 | 1 | 50 | 5 |
| 125 g + 100 ml | 28 | 96 | 5 | 96 | 5 | 100 | 3 | 45 | 10 |
| | 42 | 90 | 10 | 92 | 10 | 100 | 5 | 30 | 15 |
| | 56 | 85 | 15 | 90 | 20 | 98 | 12 | 20 | 25 |
| 6 DINAMIC ® + Galago | 14 | 96 | 5 | 99 | 5 | 100 | 3 | 55 | 1 |
| 125 g + 150 ml | 28 | 92 | 10 | 95 | 10 | 100 | 5 | 55 | 3 |
| | 42 | 90 | 12 | 92 | 15 | 94 | 10 | 45 | 10 |
| | 56 | 90 | 15 | 90 | 25 | 90 | 12 | 40 | 15 |
| 7 DINAMIC ® + Galago + TOLLA 840S | 14 | 99 | 5 | 100 | 5 | 100 | 3 | 99 | 5 |
| 75 g + 100 ml + 1.0 l | 28 | 96 | 10 | 98 | 10 | 100 | 5 | 99 | 10 |
| | 42 | 90 | 12 | 92 | 15 | 94 | 10 | 99 | 15 |
| | 56 | 85 | 15 | 88 | 25 | 92 | 15 | 98 | 25 |
| 8 DINAMIC ® + Galago + TOLLA 840S | 14 | 99 | 5 | 100 | 5 | 100 | 3 | 100 | 3 |
| 75 g + 150 ml + 1.0 l | 28 | 95 | 10 | 98 | 15 | 100 | 5 | 100 | 5 |
| | 42 | 90 | 15 | 96 | 25 | 94 | 10 | 98 | 10 |
| | 56 | 90 | 20 | 94 | 30 | 92 | 15 | 98 | 15 |
| 9 DINAMIC ® + Galago + TOLLA 840S | 14 | 100 | 3 | 98 | 3 | 100 | 1 | 100 | 5 |
| 100 g + 100 ml + 1.0 l | 28 | 99 | 5 | 95 | 5 | 100 | 3 | 100 | 10 |
| | 42 | 90 | 10 | 92 | 15 | 99 | 5 | 100 | 15 |
| | 56 | 85 | 12 | 90 | 20 | 98 | 10 | 98 | 25 |
| 10 DINAMIC ® + Galago + TOLLA 840S | 14 | 100 | 3 | 100 | 1 | 100 | 1 | 100 | 1 |
| 100 g + 150 ml + 1.0 l | 28 | 99 | 5 | 99 | 5 | 100 | 5 | 99 | 3 |
| | 42 | 96 | 10 | 95 | 10 | 99 | 10 | 98 | 10 |
| | 56 | 90 | 10 | 90 | 20 | 98 | 12 | 98 | 15 |
| 11 DINAMIC ® + Galago + TOLLA 840S | 14 | 100 | 5 | 100 | 3 | 100 | 3 | 100 | 1 |
| 125 g + 100 ml + 1.0 l | 28 | 99 | 10 | 98 | 5 | 100 | 5 | 100 | 3 |
| | 42 | 92 | 12 | 90 | 10 | 95 | 10 | 99 | 5 |
| | 56 | 85 | 15 | 88 | 20 | 90 | 15 | 98 | 15 |
| 12 DINAMIC ® + Galago + TOLLA 840S | 14 | 100 | 3 | 100 | 1 | 100 | 1 | 100 | 1 |
| 125 g + 150 ml + 1.0 l | 28 | 99 | 8 | 99 | 5 | 99 | 3 | 100 | 3 |
| | 42 | 92 | 12 | 95 | 7 | 99 | 5 | 98 | 5 |
| | 56 | 90 | 15 | 93 | 15 | 95 | 10 | 98 | 15 |
| 13 DINAMIC ® + Galago + TOLLA 840S | 14 | 100 | 3 | 100 | 3 | 100 | 1 | 100 | 3 |
| 250 g + 300 ml + 2.0 l | 28 | 100 | 5 | 100 | 5 | 100 | 3 | 100 | 5 |
| | 42 | 99 | 12 | 99 | 10 | 100 | 5 | 100 | 15 |
| | 56 | 98 | 15 | 97 | 15 | 100 | 10 | 99 | 25 |
| 14 CALLISTO ® + DUAL S GOLD ® | 14 | 99 | 5 | 100 | 3 | 100 | 3 | 100 | 5 |
| 260 ml + 710 ml | 28 | 96 | 8 | 97 | 5 | 100 | 5 | 100 | 10 |
| | 42 | 92 | 12 | 97 | 10 | 98 | 10 | 100 | 20 |
| | 56 | 92 | 15 | 94 | 20 | 96 | 15 | 99 | 25 |
| 15 Untreated control | 14 | 0 | 3 | 0 | 3 | 0 | 3 | 0 | 3 |
| | 28 | 0 | 5 | 0 | 5 | 0 | 5 | 0 | 5 |
| | 42 | 0 | 10 | 0 | 10 | 0 | 10 | 0 | 15 |
| | 56 | 0 | 15 | 0 | 20 | 0 | 15 | 0 | 25 |

The trial was conducted on a commercial maize crop produced under dry land conditions. The DINAMIC® 700WDG formulation was evaluated for herbicidal activity and crop selectivity when applied as a pre-emergence spray program in tank-mix combination with Galago and TOLLA 840S. Treatments were applied pre-emergence of crop and weeds as broadcast applications over the maize rows. Treatments were applied one day after planting. First rains (10 mm) were recorded at 6 days following application. Weather conditions were dry with infrequent showers of rain occurring for the duration of the trial. At 30 days following application heavy rains (140 mm) were recorded. Thereafter dry conditions prevailed for the remainder of the trial.

No visual symptoms of phytotoxicity in the form of stunting, chlorosis, necrosis or growth-abnormalities were observed on any of the treatments receiving the tank-mix combinations of DINAMIC® 700WDG+Galago and DINAMIC® 700WDG+Galago+TOLLA 840S, whether applied at single or double rates, respectively. The tank-mix combinations of DINAMIC® 700WDG+Galago+TOLLA 840S displayed a similar level of herbicidal selectivity as the standard tank-mix combination of CALLISTO®+DUAL S GOLD®.

The weed spectrum at the trial site consisted of broad-leaved weeds and a single grass weed (DIGSA). The broad-leaved weed spectrum was composed of Blackjack (BIDPI), Pigweed (AMAHY) and Khaki weed (TAGMI). Efficacy evaluations were conducted at 14, 28, 42 and 56 days following application, respectively.

DINAMIC® 700WDG+Galago

Tank-mix combinations of DINAMIC® 700WDG+Galago displayed a typical dosage related efficacy response between the rates of 75-125 g/ha applied. Higher rates DINAMIC® 700WDG gave improved activity against broadleaved weeds, while an increase in the rate of Galago improved herbicidal activity against broadleaved weeds and grasses. At the final assessment conducted at 56 DAA, the tank-mix combination of DINAMIC®+Galago applied at 125 g/ha+150 ml/ha exhibited commercially acceptable levels of herbicidal activity against the entire broadleaved weed spectrum consisting of BIDPI, AMAHY and TAGMI. DINAMIC® applied at the rate of 100 g/ha in combination with Galago at 150 ml/ha displayed commercial levels of herbicidal activity against the broadleaved weeds AMAHY and TAGMI at the final assessment.

DINAMIC® 700WDG+Galago+TOLLA 840S

The addition of TOLLA 840S to the tank-mix combination of DINAMIC® 700WDG+Galago greatly enhanced the herbicidal activity against the grass weed DIGSA, with all tank-mix combinations exhibiting commercial control of DIGSA at the final assessment conducted at 56 DAA. DINAMIC® 700WDG treatments applied between the rates of 75-125 g/ha in combination with Galago at 150 ml/ha and TOLLA 840S at 1.0 l/ha exhibited commercially acceptable levels of herbicidal activity against the entire weed spectrum consisting of the grass weed DIGSA and the broadleaved weeds, BIDPI, AMAHY and TAGMI, respectively. In tank-mix combinations where Galago was applied at the lower rate of 100 ml/ha and the rate of DINAMIC® 700WDG exceeded 75 g/ha, commercially acceptable levels of activity were observed for the broadleaved weeds AMAHY and TAGMI, respectively. The tank-mix combination of DINAMIC® 700WDG+Galago+TOLLA 840S applied at 125 g/ha+150 ml/ha+1.0 l/ha achieved comparable levels of herbicidal activity as the standard tank-mix combination of CALLISTO®+Dual Gold applied at 260 ml/ha+710 ml/ha.

Compatibility

No visual symptoms of incompatibility in the form of phase separation or agglomeration were observed in any of the tank-mix combinations of DINAMIC® 700WDG+Galago and DINAMIC® 700WDG+Galago+TOLLA 840S, whether applied at single or double rates.

No visual symptoms of phytotoxicity in the form of stunting, chlorosis, necrosis or growth-abnormalities were observed on any of the treatments receiving the tank-mix combinations of DINAMIC® 700WDG+Galago and DINAMIC® 700WDG+Galago+TOLLA 840S, whether applied at single or double rates, respectively.

Tank-mix combinations of DINAMIC® 700WDG+Galago displayed a typical dosage related efficacy response between the rates of 75-125 g/ha applied.

DINAMIC®+Galago applied at 125 g/ha+150 ml/ha exhibited commercially acceptable levels of herbicidal activity against the entire broadleaved weed spectrum consisting of BIDPI, AMAHY and TAGMI, but not the grass weed DIGSA.

The addition of TOLLA 840S to the tank-mix combination of DINAMIC® 700WDG+Galago greatly enhanced the herbicidal activity against the grass weed DIGSA. DINAMIC® 700WDG treatments applied between the rates of 75-125 g/ha in combination with Galago at 150 ml/ha and TOLLA 840S at 1.0 l/ha exhibited commercially acceptable levels of herbicidal activity against the entire weed spectrum consisting of the grass weed DIGSA and the broadleaved weeds, BIDPI, AMAHY and TAGMI, respectively.

No visual symptoms of incompatibility in the form of phase separation or agglomeration were observed in any of the tank-mix combinations of DINAMIC® 700WDG+Galago and DINAMIC® 700WDG+Galago+TOLLA 840S, whether applied at single or double rates.

TABLE 6-96

| Anova Table Grain yield (kg/plot) | | | | |
|---|---|---|---|---|
| Unit | Degrees of freedom | Sums of Squares | Mean Squares | F Value |
| Reps | 3 | 0.3544 | | |
| Treatments | 14 | 2.767 | 0.1976 | 3.901 |
| Error | 42 | 2.128 | 0.5066 | |
| Total | 59 | 5.249 | | |
| Overall mean | | | | 2.755 |
| S. E for Difference | | | | 0.1592 |
| Least Significant Difference (LSD) at 95% | | | | 0.3212 |

TABLE 6-97

| BBA Visual Phytotoxicity rating scale | | |
|---|---|---|
| Scale | EQUIVALENT % | Description |
| 1 | 0% | NO DAMAGE |
| 2 | 0.1-2.5% | NEGLIGIBLE DAMAGE |
| 3 | 2.5-5.0% | MODERATE DAMAGE No effects on yield and/or quality |
| 4 | 5.0-10% | Damage up to limits of commercial acceptability - if no yield loss |
| 5 | 10-15% | DISTINCT DAMAGE Commercially acceptable only under certain conditions - if no yield loss |
| 6 | 15-25% | SEVERE DAMAGE Not commercially acceptable - yield loss and quality |
| 7 | 25-35% | VERY SEVERE DAMAGE |
| 8 | 35-68% | EXTREME DAMAGE |
| 9 | 68-100% | START OF WITHERING AND DEATH |

N. Pre Emergence Application Against Weed in Maize

This Example compares the herbicidal selectivity and efficacy of DINAMIC® 700WDG applied in combination with Galago and TOLLA 840S as a pre-emergence application with regards to both crop and weeds in irrigated maize. Treatments are conditions are tabulated below.

TABLE 6-98

| Treatments | | |
|---|---|---|
| | Rate/ha | |
| TREATMENT | Product (l) | a.i. (g) |
| 1 DINAMIC ® + Galago | 75 g + 100 ml | 52.5 + 48 |
| 2 DINAMIC ® + Galago | 75 g + 150 ml | 52.5 + 72 |
| 3 DINAMIC ® + Galago | 100 g + 100 ml | 70 + 48 |
| 4 DINAMIC ® + Galago | 100 g + 150 ml | 70 + 72 |
| 5 DINAMIC ® + Galago | 125 g + 100 ml | 87.5 + 48 |
| 6 DINAMIC ® + Galago | 125 g + 150 ml | 87.5 + 72 |

TABLE 6-98-continued

Treatments

| TREATMENT | Rate/ha Product (l) | a.i. (g) |
|---|---|---|
| 7 DINAMIC ® + Galago + TOLLA 840S | 75 g + 100 ml + 1.0 l | 52.5 + 48 + 840 |
| 8 DINAMIC ® + Galago + TOLLA 840S | 75 g + 150 ml + 1.0 l | 52.5 + 72 + 840 |
| 9 DINAMIC ® + Galago + TOLLA 840S | 100 g + 100 ml + 1.0 l | 70 + 48 + 840 |
| 10 DINAMIC ® + Galago + TOLLA 840S | 100 g + 150 ml + 1.0 l | 70 + 72 + 840 |
| 11 DINAMIC ® + Galago + TOLLA 840S | 125 g + 100 ml + 1.0 l | 87.5 + 48 + 840 |
| 12 DINAMIC ® + Galago + TOLLA 840S | 125 g + 150 ml + 1.0 l | 87.5 + 72 + 840 |
| 13 DINAMIC ® + Galago + TOLLA 840S | 250 g + 300 ml + 2.0 l | 175 + 144 + 1680 |
| 14 CALLISTO ® + Dual Gold | 260 ml + 710 ml | 125 + 650 |
| 15 Untreated control | — | — |

TABLE 6-99

Test products used

| | Product | Active Ingredient | Form | Manufacturer/Supplier | Reg. No. |
|---|---|---|---|---|---|
| 1 | DINAMIC ® 700WDG | Amicarbazone 700 g/kg | WDG | Arysta Lifescience | L. 8089 |
| 2 | Galago | Mesotrione 480 g/l | SC | Arysta Lifescience | |
| 3 | TOLLA 840 S | Metolachlor 840 g/l + Safener | EC | Arysta Lifescience | L. 7374 |
| 4 | CALLISTO ® | Mesotrione 480 g/l | SC | Syngenta | L. 6795 |
| 5 | DUAL S GOLD ® | S-Metolachlor 915 g/l + Safener | EC | Syngenta | L. 5749 |

TABLE 6-100

TRIAL DESIGN

| | |
|---|---|
| Design | Completely randomized design |
| Replicates | Four |
| Plot size | 5 m × 2.5 m = Nett/plot |

TABLE 6-101

SPRAYER

| | |
|---|---|
| Sprayer | CO$_2$ Precision Sprayer |
| Boom | 2.5 m aluminium |
| Nozzle | 5 × 11002 flat fan nozzles (Teejet 11002 DG) |
| Pressure | 3.0 Bar |
| Application | 200 l/ha |

Spray Water Quality:
pH: 6.5
EC: 0.6 mS/m

TABLE 6-102

WEATHER INFORMATION AT APPLICATION:

| | |
|---|---|
| Temperature (max) | 30.4° C. |
| RH: | 35% |
| Wind: | 0-5 km/h, Variable |
| Cloud | 8/8 |

TABLE 6-103

SOIL PROPERTIES AT APPLICATION

| | |
|---|---|
| Clay Fraction | 10.3% |
| Silt Fraction | 5.8% |
| Sand Fraction | 94.8% |

TABLE 6-103-continued

SOIL PROPERTIES AT APPLICATION

| | |
|---|---|
| pH (H$_2$O) | 7.3 |
| Moisture | Surface dry, subsurface moist at 5 cm |
| Seedbed condition | Fine (no clods) |

Irrigation:
Sprinkler
Crop:
Crop: Maize
Variety: Phb 32 D 68 BR
Growth stage: Pre-emergence (BBCH growth stage 00)
Sowing depth: 5 cm
Sowing density: 90000 plants/ha

TABLE 6-104

WEED INFORMATION:

| SPECIES | COMMON NAME | ABBREVIATION |
|---|---|---|
| *Datura ferox* | Large thornapple | DATFE |
| *Portulaca oleracea* | Purslane | POROL |
| *Schkuhria pinnata* | Dwarf marigold | SCHPI |
| *Bidens pilosa* | Blackjack | BIDPI |

TABLE 6-105

ASSESSMENT DETAILS

| | |
|---|---|
| Method | Comparative Efficacy |
| Herbicide | Efficacy: Number of weeds in treated versus untreated plots Selectivity: 3. Visual phytotoxicity: BBA 1-9 scale (refer to appendix for details) |

TABLE 6-105-continued

ASSESSMENT DETAILS

4. Yield: 20 cobs harvested at random from each plot. Average grain weight per plot determined using a precision 2 decimal scale. Statistical evaluation: ANOVA at the 95% probability using Tukeys LSD formulae 5. Assessment Times-Days After Application (DAA)
   - 14 DAA - Efficacy/Selectivity
   - 28 DAA - Efficacy/Selectivity
   - 42 DAA - Efficacy/Selectivity
   - 56 DAA - Efficacy
   - Harvest - Selectivity

TABLE 6-106

Comparative yield of DINAMIC ® 700WDG programs

| | TREATMENT | YIELD (Kg/plot) Replicate I | II | III | IV | Mean |
|---|---|---|---|---|---|---|
| 1 | DINAMIC ® + Galago 75 g + 100 ml | 2.34 | 1.83 | 1.79 | 1.86 | 1.95 a |
| 2 | DINAMIC ® + Galago 75 g + 150 ml 0 | 2.10 | 2.36 | 1.96 | 2.45 | 2.21 ab |
| 3 | DINAMIC ® + Galago 100 g + 100 ml | 2.32 | 1.97 | 2.41 | 2.18 | 2.22 ab |
| 4 | DINAMIC ® + Galago 100 g + 150 ml | 2.08 | 1.96 | 2.29 | 2.26 | 2.15 ab |
| 5 | DINAMIC ® + Galago 125 g + 100 ml | 2.12 | 2.45 | 1.86 | 2.30 | 2.18 ab |
| 6 | DINAMIC ® + Galago 125 g + 150 ml | 1.97 | 1.81 | 2.02 | 1.90 | 1.92 a |
| 7 | DINAMIC ® + Galago + TOLLA 840S 75 g + 100 ml + 1.0 l | 2.72 | 2.31 | 2.00 | 2.33 | 2.34 ab |
| 8 | DINAMIC ® + Galago + TOLLA 840S 75 g + 150 ml + 1.0 l | 2.49 | 1.75 | 2.07 | 2.21 | 2.13 ab |
| 9 | DINAMIC ® + Galago + TOLLA 840S 100 g + 100 ml + 1.0 l | 2.11 | 1.74 | 1.87 | 2.07 | 1.95 a |
| 10 | DINAMIC ® + Galago + TOLLA 840S 100 g + 150 ml + 1.0 l | 2.81 | 1.98 | 2.00 | 2.37 | 2.29 ab |
| 11 | DINAMIC ® + Galago + TOLLA 840S 125 g + 100 ml + 1.0 l | 1.84 | 2.53 | 2.20 | 2.19 | 2.19 ab |
| 12 | DINAMIC ® + Galago + TOLLA 840S 125 g + 150 ml + 1.0 l | 2.99 | 2.29 | 2.94 | 2.37 | 2.65 b |
| 13 | DINAMIC ® + Galago + TOLLA 840S 250 g + 300 ml + 2.0 l | 2.96 | 2.47 | 2.38 | 2.43 | 2.56 b |
| 14 | CALLISTO ® + Dual Gold 260 ml + 710 ml | 2.55 | 1.93 | 2.25 | 2.09 | 2.20 ab |
| 15 | Untreated control | 2.30 | 2.00 | 2.25 | 2.06 | 2.15 ab |

Note:
Treatment means sharing the same letter do not differ significantly by LSD test at the 5% ($\alpha = 0.05$) level of probability

TABLE 6-107

Comparative visual phytotoxicity of DINAMIC ® 700WDG pre-emergence programs

| | TREATMENT | Timing | BBA VISUAL PHYTOTOXICITY SCALE (1 - no damage; 9 - dead) Replicate I | II | III | IV | Mean |
|---|---|---|---|---|---|---|---|
| 1 | DINAMIC ® + Galago 75 g + 100 ml | 14 | 1 | 1 | 1 | 1 | 1.0 |
| | | 28 | 1 | 1 | 1 | 1 | 1.0 |
| | | 42 | 1 | 1 | 1 | 1 | 1.0 |
| 2 | DINAMIC ® + Galago 75 g + 150 ml | 14 | 1 | 1 | 1 | 1 | 1.0 |
| | | 28 | 1 | 1 | 1 | 1 | 1.0 |
| | | 42 | 1 | 1 | 1 | 1 | 1.0 |
| 3 | DINAMIC ® + Galago 100 g + 100 ml | 14 | 2 | 2 | 2 | 2 | 2.0 |
| | | 28 | 1 | 1 | 1 | 1 | 1.0 |
| | | 42 | 1 | 1 | 1 | 1 | 1.0 |
| 4 | DINAMIC ® + Galago 100 g + 150 ml | 14 | 1 | 1 | 3 | 3 | 2.0 |
| | | 28 | 1 | 1 | 1 | 1 | 1.0 |
| | | 42 | 1 | 1 | 1 | 1 | 1.0 |

TABLE 6-107-continued

Comparative visual phytotoxicity of DINAMIC ® 700WDG pre-emergence programs

| | | BBA VISUAL PHYTOTOXICITY SCALE (1 - no damage; 9 - dead) | | | | |
|---|---|---|---|---|---|---|
| | | Replicate | | | | |
| TREATMENT | Timing | I | II | III | IV | Mean |
| 5 DINAMIC ® + Galago 125 g + 100 ml | 14 | 3 | 2 | 3 | 1 | 2.5 |
| | 28 | 3 | 2 | 3 | 2 | 2.5 |
| | 42 | 2 | 1 | 2 | 1 | 1.5 |
| 6 DINAMIC ® + Galago 125 g + 150 ml | 14 | 3 | 1 | 1 | 3 | 2.0 |
| | 28 | 3 | 3 | 3 | 3 | 1.0 |
| | 42 | 2 | 2 | 2 | 2 | 1.0 |
| 7 DINAMIC ® + Galago + TOLLA 840S 75 g + 100 ml + 1.0 l | 14 | 1 | 1 | 1 | 1 | 1.0 |
| | 28 | 1 | 1 | 1 | 1 | 1.0 |
| | 42 | 1 | 1 | 1 | 1 | 1.0 |
| 8 DINAMIC ® + Galago + TOLLA 840S 75 g + 150 ml + 1.0 l | 14 | 1 | 1 | 1 | 1 | 1.0 |
| | 28 | 1 | 1 | 1 | 1 | 1.0 |
| | 42 | 1 | 1 | 1 | 1 | 1.0 |
| 9 DINAMIC ® + Galago + TOLLA 840S 100 g + 100 ml + 1.0 l | 14 | 3 | 3 | 2 | 2 | 2.5 |
| | 28 | 3 | 3 | 3 | 3 | 3.0 |
| | 42 | 2 | 1 | 1 | 2 | 1.5 |
| 10 DINAMIC ® + Galago + TOLLA 840S 100 g + 150 ml + 1.0 l | 14 | 4 | 3 | 3 | 3 | 3.25 |
| | 28 | 4 | 3 | 2 | 3 | 3.0 |
| | 42 | 3 | 1 | 1 | 2 | 1.75 |
| 11 DINAMIC ® + Galago + TOLLA 840S 125 g + 100 ml + 1.0 l | 14 | 3 | 3 | 1 | 3 | 2.66 |
| | 28 | 1 | 1 | 1 | 1 | 1.0 |
| | 42 | 1 | 1 | 1 | 1 | 1.0 |
| 12 DINAMIC ® + Galago + TOLLA 840S 125 g + 150 ml + 1.0 l | 14 | 4 | 3 | 3 | 3 | 3.25 |
| | 28 | 3 | 3 | 2 | 1 | 2.25 |
| | 42 | 2 | 2 | 1 | 1 | 1.5 |
| 13 DINAMIC ® + Galago + TOLLA 840S 250 g + 300 ml + 2.0 l | 14 | 5 | 5 | 5 | 5 | 5.0 |
| | 28 | 6 | 6 | 4 | 4 | 5.0 |
| | 42 | 4 | 4 | 4 | 4 | 4.0 |
| 14 CALLISTO ® + Dual Gold 260 ml + 710 ml | 14 | 1 | 1 | 1 | 1 | 1.0 |
| | 28 | 1 | 1 | 1 | 1 | 1.0 |
| | 42 | 1 | 1 | 1 | 1 | 1.0 |
| 15 Untreated control | 14 | 1 | 1 | 1 | 1 | 1.0 |
| | 28 | 1 | 1 | 1 | 1 | 1.0 |
| | 42 | 1 | 1 | 1 | 1 | 1.0 |

TABLE 6-108

Comparative herbicidal activity of DINAMIC ® 700WDG pre-emergence programs

| | | AVERAGE % WEED CONTROL BY SPECIES % C = Visual % weed control % P = Visual % weed pressure | | | | | | | |
|---|---|---|---|---|---|---|---|---|---|
| | | DATE | | POROL | | SCHPI | | BIDPI | |
| TREATMENT | Timing | % C | % P | % C | % P | % C | % P | % C | % P |
| 1 DINAMIC ® + Galago 75 g + 100 ml | 14 | 95 | 10 | 99 | 5 | 100 | 3 | 100 | 3 |
| | 28 | 95 | 15 | 96 | 10 | 99 | 7 | 98 | 5 |
| | 42 | 85 | 25 | 90 | 15 | 96 | 10 | 90 | 7 |
| | 56 | 80 | 35 | 80 | 20 | 96 | 15 | 80 | 15 |
| 2 DINAMIC ® + Galago 75 g + 150 ml | 14 | 100 | 5 | 100 | 10 | 100 | 5 | 100 | 3 |
| | 28 | 98 | 10 | 100 | 15 | 100 | 5 | 100 | 5 |
| | 42 | 98 | 15 | 99 | 20 | 99 | 10 | 96 | 7 |
| | 56 | 98 | 30 | 97 | 25 | 99 | 15 | 94 | 10 |
| 3 DINAMIC ® + Galago 100 g + 100 ml | 14 | 100 | 10 | 100 | 1 | 100 | 1 | 100 | 3 |
| | 28 | 100 | 15 | 100 | 3 | 100 | 1 | 100 | 5 |
| | 42 | 97 | 25 | 100 | 5 | 100 | 3 | 95 | 7 |
| | 56 | 95 | 35 | 99 | 15 | 99 | 5 | 85 | 10 |
| 4 DINAMIC ® + Galago 100 g + 150 ml | 14 | 100 | 10 | 100 | 5 | 100 | 3 | 100 | 1 |
| | 28 | 100 | 20 | 100 | 10 | 100 | 5 | 100 | 3 |
| | 42 | 98 | 25 | 100 | 15 | 100 | 10 | 99 | 5 |
| | 56 | 96 | 30 | 99 | 20 | 99 | 15 | 98 | 7 |
| 5 DINAMIC ® + Galago 125 g + 100 ml | 14 | 100 | 5 | 100 | 10 | 100 | 5 | 100 | 3 |
| | 28 | 99 | 10 | 100 | 15 | 100 | 5 | 100 | 5 |
| | 42 | 97 | 15 | 99 | 20 | 99 | 10 | 95 | 7 |
| | 56 | 95 | 30 | 97 | 25 | 99 | 15 | 90 | 10 |

TABLE 6-108-continued

Comparative herbicidal activity of DINAMIC ® 700WDG pre-emergence programs

AVERAGE % WEED CONTROL BY SPECIES
% C = Visual % weed control
% P = Visual % weed pressure

| | | | DATE | | POROL | | SCHPI | | BIDPI | |
|---|---|---|---|---|---|---|---|---|---|---|
| TREATMENT | | Timing | % C | % P | % C | % P | % C | % P | % C | % P |
| 6 | DINAMIC ® + Galago | 14 | 100 | 5 | 100 | 5 | 100 | 1 | 100 | 1 |
| | 125 g + 150 ml | 28 | 100 | 15 | 100 | 10 | 100 | 1 | 100 | 1 |
| | | 42 | 100 | 25 | 100 | 15 | 99 | 3 | 99 | 3 |
| | | 56 | 99 | 30 | 97 | 20 | 99 | 5 | 99 | 5 |
| 7 | DINAMIC ® + Galago + | 14 | 100 | 10 | 100 | 3 | 100 | 1 | 100 | 3 |
| | TOLLA 840S | 28 | 99 | 15 | 100 | 5 | 100 | 1 | 100 | 5 |
| | 75 g + 100 ml + 1.0 l | 42 | 99 | 20 | 99 | 10 | 99 | 3 | 95 | 7 |
| | | 56 | 97 | 25 | 99 | 15 | 97 | 7 | 90 | 10 |
| 8 | DINAMIC ® + Galago + | 14 | 100 | 3 | 100 | 1 | 100 | 10 | 100 | 3 |
| | TOLLA 840S | 28 | 100 | 5 | 100 | 3 | 100 | 10 | 100 | 5 |
| | 75 g + 150 ml + 1.0 l | 42 | 98 | 10 | 99 | 10 | 100 | 15 | 98 | 10 |
| | | 56 | 96 | 20 | 99 | 15 | 99 | 20 | 96 | 15 |
| 9 | DINAMIC ® + Galago + | 14 | 100 | 5 | 100 | 3 | 100 | 1 | 100 | 3 |
| | TOLLA 840S | 28 | 100 | 10 | 100 | 10 | 100 | 3 | 100 | 3 |
| | 100 g + 100 ml + 1.0 l | 42 | 95 | 20 | 97 | 15 | 99 | 3 | 98 | 5 |
| | | 56 | 93 | 30 | 95 | 25 | 99 | 5 | 96 | 5 |
| 10 | DINAMIC ® + Galago + | 14 | 100 | 5 | 100 | 1 | 100 | 1 | 100 | 1 |
| | TOLLA 840S | 28 | 100 | 15 | 100 | 5 | 100 | 1 | 100 | 3 |
| | 100 g + 150 ml + 1.0 l | 42 | 98 | 25 | 99 | 10 | 99 | 3 | 100 | 3 |
| | | 56 | 96 | 35 | 99 | 30 | 99 | 5 | 99 | 7 |
| 11 | DINAMIC ® + Galago + | 14 | 100 | 5 | 100 | 5 | 100 | 1 | 100 | 1 |
| | TOLLA 840S | 28 | 100 | 12 | 100 | 10 | 100 | 1 | 100 | 3 |
| | 125 g + 100 ml + 1.0 l | 42 | 99 | 15 | 10 | 15 | 99 | 3 | 96 | 5 |
| | | 56 | 98 | 25 | 99 | 20 | 99 | 5 | 94 | 10 |
| 12 | DINAMIC ® + Galago + | 14 | 100 | 10 | 100 | 5 | 100 | 1 | 100 | 1 |
| | TOLLA 840S | 28 | 100 | 20 | 100 | 10 | 100 | 3 | 100 | 3 |
| | 125 g + 150 ml + 1.0 l | 42 | 99 | 25 | 99 | 15 | 100 | 5 | 99 | 5 |
| | | 56 | 97 | 30 | 97 | 25 | 99 | 10 | 99 | 10 |
| 13 | DINAMIC ® + Galago + | 14 | 100 | 1 | 100 | 3 | 100 | 1 | 100 | 1 |
| | TOLLA 840S | 28 | 100 | 5 | 100 | 5 | 100 | 5 | 100 | 3 |
| | 250 g + 300 ml + 2.0 l | 42 | 99 | 15 | 100 | 10 | 100 | 5 | 100 | 5 |
| | | 56 | 99 | 30 | 100 | 15 | 100 | 7 | 100 | 15 |
| 14 | CALLISTO ® + DUAL S | 14 | 100 | 5 | 100 | 1 | 100 | 1 | 100 | 3 |
| | GOLD ® | 28 | 99 | 15 | 100 | 5 | 100 | 3 | 100 | 5 |
| | 260 ml + 710 ml | 42 | 99 | 25 | 100 | 10 | 100 | 7 | 98 | 10 |
| | | 56 | 98 | 35 | 100 | 15 | 100 | 15 | 96 | 15 |
| 15 | Untreated control | 14 | 0 | 10 | 0 | 1 | 0 | 1 | 0 | 3 |
| | | 28 | 0 | 20 | 0 | 3 | 0 | 3 | 0 | 5 |
| | | 42 | 0 | 30 | 0 | 5 | 0 | 5 | 0 | 10 |
| | | 56 | 0 | 40 | 0 | 10 | 0 | 10 | 0 | 15 |

The trial was conducted on a commercial maize crop produced under irrigated conditions. The DINAMIC® 700WDG formulation was evaluated for herbicidal activity and crop selectivity when applied as a pre-emergence spray program in tank-mix combination with Galago and TOLLA 840S. Treatments were applied pre-emergence of crop and weeds as broadcast applications over the maize rows. Weather conditions were dry with infrequent showers of rain occurring for the duration of the trial.

Visual symptoms of phytotoxicity in the form of stunting and yellowing were observed in treatments receiving the DINAMIC® 700WDG formulation applied at the rates of 100 g/ha and 125 g/ha in combination with Galago and Galago+TOLLA 840S at 14 DAA. Visual symptoms of phytotoxicity were dosage related and ranged from negligible to moderate (class 2 to class 3) according to the BBA visual phytotoxicity rating scale (refer to appendix for details on scale). Slight chlorosis (yellowing) was only observed at 14 DAA. Visual symptoms of stunting were observed at the assessments conducted at 14, 28 and 42 DAA with a decrease in severity of stunting observed at the final visual phytotoxicity assessment conducted at 42 DAA.

The tank-mix combination of DINAMIC® 700WDG+Galago+TOLLA 840S applied at the double rate of 250 g/ha+300 ml/ha+2.0 l/ha exhibited visual symptoms of phytotoxicity in the form of stunting and slight yellowing (chlorosis) at the assessment conducted at 14 DAA. At the assessment conducted at 28 DAA, visual symptoms of stunting corresponding to a BBA scale of 5 (Commercially acceptable only under circumstances where yield losses do not occur) were observed. While at 42 DAA, severity of stunting improved from class 5 to class 4 according to the BBA visual phytotoxicity assessment scale.

Yield

None of the various DINAMIC® 700WDG tank-mix combinations exhibited significantly different yields in terms of grain yield per plot compared to the untreated control treatment or the standard tank-mix combination of CALLISTO®+DUAL S GOLD®, respectively.

The weed spectrum at the trial site consisted of broadleaved weeds only. The broadleaved weed spectrum was composed of Large thornapple (DATFE), Purslane (POROL), Dwarf marigold (SCHPI) and Blackjack (BIDPI).

Efficacy evaluations were conducted at 14, 28, 42 and 56 days following application, respectively.

DINAMIC® 700WDG+Galago

The tank-mix combinations of DINAMIC® 700WDG+Galago were efficacious and displayed excellent levels of herbicidal activity against the broadleaved weed spectrum at the trial site. Commercially acceptable levels of herbicidal activity were achieved across the entire weed spectrum where DINAMIC® 700WDG was applied at rates exceeding 75 g/ha in combination with Galago applied at either 100 ml/ha or 150 ml/ha, respectively. Commercial control of the entire broadleaved weed spectrum was observed in all treatments where Galago was applied at the rate of 150 ml/ha, regardless of the rate of DINAMIC® 700WDG applied.

DINAMIC® 700WDG+Galago+TOLLA 840S

The addition of TOLLA 840S to the tank-mix combination of DINAMIC® 700WDG+Galago greatly enhanced the herbicidal activity against the small-seeded broadleaved weeds (POROL, SCHPI and BIDPI). All of the tank-mix combinations of DINAMIC® 700WDG+Galago +TOLLA 840S exhibited commercially acceptable levels of herbicidal activity against the broadleaved weeds DATFE, POROL, SCHPI and BIDPI at the final assessment conducted at 56 DAA. The tank-mix combination of DINAMIC® 700WDG+Galago+TOLLA 840S applied at 100-125 g/ha+150 ml/ha+1.0 l/ha achieved comparable levels of herbicidal activity as the standard tank-mix combination of CALLISTO®+Dual Gold applied at 260 ml/ha+710 ml/ha.

Compatibility

No visual symptoms of incompatibility in the form of phase separation or agglomeration were observed in any of the tank-mix combinations of DINAMIC® 700WDG+Galago and DINAMIC® 700WDG+Galago+TOLLA 840S, whether applied at single or double rates.

Visual symptoms of phytotoxicity in the form of stunting were observed on treatments receiving the tank-mix combinations of DINAMIC® 700WDG+Galago and DINAMIC® 700WDG+Galago+TOLLA 840S in all cases where DINAMIC® 700WDG was applied at rates exceeding 75 g/ha. Visual symptoms of stunting were dosage related and ranged from negligible to distinct damage (class 2 to class 5) according to the BBA visual phytotoxicity rating scale.

DINAMIC®+Galago combinations displayed commercially acceptable levels of herbicidal activity against the broadleaved weed spectrum consisting of DATFE, POROL, SCHPI and BIDPI in all tank-mix treatments where DINAMIC® 700WDG was applied at rates exceeding 75 g/ha, or in tank-mix treatments where Galago was applied at the rate of 150 ml/ha.

Tank-mix combinations of DINAMIC® 700WDG+Galago+TOLLA 840S were efficacious and exhibited commercial control of DATFE, POROL, SCHPI and BIDPI across all rates applied. The tank-mix combination of DINAMIC® 700WDG+Galago+TOLLA 840S applied at 100-125 g/ha+150 ml/ha+1.0 l/ha achieved comparable levels of herbicidal activity as the standard tank-mix combination of CALLISTO®+Dual Gold applied at 260 ml/ha+710 ml/ha.

No visual symptoms of incompatibility in the form of phase separation or agglomeration were observed in any of the tank-mix combinations of DINAMIC® 700WDG+Galago and DINAMIC® 700WDG+Galago+TOLLA 840S, whether applied at single or double rates.

None of the various DINAMIC® 700WDG tank-mix combinations exhibited significantly different yields in terms of grain yield per plot compared to the untreated control treatment or the standard tank-mix combination of CALLISTO®+DUAL S GOLD®, respectively.

TABLE 6-109

| Anova Table Grain yield (kg/plot) | | | | |
|---|---|---|---|---|
| Unit | Degrees of freedom | Sums of Squares | Mean Squares | F Value |
| Reps | 3 | .6917 | | |
| Treatments | 14 | 2.269 | .1621 | 2.969 |
| Error | 42 | 2.293 | .5459 | |
| Total | 59 | 5.253 | | |
| Overall mean | | | | 2.207 |
| S. E for Difference | | | | .1652 |
| Least Significant Difference (LSD) at 95% | | | | .3334 |

TABLE 6-110

| BBA Visual Phytotoxicity rating scale | | |
|---|---|---|
| Scale | EQUIVALENT % | Description |
| 1 | 0% | NO DAMAGE |
| 2 | 0.1-2.5% | NEGLIGIBLE DAMAGE |
| 3 | 2.5-5.0% | MODERATE DAMAGE No effects on yield and/or quality |
| 4 | 5.0-10% | Damage up to limits of commercial acceptability - if no yield loss |
| 5 | 10-15% | DISTINCT DAMAGE Commercially acceptable only under certain conditions - if no yield loss |
| 6 | 15-25% | SEVERE DAMAGE Not commercially acceptable - yield loss and quality |
| 7 | 25-35% | VERY SEVERE DAMAGE |
| 8 | 35-68% | EXTREME DAMAGE |
| 9 | 68-100% | START OF WITHERING AND DEATH |

O. Pre Emergence Application Against Weed in Maize

This Example compares the herbicidal selectivity and efficacy of DINAMIC® 700WDG applied in combination with Galago and TOLLA 840S as a pre-emergence application with regards to both crop and weeds in irrigated maize. Treatments and conditions are tabulated below.

TABLE 6-111

| TREATMENTS | | | |
|---|---|---|---|
| | | Rate/ha | |
| | TREATMENT | Product (l) | a.i. (g) |
| 1 | DINAMIC ® + Galago | 75 g + 100 ml | 52.5 + 48 |
| 2 | DINAMIC ® + Galago | 75 g + 150 ml | 52.5 + 72 |
| 3 | DINAMIC ® + Galago | 100 g + 100 ml | 70 + 48 |
| 4 | DINAMIC ® + Galago | 100 g + 150 ml | 70 + 72 |

TABLE 6-111-continued

TREATMENTS

| | | Rate/ha | |
|---|---|---|---|
| | TREATMENT | Product (l) | a.i. (g) |
| 5 | DINAMIC ® + Galago | 125 g + 100 ml | 87.5 + 48 |
| 6 | DINAMIC ® + Galago | 125 g + 150 ml | 87.5 + 72 |
| 7 | DINAMIC ® + Galago + TOLLA 840S | 75 g + 100 ml + 1.0 l | 52.5 + 48 + 840 |
| 8 | DINAMIC ® + Galago + TOLLA 840S | 75 g + 150 ml + 1.0 l | 52.5 + 72 + 840 |
| 9 | DINAMIC ® + Galago + TOLLA 840S | 100 g + 100 ml + 1.0 l | 70 + 48 + 840 |
| 10 | DINAMIC ® + Galago + TOLLA 840S | 100 g + 150 ml + 1.0 l | 70 + 72 + 840 |
| 11 | DINAMIC ® + Galago + TOLLA 840S | 125 g + 100 ml + 1.0 l | 87.5 + 48 + 840 |
| 12 | DINAMIC ® + Galago + TOLLA 840S | 125 g + 150 ml + 1.0 l | 87.5 + 72 + 840 |
| 13 | DINAMIC ® + Galago + TOLLA 840S | 250 g + 300 ml + 2.0 l | 175 + 144 + 1680 |
| 14 | CALLISTO ® + Dual Gold | 260 ml + 710 ml | 125 + 650 |
| 15 | Untreated control | — | — |

TABLE 6-112

Test products used

| | Product | Active Ingredient | Form | Manufacturer/ Supplier | Reg. No. |
|---|---|---|---|---|---|
| 1 | DINAMIC ® 700WDG | Amicarbazone 700 g/kg | WDG | Arysta Lifescience | |
| 2 | Galago | Mesotrione 480 g/l | SC | Arysta Lifescience | L. 8089 |
| 3 | TOLLA 840 S | Metolachlor 840 g/l + Safener | EC | Arysta Lifescience | L. 7374 |
| 4 | CALLISTO ® | Mesotrione 480 g/l | SC | Syngenta | L. 6795 |
| 5 | DUAL S GOLD ® | S-Metolachlor 915 g/l + Safener | EC | Syngenta | L. 5749 |

TABLE 6-113

TRIAL DESIGN

| | |
|---|---|
| Design | Completely randomized design |
| Replicates | Four |
| Plot size | 5 m × 2 m = Nett/plot |

TABLE 6-114

SPRAYER

| | |
|---|---|
| Sprayer | CO$_2$ Precision Sprayer |
| Boom | 2.0 m aluminium |
| Nozzle | 4 × 11002 flat fan nozzles (Teejet 11002 DG) |
| Pressure | 2.55 Bar |
| Application | 200 l/ha |

Spray Water Quality:
pH: 6.6
EC: 0.5 mS/m

TABLE 6-115

WEATHER INFORMATION AT APPLICATION

| | |
|---|---|
| Temperature (max) | 31.6° C. |
| RH: | 34% |
| Wind: | 0-5 km/h, NW |
| Cloud | 8/8 |

TABLE 6-116

SOIL PROPERTIES AT APPLICATION:

| | |
|---|---|
| Clay Fraction | 9% |
| Silt Fraction | 5% |
| Sand Fraction | 86% |
| pH (H$_2$O) | 6.01 |
| Moisture | Field capacity |
| Seedbed condition | Fine (no clods) |

Irrigation:
Sprinkler
Crop:
Crop: Maize
Variety: Pan 3P-736BR
Growth stage: Pre-emergence (BBCH growth stage 00)
Sowing depth: 5 cm
Sowing density: 80 000 plants/ha

TABLE 6-117

WEED INFORMATION:

| SPECIES | COMMON NAME | ABBREVIATION |
|---|---|---|
| *Bidens pilosa* | Blackjack | BIDPI |
| *Portulaca oleracea* | Purslane | POROL |
| *Convolvulus arvensis* | Field bindweed | CONAR |
| *Anoda cristata* | Anoda weed | ANOCR |

TABLE 6-118

ASSESSMENT DETAILS

| | |
|---|---|
| Method | Comparative Efficacy |
| Herbicide | Efficacy: Number of weeds in treated versus untreated plots |
| | Selectivity: |
| | 5. Visual phytotoxicity: BBA 1-9 scale (refer to appendix for details) |

TABLE 6-118-continued

ASSESSMENT DETAILS

| | | |
|---|---|---|
| | 6. | Yield: 40 cobs harvested at random from each plot. Average grain weight per plot determined using a precision 2 decimal scale. Statistical evaluation: ANOVA at the 95% probability using Tukeys LSD formulae |
| Assessment Times-Days After Application (DAA) | 14 DAA - Efficacy/Selectivity 28 DAA - Efficacy/Selectivity 42 DAA - Efficacy/Selectivity 56 DAA - Efficacy Harvest - Selectivity | |

TABLE 6-119

Comparative yield of DINAMIC ® 700WDG programs

| | | YIELD (Kg/plot) | | | | |
|---|---|---|---|---|---|---|
| | | Replicate | | | | |
| | TREATMENT | I | II | III | IV | Mean |
| 1 | DINAMIC ® + Galago 75 g + 100 ml | 4.06 | 3.52 | 4.59 | 4.22 | 4.10 a |
| 2 | DINAMIC ® + Galago 75 g + 150 ml 0 | 3.59 | 3.21 | 3.90 | 4.19 | 3.72 a |
| 3 | DINAMIC ® + Galago 100 g + 100 ml | 4.30 | 3.43 | 3.97 | 3.91 | 3.90 a |
| 4 | DINAMIC ® + Galago 100 g + 150 ml | 3.47 | 3.00 | 3.70 | 3.56 | 3.43 a |
| 5 | DINAMIC ® + Galago 125 g + 100 ml | 3.68 | 3.04 | 4.01 | 3.69 | 3.61 a |
| 6 | DINAMIC ® + Galago 125 g + 150 ml | 3.69 | 3.34 | 3.59 | 3.78 | 3.60 a |
| 7 | DINAMIC ® + Galago + TOLLA 840S 75 g + 100 ml + 1.0 l | 3.64 | 3.16 | 3.48 | 4.37 | 3.66 a |
| 8 | DINAMIC ® + Galago + TOLLA 840S 75 g + 150 ml + 1.0 l | 3.01 | 3.45 | 3.56 | 4.82 | 3.71 a |
| 9 | DINAMIC ® + Galago + TOLLA 840S 100 g + 100 ml + 1.0 l | 3.52 | 3.22 | 4.00 | 3.90 | 3.66 a |
| 10 | DINAMIC ® + Galago + TOLLA 840S 100 g + 150 ml + 1.0 l | 3.91 | 4.20 | 3.50 | 3.91 | 3.88 a |
| 11 | DINAMIC ® + Galago + TOLLA 840S 125 g + 100 ml + 1.0 l | 3.71 | 4.84 | 3.58 | 3.48 | 3.90 a |
| 12 | DINAMIC ® + Galago + TOLLA 840S 125 g + 150 ml + 1.0 l | 3.36 | 3.54 | 4.75 | 3.95 | 3.90 a |
| 13 | DINAMIC ® + Galago + TOLLA 840S 250 g + 300 ml + 2.0 l | 3.49 | 3.85 | 4.42 | 3.48 | 3.81 a |
| 14 | CALLISTO ® + Dual Gold 260 ml + 710 ml | 3.73 | 4.40 | 4.09 | 4.06 | 4.07 a |
| 15 | Untreated control | 4.00 | 4.32 | 4.37 | 4.02 | 4.18 a |

Note:
Treatment means sharing the same letter do not differ significantly by LSD test at the 5% ($\alpha = 0.05$) level of probability

TABLE 6-120

Comparative visual phytotoxicity of DINAMIC ® 700WDG pre-emergence programs

| | | | BBA VISUAL PHYTOTOXICITY SCALE (1 - no damage; 9 - dead) | | | | |
|---|---|---|---|---|---|---|---|
| | | | Replicate | | | | |
| | TREATMENT | Timing | I | II | III | IV | Mean |
| 1 | DINAMIC ® + Galago 75 g + 100 ml | 14 | 1 | 1 | 1 | 1 | 1.0 |
| | | 28 | 1 | 1 | 1 | 1 | 1.0 |
| | | 42 | 1 | 1 | 1 | 1 | 1.0 |
| 2 | DINAMIC ® + Galago 75 g + 150 ml | 14 | 1 | 1 | 1 | 1 | 1.0 |
| | | 28 | 1 | 1 | 1 | 1 | 1.0 |
| | | 42 | 1 | 1 | 1 | 1 | 1.0 |
| 3 | DINAMIC ® + Galago 100 g + 100 ml | 14 | 1 | 1 | 1 | 1 | 1.0 |
| | | 28 | 1 | 1 | 1 | 1 | 1.0 |
| | | 42 | 1 | 1 | 1 | 1 | 1.0 |
| 4 | DINAMIC ® + Galago 100 g + 150 ml | 14 | 1 | 1 | 1 | 1 | 1.0 |
| | | 28 | 1 | 1 | 1 | 1 | 1.0 |
| | | 42 | 1 | 1 | 1 | 1 | 1.0 |
| 5 | DINAMIC ® + Galago 125 g + 100 ml | 14 | 1 | 1 | 1 | 1 | 1.0 |
| | | 28 | 1 | 1 | 1 | 1 | 1.0 |
| | | 42 | 1 | 1 | 1 | 1 | 1.0 |
| 6 | DINAMIC ® + Galago 125 g + 150 ml | 14 | 1 | 1 | 1 | 1 | 1.0 |
| | | 28 | 1 | 1 | 1 | 1 | 1.0 |
| | | 42 | 1 | 1 | 1 | 1 | 1.0 |
| 7 | DINAMIC ® + Galago + TOLLA 840S 75 g + 100 ml + 1.0 l | 14 | 1 | 1 | 1 | 1 | 1.0 |
| | | 28 | 1 | 1 | 1 | 1 | 1.0 |
| | | 42 | 1 | 1 | 1 | 1 | 1.0 |
| 8 | DINAMIC ® + Galago + TOLLA 840S 75 g + 150 ml + 1.0 l | 14 | 1 | 1 | 1 | 1 | 1.0 |
| | | 28 | 1 | 1 | 1 | 1 | 1.0 |
| | | 42 | 1 | 1 | 1 | 1 | 1.0 |
| 9 | DINAMIC ® + Galago + TOLLA 840S 100 g + 100 ml + 1.0 l | 14 | 1 | 1 | 1 | 1 | 1.0 |
| | | 28 | 1 | 1 | 1 | 1 | 1.0 |
| | | 42 | 1 | 1 | 1 | 1 | 1.0 |

TABLE 6-120-continued

Comparative visual phytotoxicity of DINAMIC ® 700WDG pre-emergence programs

| | | | BBA VISUAL PHYTOTOXICITY SCALE (1 - no damage; 9 - dead) | | | | |
|---|---|---|---|---|---|---|---|
| | | | Replicate | | | | |
| | TREATMENT | Timing | I | II | III | IV | Mean |
| 10 | DINAMIC ® + Galago + TOLLA 840S 100 g + 150 ml + 1.0 l | 14 28 42 | 1 1 1 | 1 1 1 | 1 1 1 | 1 1 1 | 1.0 1.0 1.0 |
| 11 | DINAMIC ® + Galago + TOLLA 840S 125 g + 100 ml + 1.0 l | 14 28 42 | 3 1 1 | 3 1 1 | 1 1 1 | 1 1 1 | 2.0 1.0 1.0 |
| 12 | DINAMIC ® + Galago + TOLLA 840S 125 g + 150 ml + 1.0 l | 14 28 42 | 3 1 1 | 1 1 1 | 1 1 1 | 3 1 1 | 2.0 1.0 1.0 |
| 13 | DINAMIC ® + Galago + TOLLA 840S 250 g + 300 ml + 2.0 l | 14 28 42 | 3 2 4 | 2 2 4 | 1 1 1 | 3 2 2 | 2.25 1.75 2.75 |
| 14 | CALLISTO ® + Dual Gold 260 ml + 710 ml | 14 28 42 | 1 1 1 | 1 1 1 | 1 1 1 | 1 1 1 | 1.0 1.0 1.0 |
| 15 | Untreated control | 14 28 42 | 1 1 1 | 1 1 1 | 1 1 1 | 1 1 1 | 1.0 1.0 1.0 |

TABLE 6-121

Comparative herbicidal activity of DINAMIC ® 700WDG pre-emergence programs

| | | | AVERAGE % WEED CONTROL BY SPECIES % C = Visual % weed control % P = Visual % weed pressure | | | | | | | |
|---|---|---|---|---|---|---|---|---|---|---|
| | | | BIDPI | | POROL | | ANOCR | | CONAR | |
| | TREATMENT | Timing | % C | % P | % C | % P | % C | % P | % C | % P |
| 1 | DINAMIC ® + Galago 75 g + 100 ml | 14 28 42 56 | 100 100 96 85 | 5 10 15 20 | 100 100 100 90 | 3 10 15 25 | 100 100 80 70 | 1 3 5 10 | 100 100 100 80 | 1 1 3 10 |
| 2 | DINAMIC ® + Galago 75 g + 150 ml | 14 28 42 56 | 100 100 100 94 | 5 10 15 20 | 100 100 100 98 | 5 10 15 20 | 100 100 100 90 | 1 3 5 10 | 100 100 100 90 | 1 3 7 10 |
| 3 | DINAMIC ® + Galago 100 g + 100 ml | 14 28 42 56 | 100 100 100 90 | 5 10 20 25 | 100 100 100 98 | 1 3 5 15 | 100 98 90 90 | 1 5 10 10 | 100 100 100 85 | 2 5 10 10 |
| 4 | DINAMIC ® + Galago 100 g + 150 ml | 14 28 42 56 | 100 100 100 98 | 3 5 10 15 | 100 100 100 99 | 3 5 10 20 | 100 100 100 98 | 1 1 3 5 | 100 100 100 96 | 1 1 3 5 |
| 5 | DINAMIC ® + Galago 125 g + 100 ml | 14 28 42 56 | 100 100 100 96 | 1 5 10 15 | 100 100 100 98 | 1 5 10 15 | 100 100 100 96 | 1 1 3 7 | 100 100 100 94 | 1 1 3 5 |
| 6 | DINAMIC ® + Galago 125 g + 150 ml | 14 28 42 56 | 100 100 100 99 | 5 10 15 20 | 100 100 100 99 | 1 3 5 15 | 100 100 100 98 | 1 3 5 10 | 100 100 100 98 | 2 5 10 10 |
| 7 | DINAMIC ® + Galago + TOLLA 840S 75 g + 100 ml + 1.0 l | 14 28 42 56 | 100 100 94 90 | 5 10 20 25 | 100 100 100 98 | 3 5 10 20 | 100 90 90 80 | 1 3 5 10 | 100 100 100 90 | 2 5 7 10 |
| 8 | DINAMIC ® + Galago + TOLLA 840S 75 g + 150 ml + 1.0 l | 14 28 42 56 | 100 100 100 99 | 3 5 10 20 | 100 100 100 99 | 3 5 10 20 | 100 100 100 90 | 1 3 5 10 | 100 100 100 94 | 2 5 10 10 |

TABLE 6-121-continued

Comparative herbicidal activity of DINAMIC ® 700WDG pre-emergence programs

AVERAGE % WEED CONTROL BY SPECIES
% C = Visual % weed control
% P = Visual % weed pressure

| TREATMENT | Timing | BIDPI % C | BIDPI % P | POROL % C | POROL % P | ANOCR % C | ANOCR % P | CONAR % C | CONAR % P |
|---|---|---|---|---|---|---|---|---|---|
| 9 DINAMIC ® + Galago + TOLLA 840S 100 g + 100 ml + 1.0 l | 14 | 100 | 5 | 100 | 3 | 100 | 2 | 100 | 1 |
| | 28 | 100 | 10 | 100 | 5 | 96 | 5 | 100 | 1 |
| | 42 | 96 | 20 | 100 | 10 | 96 | 10 | 100 | 3 |
| | 56 | 96 | 25 | 96 | 20 | 90 | 10 | 90 | 5 |
| 10 DINAMIC ® + Galago + TOLLA 840S 100 g + 150 ml + 1.0 l | 14 | 100 | 3 | 100 | 1 | 100 | 1 | 100 | 1 |
| | 28 | 100 | 5 | 100 | 3 | 100 | 1 | 100 | 3 |
| | 42 | 100 | 10 | 100 | 5 | 100 | 3 | 100 | 5 |
| | 56 | 99 | 20 | 98 | 15 | 94 | 7 | 94 | 10 |
| 11 DINAMIC ® + Galago + TOLLA 840S 125 g + 100 ml + 1.0 l | 14 | 100 | 5 | 100 | 1 | 100 | 1 | 100 | 1 |
| | 28 | 100 | 10 | 100 | 3 | 100 | 1 | 98 | 3 |
| | 42 | 99 | 15 | 100 | 5 | 100 | 3 | 90 | 3 |
| | 56 | 98 | 20 | 100 | 15 | 96 | 10 | 90 | 10 |
| 12 DINAMIC ® + Galago + TOLLA 840S 125 g + 150 ml + 1.0 l | 14 | 100 | 5 | 100 | 3 | 100 | 2 | 100 | 2 |
| | 28 | 100 | 10 | 100 | 5 | 100 | 5 | 100 | 5 |
| | 42 | 100 | 15 | 100 | 10 | 100 | 10 | 100 | 10 |
| | 56 | 100 | 20 | 100 | 20 | 98 | 15 | 96 | 12 |
| 13 DINAMIC ® + Galago + TOLLA 840S 250 g + 300 ml + 2.0 l | 14 | 100 | 5 | 100 | 3 | 100 | 0 | 100 | 1 |
| | 28 | 100 | 10 | 100 | 5 | 100 | 0 | 100 | 3 |
| | 42 | 100 | 20 | 100 | 10 | 100 | 1 | 100 | 5 |
| | 56 | 100 | 25 | 100 | 20 | 100 | 5 | 100 | 10 |
| 14 CALLISTO ® + DUAL S GOLD ® 260 ml + 710 ml | 14 | 100 | 1 | 100 | 1 | 100 | 1 | 100 | 2 |
| | 28 | 100 | 5 | 100 | 3 | 100 | 3 | 100 | 5 |
| | 42 | 100 | 10 | 100 | 5 | 100 | 5 | 100 | 10 |
| | 56 | 100 | 15 | 100 | 15 | 100 | 10 | 100 | 10 |
| 15 Untreated control | 14 | 0 | 5 | 0 | 1 | 0 | 1 | 0 | 1 |
| | 28 | 0 | 10 | 0 | 3 | 0 | 3 | 0 | 3 |
| | 42 | 0 | 15 | 0 | 5 | 0 | 5 | 0 | 5 |
| | 56 | 0 | 20 | 0 | 15 | 0 | 10 | 0 | 10 |

The trial was conducted on a commercial maize crop produced under irrigated conditions. The DINAMIC® 700WDG formulation was evaluated for herbicidal activity and crop selectivity when applied as a pre-emergence spray program in tank-mix combination with Galago and TOLLA 840S. Treatments were applied pre-emergence of crop and weeds as broadcast applications over the maize rows.

No visual symptoms of phytotoxicity in the form of stunting, chlorosis or growth abnormalities were observed on any of the treatments receiving the tank-mix combination of DINAMIC® 700WDG+Galago across all rates applied.

The tank-mix combination of DINAMIC® 700WDG+Galago+TOLLA 840S exhibited symptoms of phytotoxicity in the form of stunting in treatments receiving the DINAMIC® 700WDG formulation applied at the rate of 125 g/ha and the double rate of 250 g/ha, respectively. At 125 g/ha, stunting was only observed at the first assessment conducted at 14 DAA. At the double rate of 250 g/ha, stunting was observed at each of the assessments conducted. No visual symptoms of phytotoxicity were observed in tank-mix combinations of DINAMIC® 700WDG+Galago+TOLLA 840S where the DINAMIC® 700WDG formulation was applied at rates of 75 g/ha and 100 g/ha, respectively.

In terms of yield, tank-mix combinations of DINAMIC® 700WDG+Galago and DINAMIC® 700WDG+Galago+TOLLA 840S did not significantly increase or decrease yield compared to the untreated control treatments and the standard tank-mix combination of CALLISTO®+DUAL S GOLD®.

The weed spectrum at the trial site consisted mainly of broadleaved weeds namely; Blackjack (BIDPI), Purslane (POROL), Anoda weed (ANOCR) and Field bindweed (CONAR). Efficacy evaluations were conducted at 14, 28, 42 and 56 days following application, respectively. Blackjack (BIDPI) and Purslane (POROL) were well represented in each plot with 15-25% soil cover of each weed observed in the untreated control strips at the final assessment, respectively. The weeds ANOCR and CONAR represented a smaller portion of the weed population with 5-15% and 5-10% soil cover of each weed observed in the untreated control strips at the final assessment conducted at 56 DAA, respectively.

DINAMIC® 700WDG+Galago

The tank-mix combinations of DINAMIC® 700WDG+Galago exhibited commercially acceptable levels of herbicidal activity against the broadleaved weed POROL across all rates applied. Commercially acceptable levels of herbicidal activity were achieved for BIDPI and ANOCR where DINAMIC® 700WDG was applied at rates exceeding 75 g/ha in combination with Galago applied at either 100 ml/ha or 150 ml/ha, respectively. Generally, weed control was greatest with increasing rates of Galago applied and commercial control of the entire broadleaved weed spectrum was observed in all treatments where Galago was applied at the rate of 150 ml/ha, regardless of the rate of DINAMIC® 700WDG applied.

DINAMIC® 700WDG+Galago+TOLLA 840S

The addition of TOLLA 840S to the tank-mix combination of DINAMIC® 700WDG+Galago greatly enhanced the herbicidal activity against the small-seeded broadleaved weeds (POROL and BIDPI). All of the tank-mix combinations of DINAMIC® 700WDG+Galago+TOLLA 840S exhibited commercially acceptable levels of herbicidal activity against the broadleaved weeds BIDPI, POROL and CONAR at the final assessment conducted at 56 DAA. The broadleaved weed CONAR was commercially controlled by all tank-mix combinations of DINAMIC® 700WDG+Galago+TOLLA 840S where Galago was applied at the rate of 150 ml/ha or where the rate of DINAMIC® 700WDG exceeded 75 g/ha. The tank-mix combination of DINAMIC® 700WDG+Galago+TOLLA 840S applied at 125 g/ha+150 ml/ha+1.0 l/ha achieved comparable levels of herbicidal activity as the standard tank-mix combination of CALLISTO®+Dual Gold applied at 260 ml/ha+710 ml/ha.

Compatibility

No visual symptoms of incompatibility in the form of phase separation or agglomeration were observed in any of the tank-mix combinations of DINAMIC® 700WDG+Galago and DINAMIC® 700WDG+Galago+TOLLA 840S, whether applied at single or double rates.

No visual symptoms of phytotoxicity in the form of stunting, chlorosis or growth abnormalities were observed on any of the treatments receiving the tank-mix combination of DINAMIC® 700WDG+Galago across all rates applied. DINAMIC®+Galago tank-mix combinations displayed commercially acceptable levels of herbicidal activity against the broadleaved weed POROL across all rates applied, while commercially acceptable levels of herbicidal activity were observed for BIDPI and ANOCR where DINAMIC® 700WDG was applied at rates exceeding 75 g/ha in combination with Galago applied at either 100 ml/ha or 150 ml/ha.

The tank-mix combination of DINAMIC® 700WDG+Galago+TOLLA 840S exhibited symptoms of phytotoxicity in the form of stunting in treatments receiving the DINAMIC® 700WDG formulation applied at the rate of 125 g/ha and the double rate of 250 g/ha, respectively. No visual symptoms of phytotoxicity were observed in tank-mix combinations of DINAMIC® 700WDG+Galago+TOLLA 840S where the DINAMIC® 700WDG formulation was applied at rates of 75 g/ha and 100 g/ha, respectively.

Tank-mix combinations of DINAMIC® 700WDG+Galago+TOLLA 840S were efficacious and exhibited commercial control of BIDPI, POROL and CONAR across all rates applied. CONAR was commercially controlled by all tank-mix combinations of DINAMIC® 700WDG+Galago+TOLLA 840S where Galago was applied at the rate of 150 ml/ha or where the rate of DINAMIC® 700WDG exceeded 75 g/ha. The tank-mix combination of DINAMIC® 700WDG+Galago+TOLLA 840S applied at 125 g/ha+150 ml/ha+1.0 l/ha achieved comparable levels of herbicidal activity as the standard tank-mix combination of CALLISTO®+Dual Gold applied at 260 ml/ha+710 ml/ha.

No visual symptoms of incompatibility in the form of phase separation or agglomeration were observed in any of the tank-mix combinations of DINAMIC® 700WDG+Galago and DINAMIC® 700WDG+Galago+TOLLA 840S, whether applied at single or double rates.

Tank-mix combinations of DINAMIC® 700WDG+Galago and DINAMIC® 700WDG+Galago+TOLLA 840S did not significantly increase or decrease yield compared to the untreated control treatments and the standard tank-mix combination of CALLISTO®+DUAL S GOLD®.

TABLE 6-122

Anova Table Grain yield (kg/plot)

| Unit | Degrees of freedom | Sums of Squares | Mean Squares | F Value |
|---|---|---|---|---|
| Reps | 3 | 1.416 | | |
| Treatments | 14 | 2.424 | 0.1731 | 0.9727 |
| Error | 42 | 7.476 | 0.1780 | |
| Total | 59 | 11.32 | | |
| Overall mean | | | | 3.809 |
| S. E for Difference | | | | 0.2983 |
| Least Significant Difference (LSD) at 95% | | | | 0.6020 |

TABLE 6-123

BBA Visual Phytotoxicity rating scale

| Scale | EQUIVALENT % | Description |
|---|---|---|
| 1 | 0% | NO DAMAGE |
| 2 | 0.1-2.5% | NEGLIGIBLE DAMAGE |
| 3 | 2.5-5.0% | MODERATE DAMAGE No effects on yield and/or quality |
| 4 | 5.0-10% | Damage up to limits of commercial acceptability - if no yield loss |
| 5 | 10-15% | DISTINCT DAMAGE Commercially acceptable only under certain conditions - if no yield loss |
| 6 | 15-25% | SEVERE DAMAGE Not commercially acceptable - yield loss and quality |
| 7 | 25-35% | VERY SEVERE DAMAGE |
| 8 | 35-68% | EXTREME DAMAGE |
| 9 | 68-100% | START OF WITHERING AND DEATH |

P. Post Emergence Application Against Weed in Maize

This Example compares the herbicidal selectivity and efficacy of DINAMIC® 700WDG applied in combination with Galago and TOLLA 960 as a post-emergence application with regards to both crop and weeds in irrigated maize. Treatments and conditions are tabulated below.

TABLE 6-124

TREATMENTS

| | TREATMENT | Rate/ha Product (l) | a.i. (g) |
|---|---|---|---|
| 1 | DINAMIC ® + Galago + Wet-All | 75 g + 100 ml + 100 ml/100 l | 52.5 + 48 + 180 |
| 2 | DINAMIC ® + Galago + Wet-All | 75 g + 150 ml + 100 ml/100 l | 52.5 + 72 |
| 3 | DINAMIC ® + Galago + Wet-All | 100 g + 100 ml + 100 ml/100 l | 70 + 48 |
| 4 | DINAMIC ® + Galago + Wet-All | 100 g + 150 ml + 100 ml/100 l | 70 + 72 |
| 5 | DINAMIC ® + Galago + Wet-All | 125 g + 100 ml + 100 ml/100 l | 87.5 + 48 |
| 6 | DINAMIC ® + Galago + Wet-All | 125 g + 150 ml + 100 ml/100 l | 87.5 + 72 |

TABLE 6-124-continued

| | TREATMENTS | | |
|---|---|---|---|
| | | Rate/ha | |
| TREATMENT | | Product (l) | a.i. (g) |
| 7 DINAMIC ® + Galago + TOLLA 960 + Wet-All | | 75 g + 100 ml + 1.0 l + 100 ml/100 l | 52.5 + 48 + 960 + 180 |
| 8 DINAMIC ® + Galago + TOLLA 960 + Wet-All | | 75 g + 150 ml + 1.0 l + 100 ml/100 l | 52.5 + 72 + 960 + 180 |
| 9 DINAMIC ® + Galago + TOLLA 960 + Wet-All | | 100 g + 100 ml + 1.0 l + 100 ml/100 l | 70 + 48 + 960 + 180 |
| 10 DINAMIC ® + Galago + TOLLA 960 + Wet-All | | 100 g + 150 ml + 1.0 l + 100 ml/100 l | 70 + 72 + 960 + 180 |
| 11 DINAMIC ® + Galago + TOLLA 960 + Wet-All | | 125 g + 100 ml + 1.0 l + 100 ml/100 l | 87.5 + 48 + 960 + 180 |
| 12 DINAMIC ® + Galago + TOLLA 960 + Wet-All | | 125 g + 150 ml + 1.0 l + 100 ml/100 l | 87.5 + 72 + 960 + 180 |
| 13 DINAMIC ® + Galago + TOLLA 960 + Wet-All | | 250 g + 300 ml + 2.0 l + 200 ml/100 l | 175 + 144 + 1920 + 360 |
| 14 CALLISTO ® + Gardo Gold + Complement super | | 260 ml + 1562 ml + 100 ml | 125 + 488/293 + 100 |
| 15 Untreated control | | — | — |

TABLE 6-125

| | Test products used | | | |
|---|---|---|---|---|
| Product | Active Ingredient | Formulation | Manufacturer/Supplier | Registration No. |
| 1 DINAMIC ® 700WDG | Amicarbazone 700 g/kg | WDG | Arysta Lifescience | |
| 2 Galago | Mesotrione 480 g/l | SC | Arysta Lifescience | L. 8089 |
| 3 TOLLA 960 | Metolachlor 960 g/l | EC | Arysta Lifescience | L. 6794 |
| 4 Wet-All | Adjuvant | SL | Arysta Lifescience | L. 8361 |
| 5 CALLISTO ® | Mesotrione 480 g/l | SC | Syngenta | L. 6795 |
| 6 Gardo Gold | S-Metolachlor 312.5 g/l Terbuthylazine 187.5 g/l | SC | Syngenta | L. 7763 |
| 7 COMPLEMENT ® Super | Adjuvant | SL | Syngenta | L. 8169 |

TABLE 6-126

| TRIAL DESIGN | |
|---|---|
| Design | Completely randomized design |
| Replicates | Four |
| Plot size | 5 m × 2.5 m = Nett/plot |

TABLE 6-127

| SPRAYER | |
|---|---|
| Sprayer | $CO_2$ Precision Sprayer |
| Boom | 2 m aluminium |
| Nozzle | 5 × 11002 flat fan nozzles (Teejet 11002 DG) |
| Pressure | 2.7 Bar |
| Application | 200 l/ha |

Spray Water Quality:

pH: 6.5

EC: 0.7 mS/m

Spray Volume:

200 l/ha at 2.7 Bar

TABLE 6-128

| WEATHER INFORMATION AT APPLICATION | |
|---|---|
| Temperature (max) | 25.9° C. |
| RH: | 57% |
| Wind: | 0-5 km/h, W |
| Cloud | 7/8 |

TABLE 6-129

| SOIL PROPERTIES AT APPLICATION | |
|---|---|
| Clay Fraction | 10.3% |
| Silt Fraction | 5.8% |
| Sand Fraction | 94.8% |
| pH (KCl) | 7.3 |
| Moisture | Field capacity (one day after irrigation) |

Irrigation:

None (rain-fed)

Crop:

Crop: Maize

Variety: Phb 32 P 68 R

Growth stage: 4-5 leaf (BBCH growth stage 14/15)

Sowing depth: 5 cm

Sowing density: 90 000 plants/ha

TABLE 6-130

| WEED INFORMATION | | | | |
|---|---|---|---|---|
| SPECIES | COMMON NAME | CODE | GROWTH STAGE | % SOIL COVER |
| *Datura ferox* | Large thornapple | DATFE | 2-4 leaf | 20% |
| *Portulaca oleracea* | Purslane | POROL | 8-12 leaf + 2 sideshoots | 5% |
| *Schkuhria pinnata* | Dwarf marigold | SCHPI | 2-6 leaf | 10% |
| *Bidens pilosa* | Blackjack | BIDPI | 4-12 leaf + 2 sideshoots | 5% |

TABLE 6-131

ASSESSMENT DETAILS

| | |
|---|---|
| Method | Comparative Efficacy |
| Herbicide | Efficacy: Number of weeds in treated versus untreated plots |
| | Selectivity: Visual phytotoxicity and yield |
| | 7. Visual phytotoxicity: BBA 1-9 scale (refer to appendix for details) |
| | 8. Yield: 20 cobs harvested at random from each plot. Average grain weight per plot determined using a precision 2 decimal scale. Statistical evaluation: |
| | ANOVA at the 95% probability using Tukeys LSD formulae |
| Assessment Times-Days After Application (DAA) | 14 DAA - Efficacy/Selectivity<br>28 DAA - Efficacy/Selectivity<br>56 DAA - Efficacy/Selectivity<br>Harvest - Selectivity |

TABLE 6-132

Comparative yield of DINAMIC ® 700WDG programs

| | TREATMENT | YIELD (Kg/plot) Replicate | | | | |
|---|---|---|---|---|---|---|
| | | I | II | III | IV | Mean |
| 1 | DINAMIC ® + Galago + Wet-All<br>75 g + 100 ml + 100 ml/100 l | 2.04 | 2.13 | 2.30 | 1.60 | 2.02 a |
| 2 | DINAMIC ® + Galago + Wet-All<br>75 g + 150 ml + 100 ml/100 l | 2.31 | 2.31 | 2.31 | 1.72 | 2.16 a |
| 3 | DINAMIC ® + Galago + Wet-All<br>100 g + 100 ml + 100 ml/100 l | 2.62 | 1.95 | 2.27 | 1.79 | 2.16 a |
| 4 | DINAMIC ® + Galago + Wet-All<br>100 g + 150 ml + 100 ml/100 l | 2.49 | 1.97 | 2.39 | 1.93 | 2.20 a |
| 5 | DINAMIC ® + Galago + Wet-All<br>125 g + 100 ml + 100 ml/100 l | 2.09 | 2.27 | 2.37 | 2.07 | 2.20 a |
| 6 | DINAMIC ® + Galago + Wet-All<br>125 g + 150 ml + 100 ml/100 l | 2.35 | 2.17 | 1.84 | 2.22 | 2.14 a |
| 7 | DINAMIC ® + Galago + TOLLA 960 + Wet-All<br>75 g + 100 ml + 1.0 l + 100 ml/100 l | 2.61 | 1.88 | 2.23 | 2.12 | 2.21 a |
| 8 | DINAMIC ® + Galago + TOLLA 960 + Wet-All<br>75 g + 150 ml + 1.0 l + 100 ml/100 l | 2.33 | 2.03 | 2.05 | 1.91 | 2.08 a |
| 9 | DINAMIC ® + Galago + TOLLA 960 + Wet-All<br>100 g + 100 ml + 1.0 l + 100 ml/100 l | 2.20 | 1.92 | 2.66 | 1.96 | 2.18 a |
| 10 | DINAMIC ® + Galago + TOLLA 960 + Wet-All<br>100 g + 150 ml + 1.0 l + 100 ml/100 l | 2.21 | 2.24 | 2.31 | 2.58 | 2.34 a |
| 11 | DINAMIC ® + Galago + TOLLA 960 + Wet-All<br>125 g + 100 ml + 1.0 l + 100 ml/100 l | 1.84 | 2.03 | 2.63 | 2.80 | 2.33 a |
| 12 | DINAMIC ® + Galago + TOLLA 960 + Wet-All<br>125 g + 150 ml + 1.0 l + 100 ml/100 l | 1.50 | 2.29 | 2.19 | 2.74 | 2.18 a |
| 13 | DINAMIC ® + Galago + TOLLA 960 + Wet-All<br>250 g + 300 ml + 2.0 l + 200 ml/100 l | 1.57 | 1.92 | 1.90 | 2.07 | 1.87 a |
| 14 | CALLISTO ® + Gardo Gold + COMPLIMENT ® Super<br>260 ml + 1562 ml + 100 ml/100 l | 1.80 | 2.64 | 2.85 | 2.52 | 2.46 a |
| 15 | Untreated control | 2.12 | 2.67 | 2.68 | 2.45 | 2.48 a |

TABLE 6-133

Comparative visual phytotoxicity of DINAMIC ® 700WDG post-emergence programs

| | TREATMENT | Timing | BBA VISUAL PHYTOTOXICITY SCALE (1 - no damage; 9 - dead) Replicate | | | | |
|---|---|---|---|---|---|---|---|
| | | | I | II | III | IV | Mean |
| 1 | DINAMIC ® + Galago + Wet-All<br>75 g + 100 ml + 100 ml/100 ml | 14 DAA | 1 | 1 | 1 | 1 | 1.0 |
| | | 28 DAA | 1 | 1 | 1 | 1 | 1.0 |
| | | 42 DAA | 1 | 1 | 1 | 1 | 1.0 |

TABLE 6-133-continued

Comparative visual phytotoxicity of DINAMIC ® 700WDG post-emergence programs

| | | | BBA VISUAL PHYTOTOXICITY SCALE (1 - no damage; 9 - dead) | | | | |
|---|---|---|---|---|---|---|---|
| | | | Replicate | | | | |
| | TREATMENT | Timing | I | II | III | IV | Mean |
| 2 | DINAMIC ® + Galago + Wet-All | 14 DAA | 1 | 1 | 1 | 1 | 1.0 |
| | 75 g + 150 ml + 100 ml/100 ml | 28 DAA | 1 | 1 | 1 | 1 | 1.0 |
| | | 42 DAA | 1 | 1 | 1 | 1 | 1.0 |
| 3 | DINAMIC ® + Galago + Wet-All | 14 DAA | 1 | 1 | 1 | 1 | 1.0 |
| | 100 g + 100 ml + 100 ml/100 ml | 28 DAA | 1 | 1 | 1 | 1 | 1.0 |
| | | 42 DAA | 1 | 1 | 1 | 1 | 1.0 |
| 4 | DINAMIC ® + Galago + Wet-All | 14 DAA | 1 | 1 | 1 | 1 | 1.0 |
| | 100 g + 150 ml + 100 ml/100 ml | 28 DAA | 1 | 1 | 1 | 1 | 1.0 |
| | | 42 DAA | 1 | 1 | 1 | 1 | 1.0 |
| 5 | DINAMIC ® + Galago + Wet-All | 14 DAA | 1 | 1 | 1 | 1 | 1.0 |
| | 125 g + 100 ml + 100 ml/100 ml | 28 DAA | 1 | 1 | 1 | 1 | 1.0 |
| | | 42 DAA | 1 | 1 | 1 | 1 | 1.0 |
| 6 | DINAMIC ® + Galago + Wet-All | 14 DAA | 3 | 1 | 1 | 3 | 2.0 |
| | 125 g + 150 ml + 100 ml/100 ml | 28 DAA | 1 | 1 | 1 | 1 | 1.0 |
| | | 42 DAA | 1 | 1 | 1 | 1 | 1.0 |
| 7 | DINAMIC ® + Galago + TOLLA 960 + Wet-All | 14 DAA | 1 | 1 | 1 | 1 | 1.0 |
| | | 28 DAA | 1 | 1 | 1 | 1 | 1.0 |
| | 75 g + 100 ml + 1.0 l + 100 ml/100 ml | 42 DAA | 1 | 1 | 1 | 1 | 1.0 |
| 8 | DINAMIC ® + Galago + TOLLA 960 + Wet-All | 14 DAA | 1 | 1 | 1 | 1 | 1.0 |
| | | 28 DAA | 1 | 1 | 1 | 1 | 1.0 |
| | 75 g + 150 ml + 1.0 l + 100 ml/100 ml | 42 DAA | 1 | 1 | 1 | 1 | 1.0 |
| 9 | DINAMIC ® + Galago + TOLLA 960 + Wet-All | 14 DAA | 1 | 1 | 1 | 1 | 1.0 |
| | | 28 DAA | 1 | 1 | 1 | 1 | 1.0 |
| | 100 g + 100 ml + 1.0 l + 100 ml/100 ml | 42 DAA | 1 | 1 | 1 | 1 | 1.0 |
| 10 | DINAMIC ® + Galago + TOLLA 960 + Wet-All | 14 DAA | 1 | 1 | 1 | 1 | 1.5 |
| | | 28 DAA | 1 | 1 | 1 | 1 | 1.0 |
| | 100 g + 150 ml + 1.0 l + 100 ml/100 ml | 42 DAA | 1 | 1 | 1 | 1 | 1.0 |
| 11 | DINAMIC ® + Galago + TOLLA 960 + Wet-All | 14 DAA | 3 | 3 | 1 | 1 | 2.0 |
| | | 28 DAA | 2 | 3 | 1 | 1 | 1.75 |
| | 125 g + 100 ml + 1.0 l + 100 ml/100 ml | 42 DAA | 1 | 1 | 1 | 1 | 1.0 |
| 12 | DINAMIC ® + Galago + TOLLA 960 + Wet-All | 14 DAA | 3 | 3 | 1 | 1 | 2.0 |
| | | 28 DAA | 2 | 2 | 1 | 1 | 1.5 |
| | 125 g + 150 ml + 1.0 l + 100 ml/100 ml | 42 DAA | 1 | 1 | 1 | 1 | 1.0 |
| 13 | DINAMIC ® + Galago + TOLLA 960 + Wet-All | 14 DAA | 5 | 6 | 6 | 5 | 5.5 |
| | | 28 DAA | 3 | 4 | 4 | 3 | 3.5 |
| | 250 g + 300 ml + 2.0 l + 200 ml/100 ml | 42 DAA | 2 | 3 | 3 | 2 | 2.5 |
| 14 | CALLISTO ® + Gardo Gold + COMPLEMENT ® Super | 14 DAA | 1 | 1 | 1 | 1 | 1.0 |
| | | 28 DAA | 1 | 1 | 1 | 1 | 1.0 |
| | 260 ml + 1562 ml + 100 ml | 42 DAA | 1 | 1 | 1 | 1 | 1.0 |
| 15 | Untreated control | 14 DAA | 1 | 1 | 1 | 1 | 1.0 |
| | | 28 DAA | 1 | 1 | 1 | 1 | 1.0 |
| | | 42 DAA | 1 | 1 | 1 | 1 | 1.0 |

Note:
Treatment means sharing the same letter do not differ significantly by LSD test at the 5% ($\alpha = 0.05$) level of probability

TABLE 6-134

Comparative visual phytotoxicity of DINAMIC ® 700WDG post-emergence programs

| | | | AVERAGE % WEED CONTROL BY SPECIES | | | |
|---|---|---|---|---|---|---|
| | TREATMENT | Timing | DATFE | SCHPI | POROL | CYPES |
| 1 | DINAMIC ® + Galago + Wet-All | 14 DAA | 99 | 100 | 60 | 30 |
| | 75 g + 100 ml + 100 ml/100 ml | 28 DAA | 100 | 100 | 40 | 40 |
| | | 56 DAA | 100 | 100 | 30 | 30 |
| 2 | DINAMIC ® + Galago + Wet-All | 14 DAA | 100 | 100 | 70 | 50 |
| | 75 g + 150 ml + 100 ml/100 ml | 28 DAA | 100 | 100 | 50 | 70 |
| | | 56 DAA | 100 | 100 | 30 | 50 |
| 3 | DINAMIC ® + Galago + Wet-All | 14 DAA | 99 | 100 | 65 | 35 |
| | 100 g + 100 ml + 100 ml/100 ml | 28 DAA | 100 | 100 | 50 | 40 |
| | | 56 DAA | 100 | 100 | 35 | 35 |
| 4 | DINAMIC ® + Galago + Wet-All | 14 DAA | 100 | 100 | 70 | 55 |
| | 100 g + 150 ml + 100 ml/100 ml | 28 DAA | 100 | 100 | 60 | 70 |
| | | 56 DAA | 100 | 100 | 40 | 50 |

TABLE 6-134-continued

Comparative visual phytotoxicity of DINAMIC ® 700WDG post-emergence programs

|   | TREATMENT | Timing | AVERAGE % WEED CONTROL BY SPECIES | | | |
|---|---|---|---|---|---|---|
|   |   |   | DATFE | SCHPI | POROL | CYPES |
| 5 | DINAMIC ® + Galago + Wet-All | 14 DAA | 100 | 100 | 70 | 40 |
|   | 125 g + 100 ml + 100 ml/100 ml | 28 DAA | 100 | 100 | 60 | 50 |
|   |   | 56 DAA | 100 | 100 | 50 | 40 |
| 6 | DINAMIC ® + Galago + Wet-All | 14 DAA | 100 | 100 | 75 | 40 |
|   | 125 g + 150 ml + 100 ml/100 ml | 28 DAA | 100 | 100 | 70 | 70 |
|   |   | 56 DAA | 100 | 100 | 55 | 60 |
| 7 | DINAMIC ® + Galago + TOLLA 960 + | 14 DAA | 100 | 100 | 70 | 40 |
|   | Wet-All | 28 DAA | 100 | 100 | 55 | 50 |
|   | 75 g + 100 ml + 1.0 l + 100 ml/100 ml | 56 DAA | 100 | 100 | 45 | 40 |
| 8 | DINAMIC ® + Galago + TOLLA 960 + | 14 DAA | 100 | 100 | 75 | 60 |
|   | Wet-All | 28 DAA | 100 | 100 | 65 | 80 |
|   | 75 g + 150 ml + 1.0 l + 100 ml/100 ml | 56 DAA | 100 | 100 | 50 | 70 |
| 9 | DINAMIC ® + Galago + TOLLA 960 + | 14 DAA | 100 | 100 | 75 | 50 |
|   | Wet-All | 28 DAA | 100 | 100 | 75 | 60 |
|   | 100 g + 100 ml + 1.0 l + 100 ml/100 ml | 56 DAA | 100 | 100 | 60 | 45 |
| 10 | DINAMIC ® + Galago + TOLLA 960 + | 14 DAA | 100 | 100 | 80 | 65 |
|   | Wet-All | 28 DAA | 100 | 100 | 75 | 80 |
|   | 100 g + 150 ml + 1.0 l + 100 ml/100 ml | 56 DAA | 100 | 100 | 65 | 70 |
| 11 | DINAMIC ® + Galago + TOLLA 960 + | 14 DAA | 100 | 100 | 80 | 50 |
|   | Wet-All | 28 DAA | 100 | 100 | 80 | 70 |
|   | 125 g + 100 ml + 1.0 l + 100 ml/100 ml | 56 DAA | 100 | 100 | 70 | 55 |
| 12 | DINAMIC ® + Galago + TOLLA 960 + | 14 DAA | 100 | 100 | 85 | 60 |
|   | Wet-All | 28 DAA | 100 | 100 | 85 | 85 |
|   | 125 g + 150 ml + 1.0 l + 100 ml/100 ml | 56 DAA | 100 | 100 | 80 | 70 |
| 13 | DINAMIC ® + Galago + TOLLA 960 + | 14 DAA | 100 | 100 | 100 | 70 |
|   | Wet-All | 28 DAA | 100 | 100 | 100 | 95 |
|   | 250 g + 300 ml + 2.0 l + 200 ml/100 ml | 56 DAA | 100 | 100 | 100 | 90 |
| 14 | CALLISTO ® + Gardo Gold + | 14 DAA | 100 | 100 | 85 | 65 |
|   | COMPLEMENT ® Super | 28 DAA | 100 | 100 | 90 | 90 |
|   | 260 ml + 1562 ml + 100 ml | 56 DAA | 100 | 100 | 90 | 90 |
| 15 | Untreated Control | 14 DAA | 0 | 0 | 0 | 0 |
|   |   | 28 DAA | 0 | 0 | 0 | 0 |
|   |   | 56 DAA | 0 | 0 | 0 | 0 |

The trial was conducted on a commercial maize crop produced under sprinkler irrigation. The DINAMIC® 700WDG formulation was evaluated for herbicidal activity and crop selectivity when applied as a post-emergence spray program in tank-mix combination with Galago and TOLLA 960. The adjuvant Wet-All was applied to all treatments receiving DINAMIC® 700WDG as standard practice. Treatments were applied post-emergence of crop and weeds as broadcast applications over the maize rows when the maize crop was in the 4-5 leaf stage.

No visual symptoms of phytotoxicity in the form of stunting, chlorosis, necrosis or growth-abnormalities were observed on treatments receiving the tank-mix combinations of DINAMIC® 700WDG+Galago+Wet-All where DINAMIC® 700WDG was applied at rates of 75 g/ha and 100 g/ha, respectively Tank-mix combinations of DINAMIC® 700WDG+Galago+Wet-All applied at rates of 125 g/ha+150 ml+100 ml/100 l exhibited slight visual symptoms of stunting on isolated plots at the first assessment only. No visual symptoms of stunting were observed on any of the subsequent evaluations conducted at 28 DAA and 42 DAA, respectively.

Visual symptoms of phytotoxicity in the form of stunting were observed at the assessments conducted at 14 and 28 DAA in treatments receiving the tank-mix combination of DINAMIC® 700WDG+Galago+TOLLA 960+Wet-All where DINAMIC® 700WDG was applied at the rate of 125 g/ha and the double rate of 250 g/ha. Symptoms of phytotoxicity were not severe and ranged from negligible to moderate (BBA visual phytotoxicity rating of 2 to 3) in tank-mix treatments receiving DINAMIC® 700WDG at the rate of 125 g/ha. No visual symptoms of phytotoxicity of any nature were observed at the final assessment conducted at 56 DAA.

Tank-mix combinations of DINAMIC® 700WDG+Galago+TOLLA 960+Wet-All applied at the double rate of 250 g/ha+300 ml/ha+1.0 l/ha+200 ml/100 l exhibited distinct symptoms of stunting (BBA class 5-6) at the first assessment conducted at 14 DAA. Severity of stunting improved at the subsequent evaluations conducted at 28 DAA (BBA class 3-4) and 56 DAA (BBA class 2-3).

Yield:

None of the various DINAMIC® 700WDG+Galago+TOLLA 960+Wet-All tank-mix combinations exhibited a significant reduction in yield compared to the untreated control and the standard CALLISTO®+Gardo Gold+COMPLEMENT® Super treatments.

The weed spectrum at the trial site was composed of yellow nutsedge (CYPES) and broadleaved weeds namely Large thornapple (DATFE), Dwarf marigold (SCHPI) and Purslane (POROL). The broadleaved weed POROL was in an advanced growth stage at application and considered to be beyond acceptable post-emergence application size. Efficacy evaluations were conducted at 14, 28 and 56 days following application, respectively.

DINAMIC® 700WDG+Galago

Tank-mix combinations of DINAMIC® 700WDG+Galago+Wet-all exhibited commercially acceptable levels of herbicidal activity against the broadleaved weeds DATFE and SCHPI across all rates applied. None of the treatments exhibited commercially acceptable levels of herbicidal activity against CYPES and POROL.

DINAMIC® 700WDG+Galago+TOLLA 960

Tank-mix combinations of DINAMIC® 700WDG+Galago+TOLLA 960+Wet-All were efficacious and exhibited commercially acceptable levels of herbicidal activity against the broadleaved weeds DATFE and SCHPI across all rates applied. The broadleaved weed POROL was suppressed (efficacy between 80-89%) in treatments receiving DINAMIC® 700WDG applied at the rate of 125 g/ha in combination with Galago at 150 ml/ha. The double rate of DINAMIC® 700WDG+Galago+TOLLA 960+Wet-All and the standard tank-mix combination of CALLISTO®+Gardo Gold+COMPLEMENT® Super were the only treatments to display commercially acceptable levels of herbicidal activity against yellow nutsedge (CYPES) as a result of the higher rate of mesotrione in these treatments. The standard tank-mix combination of CALLISTO®+Gardo Gold+COMPLEMENT® Super applied at 260 ml/ha+1562 ml/ha+100 ml/100 l displayed superior levels of herbicidal activity with commercial control achieved for all weed species at the final assessment conducted at 56 DAA.

Compatibility

No visual symptoms of incompatibility in the form of phase separation or agglomeration were observed in any of the tank-mix combinations of DINAMIC® 700WDG+Galago+Wet-All and DINAMIC® 700WDG+Galago+TOLLA 960+Wet-All, whether applied at single or double rates.

No visual symptoms of phytotoxicity in the form of stunting, chlorosis, necrosis or growth-abnormalities were observed on treatments receiving the tank-mix combinations of DINAMIC® 700WDG+Galago+Wet-All where DINAMIC® 700WDG was applied at the rates of 75 g/ha and 100 g/ha. Negligible levels of stunting were observed in treatments receiving the tank-mix combination of DINAMIC® 700WDG+Galago+Wet-All at the rate of 125 g/ha+150 ml/ha+100 ml/100 l at the first assessment only, after which no further symptoms of phytotoxicity were observed.

Visual symptoms of phytotoxicity in the form of stunting were observed at the assessments conducted at 14 and 28 DAA in treatments receiving the tank-mix combination of DINAMIC® 700WDG+Galago+TOLLA 960+Wet-All where DINAMIC® 700WDG was applied at the rate of 125 g/ha. Stunting was not severe and ranged from negligible to moderate according to BBA visual phytotoxicity scale. Tank-mix combinations of DINAMIC® 700WDG+Galago+TOLLA 960+Wet-All applied at the rate of 250 g/ha+300 ml/ha+1.0 l/ha+200 ml/100 l exhibited distinct symptoms of stunting (BBA class 5-6) at the first assessment conducted at 14 DAA. Severity of stunting improved at the subsequent evaluations conducted at 28 DAA (BBA class 3-4) and 56 DAA (BBA class 2-3).

None of the various DINAMIC® 700WDG+Galago+TOLLA 960+Wet-All tank-mix combinations exhibited a significant reduction in yield compared to the untreated control and the standard CALLISTO®+Gardo Gold+COMPLEMENT® Super treatments.

Tank-mix combinations of DINAMIC® 700WDG+Galago+TOLLA 960+Wet-All were efficacious and exhibited commercially acceptable levels of herbicidal activity against the broadleaved weeds DATFE and SCHPI across all rates applied. Yellow nutsedge (CYPES) was only controlled by the double rate of DINAMIC®+Galago+TOLLA 960+Wet-All and the standard tank-mix combination of CALLISTO®+Gardo Gold+COMPLEMENT® Super as a result of the higher rate of mesotrione in these treatments.

No visual symptoms of incompatibility in the form of phase separation or agglomeration were observed in any of the tank-mix combinations of DINAMIC® 700WDG+Galago+Wet-All and DINAMIC® 700WDG+Galago+TOLLA 960+Wet-All, whether applied at single or double rates.

TABLE 6-135

Anova Table Grain yield (kg/plot)

| Unit | Degrees of freedom | Sums of Squares | Mean Squares | F Value |
|---|---|---|---|---|
| Reps | 3 | 0.3582 | | |
| Treatments | 14 | 1.372 | 0.9798 | 0.9748 |
| Error | 42 | 4.221 | 0.1005 | |
| Total | 59 | 5.951 | | |
| Overall mean | | | | 2.199 |
| S. E for Difference | | | | 0.2242 |
| Least Significant Difference (LSD) at 95% | | | | 0.4524 |

TABLE 6-136

BBA Visual Phytotoxicity rating scale

| Scale | EQUIVALENT % | Description |
|---|---|---|
| 1 | 0% | NO DAMAGE |
| 2 | 0.1-2.5% | NEGLIGIBLE DAMAGE |
| 3 | 2.5-5.0% | MODERATE DAMAGE No effects on yield and/or quality |
| 4 | 5.0-10% | Damage up to limits of commercial acceptability - if no yield loss |
| 5 | 10-15% | DISTINCT DAMAGE Commercially acceptable only under certain conditions- if no yield loss |
| 6 | 15-25% | SEVERE DAMAGE Not commercially acceptable - yield loss and quality |
| 7 | 25-35% | VERY SEVERE DAMAGE |
| 8 | 35-68% | EXTREME DAMAGE |
| 9 | 68-100% | START OF WITHERING AND DEATH |

Q. Post-Emergence Application Against Weed in Maize

This Example compares the herbicidal selectivity and efficacy of DINAMIC® 700WDG applied in combination with Galago and TOLLA 960 as a post-emergence application with regards to both crop and weeds in dry land maize. Treatments and conditions are tabulated below.

TABLE 6-137

TREATMENTS

| | TREATMENT | Rate/ha Product (l) | a.i. (g) |
|---|---|---|---|
| 1 | DINAMIC ® + Galago + Wet-All | 75 g + 100 ml + 100 ml/100 l | 52.5 + 48 + 180 |
| 2 | DINAMIC ® + Galago + Wet-All | 75 g + 150 ml + 100 ml/100 l | 52.5 + 72 |
| 3 | DINAMIC ® + Galago + Wet-All | 100 g + 100 ml + 100 ml/100 l | 70 + 48 |

TABLE 6-137-continued

| | TREATMENTS | |
|---|---|---|
| | | Rate/ha |
| TREATMENT | Product (l) | a.i. (g) |
| 4 DINAMIC ® + Galago + Wet-All | 100 g + 150 ml + 100 ml/100 l | 70 + 72 |
| 5 DINAMIC ® + Galago + Wet-All | 125 g + 100 ml + 100 ml/100 l | 87.5 + 48 |
| 6 DINAMIC ® + Galago + Wet-All | 125 g + 150 ml + 100 ml/100 l | 87.5 + 72 |
| 7 DINAMIC ® + Galago + TOLLA 960 + Wet-All | 75 g + 100 ml + 1.0 l + 100 ml/100 l | 52.5 + 48 + 960 + 180 |
| 8 DINAMIC ® + Galago + TOLLA 960 + Wet-All | 75 g + 150 ml + 1.0 l + 100 ml/100 l | 52.5 + 72 + 960 + 180 |
| 9 DINAMIC ® + Galago + TOLLA 960 + Wet-All | 100 g + 100 ml + 1.0 l + 100 ml/100 l | 70 + 48 + 960 + 180 |
| 10 DINAMIC ® + Galago + TOLLA 960 + Wet-All | 100 g + 150 ml + 1.0 l + 100 ml/100 l | 70 + 72 + 960 + 180 |
| 11 DINAMIC ® + Galago + TOLLA 960 + Wet-All | 125 g + 100 ml + 1.0 l + 100 ml/100 l | 87.5 + 48 + 960 + 180 |
| 12 DINAMIC ® + Galago + TOLLA 960 + Wet-All | 125 g + 150 ml + 1.0 l + 100 ml/100 l | 87.5 + 72 + 960 + 180 |
| 13 DINAMIC ® + Galago + TOLLA 960 + Wet-All | 250 g + 300 ml + 2.0 l + 200ml/100 l | 175 + 144 + 1920 + 360 |
| 14 CALLISTO ® + Gardo Gold + Complement super | 260 ml + 1562 ml + 100 ml/100 l | 125 + 488/293 + 100 |
| 15 Untreated control | — | — |

TABLE 6-138 est products used:

| | Product | Active Ingredient | Formulation | Manufacturer/Supplier | Registration No. |
|---|---|---|---|---|---|
| 1 | DINAMIC ® 700WDG | Amicarbazone 700 g/kg | WDG | Arysta Lifescience | |
| 2 | Galago | Mesotrione 480 g/l | SC | Arysta Lifescience | L. 8089 |
| 3 | TOLLA 960 | Metolachlor 960 g/l | EC | Arysta Lifescience | L. 6794 |
| 4 | Wet-All | Adjuvant | SL | Arysta Lifescience | L. 8361 |
| 5 | CALLISTO ® | Mesotrione 480 g/l | SC | Syngenta | L. 6795 |
| 6 | Gardo Gold | S-Metolachlor 312.5 g/l Terbuthylazine 187.5 g/l | SC | Syngenta | L. 7763 |
| 7 | COMPLEMENT ® Super | Adjuvant | SL | Syngenta | L. 8169 |

TABLE 6-139

| TRIAL DESIGN | |
|---|---|
| Design | Completely randomized design |
| Replicates | Four |
| Plot size | 5 m × 2.5 m = Nett/plot |

TABLE 6-140

| SPRAYER | |
|---|---|
| Sprayer | $CO_2$ Precision Sprayer |
| Boom | 2 m aluminium |
| Nozzle | 5 x 11002 flat fan nozzles (Teejet 11002 DG) |
| Pressure | 2.7 Bar |
| Application | 200 l/ha |

Spray Water Quality:
pH: 6.5
EC: 0.7 mS/m
Spray Volume:
200 l/ha at 2.7 Bar

TABLE 6-141

| WEATHER INFORMATION AT APPLICATION | |
|---|---|
| Time: | 10:00 |
| Temperature (max) | 28.3° C. |
| RH: | 44% |
| Wind: | 0-5 km/h, NE |
| Cloud | 3/8 |

TABLE 6-142

| SOIL PROPERTIES AT APPLICATION | |
|---|---|
| Clay Fraction | 16.0% |
| Silt Fraction | 3.5% |
| Sand Fraction | 80.5% |
| pH (KCl) | 5.1 |
| Moisture | Surface dry, subsurface moist at 6 cm |

Irrigation:
None (rain-fed)
Crop:
Crop: Maize
Variety: Phb 31 G 54 BR
Growth stage: 6-7 leaf (BBCH growth stage 16/17)
Sowing depth: 5 cm
Sowing density: 45000 plants/ha

TABLE 6-143

| WEED INFORMATION | | | | |
|---|---|---|---|---|
| SPECIES | COMMON NAME | CODE | GROWTH STAGE | % SOIL COVER |
| *Bidens pilosa* | Blackjack | BIDPI | 2-4 leaf | 10% |
| *Amaranthus hybridus* | Pigweed | AMAHY | 2-4 leaf | 10% |
| *Tagetes minuta* | Khaki weed | TAGMI | 2-6 leaf | 5% |
| *Portulaca oleracea* | Purslane | POROL | 4-12 leaf + 2 sideshoots | 5% |
| *Commelina benghalensis* | Wandering Jew | COMBE | 4-8 leaf | 5% |

TABLE 6-144

ASSESSMENT DETAILS

| | |
|---|---|
| Method Herbicide | Comparative Efficacy<br>Efficacy: Number of weeds in treated versus untreated plots<br>Selectivity: Visual phytotoxicity and yield<br>9. Visual phytotoxicity: BBA 1-9 scale (refer to appendix for details)<br>10. Yield: 20 cobs harvested at random from each plot. Average grain weight per plot determined using a precision 2 decimal scale. Statistical evaluation: |
| Assessment Times- Days After Application (DAA) | ANOVA at the 95% probability using Tukeys LSD formulae<br>14 DAA - Efficacy/Selectivity<br>28 DAA - Efficacy/Selectivity<br>42 DAA - Efficacy/Selectivity<br>Harvest - Selectivity |

TABLE 6-145

Comparative yield of DINAMIC ® 700WDG programs

| | | YIELD (Kg/plot) | | | | |
|---|---|---|---|---|---|---|
| | | Replicate | | | | |
| | TREATMENT | I | II | III | IV | Mean |
| 1 | DINAMIC ® + Galago + Wet-All<br>75 g + 100 ml + 100 ml/100 l | 2.63 | 2.65 | 2.63 | 1.71 | 2.41 a |
| 2 | DINAMIC ® + Galago + Wet-All<br>75 g + 150 ml + 100 ml/100 l | 2.95 | 2.87 | 2.24 | 2.55 | 2.65 a |
| 3 | DINAMIC ® + Galago + Wet-All<br>100 g + 100 ml + 100 ml/100 l | 2.29 | 2.67 | 2.67 | 2.01 | 2.41 a |
| 4 | DINAMIC ® + Galago + Wet-All<br>100 g + 150 ml + 100 ml/100 l | 2.47 | 2.85 | 1.79 | 2.22 | 2.33 a |
| 5 | DINAMIC ® + Galago + Wet-All<br>125 g + 100 ml + 100 ml/100 l | 2.64 | 2.58 | 2.71 | 2.48 | 2.60 a |
| 6 | DINAMIC ® + Galago + Wet-All<br>125 g + 150 ml + 100 ml/100 l | 2.43 | 2.77 | 2.69 | 2.15 | 2.51 a |
| 7 | DINAMIC ® + Galago + TOLLA 960 + Wet-All<br>75 g + 100 ml + 1.0 l + 100 ml/100 l | 2.47 | 2.72 | 2.62 | 2.44 | 2.57 a |
| 8 | DINAMIC ® + Galago + TOLLA 960 + Wet-All<br>75 g + 150 ml + 1.0 l + 100 ml/100 l | 2.52 | 2.66 | 2.09 | 2.88 | 2.54 a |
| 9 | DINAMIC ® + Galago + TOLLA 960 + Wet-All<br>100 g + 100 ml + 1.0 l + 100 ml/100 l | 2.84 | 2.49 | 2.47 | 2.97 | 2.69 a |
| 10 | DINAMIC ® + Galago + TOLLA 960 + Wet-All<br>100 g + 150 ml + 1.0 l + 100 ml/100 l | 2.72 | 2.82 | 2.28 | 2.69 | 2.63 a |
| 11 | DINAMIC ® + Galago + TOLLA 960 + Wet-All<br>125 g + 100 ml + 1.0 l + 100 ml/100 l | 2.52 | 2.42 | 2.41 | 2.78 | 2.53 a |
| 12 | DINAMIC ® + Galago + TOLLA 960 + Wet-All<br>125 g + 150 ml + 1.0 l + 100 ml/100 l | 2.51 | 2.53 | 1.95 | 2.53 | 2.38 a |
| 13 | DINAMIC ® + Galago + TOLLA 960 + Wet-All<br>250 g + 300 ml + 2.0 l + 200 ml/100 l | 2.10 | 2.41 | 2.61 | 2.51 | 2.41 a |
| 14 | CALLISTO ® + Gardo Gold + COMPLIMENT ® Super<br>260 ml + 1562 ml + 100 ml/100 l | 2.30 | 2.30 | 1.68 | 3.17 | 2.36 a |
| 15 | Untreated control | 2.32 | 2.42 | 2.92 | 3.14 | 2.70 a |

Note:
Treatment means sharing the same letter do not differ significantly by LSD test at the 5% ($\alpha = 0.05$) level of probability

TABLE 6-146

Comparative visual phytotoxicity of DINAMIC ® 700WDG post-emergence programs

| | | BBA VISUAL PHYTOTOXICITY SCALE<br>(1 - no damage; 9 - dead) | | | | |
|---|---|---|---|---|---|---|
| | | Replicate | | | | |
| TREATMENT | Timing | I | II | III | IV | Mean |
| 1. DINAMIC ® + Galago + Wet-All<br>75 g + 100 ml + 100 ml/100 ml | 14 DAA<br>28 DAA<br>42 DAA | 1<br>1<br>1 | 1<br>1<br>1 | 1<br>1<br>1 | 1<br>1<br>1 | 1.0<br>1.0<br>1.0 |
| 2. DINAMIC ® + Galago + Wet-All<br>75 g + 150 ml + 100 ml/100 ml | 14 DAA<br>28 DAA<br>42 DAA | 1<br>1<br>1 | 1<br>1<br>1 | 1<br>1<br>1 | 1<br>1<br>1 | 1.0<br>1.0<br>1.0 |
| 3. DINAMIC ® + Galago + Wet-All<br>100 g + 100 ml + 100 ml/100 ml | 14 DAA<br>28 DAA<br>42 DAA | 1<br>1<br>1 | 1<br>1<br>1 | 1<br>1<br>1 | 1<br>1<br>1 | 1.0<br>1.0<br>1.0 |

TABLE 6-146-continued

Comparative visual phytotoxicity of DINAMIC ® 700WDG post-emergence programs

|  |  | BBA VISUAL PHYTOTOXICITY SCALE (1 - no damage; 9 - dead) | | | | |
|--|--|--|--|--|--|--|
|  |  | Replicate | | | | |
| TREATMENT | Timing | I | II | III | IV | Mean |
| 4. DINAMIC ® + Galago + Wet-All<br>100 g + 150 ml + 100 ml/100 ml | 14 DAA<br>28 DAA<br>42 DAA | 1<br>1<br>1 | 1<br>1<br>1 | 1<br>1<br>1 | 1<br>1<br>1 | 1.0<br>1.0<br>1.0 |
| 5. DINAMIC ® + Galago + Wet-All<br>125 g + 100 ml + 100 ml/100 ml | 14 DAA<br>28 DAA<br>42 DAA | 1<br>1<br>1 | 1<br>1<br>1 | 1<br>1<br>1 | 1<br>1<br>1 | 1.0<br>1.0<br>1.0 |
| 6. DINAMIC ® + Galago + Wet-All<br>125 g + 150 ml + 100 ml/100 ml | 14 DAA<br>28 DAA<br>42 DAA | 1<br>1<br>1 | 1<br>1<br>1 | 1<br>1<br>1 | 1<br>1<br>1 | 1.0<br>1.0<br>1.0 |
| 7. DINAMIC ® + Galago + TOLLA 960 + Wet-All<br>75 g + 100 ml + 1.0 l + 100 ml/100 ml | 14 DAA<br>28 DAA<br>42 DAA | 1<br>1<br>1 | 1<br>1<br>1 | 1<br>1<br>1 | 1<br>1<br>1 | 1.0<br>1.0<br>1.0 |
| 8. DINAMIC ® + Galago + TOLLA 960 + Wet-All<br>75 g + 150 ml + 1.0 l + 100 ml/100 ml | 14 DAA<br>28 DAA<br>42 DAA | 1<br>1<br>1 | 1<br>1<br>1 | 1<br>1<br>1 | 1<br>1<br>1 | 1.0<br>1.0<br>1.0 |
| 9. DINAMIC ® + Galago + TOLLA 960 + Wet-All<br>100 g + 100 ml + 1.0 l + 100 ml/100 ml | 14 DAA<br>28 DAA<br>42 DAA | 1<br>1<br>1 | 1<br>1<br>1 | 1<br>1<br>1 | 1<br>1<br>1 | 1.0<br>1.0<br>1.0 |
| 10. DINAMIC ® + Galago + TOLLA 960 + Wet-All<br>100 g + 150 ml + 1.0 l + 100 ml/100 ml | 14 DAA<br>28 DAA<br>42 DAA | 2<br>1<br>1 | 1<br>1<br>1 | 1<br>1<br>1 | 2<br>1<br>1 | 1.5<br>1.0<br>1.0 |
| 11. DINAMIC ® + Galago + TOLLA 960 + Wet-All<br>125 g + 100 ml + 1.0 l + 100 ml/100 ml | 14 DAA<br>28 DAA<br>42 DAA | 3<br>2<br>1 | 1<br>1<br>1 | 2<br>2<br>1 | 1<br>1<br>1 | 1.75<br>1.5<br>1.0 |
| 12. DINAMIC ® + Galago + TOLLA 960 + Wet-All<br>125 g + 150 ml + 1.0 l + 100 ml/100 ml | 14 DAA<br>28 DAA<br>42 DAA | 3<br>3<br>1 | 3<br>2<br>1 | 2<br>2<br>1 | 2<br>2<br>1 | 2.5<br>2.25<br>1.0 |
| 13. DINAMIC ® + Galago + TOLLA 960 + Wet-All<br>250 g + 300 ml + 2.0 l + 200 ml/100 ml | 14 DAA<br>28 DAA<br>42 DAA | 4<br>3<br>1 | 3<br>3<br>1 | 3<br>3<br>1 | 3<br>3<br>1 | 3.25<br>3.0<br>1.0 |
| 14. CALLISTO ® + Gardo Gold + COMPLEMENT ® Super<br>260 ml + 1562 ml + 100 ml | 14 DAA<br>28 DAA<br>42 DAA | 1<br>1<br>1 | 1<br>1<br>1 | 1<br>1<br>1 | 1<br>1<br>1 | 1.0<br>1.0<br>1.0 |
| 15. Untreated control | 14 DAA<br>28 DAA<br>42 DAA | 1<br>1<br>1 | 1<br>1<br>1 | 1<br>1<br>1 | 1<br>1<br>1 | 1.0<br>1.0<br>1.0 |

TABLE 6-147

Comparative visual phytotoxicity of DINAMIC ® 700WDG post-emergence programs

|  | | | AVERAGE % WEED CONTROL BY SPECIES | | | | |
|--|--|--|--|--|--|--|--|
|  | TREATMENT | DAA | AMAHY | BIDPI | TAGMI | POROL | COMBE |
| 1 | DINAMIC ® + Galago + Wet-All<br>75 g + 100 ml + 100 ml/100 ml | 14<br>28<br>56 | 70<br>80<br>65 | 90<br>90<br>80 | 94<br>100<br>100 | 40<br>50<br>30 | 40<br>40<br>30 |
| 2 | DINAMIC ® + Galago + Wet-All<br>75 g + 150 ml + 100 ml/100 ml | 14<br>28<br>56 | 90<br>85<br>80 | 96<br>100<br>100 | 98<br>100<br>100 | 60<br>60<br>35 | 60<br>60<br>40 |
| 3 | DINAMIC ® + Galago + Wet-All<br>100 g + 100 ml + 100 ml/100 ml | 14<br>28<br>56 | 85<br>85<br>75 | 98<br>94<br>90 | 98<br>100<br>100 | 50<br>60<br>30 | 50<br>55<br>30 |
| 4 | DINAMIC ® + Galago + Wet-All<br>100 g + 150 ml + 100 ml/100 ml | 14<br>28<br>56 | 92<br>96<br>85 | 98<br>100<br>100 | 98<br>100<br>100 | 60<br>65<br>40 | 65<br>60<br>45 |
| 5 | DINAMIC ® + Galago + Wet-All<br>125 g + 100 ml + 100 ml/100 ml | 14<br>28<br>56 | 90<br>92<br>85 | 98<br>100<br>100 | 99<br>100<br>100 | 65<br>60<br>40 | 65<br>60<br>45 |
| 6 | DINAMIC ® + Galago + Wet-All<br>125 g + 150 ml + 100 ml/100 ml | 14<br>28<br>56 | 98<br>98<br>90 | 99<br>100<br>100 | 99<br>100<br>100 | 70<br>65<br>45 | 70<br>70<br>45 |
| 7 | DINAMIC ® + Galago + TOLLA 960 + Wet-All<br>75 g + 100 ml + 1.0 l + 100 ml/100 ml | 14<br>28<br>56 | 90<br>85<br>80 | 98<br>100<br>100 | 99<br>100<br>100 | 60<br>65<br>35 | 70<br>60<br>30 |

TABLE 6-147-continued

Comparative visual phytotoxicity of DINAMIC ® 700WDG post-emergence programs

| | TREATMENT | DAA | AVERAGE % WEED CONTROL BY SPECIES | | | | |
|---|---|---|---|---|---|---|---|
| | | | AMAHY | BIDPI | TAGMI | POROL | COMBE |
| 8 | DINAMIC ® + Galago + TOLLA 960 + Wet-All | 14 | 98 | 99 | 99 | 70 | 80 |
| | 75 g + 150 ml + 1.0 l + 100 ml/100 ml | 28 | 96 | 100 | 100 | 80 | 70 |
| | | 56 | 90 | 100 | 100 | 40 | 40 |
| 9 | DINAMIC ® + Galago + TOLLA 960 + Wet-All | 14 | 99 | 99 | 99 | 75 | 85 |
| | 100 g + 100 ml + 1.0 l + 100 ml/100 ml | 28 | 92 | 100 | 100 | 70 | 70 |
| | | 56 | 90 | 100 | 100 | 45 | 50 |
| 10 | DINAMIC ® + Galago + TOLLA 960 + Wet-All | 14 | 99 | 99 | 99 | 85 | 90 |
| | 100 g + 150 ml + 1.0 l + 100 ml/100 ml | 28 | 100 | 100 | 100 | 80 | 80 |
| | | 56 | 100 | 100 | 100 | 55 | 60 |
| 11 | DINAMIC ® + Galago + TOLLA 960 + Wet-All | 14 | 99 | 99 | 99 | 85 | 90 |
| | 125 g + 100 ml + 1.0 l + 100 ml/100 ml | 28 | 100 | 100 | 100 | 80 | 85 |
| | | 56 | 100 | 100 | 100 | 60 | 60 |
| 12 | DINAMIC ® + Galago + TOLLA 960 + Wet-All | 14 | 99 | 99 | 99 | 90 | 90 |
| | 125 g + 150 ml + 1.0 l + 100 ml/100 ml | 28 | 100 | 100 | 100 | 90 | 90 |
| | | 56 | 100 | 100 | 100 | 80 | 80 |
| 13 | DINAMIC ® + Galago + TOLLA 960 + Wet-All | 14 | 100 | 100 | 100 | 98 | 99 |
| | 250 g + 300 ml + 2.0 l + 200 ml/100 ml | 28 | 100 | 100 | 100 | 94 | 96 |
| | | 56 | 100 | 100 | 100 | 92 | 100 |
| 14 | CALLISTO ® + Gardo Gold + COMPLIMENT ® Super | 14 | 100 | 100 | 100 | 94 | 94 |
| | | 28 | 100 | 100 | 100 | 94 | 92 |
| | 260 ml + 1562 ml + 100 ml/100 ml | 56 | 100 | 100 | 100 | 90 | 95 |
| 15 | Untreated Control | 14 | 0 | 0 | 0 | 0 | 0 |
| | | 28 | 0 | 0 | 0 | 0 | 0 |
| | | 56 | 0 | 0 | 0 | 0 | 0 |

The trial was conducted on a commercial maize crop produced under dry land conditions. The DINAMIC® 700WDG formulation was evaluated for herbicidal activity and crop selectivity when applied as a post-emergence spray program in tank-mix combination with Galago and TOLLA 960. The adjuvant Wet-All was applied to all treatments receiving DINAMIC® 700WDG as standard practice. Treatments were applied post-emergence of crop and weeds as broadcast applications over the maize rows when the maize crop was in the 6-7 leaf stage.

No visual symptoms of phytotoxicity in the form of stunting, chlorosis, necrosis or growth-abnormalities were observed on any of the treatments receiving the tank-mix combinations of DINAMIC® 700WDG+Galago+Wet-All across all rates applied.

Visual symptoms of phytotoxicity in the form of stunting were observed at the assessments conducted at 14 and 28 DAA in treatments receiving the tank-mix combination of DINAMIC® 700WDG+Galago+TOLLA 960+Wet-All where DINAMIC® 700WDG was applied at the rate of 125 g/ha and the double rate of 250 g/ha. Symptoms of phytotoxicity were not severe and ranged from negligible to moderate (BBA visual phytotoxicity rating of 2 to 3) depending on the dosage rate of DINAMIC® 700WDG applied. No visual symptoms of phytotoxicity of any nature were observed at the final assessment conducted at 56 DAA.

The weed spectrum at the trial site was dominated by broadleaved weeds namely Blackjack (BIDPI), Pigweed (AMAHY), Khaki weed (TAGMI) and Wandering jew (COMBE). The broadleaved weed POROL was in an advanced growth stage at application and considered to be beyond acceptable post-emergence application size. Efficacy evaluations were conducted at 14, 28 and 56 days following application, respectively.

DINAMIC® 700WDG+Galago

Tank-mix combinations of DINAMIC® 700WDG+Galago+Wet-all exhibited commercially acceptable levels of herbicidal activity against the broadleaved weeds BIDPI and TAGMI in treatments receiving DINAMIC® 700WDG applied at the higher rates of 100 g/ha and 125 g/ha. The broadleaved weed AMAHY was only commercially controlled at the higher tank-mix rate of DINAMIC® 700WDG+Galago applied at 125 g/ha+150 ml/ha. None of the treatments displayed commercially acceptable levels of herbicidal activity against the broadleaved weeds COMBE and POROL.

DINAMIC® 700WDG+Galago+TOLLA 960

Tank-mix combinations of DINAMIC® 700WDG+Galago+TOLLA 960+Wet-All were efficacious and exhibited commercially acceptable levels of herbicidal activity against the broadleaved weeds BIDPI and TAGMI across all rates applied. The broadleaved weed AMAHY was commercially controlled by all tank-mix combinations where DINAMIC® 700WDG was applied at rates exceeding 75 g/ha or where Galago was applied at 150 ml/ha. The broadleaved weeds POROL and COMBE were only commercially controlled by the double rate of DINAMIC®+Galago+TOLLA+Wet-All applied at 250 g/ha+300 ml/ha+2.0 l/ha+200 ml/100 l and the standard tank-mix combination of CALLISTO®+Gardo Gold+COMPLEMENT® Super applied at 260 ml/ha+1562 ml/ha+100 ml/100 l due to the higher rate of the active ingredient Mesotrione in these treatments.

Compatibility

No visual symptoms of incompatibility in the form of phase separation or agglomeration were observed in any of the tank-mix combinations of DINAMIC® 700WDG+Galago+Wet-All and DINAMIC® 700WDG+Galago+TOLLA 960+Wet-All, whether applied at single or double rates.

No visual symptoms of phytotoxicity in the form of stunting, chlorosis, necrosis or growth-abnormalities were observed on any of the treatments receiving the tank-mix combinations of DINAMIC® 700WDG+Galago+Wet-All across all rates applied.

Visual symptoms of phytotoxicity in the form of stunting were observed at the assessments conducted at 14 and 28 DAA in treatments receiving the tank-mix combination of DINAMIC® 700WDG+Galago+TOLLA 960+Wet-All where DINAMIC® 700WDG was applied at the rate of 125 g/ha and the double rate of 250 g/ha. Stunting was not severe and ranged from negligible to moderate according to BBA visual phytotoxicity scale.

Tank-mix combinations of DINAMIC® 700WDG+Galago+TOLLA 960+Wet-All were efficacious and exhibited commercially acceptable levels of herbicidal activity against the broadleaved weeds BIDPI and TAGMI across all rates applied. AMAHY was commercially controlled by all tank-mix combinations where DINAMIC® 700WDG was applied at rates exceeding 75 g/ha or where Galago was applied at 150 ml/ha. The broadleaved weeds POROL and COMBE were only commercially controlled by the double rate of DINAMIC®+Galago+TOLLA+Wet-All and the standard tank-mix combination of CALLISTO®+Gardo Gold+COMPLEMENT® Super.

No visual symptoms of incompatibility in the form of phase separation or agglomeration were observed in any of the tank-mix combinations of DINAMIC® 700WDG+Galago+Wet-All and DINAMIC® 700WDG+Galago+TOLLA 960+Wet-All, whether applied at single or double rates.

TABLE 6-148

Anova Table Grain yield (kg/plot)

| Unit | Degrees of freedom | Sums of Squares | Mean Squares | F Value |
|---|---|---|---|---|
| Reps | 3 | .4117 | | |
| Treatments | 14 | .8700 | .6214 | .5757 |
| Error | 42 | 4.533 | .1079 | |
| Total | 59 | 5.815 | | |
| Overall mean | | | | 2.514 |
| S. E for Difference | | | | 0.2323 |
| Least Significant Difference (LSD) at 95% | | | | 0.4688 |

TABLE 6-149

BBA Visual Phytotoxicity rating scale

| Scale | EQUIVALENT % | Description |
|---|---|---|
| 1 | 0% | NO DAMAGE |
| 2 | 0.1-2.5% | NEGLIGIBLE DAMAGE |
| 3 | 2.5-5.0% | MODERATE DAMAGE No effects on yield and/or quality |
| 4 | 5.0-10% | Damage up to limits of commercial acceptability - if no yield loss |
| 5 | 10-15% | DISTINCT DAMAGE Commercially acceptable only under certain conditions- if no yield loss |
| 6 | 15-25% | SEVERE DAMAGE Not commercially acceptable - yield loss and quality |
| 7 | 25-35% | VERY SEVERE DAMAGE |
| 8 | 35-68% | EXTREME DAMAGE |
| 9 | 68-100% | START OF WITHERING AND DEATH |

R. Post-Emergence Application Against Weed in Maize

This Example compares the herbicidal selectivity and efficacy of DINAMIC® 700WDG applied in combination with Galago and TOLLA 960 as a post-emergence application with regards to both crop and weeds in irrigated maize. Treatments and conditions are tabulated below.

TABLE 6-150

TREATMENTS

| | TREATMENT | Rate/ha Product (l) | a.i. (g) |
|---|---|---|---|
| 1 | DINAMIC ® + Galago + Wet-All | 75 g + 100 ml + 100 ml/100 l | 52.5 + 48 + 180 |
| 2 | DINAMIC ® + Galago + Wet-All | 75 g + 150 ml + 100 ml/100 l | 52.5 + 72 |
| 3 | DINAMIC ® + Galago + Wet-All | 100 g + 100 ml + 100 ml/100 l | 70 + 48 |
| 4 | DINAMIC ® + Galago + Wet-All | 100 g + 150 ml + 100 ml/100 l | 70 + 72 |
| 5 | DINAMIC ® + Galago + Wet-All | 125 g + 100 ml + 100 ml/100 l | 87.5 + 48 |
| 6 | DINAMIC ® + Galago + Wet-All | 125 g + 150 ml + 100 ml/100 l | 87.5 + 72 |
| 7 | DINAMIC ® + Galago + TOLLA 960 + Wet-All | 75 g + 100 ml + 1.0 l + 100 ml/100 l | 52.5 + 48 + 960 + 180 |
| 8 | DINAMIC ® + Galago + TOLLA 960 + Wet-All | 75 g + 150 ml + 1.0 l + 100 ml/100 l | 52.5 + 72 + 960 + 180 |
| 9 | DINAMIC ® + Galago + TOLLA 960 + Wet-All | 100 g + 100 ml + 1.0 l + 100 ml/100 l | 70 + 48 + 960 + 180 |
| 10 | DINAMIC ® + Galago + TOLLA 960 + Wet-All | 100 g + 150 ml + 1.0 l + 100 ml/100 l | 70 + 72 + 960 + 180 |
| 11 | DINAMIC ® + Galago + TOLLA 960 + Wet-All | 125 g + 100 ml + 1.0 l + 100 ml/100 l | 87.5 + 48 + 960 + 180 |
| 12 | DINAMIC ® + Galago + TOLLA 960 + Wet-All | 125 g + 150 ml + 1.0 l + 100 ml/100 l | 87.5 + 72 + 960 + 180 |
| 13 | DINAMIC ® + Galago + TOLLA 960 + Wet-All | 250 g + 300 ml + 2.0 l + 200 ml/100 l | 175 + 144 + 1920 + 360 |
| 14 | CALLISTO ® + Gardo Gold + Complement super | 260 ml + 1562 ml + 100 ml/100 l | 125 + 488/293 + 100 |
| 15 | Untreated control | — | — |

TABLE 6-151

Test products used

| | Product | Active Ingredient | Formulation | Manufacturer/ Supplier | Registration No. |
|---|---|---|---|---|---|
| 1 | DINAMIC ® 700WDG | Amicarbazone 700 g/kg | WDG | Arysta Lifescience | |
| 2 | Galago | Mesotrione 480 g/l | SC | Arysta Lifescience | L. 8089 |
| 3 | TOLLA 960 | Metolachlor 960 g/l | EC | Arysta Lifescience | L. 6794 |
| 4 | Wet-All | Adjuvant | SL | Arysta Lifescience | L. 8361 |
| 5 | CALLISTO ® | Mesotrione 480 g/l | SC | Syngenta | L. 6795 |

TABLE 6-151-continued

| | | Test products used | | | |
|---|---|---|---|---|---|
| | Product | Active Ingredient | Formulation | Manufacturer/ Supplier | Registration No. |
| 6 | Gardo Gold | S-Metolachlor 312.5 g/l Terbuthylazine 187.5 g/l | SC | Syngenta | L. 7763 |
| 7 | COMPLEMENT ® Super | Adjuvant | SL | Syngenta | L. 8169 |

TABLE 6-152

| TRIAL DESIGN | |
|---|---|
| Design | Completely randomized design |
| Replicates | Four |
| Plot size | 5 m × 2.5 m = Nett/plot |

TABLE 6-153

| SPRAYER | |
|---|---|
| Sprayer | $CO_2$ Precision Sprayer |
| Boom | 2 m aluminium |
| Nozzle | 5 × 11002 flat fan nozzles (Teejet 11002 DG) |
| Pressure | 2.7 Bar |
| Application | 200 l/ha |

Spray Water Quality:
pH: 6.5
EC: 0.7 mS/m
Spray Volume:
200 l/ha at 2.7 Bar

TABLE 6-154

| WEATHER INFORMATION AT APPLICATION | |
|---|---|
| Temperature (max) | 21.7° C. |
| RH: | 65% |
| Wind: | 0-5 km/h, NE |
| Cloud | 8/8 |

TABLE 6-155

| SOIL PROPERTIES AT APPLICATION | |
|---|---|
| Clay Fraction | 9% |
| Silt Fraction | 5% |
| Sand Fraction | 86% |
| pH (KCl) | 6.01 |
| Moisture | Field capacity |

Irrigation

None (rain-fed)

Crop

Crop: Maize

Variety: Pan 3P-736BR

Growth stage: 4-5 leaf (BBCH growth stage 14/15)

Sowing depth: 5 cm

Sowing density: 80 000 plants/ha

TABLE 6-156

| | WEED INFORMATION | | | |
|---|---|---|---|---|
| SPECIES | COMMON NAME | CODE | GROWTH STAGE | % SOIL COVER |
| *Bidens polosa* | Blackjack | BIDPI | 2-4 leaf | 25% |
| *Portulaca oleracea* | Purslane | POROL | 4-6 leaf | 5% |
| *Convolvulus arvensis* | Field bindweed | CONAR | 2-4 leaf | 5% |
| *Anoda cristata* | Anoda weed | ANOCR | 2-4 leaf | 5% |

TABLE 6-157

| | ASSESSMENT DETAILS | | | | | |
|---|---|---|---|---|---|---|
| | | YIELD (Kg/plot) | | | | |
| | | Replicate | | | | |
| | TREATMENT | I | II | III | IV | Mean |
| 1 | DINAMIC ® + Galago + Wet-All 75 g + 100 ml + 100 ml/100 l | 3.89 | 4.00 | 3.68 | 3.43 | 3.75 ab |
| 2 | DINAMIC ® + Galago + Wet-All 75 g + 150 ml + 100 ml/100 l | 3.61 | 3.56 | 3.72 | 3.34 | 3.56 ab |
| 3 | DINAMIC ® + Galago + Wet-All 100 g + 100 ml + 100 ml/100 l | 3.81 | 4.06 | 3.43 | 2.78 | 3.52 ab |
| 4 | DINAMIC ® + Galago + Wet-All 100 g + 150 ml + 100 ml/100 l | 3.99 | 4.01 | 3.98 | 3.27 | 3.81 ab |
| 5 | DINAMIC ® + Galago + Wet-All 125 g + 100 ml + 100 ml/100 l | 3.57 | 3.78 | 3.60 | 3.66 | 3.65 ab |
| 6 | DINAMIC ® + Galago + Wet-All 125 g + 150 ml + 100 ml/100 l | 3.43 | 3.92 | 3.92 | 4.04 | 3.83 ab |
| 7 | DINAMIC ® + Galago + TOLLA 960 + Wet-All 75 g + 100 ml + 1.0 l + 100 ml/100 l | 3.54 | 4.06 | 3.70 | 3.50 | 3.70 ab |
| 8 | DINAMIC ® + Galago + TOLLA 960 + Wet-All 75 g + 150 ml + 1.0 l + 100 ml/100 l | 3.90 | 4.06 | 3.33 | 2.93 | 3.55 ab |

TABLE 6-157-continued

ASSESSMENT DETAILS

| | YIELD (Kg/plot) | | | | |
|---|---|---|---|---|---|
| | Replicate | | | | |
| TREATMENT | I | II | III | IV | Mean |
| 9 DINAMIC ® + Galago + TOLLA 960 + Wet-All 100 g + 100 ml + 1.0 l + 100 ml/100 l | 3.52 | 4.27 | 3.80 | 3.32 | 3.73 ab |
| 10 DINAMIC ® + Galago + TOLLA 960 + Wet-All 100 g + 150 ml + 1.0 l + 100 ml/100 l | 4.01 | 3.92 | 3.53 | 4.04 | 3.87 ab |
| 11 DINAMIC ® + Galago + TOLLA 960 + Wet-All 125 g + 100 ml + 1.0 l + 100 ml/100 l | 3.28 | 3.46 | 3.37 | 4.07 | 3.55 ab |
| 12 DINAMIC ® + Galago + TOLLA 960 + Wet-All 125 g + 150 ml + 1.0 l + 100 ml/100 l | 2.94 | 4.14 | 3.39 | 4.01 | 3.62 ab |
| 13 DINAMIC ® + Galago + TOLLA 960 + Wet-All 250 g + 300 ml + 2.0 l + 200 ml/100 l | 2.62 | 3.36 | 3.52 | 3.74 | 3.31 a |
| 14 CALLISTO ® + Gardo Gold + COMPLIMENT ® Super 260 ml + 1562 ml + 100 ml/100 l | 3.75 | 4.50 | 4.73 | 4.50 | 4.37 b |
| 15 Untreated control | 3.99 | 3.28 | 3.60 | 3.15 | 3.50 ab |

TABLE 6-158

Comparative yield of DINAMIC ® 700WDG programs

| Method Herbicide | Comparative Efficacy Efficacy: Number of weeds in treated versus untreated plots Selectivity: Visual phytotoxicity and yield |
|---|---|
| 11. | Visual phytotoxicity: BBA 1-9 scale (refer to appendix for details) |
| 12. | Yield: 40 cobs harvested at random from each plot. Average grain weight per plot determined using a precision 2 decimal scale. Statistical evaluation: ANOVA at the 95% probability using Tukeys LSD formulae |
| Assessment Times-Days After Application (DAA) | 14 DAA - Efficacy/Selectivity 28 DAA - Efficacy/Selectivity 42 DAA - Efficacy/Selectivity Harvest - Selectivity |

Note:
Treatment means sharing the same letter do not differ significantly by LSD test at the 5% ($\alpha = 0.05$) level of probability

TABLE 6-159

Comparative visual phytotoxicity of DINAMIC ® 700WDG post-emergence programs

| | | BBA VISUAL PHYTOTOXICITY SCALE (1 - no damage; 9 - dead) | | | | |
|---|---|---|---|---|---|---|
| | | Replicate | | | | |
| TREATMENT Rate/ha | Timing | I | II | III | IV | Mean |
| 1 DINAMIC ® + Galago + Wet-All 75 g + 100 ml + 100 ml/100 ml | 14 DAA | 3 | 2 | 2 | 3 | 2.5 |
| | 28 DAA | 1 | 1 | 1 | 3 | 1.5 |
| | 42 DAA | 1 | 1 | 1 | 1 | 1.0 |
| 2 DINAMIC ® + Galago + Wet-All 75 g + 150 ml + 100 ml/100 ml | 14 DAA | 3 | 2 | 4 | 3 | 3.0 |
| | 28 DAA | 1 | 1 | 1 | 1 | 1.0 |
| | 42 DAA | 1 | 1 | 1 | 1 | 1.0 |
| 3 DINAMIC ® + Galago + Wet-All 100 g + 100 ml + 100 ml/100 ml | 14 DAA | 3 | 3 | 2 | 4 | 3.0 |
| | 28 DAA | 2 | 1 | 2 | 2 | 1.75 |
| | 42 DAA | 1 | 1 | 1 | 1 | 1.0 |
| 4 DINAMIC ® + Galago + Wet-All 100 g + 150 ml + 100 ml/100 ml | 14 DAA | 3 | 3 | 4 | 3 | 3.25 |
| | 28 DAA | 3 | 1 | 1 | 1 | 1.5 |
| | 42 DAA | 1 | 1 | 1 | 1 | 1.0 |
| 5 DINAMIC ® + Galago + Wet-All 125 g + 100 ml + 100 ml/100 ml | 14 DAA | 4 | 4 | 3 | 3 | 3.5 |
| | 28 DAA | 1 | 3 | 2 | 3 | 2.25 |
| | 42 DAA | 1 | 1 | 1 | 1 | 1.0 |
| 6 DINAMIC ® + Galago + Wet-All 125 g + 150 ml + 100 ml/100 ml | 14 DAA | 4 | 4 | 4 | 2 | 3.5 |
| | 28 DAA | 3 | 3 | 2 | 3 | 2.75 |
| | 42 DAA | 1 | 1 | 1 | 1 | 1.0 |
| 7 DINAMIC ® + Galago + TOLLA 960 + Wet-All 75 g + 100 ml + 1.0 l + 100 ml/100 ml | 14 DAA | 2 | 2 | 3 | 2 | 2.25 |
| | 28 DAA | 1 | 1 | 1 | 2 | 1.25 |
| | 42 DAA | 1 | 1 | 1 | 1 | 1.0 |
| 8 DINAMIC ® + Galago + TOLLA 960 + Wet-All 75 g + 150 ml + 1.0 l + 100 ml/100 ml | 14 DAA | 2 | 2 | 3 | 3 | 2.5 |
| | 28 DAA | 1 | 1 | 1 | 1 | 1.0 |
| | 42 DAA | 1 | 1 | 1 | 1 | 1.0 |

TABLE 6-159-continued

Comparative visual phytotoxicity of DINAMIC ® 700WDG post-emergence programs

| | | BBA VISUAL PHYTOTOXICITY SCALE (1 - no damage; 9 - dead) | | | | |
|---|---|---|---|---|---|---|
| | | Replicate | | | | |
| TREATMENT Rate/ha | Timing | I | II | III | IV | Mean |
| 9 DINAMIC ® + Galago + TOLLA 960 + Wet-All 100 g + 100 ml + 1.0 l + 100 ml/100 ml | 14 DAA 28 DAA 42 DAA | 4 1 1 | 3 3 1 | 4 3 1 | 4 2 1 | 3.75 2.25 1.0 |
| 10 DINAMIC ® + Galago + TOLLA 960 + Wet-All 100 g + 150 ml + 1.0 l + 100 ml/100 ml | 14 DAA 28 DAA 42 DAA | 4 1 1 | 3 2 1 | 3 1 1 | 4 3 1 | 3.5 1.75 1.0 |
| 11 DINAMIC ® + Galago + TOLLA 960 + Wet-All 125 g + 100 ml + 1.0 l + 100 ml/100 ml | 14 DAA 28 DAA 42 DAA | 4 3 1 | 3 3 1 | 4 3 1 | 4 3 1 | 3.75 3.0 1.0 |
| 12 DINAMIC ® + Galago + TOLLA 960 + Wet-All 125 g + 150 ml + 1.0 l + 100 ml/100 ml | 14 DAA 28 DAA 42 DAA | 4 3 1 | 4 3 1 | 4 3 1 | 3 3 1 | 3.75 3.0 1.0 |
| 13 DINAMIC ® + Galago + TOLLA 960 + Wet-All 250 g + 300 ml + 2.0 l + 200 ml/100 ml | 14 DAA 28 DAA 42 DAA | 6 5 4 | 6 5 4 | 6 4 4 | 6 5 4 | 6.0 4.75 4.0 |
| 14 CALLISTO ® + Gardo Gold + COMPLEMENT ® Super 260 ml + 1562 ml + 100 ml | 14 DAA 28 DAA 42 DAA | 3 1 1 | 1 1 1 | 1 1 1 | 1 1 1 | 1.5 1.0 1.0 |
| 15 Untreated control | 14 DAA 28 DAA 42 DAA | 1 1 1 | 1 1 1 | 1 1 1 | 1 1 1 | 1.0 1.0 1.0 |

TABLE 6-160

Comparative visual phytotoxicity of DINAMIC ® 700WDG post-emergence programs

| | | AVERAGE % WEED CONTROL BY SPECIES | | | |
|---|---|---|---|---|---|
| TREATMENT Rate/ha | TIMING | BIDPI | ANOCR | CONAR | POROL |
| 1. DINAMIC ® + Galago + Wet-All 75 g + 100 ml + 100 ml/100 ml | 14 DAA 28 DAA 56 DAA | 94 96 90 | 100 100 100 | 100 100 100 | 70 60 60 |
| 2. DINAMIC ® + Galago + Wet-All 75 g + 150 ml + 100 ml/100 ml | 14 DAA 28 DAA 56 DAA | 98 100 100 | 98 100 100 | 100 100 100 | 80 70 80 |
| 3. DINAMIC ® + Galago + Wet-All 100 g + 100 ml + 100 ml/100 ml | 14 DAA 28 DAA 56 DAA | 99 99 96 | 98 98 100 | 100 100 100 | 80 70 70 |
| 4. DINAMIC ® + Galago + Wet-All 100 g + 150 ml + 100 ml/100 ml | 14 DAA 28 DAA 56 DAA | 98 99 100 | 100 100 100 | 100 100 100 | 75 70 85 |
| 5. DINAMIC ® + Galago + Wet-All 125 g + 100 ml + 100 ml/100 ml | 14 DAA 28 DAA 56 DAA | 100 100 100 | 100 100 100 | 100 100 100 | 80 75 80 |
| 6. DINAMIC ® + Galago + Wet-All 125 g + 150 ml + 100 ml/100 ml | 14 DAA 28 DAA 56 DAA | 100 100 100 | 100 100 100 | 100 100 100 | 80 80 94 |
| 7. DINAMIC ® + Galago + TOLLA 960 + Wet-All 75 g + 100 ml + 1.0 l + 100 ml/100 ml | 14 DAA 28 DAA 56 DAA | 100 100 100 | 99 100 100 | 100 100 100 | 85 80 85 |
| 8. DINAMIC ® + Galago + TOLLA 960 + Wet-All 75 g + 150 ml + 1.0 l + 100 ml/100 ml | 14 DAA 28 DAA 56 DAA | 100 100 100 | 100 100 100 | 100 100 100 | 85 80 85 |
| 9. DINAMIC ® + Galago + TOLLA 960 + Wet-All 100 g + 100 ml + 1.0 l + 100 ml/100 ml | 14 DAA 28 DAA 56 DAA | 100 100 100 | 100 100 100 | 100 100 100 | 85 80 90 |
| 10. DINAMIC ® + Galago + TOLLA 960 + Wet-All 100 g + 150 ml + 1.0 l + 100 ml/100 ml | 14 DAA 28 DAA 56 DAA | 100 100 100 | 100 100 100 | 100 100 100 | 90 99 90 |
| 11. DINAMIC ® + Galago + TOLLA 960 + Wet-All 125 g + 100 ml + 1.0 l + 100 ml/100 ml | 14 DAA 28 DAA 56 DAA | 100 100 100 | 100 100 100 | 100 100 100 | 96 94 92 |

TABLE 6-160-continued

Comparative visual phytotoxicity of DINAMIC ® 700WDG post-emergence programs

|  |  | AVERAGE % WEED CONTROL BY SPECIES | | | |
|---|---|---|---|---|---|
| TREATMENT Rate/ha | TIMING | BIDPI | ANOCR | CONAR | POROL |
| 12. DINAMIC ® + Galago + TOLLA 960 + | 14 DAA | 100 | 100 | 100 | 94 |
| Wet-All | 28 DAA | 100 | 100 | 100 | 100 |
| 125 g + 150 ml + 1.0 l + 100 ml/100 ml | 56 DAA | 100 | 100 | 100 | 96 |
| 13. DINAMIC ® + Galago + TOLLA 960 + | 14 DAA | 100 | 100 | 100 | 90 |
| Wet-All | 28 DAA | 100 | 100 | 100 | 100 |
| 250 g + 300 ml + 2.0 l + 200 ml/100 ml | 56 DAA | 100 | 100 | 100 | 100 |
| 14. CALLISTO ® + Gardo Gold + | 14 DAA | 100 | 100 | 100 | 95 |
| COMPLEMENT ® Super | 28 DAA | 100 | 100 | 100 | 90 |
| 260 ml + 1562 ml + 100 ml | 56 DAA | 100 | 100 | 100 | 100 |
| 15. Untreated Control | 14 DAA | 0 | 0 | 0 | 0 |
|  | 28 DAA | 0 | 0 | 0 | 0 |
|  | 56 DAA | 0 | 0 | 0 | 0 |

The trial was conducted on a commercial maize crop produced under centre pivot irrigation. The DINAMIC® 700WDG formulation was evaluated for herbicidal efficacy and crop selectivity when applied as a post-emergence spray program in tank-mix combination with Galago and TOLLA 960. The adjuvant Wet-All was applied to all treatments containing DINAMIC® 700WDG as standard practice. Treatments were applied post-emergence of crop and weeds as broadcast applications over the maize rows when the maize crop was in the 4-5 leaf stage. Weather conditions on the day of application were overcast and cool.

At the first assessment conducted at 14 DAA, all DINAMIC® 700WDG treatments displayed visual symptoms of phytotoxicity in the form of leaf scorching. Scorching appeared to be dosage related, with the severity of scorching increasing along with an increase in the rate of DINAMIC® 700WDG applied. Visual symptoms of stunting were also observed on treatments receiving DINAMIC® 700WDG at rates exceeding 75 g/ha. At the second assessment conducted at 28 DAA, visual symptoms of phytotoxicity in the form of stunting were observed in tank-mix combinations receiving the DINAMIC® 700WDG formulation exceeding the rate of 75 g/ha applied. Stunting was distinct (BBA phytotoxicity class 5) in tank-mix treatments receiving the double rate of DINAMIC® 700WDG applied at 250 g/ha. Stunting was negligible to moderate (BBA class 2-3) across all other DINAMIC® 700WDG tank-mix combinations applied between the rates 100-125 g/ha.

At the final assessment conducted at 42 DAA, no visual symptoms of phytotoxicity of any nature were observed on any of the treatments applied.

Yield

Tank-mix combinations of the test product DINAMIC® 700WDG applied between the rates of 75-125 g/ha did not exhibit significantly different yields compared to the standard tank-mix combination of CALLISTO®+Gardo Gold+COMPLEMENT® Super and the untreated control treatment.

The tank-mix combination of DINAMIC® 700WDG+Galago+TOLLA 960+Wet-All applied at the double rate of 250 g/ha+300 ml/ha+1.0 l/ha+200 ml/100 l displayed significantly lower yields compared to the standard tank-mix combination of CALLISTO®+Gardo Gold+COMPLEMENT® Super. However, no significant yield reduction occurred when compared to the untreated control treatment.

The weed spectrum at the trial site was dominated by broadleaved weeds namely Blackjack (BIDPI), Field bindweed (CONAR), Anoda weed (ANOCR) and Purslane (POROL). The weed spectrum varied from 2-6 leaf stage at application. Efficacy evaluations were conducted at 14, 28 and 56 days following application, respectively.

DINAMIC® 700WDG+Galago

Tank-mix combinations of DINAMIC® 700WDG+Galago+Wet-all exhibited commercially acceptable levels of herbicidal activity against the broadleaved weeds BIDPI, CONAR and ANOCR across all rates applied. The broadleaved weed POROL was only commercially controlled at the higher tank-mix rate of DINAMIC® 700WDG+Galago+Wet-All applied at 125 g/ha+150 ml/ha+100 ml/100 l.

DINAMIC® 700WDG+Galago+TOLLA 960

Tank-mix combinations of DINAMIC® 700WDG+Galago+TOLLA 960+Wet-All were efficacious and exhibited total control (100% efficacy) of the broadleaved weeds BIDPI, CONAR and ANOCR across all rates applied. The broadleaved weed POROL was commercially controlled by all tank-mix combinations where DINAMIC® 700WDG was applied at rates exceeding 75 g/ha. Herbicidal activity was greatest where DINAMIC® 700WDG was applied in tank-mix combinations with Galago at the higher rate of 150 ml/ha. The tank-mix combination of DINAMIC® 700WDG+Galago+TOLLA 960+Wet-All applied at the rate of 125 g/ha+150 ml/ha+1.0 l/ha+100 ml/100 l displayed a similar level of herbicidal activity as the standard tank-mix combination of CALLISTO®+Gardo Gold+COMPLEMENT® Super applied at the registered rate of 260 ml/ha+1562 ml/ha+100 ml/ha.

Compatibility

No visual symptoms of incompatibility in the form of phase separation or agglomeration were observed in any of the tank-mix combinations of DINAMIC® 700WDG+Galago+Wet-All and DINAMIC® 700WDG+Galago+TOLLA 960+Wet-All, whether applied at single or double rates.

All DINAMIC® 700WDG tank-mix combinations displayed visual symptoms of phytotoxicity in the form of leaf scorching at 14 days following application. Scorching appeared to be dosage related, with the severity of scorching increasing along with an increase in the rate of DINAMIC® 700WDG applied.

Visual symptoms of phytotoxicity in the form of stunting were observed at the assessments conducted at 14 and 28 DAA in treatments receiving the tank-mix combination of DINAMIC® 700WDG+Galago+TOLLA 960+Wet-All where DINAMIC® 700WDG was applied at the rates exceeding 75 g/ha. Stunting observed in plots treated with the DINAMIC® 700WDG formulation applied between the rates of 100-125 g/ha was not severe and ranged from negligible to moderate according to the BBA visual phytotoxicity scale. Symptoms of stunting were distinct in treatments receiving the double rate of DINAMIC® 700WDG applied. No visual symptoms of phytotoxicity of any nature were observed at the assessment conducted at 42 DAA.

Tank-mix combinations of DINAMIC® 700WDG+Galago+TOLLA 960+Wet-All were efficacious and exhibited commercially acceptable levels of herbicidal activity against the broadleaved weeds BIDPI, CONAR and ANOCR across all rates applied. POROL was commercially controlled by all tank-mix combinations where DINAMIC® 700WDG was applied at rates exceeding 75 g/ha.

Likewise, tank-mix combinations of DINAMIC® 700WDG+Galago+Wet-all exhibited commercially acceptable levels of herbicidal activity against the broadleaved weeds BIDPI, CONAR and ANOCR across all rates applied. The broadleaved weed POROL was only commercially controlled at the higher tank-mix rate of DINAMIC® 700WDG+Galago+Wet-All applied at 125 g/ha+150 ml/ha+100 ml/100 l.

No visual symptoms of incompatibility in the form of phase separation or agglomeration were observed in any of the tank-mix combinations of DINAMIC® 700WDG+Galago+Wet-All and DINAMIC® 700WDG+Galago+TOLLA 960+Wet-All, whether applied at single or double rates.

TABLE 6-161

Anova Table Grain yield (kg/plot)

| Unit | Degrees of freedom | Sums of Squares | Mean Squares | F Value |
|---|---|---|---|---|
| Reps | 3 | 0.9264 | | |
| Treatments | 14 | 3.225 | 0.2304 | 1.730 |
| Error | 42 | 5.593 | 0.1332 | |
| Total | 59 | 9.745 | | |
| Overall mean | | | 3.688 | |
| S. E for Difference | | | 0.2580 | |
| Least Significant Difference (LSD) at 95% | | | 0.5208 | |

TABLE 6-162

BBA Visual Phytotoxicity rating scale

| Scale | EQUIVALENT % | Description |
|---|---|---|
| 1 | 0% | NO DAMAGE |
| 2 | 0.1-2.5% | NEGLIGIBLE DAMAGE |
| 3 | 2.5-5.0% | MODERATE DAMAGE No effects on yield and/or quality |
| 4 | 5.0-10% | Damage up to limits of commercial acceptability - if no yield loss |
| 5 | 10-15% | DISTINCT DAMAGE Commercially acceptable only under certain conditions- if no yield loss |
| 6 | 15-25% | SEVERE DAMAGE Not commercially acceptable - yield loss and quality |
| 7 | 25-35% | VERY SEVERE DAMAGE |
| 8 | 35-68% | EXTREME DAMAGE |
| 9 | 68-100% | START OF WITHERING AND DEATH |

Example 7

Evaluation of Synergistic Action Between Amicarbazone and TENACITY® (Mesotrione 40%)

This Example shows the synergism in the use of the combination of amicarbazone and mesotrione. In evaluating synergism, the data from Example 5 above were converted to % of control. This was done based on the data provided on a 1-9 scale detailed in Example 5. Expected values were computed from the % of control data by the formula for expected control=A*B/100, where A is the % of control value for herbicide A alone and B is the % of control value for herbicide B alone.

In this Example, the source of mesotrione was TENACITY®, available from Syngenta (Greensboro, N.C.). Rates appear as pounds of active ingredient (ai), rates as ounces per acre. Results are tabulated in Tables 7-1 through 7-17 below.

TABLE 7-1

Kentucky Bluegrass Bleaching from Tenacity + Amicarbazone applications plus the expected responses calculated from the responses to each herbicide applied singly.

| Treatment | Rate (lbs ai/A) | Rate (oz/A) | 1 | Exp | 2 | Exp | 3 | Exp | 3/27 | Exp |
|---|---|---|---|---|---|---|---|---|---|---|
| Control | — | | 100 | | 100 | | 100 | | 100 | |
| Amicarbazone | 0.022 | 0.5 | 100 | | 100 | | 100 | | 100 | |
| Amicarbazone | 0.13 | 3 | 100 | | 100 | | 100 | | 94 | |
| Tenacity | 0.125 | 4 | 100 | | 100 | | 100 | | 100 | |
| Tenacity | 0.25 | 8 | 100 | | 100 | | 91 | | 91 | |
| Tenacity + Amicarbazone | 0.125 + 0.022 | 4 + 0.5 | 100 | 100 | 100 | 100 | 100 | 100 | 100 | 100 |
| Tenacity + Amicarbazone | 0.125 + 0.13 | 4 + 3 | 100 | 100 | 100 | 100 | 100 | 100 | 97 | 94 |
| Tenacity + Amicarbazone | 0.25 + 0.022 | 8 + 0.5 | 100 | 100 | 100 | 100 | 100 | 100 | 91 | 97 | 91 |
| Tenacity + Amicarbazone | 0.25 + 0.13 | 8 + 3 | 100 | 100 | 100 | 100 | 100 | 100 | 91 | 97 | 85 |

TABLE 7-2

Kentucky bluegrass injury from Tenacity + Amicarbazone applications plus

| Treatment | Rate (lbs ai/A) | Rate (oz/A) | 1 | Exp | 2 | Exp |
|---|---|---|---|---|---|---|
| Control | — | | 100 | | 100 | |
| Amicarbazone | 0.022 | 0.5 | 100 | | 100 | |
| Amicarbazone | 0.13 | 3 | 91 | | 83 | |
| Tenacity | 0.125 | 4 | 100 | | 100 | |
| Tenacity | 0.25 | 8 | 94 | | 90 | |
| Tenacity + Amicarbazone | 0.125 + 0.022 | 4 + 0.5 | 97 | 100 | 94 | 101 |
| Tenacity + Amicarbazone | 0.125 + 0.13 | 4 + 3 | 63 | 91 | 59 | 84 |
| Tenacity + Amicarbazone | 0.25 + 0.022 | 8 + 0.5 | 84 | 94 | 79 | 91 |
| Tenacity + Amicarbazone | 0.25 + 0.13 | 8 + 3 | 13 | 85 | 6 | 75 |

TABLE 7-3

Kentucky Bluegrass percent cover from Tenacity + Amicarbazone applications plus the expected responses calculated from the responses to each herbicide applied singly.

| Treatment | Rate (lbs ai/A) | Rate (oz/A) | 1 | Exp | 2 | Exp | 3 | Exp |
|---|---|---|---|---|---|---|---|---|
| Control | — | | 100 | | 100 | | 100 | |
| Amicarbazone | 0.022 | 0.5 | 85 | | 85 | | 100 | |
| Amicarbazone | 0.13 | 3 | 55 | | 53 | | 83 | |
| Tenacity | 0.125 | 4 | 67 | | 66 | | 91 | |
| Tenacity | 0.25 | 8 | 77 | | 81 | | 89 | |
| Tenacity + Amicarbazone | 0.125 + 0.022 | 4 + 0.5 | 74 | 57 | 76 | 56 | 97 | 91 |
| Tenacity + Amicarbazone | 0.125 + 0.13 | 4 + 3 | 31 | 37 | 41 | 35 | 55 | 75 |
| Tenacity + Amicarbazone | 0.25 + 0.022 | 8 + 0.5 | 61 | 65 | 61 | 69 | 87 | 90 |
| Tenacity + Amicarbazone | 0.25 + 0.13 | 8 + 3 | 3 | 42 | 7 | 43 | 3 | 74 |

TABLE 7-4

Kentucky Bluegrass Bleaching from Tenacity + Amicarbazone applications plus the expected responses calculated from the responses to each herbicide applied singly.

| Treatment | Rate (lbs ai/A) | Rate (oz/A) | 1 | Exp | 2 | Exp | 3 | Exp | 4 | Exp | 5 | Exp | 6 | Exp |
|---|---|---|---|---|---|---|---|---|---|---|---|---|---|---|
| Control | — | | 100 | | 100 | | 100 | | 100 | | 100 | | 100 | |
| Amicarbazone | 0.022 | 0.5 | 100 | | 100 | | 100 | | 100 | | 97 | | 100 | |
| Amicarbazone | 0.13 | 3 | 97 | | 97 | | 97 | | 100 | | 100 | | 100 | |
| Tenacity | 0.125 | 4 | 94 | | 94 | | 100 | | 100 | | 94 | | 100 | |
| Tenacity | 0.25 | 8 | 97 | | 97 | | 97 | | 97 | | 100 | | 100 | |
| Tenacity + Amicarbazone | 0.125 + 0.022 | 4 + 0.5 | 97 | 94 | 97 | 94 | 94 | 100 | 100 | 100 | 94 | 91 | 100 | 100 |
| Tenacity + Amicarbazone | 0.125 + 0.13 | 4 + 3 | 97 | 91 | 97 | 91 | 97 | 97 | 94 | 100 | 97 | 94 | 100 | 100 |
| Tenacity + Amicarbazone | 0.25 + 0.022 | 8 + 0.5 | 91 | 97 | 91 | 97 | 94 | 97 | 94 | 97 | 94 | 97 | 100 | 100 |
| Tenacity + Amicarbazone | 0.25 + 0.13 | 8 + 3 | 97 | 94 | 97 | 94 | 94 | 94 | 91 | 97 | 94 | 100 | 100 | 100 |

TABLE 7-5

Mustard bleaching from Tenacity + Amicarbazone applications plus the expected responses calculated from the responses to each herbicide applied singly.

| Treatment | Rate (lbs ai/A) | Rate (oz/A) | 1 | Exp | 2 | Exp |
|---|---|---|---|---|---|---|
| Control | — | | 100 | | 100 | |
| Amicarbazone | 0.022 | 0.5 | 119 | | 94 | |
| Amicarbazone | 0.13 | 3 | 132 | | 94 | |
| Tenacity | 0.125 | 4 | 64 | | 54 | |
| Tenacity | 0.25 | 8 | 54 | | 53 | |
| Tenacity + Amicarbazone | 0.125 + 0.022 | 4 + 0.5 | 119 | 76 | 94 | 50 |
| Tenacity + Amicarbazone | 0.125 + 0.13 | 4 + 3 | 132 | 85 | 94 | 50 |

TABLE 7-5-continued

Mustard bleaching from Tenacity + Amicarbazone applications plus the expected responses calculated from the responses to each herbicide applied singly.

| Treatment | Rate (lbs ai/A) | Rate (oz/A) | 1 | Exp | 2 | Exp |
|---|---|---|---|---|---|---|
| Tenacity + Amicarbazone | 0.25 + 0.022 | 8 + 0.5 | 115 | 65 | 90 | 50 |
| Tenacity + Amicarbazone | 0.25 + 0.13 | 8 + 3 | 132 | 72 | 94 | 50 |

TABLE 7-6

Mustard injury from Tenacity + Amicarbazone applications plus the expected responses calculated from the responses to each herbicide applied singly.

| Treatment | Rate (lbs ai/A) | Rate (oz/A) | 1 | Exp | 2 | Exp | 3 | Exp | 4 | Exp | 5 | Exp |
|---|---|---|---|---|---|---|---|---|---|---|---|---|
| Control | — | | 100 | | 100 | | 100 | | 100 | | 100 | |
| Amicarbazone | 0.022 | 0.5 | 78 | | 78 | | 61 | | 39 | | 42 | |
| Amicarbazone | 0.13 | 3 | 28 | | 31 | | 26 | | 3 | | 3 | |
| Tenacity | 0.125 | 4 | 72 | | 78 | | 62 | | 25 | | 10 | |
| Tenacity | 0.25 | 8 | 84 | | 81 | | 62 | | 33 | | 17 | |
| Tenacity + Amicarbazone | 0.125 + 0.022 | 4 + 0.5 | 44 | 56 | 44 | 61 | 39 | 38 | 6 | 10 | 0 | 4 |
| Tenacity + Amicarbazone | 0.125 + 0.13 | 4 + 3 | 31 | 20 | 28 | 24 | 26 | 16 | 4 | 1 | 0 | 0 |
| Tenacity + Amicarbazone | 0.25 + 0.022 | 8 + 0.5 | 41 | 66 | 44 | 63 | 39 | 37 | 7 | 13 | 0 | 7 |
| Tenacity + Amicarbazone | 0.25 + 0.13 | 8 + 3 | 19 | 24 | 13 | 25 | 3 | 16 | 0 | 1 | 0 | 1 |

TABLE 7-7

Annual bluegrass bleaching from Tenacity + Amicarbazone applications plus the expected responses calculated from the responses to each herbicide applied singly.

| Treatment | Rate (lbs ai/A) | Rate (oz/A) | 1 | Exp | 2 | Exp | 3 | Exp | 4 | Exp | 4/2 | Exp |
|---|---|---|---|---|---|---|---|---|---|---|---|---|
| Control | — | | 100 | | 100 | | 100 | | 100 | | 100 | |
| Amicarbazone | 0.022 | 0.5 | 100 | | 100 | | 100 | | 107 | | 100 | |
| Amicarbazone | 0.13 | 3 | 100 | | 100 | | 91 | | 94 | | 88 | |
| Tenacity | 0.125 | 4 | 100 | | 100 | | 97 | | 91 | | 94 | |
| Tenacity | 0.25 | 8 | 97 | | 97 | | 91 | | 83 | | 91 | |
| Tenacity + Amicarbazone | 0.125 + 0.022 | 4 + 0.5 | 97 | 100 | 94 | 100 | 78 | 97 | 82 | 97 | 88 | 94 |
| Tenacity + Amicarbazone | 0.125 + 0.13 | 4 + 3 | 100 | 100 | 100 | 100 | 84 | 88 | 87 | 85 | 84 | 82 |
| Tenacity + Amicarbazone | 0.25 + 0.022 | 8 + 0.5 | 100 | 97 | 100 | 97 | 91 | 91 | 93 | 89 | 94 | 91 |
| Tenacity + Amicarbazone | 0.25 + 0.13 | 8 + 3 | 97 | 97 | 100 | 97 | 56 | 82 | 71 | 78 | 84 | 79 |

TABLE 7-8

Annual bluegrass injury from Tenacity + Amicarbazone applications plus the expected responses calculated from the responses to each herbicide applied singly.

| Treatment | Rate (lbs ai/A) | Rate (oz/A) | 1 | Exp | 2 | Exp | 3 | Exp | 4 | Exp | 5 | Exp |
|---|---|---|---|---|---|---|---|---|---|---|---|---|
| Control | — | | 100 | | 100 | | 100 | | 100 | | 100 | |
| Amicarbazone | 0.022 | 0.5 | 104 | | 104 | | 108 | | 96 | | 90 | |
| Amicarbazone | 0.13 | 3 | 71 | | 61 | | 67 | | 53 | | 52 | |
| Tenacity | 0.125 | 4 | 100 | | 104 | | 113 | | 104 | | 97 | |
| Tenacity | 0.25 | 8 | 88 | | 89 | | 104 | | 93 | | 86 | |
| Tenacity + Amicarbazone | 0.125 + 0.022 | 4 + 0.5 | 84 | 104 | 71 | 107 | 83 | 122 | 64 | 100 | 70 | 87 |
| Tenacity + Amicarbazone | 0.125 + 0.13 | 4 + 3 | 61 | 72 | 50 | 63 | 46 | 75 | 33 | 55 | 28 | 50 |
| Tenacity + Amicarbazone | 0.25 + 0.022 | 8 + 0.5 | 81 | 91 | 68 | 92 | 71 | 113 | 60 | 90 | 59 | 78 |
| Tenacity + Amicarbazone | 0.25 + 0.13 | 8 + 3 | 38 | 62 | 29 | 54 | 21 | 69 | 11 | 50 | 14 | 45 |

| Treatment | Rate (lbs ai/A) | Rate (oz/A) | 6 | Exp | 7 | Exp |
|---|---|---|---|---|---|---|
| Control | — | | 100 | | 100 | |
| Amicarbazone | 0.022 | 0.5 | 85 | | 85 | |
| Amicarbazone | 0.13 | 3 | 31 | | 24 | |
| Tenacity | 0.125 | 4 | 93 | | 101 | |

TABLE 7-8-continued

Annual bluegrass injury from Tenacity + Amicarbazone applications plus the expected responses calculated from the responses to each herbicide applied singly.

| Tenacity | 0.25 | 8 | 93 | | 102 | |
|---|---|---|---|---|---|---|
| Tenacity + Amicarbazone | 0.125 + 0.022 | 4 + 0.5 | 41 | 79 | 40 | 85 |
| Tenacity + Amicarbazone | 0.125 + 0.13 | 4 + 3 | 11 | 29 | 11 | 25 |
| Tenacity + Amicarbazone | 0.25 + 0.022 | 8 + 0.5 | 43 | 80 | 45 | 86 |
| Tenacity + Amicarbazone | 0.25 + 0.13 | 8 + 3 | 8 | 29 | 13 | 25 |

TABLE 7-9

Green Foxtail bleaching from Tenacity + Amicarbazone applications plus the expected responses calculated from the responses to each herbicide applied singly.

| Treatment | Rate (lbs ai/A) | Rate (oz/A) | 1 | Exp | 2 | Exp | 3 | Exp | 4 | Exp | 5 | Exp |
|---|---|---|---|---|---|---|---|---|---|---|---|---|
| Control | — | | 100 | | 100 | | 100 | | 100 | | 100 | |
| Amicarbazone | 0.022 | 0.5 | 100 | | 104 | | 104 | | 104 | | 160 | |
| Amicarbazone | 0.13 | 3 | 100 | | 104 | | 104 | | 104 | | 106 | |
| Tenacity | 0.125 | 4 | 50 | | 52 | | 65 | | 80 | | 142 | |
| Tenacity | 0.25 | 8 | 41 | | 38 | | 49 | | 71 | | 159 | |
| Tenacity + Amicarbazone | 0.125 + 0.022 | 4 + 0.5 | 78 | 50 | 81 | 54 | 81 | 68 | 94 | 83 | 164 | 227 |
| Tenacity + Amicarbazone | 0.125 + 0.13 | 4 + 3 | 100 | 50 | 104 | 54 | 100 | 68 | 100 | 83 | 109 | 151 |
| Tenacity + Amicarbazone | 0.25 + 0.022 | 8 + 0.5 | 78 | 41 | 84 | 40 | 77 | 51 | 90 | 73 | 164 | 256 |
| Tenacity + Amicarbazone | 0.25 + 0.13 | 8 + 3 | 97 | 41 | 97 | 40 | 97 | 51 | 104 | 73 | 179 | 169 |

TABLE 7-10

Green Foxtail injury from Tenacity + Amicarbazone applications plus the expected responses calculated from the responses to each herbicide applied singly.

| Treatment | Rate (lbs ai/A) | Rate (oz/A) | 1 | Exp | 2 | Exp | 3 | Exp | 4 | Exp | 5 | Exp |
|---|---|---|---|---|---|---|---|---|---|---|---|---|
| Control | — | | 100 | | 100 | | 100 | | 100 | | 100 | |
| Amicarbazone | 0.022 | 0.5 | 97 | | 94 | | 97 | | 97 | | 102 | |
| Amicarbazone | 0.13 | 3 | 67 | | 69 | | 81 | | 84 | | 77 | |
| Tenacity | 0.125 | 4 | 74 | | 66 | | 59 | | 70 | | 71 | |
| Tenacity | 0.25 | 8 | 66 | | 56 | | 41 | | 40 | | 48 | |
| Tenacity + Amicarbazone | 0.125 + 0.022 | 4 + 0.5 | 49 | 72 | 38 | 62 | 31 | 58 | 46 | 68 | 49 | 72 |
| Tenacity + Amicarbazone | 0.125 + 0.13 | 4 + 3 | 19 | 50 | 13 | 45 | 16 | 48 | 20 | 59 | 21 | 55 |
| Tenacity + Amicarbazone | 0.25 + 0.022 | 8 + 0.5 | 32 | 64 | 25 | 53 | 25 | 39 | 17 | 39 | 21 | 49 |
| Tenacity + Amicarbazone | 0.25 + 0.13 | 8 + 3 | 10 | 44 | 13 | 39 | 6 | 33 | 7 | 33 | 11 | 37 |

| Treatment | Rate (lbs ai/A) | Rate (oz/A) | 6 | Exp | 7 | Exp |
|---|---|---|---|---|---|---|
| Control | — | | 100 | | 100 | |
| Amicarbazone | 0.022 | 0.5 | 97 | | 268 | |
| Amicarbazone | 0.13 | 3 | 73 | | 144 | |
| Tenacity | 0.125 | 4 | 68 | | 109 | |
| Tenacity | 0.25 | 8 | 45 | | 64 | |
| Tenacity + Amicarbazone | 0.125 + 0.022 | 4 + 0.5 | 38 | 66 | 81 | 291 |
| Tenacity + Amicarbazone | 0.125 + 0.13 | 4 + 3 | 21 | 50 | 37 | 156 |
| Tenacity + Amicarbazone | 0.25 + 0.022 | 8 + 0.5 | 24 | 44 | 46 | 170 |
| Tenacity + Amicarbazone | 0.25 + 0.13 | 8 + 3 | 4 | 33 | 34 | 91 |

TABLE 7-11

Crabgrass bleaching from Tenacity + Amicarbazone applications plus the expected responses calculated from the responses to each herbicide applied singly.

| Treatment | Rate (lbs ai/A) | Rate (oz/A) | 1 | Exp | 2 | Exp | 3 | Exp | 4 | Exp | 5 | Exp |
|---|---|---|---|---|---|---|---|---|---|---|---|---|
| Control | — | | 100 | | 100 | | 100 | | 100 | | 100 | |
| Amicarbazone | 0.022 | 0.5 | 97 | | 100 | | 100 | | 100 | | 97 | |
| Amicarbazone | 0.13 | 3 | 100 | | 100 | | 100 | | 100 | | 100 | |
| Tenacity | 0.125 | 4 | 38 | | 31 | | 22 | | 25 | | 22 | |
| Tenacity | 0.25 | 8 | 47 | | 38 | | 28 | | 31 | | 31 | |
| Tenacity + Amicarbazone | 0.125 + 0.022 | 4 + 0.5 | 75 | 36 | 59 | 31 | 50 | 22 | 59 | 25 | 69 | 21 |

TABLE 7-11-continued

Crabgrass bleaching from Tenacity + Amicarbazone applications plus the expected
responses calculated from the responses to each herbicide applied singly.

| | | | | | | | | | | | |
|---|---|---|---|---|---|---|---|---|---|---|---|
| Tenacity + Amicarbazone | 0.125 + 0.13 | 4 + 3 | 84 | 38 | 81 | 31 | 91 | 22 | 88 | 25 | 84 | 22 |
| Tenacity + Amicarbazone | 0.25 + 0.022 | 8 + 0.5 | 66 | 45 | 56 | 38 | 59 | 28 | 69 | 31 | 66 | 30 |
| Tenacity + Amicarbazone | 0.25 + 0.13 | 8 + 3 | 94 | 47 | 97 | 38 | 100 | 28 | 100 | 31 | 97 | 31 |

| Treatment | Rate (lbs ai/A) | Rate (oz/A) | 6 | Exp | 7 | Exp | 8 | Exp |
|---|---|---|---|---|---|---|---|---|
| Control | — | | 100 | | 100 | | 100 | |
| Amicarbazone | 0.022 | 0.5 | 97 | | 100 | | 100 | |
| Amicarbazone | 0.13 | 3 | 100 | | 100 | | 100 | |
| Tenacity | 0.125 | 4 | 22 | | 84 | | 100 | |
| Tenacity | 0.25 | 8 | 44 | | 81 | | 100 | |
| Tenacity + Amicarbazone | 0.125 + 0.022 | 4 + 0.5 | 66 | 21 | 97 | 84 | 100 | 100 |
| Tenacity + Amicarbazone | 0.125 + 0.13 | 4 + 3 | 78 | 22 | 97 | 84 | 100 | 100 |
| Tenacity + Amicarbazone | 0.25 + 0.022 | 8 + 0.5 | 59 | 42 | 97 | 81 | 100 | 100 |
| Tenacity + Amicarbazone | 0.25 + 0.13 | 8 + 3 | 94 | 44 | 100 | 81 | 100 | 100 |

TABLE 7-12

Crabgrass injury from Tenacity + Amicarbazone applications plus the expected
responses calculated from the responses to each herbicide applied singly.

| Treatment | Rate (lbs ai/A) | Rate (oz/A) | 1 | Exp | 2 | Exp | 3 | Exp | 4 | Exp | 5 | Exp | 6 | Exp |
|---|---|---|---|---|---|---|---|---|---|---|---|---|---|---|
| Control | — | | 100 | | 100 | | 100 | | 100 | | 100 | | 100 | |
| Amicarbazone | 0.022 | 0.5 | 94 | | 100 | | 100 | | 97 | | 97 | | 94 | |
| Amicarbazone | 0.13 | 3 | 100 | | 100 | | 100 | | 94 | | 94 | | 94 | |
| Tenacity | 0.125 | 4 | 47 | | 47 | | 41 | | 19 | | 16 | | 25 | |
| Tenacity | 0.25 | 8 | 41 | | 38 | | 34 | | 19 | | 19 | | 25 | |
| Tenacity + Amicarbazone | 0.125 + 0.022 | 4 + 0.5 | 50 | 44 | 28 | 47 | 25 | 41 | 22 | 18 | 13 | 15 | 16 | 23 |
| Tenacity + Amicarbazone | 0.125 + 0.13 | 4 + 3 | 28 | 47 | 22 | 47 | 6 | 41 | 6 | 18 | 6 | 15 | 9 | 23 |
| Tenacity + Amicarbazone | 0.25 + 0.022 | 8 + 0.5 | 44 | 38 | 38 | 38 | 22 | 34 | 9 | 18 | 6 | 18 | 13 | 23 |
| Tenacity + Amicarbazone | 0.25 + 0.13 | 8 + 3 | 9 | 41 | 9 | 38 | 0 | 34 | 0 | 18 | 0 | 18 | 0 | 23 |

TABLE 7-13

Crabgrass cover from Tenacity + Amicarbazone applications plus the expected
responses calculated from the responses to each herbicide applied singly.

| Treatment | Rate (lbs ai/A) | Rate (oz/A) | 1 | Exp | 2 | Exp | 3 | Exp |
|---|---|---|---|---|---|---|---|---|
| Control | — | | 100 | | 100 | | 100 | |
| Amicarbazone | 0.022 | 0.5 | 88 | | 94 | | 100 | |
| Amicarbazone | 0.13 | 3 | 67 | | 67 | | 72 | |
| Tenacity | 0.125 | 4 | 22 | | 28 | | 13 | |
| Tenacity | 0.25 | 8 | 10 | | 13 | | 6 | |
| Tenacity + Amicarbazone | 0.125 + 0.022 | 4 + 0.5 | 4 | 19 | 0 | 26 | 3 | 13 |
| Tenacity + Amicarbazone | 0.125 + 0.13 | 4 + 3 | 0 | 15 | 0 | 19 | 3 | 9 |
| Tenacity + Amicarbazone | 0.25 + 0.022 | 8 + 0.5 | 7 | 9 | 0 | 12 | 3 | 6 |
| Tenacity + Amicarbazone | 0.25 + 0.13 | 8 + 3 | 0 | 7 | 0 | 9 | 9 | 4 |

TABLE 7-14

Floratam St. Augustine bleaching from Tenacity + Amicarbazone applications plus the
expected responses calculated from the responses to each herbicide applied singly.

| Treatment | Rate (lbs ai/A) | Rate (oz/A) | 1 | Exp | 2 | Exp | 3 | Exp | 4 | Exp | 5 | Exp |
|---|---|---|---|---|---|---|---|---|---|---|---|---|
| Control | — | | 100 | | 100 | | 100 | | 100 | | 100 | |
| Amicarbazone | 0.022 | 0.5 | 100 | | 100 | | 100 | | 100 | | 100 | |
| Amicarbazone | 0.13 | 3 | 100 | | 100 | | 100 | | 100 | | 97 | |

TABLE 7-14-continued

Floratam St. Augustine bleaching from Tenacity + Amicarbazone applications plus the expected responses calculated from the responses to each herbicide applied singly.

| Treatment | Rate (lbs ai/A) | Rate (oz/A) | | | | | | | | |
|---|---|---|---|---|---|---|---|---|---|---|
| Tenacity | 0.125 | 4 | 97 | | 88 | | 75 | | 78 | 78 |
| Tenacity | 0.25 | 8 | 88 | | 78 | | 63 | | 66 | 53 |
| Tenacity + Amicarbazone | 0.125 + 0.022 | 4 + 0.5 | 88 | 97 | 84 | 88 | 69 | 75 | 78 | 78 | 63 | 78 |
| Tenacity + Amicarbazone | 0.125 + 0.13 | 4 + 3 | 97 | 97 | 91 | 88 | 81 | 75 | 88 | 78 | 84 | 76 |
| Tenacity + Amicarbazone | 0.25 + 0.022 | 8 + 0.5 | 88 | 88 | 72 | 78 | 56 | 63 | 69 | 66 | 69 | 53 |
| Tenacity + Amicarbazone | 0.25 + 0.13 | 8 + 3 | 88 | 88 | 81 | 78 | 66 | 63 | 72 | 66 | 56 | 51 |

| Treatment | Rate (lbs ai/A) | Rate (oz/A) | 6 | Exp | 7 | Exp | 8 | Exp |
|---|---|---|---|---|---|---|---|---|
| Control | — | | 100 | | 100 | | 100 | |
| Amicarbazone | 0.022 | 0.5 | 100 | | 100 | | 100 | |
| Amicarbazone | 0.13 | 3 | 97 | | 100 | | 100 | |
| Tenacity | 0.125 | 4 | 72 | | 81 | | 100 | |
| Tenacity | 0.25 | 8 | 56 | | 63 | | 100 | |
| Tenacity + Amicarbazone | 0.125 + 0.022 | 4 + 0.5 | 59 | 72 | 66 | 81 | 100 | 100 |
| Tenacity + Amicarbazone | 0.125 + 0.13 | 4 + 3 | 78 | 70 | 91 | 81 | 100 | 100 |
| Tenacity + Amicarbazone | 0.25 + 0.022 | 8 + 0.5 | 72 | 56 | 78 | 63 | 100 | 100 |
| Tenacity + Amicarbazone | 0.25 + 0.13 | 8 + 3 | 56 | 54 | 63 | 63 | 100 | 100 |

TABLE 7-15

Floratam St. Augustine turf quality as affected by Tenacity + Amicarbazone applications plus the expected responses calculated from the responses to each herbicide applied singly.

| Treatment | Rate (lbs ai/A) | Rate (oz/A) | 1 | Exp |
|---|---|---|---|---|
| Control | — | | 100 | |
| Amicarbazone | 0.022 | 0.5 | 75 | |
| Amicarbazone | 0.13 | 3 | 58 | |
| Tenacity | 0.125 | 4 | 83 | |
| Tenacity | 0.25 | 8 | 83 | |
| Tenacity + Amicarbazone | 0.125 + 0.022 | 4 + 0.5 | 67 | 63 |
| Tenacity + Amicarbazone | 0.125 + 0.13 | 4 + 3 | 42 | 49 |
| Tenacity + Amicarbazone | 0.25 + 0.022 | 8 + 0.5 | 83 | 63 |
| Tenacity + Amicarbazone | 0.25 + 0.13 | 8 + 3 | 67 | 49 |

TABLE 7-17

Sapphire St. Augustine turf quality as affected by Tenacity + Amicarbazone applications plus the expected responses calculated from the responses to each herbicide applied singly.

| Treatment | Rate (lbs ai/A) | Rate (oz/A) | 1 | Exp |
|---|---|---|---|---|
| Control | — | | 100 | |
| Amicarbazone | 0.022 | 0.5 | 100 | |
| Amicarbazone | 0.13 | 3 | 75 | |
| Tenacity | 0.125 | 4 | 100 | |
| Tenacity | 0.25 | 8 | 100 | |
| Tenacity + Amicarbazone | 0.125 + 0.022 | 4 + 0.5 | 100 | 100 |
| Tenacity + Amicarbazone | 0.125 + 0.13 | 4 + 3 | 75 | 75 |
| Tenacity + Amicarbazone | 0.25 + 0.022 | 8 + 0.5 | 100 | 100 |
| Tenacity + Amicarbazone | 0.25 + 0.13 | 8 + 3 | 75 | 75 |

TABLE 7-16

Sapphire St. Augustine bleaching from Tenacity + Amicarbazone applications plus the expected responses calculated from the responses to each herbicide applied singly.

| Treatment | Rate (lbs ai/A) | Rate (oz/A) | 1 | Exp | 2 | Exp | 3 | Exp | 4 | Exp | 5 | Exp |
|---|---|---|---|---|---|---|---|---|---|---|---|---|
| Control | — | | 100 | | 100 | | 100 | | 100 | | 100 | |
| Amicarbazone | 0.022 | 0.5 | 100 | | 100 | | 100 | | 100 | | 100 | |
| Amicarbazone | 0.13 | 3 | 94 | | 100 | | 100 | | 100 | | 100 | |
| Tenacity | 0.125 | 4 | 88 | | 88 | | 94 | | 100 | | 100 | |
| Tenacity | 0.25 | 8 | 88 | | 88 | | 69 | | 81 | | 75 | |
| Tenacity + Amicarbazone | 0.125 + 0.022 | 4 + 0.5 | 88 | 88 | 88 | 88 | 81 | 94 | 88 | 100 | 88 | 100 |
| Tenacity + Amicarbazone | 0.125 + 0.13 | 4 + 3 | 94 | 82 | 94 | 88 | 88 | 94 | 94 | 100 | 88 | 100 |
| Tenacity + Amicarbazone | 0.25 + 0.022 | 8 + 0.5 | 94 | 88 | 88 | 88 | 88 | 69 | 94 | 81 | 94 | 75 |
| Tenacity + Amicarbazone | 0.25 + 0.13 | 8 + 3 | 100 | 82 | 88 | 88 | 75 | 69 | 75 | 81 | 63 | 75 |

| Treatment | Rate (lbs ai/A) | Rate (oz/A) | 6 | Exp | 7 | Exp | 8 | Exp |
|---|---|---|---|---|---|---|---|---|
| Control | — | | 100 | | 100 | | 100 | |
| Amicarbazone | 0.022 | 0.5 | 94 | | 100 | | 100 | |
| Amicarbazone | 0.13 | 3 | 100 | | 100 | | 100 | |
| Tenacity | 0.125 | 4 | 100 | | 94 | | 100 | |
| Tenacity | 0.25 | 8 | 75 | | 81 | | 100 | |
| Tenacity + Amicarbazone | 0.125 + 0.022 | 4 + 0.5 | 81 | 94 | 81 | 94 | 100 | 100 |
| Tenacity + Amicarbazone | 0.125 + 0.13 | 4 + 3 | 88 | 100 | 100 | 94 | 100 | 100 |
| Tenacity + Amicarbazone | 0.25 + 0.022 | 8 + 0.5 | 81 | 70 | 88 | 81 | 100 | 100 |
| Tenacity + Amicarbazone | 0.25 + 0.13 | 8 + 3 | 69 | 75 | 75 | 81 | 100 | 100 |

The Kentucky bluegrass data shows that the high rate of Tenacity+Amicarbazone is injurious and synergistic to Kentucky bluegrass. The high rate of amicarbazone appears to be the driver of this response. Bleaching in mustard was reduced by the combination treatment, indicating that amicarbazone prevents some of the bleaching responses typical from mesotrione. Injury data shows some synergism initially. Annual bluegrass clearly shows synergism, particularly from the low rate of amicarbazone. The high rate of amicarbazone was sufficient to get reasonable control of annual bluegrass by itself.

Green foxtail results indicate syngergism, both in terms of increased injury from the combination treatments and in terms of reduction in bleaching from the combination.

What is claimed is:

1. A method for selective control of weeds in a turf grass, comprising contacting a weed in the turf grass with an herbicidal composition comprising amicarbazone and mesotrione; an adjuvant and a diluent carrier, wherein the application rate of amicarbazone is between about 0.025 and about 0.15 kg/ha and the application rate of mesotrione is between about 0.14 and 0.28 kg/ha; and wherein the herbicidal composition provides synergistic control of the weed.

2. The method according to claim 1, wherein the weed is a broadleaf weed.

3. The method according to claim 1, wherein the weed is selected from the group consisting of mustard, *Poa annua*, green foxtail, crabgrass, blackjack, pigweed, khaki weed, crab-finger grass, large thornapple, purslane, dwarf marigold, field bindweed, anoda weed, *Rottboelia exaltata, Ipomeoea purpurea, Eleusine indica, Amaranthus spinosus, Commelina benghalensis*, and combinations thereof.

4. The method according to claim 1, wherein the composition is applied as a pre-emergence treatment.

5. The method according to claim 1, wherein the composition is applied as a post-emergence treatment.

6. The method according to claims 1, wherein the composition is applied at an application rate of about 0.15 kg/ha of amicarbazone and about 0.14 kg/ha of mesotrione to the crop.

7. The method according to claim 1, wherein the composition is applied at an application rate of about 0.15 kg/ha of amicarbazone and about 0.280 kg/ha of mesotrione to the crop.

8. The method according to claims 1, wherein the composition is applied at an application rate of about 0.025 kg/ha of amicarbazone and about 0.14 kg/ha of mesotrione to the crop.

9. The method according to claims 1, wherein the composition is applied at an application rate of about 0.025 kg/ha of amicarbazone and about 0.28 kg/ha of mesotrione to the crop.

10. The method according to claim 1, wherein the herbicidal composition is applied as a ready mixture or as a tank mixture.

* * * * *